(12) United States Patent
Oh et al.

(10) Patent No.: US 10,993,990 B2
(45) Date of Patent: May 4, 2021

(54) METHODS AND COMPOSITIONS FOR TREATING AUTOIMMUNE AND INFLAMMATORY CONDITIONS

(71) Applicant: Baylor Research Institute, Dallas, TX (US)

(72) Inventors: SangKon Oh, Baltimore, MD (US); Sandra Zurawski, Midlothian, TX (US); Hyemee Joo, Dallas, TX (US); Gerard Zurawski, Midlothian, TX (US)

(73) Assignee: Baylor Research Institute, Dallas, TX (US)

( * ) Notice: Subject to any disclaimer, the term of this patent is extended or adjusted under 35 U.S.C. 154(b) by 327 days.

(21) Appl. No.: 15/311,572

(22) PCT Filed: May 15, 2015

(86) PCT No.: PCT/US2015/031117
§ 371 (c)(1),
(2) Date: Nov. 16, 2016

(87) PCT Pub. No.: WO2015/175957
PCT Pub. Date: Nov. 19, 2015

(65) Prior Publication Data
US 2017/0106051 A1  Apr. 20, 2017

Related U.S. Application Data

(60) Provisional application No. 61/994,239, filed on May 16, 2014, provisional application No. 62/014,504, filed on Jun. 19, 2014.

(51) Int. Cl.
*A61K 38/20* (2006.01)
*C07K 14/54* (2006.01)
*A61K 39/00* (2006.01)
*C07K 16/28* (2006.01)

(52) U.S. Cl.
CPC ...... *A61K 38/2066* (2013.01); *A61K 39/0008* (2013.01); *C07K 14/5428* (2013.01); *C07K 16/2851* (2013.01); *C07K 16/2878* (2013.01); *A61K 2039/505* (2013.01); *A61K 2039/54* (2013.01); *A61K 2039/57* (2013.01); *C07K 2317/24* (2013.01); *C07K 2317/40* (2013.01); *C07K 2317/52* (2013.01); *C07K 2317/53* (2013.01); *C07K 2317/56* (2013.01); *C07K 2317/565* (2013.01); *C07K 2317/73* (2013.01); *C07K 2317/75* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 3,791,932 A | 2/1974 | Schuurs | 435/7.8 |
| 3,949,064 A | 4/1976 | Bornstein | 436/527 |
| 4,174,384 A | 11/1979 | Ullman | 436/537 |
| 4,554,101 A | 11/1985 | Hopp | 530/324 |
| 5,738,985 A | 4/1998 | Miles et al. | 435/5 |
| 5,945,308 A | 8/1999 | Tang | 435/69.1 |
| 6,046,158 A | 4/2000 | Ariizumi | 514/21.2 |
| 6,277,959 B1 | 8/2001 | Valladeau | 530/350 |
| 6,410,241 B1 | 6/2002 | Sykes | 435/6.13 |
| 6,451,995 B1 | 9/2002 | Cheung | 536/23.53 |
| 6,541,011 B2 | 4/2003 | Punnonen | 424/204.1 |
| 6,738,985 B2 | 5/2004 | Hahn | 2/181 |
| 7,129,039 B2 | 10/2006 | Ariizumi | 435/4 |
| 7,179,595 B2 | 2/2007 | Li | 435/6.16 |
| 7,592,003 B2 | 9/2009 | Nagai | 424/93.7 |
| 7,666,596 B2 | 2/2010 | Halloran | 435/6.16 |
| 7,786,267 B2 | 8/2010 | Flamar | 530/387.1 |
| 8,236,934 B2 | 8/2012 | Banchereau et al. | 530/388.7 |
| 8,449,888 B2 | 5/2013 | Zurawski et al. | 424/179.1 |
| 8,481,314 B2 | 7/2013 | Banchereau et al. | 435/372 |
| 8,728,481 B2 | 5/2014 | Banchereau et al. | 424/178.1 |
| 9,339,556 B2 | 5/2016 | Banchereau et al. | |
| 9,453,074 B2 | 9/2016 | Oh et al. | |
| 2002/0055618 A1 | 5/2002 | Langridge et al. | |
| 2004/0126357 A1 | 7/2004 | Segal | 424/85.1 |
| 2004/0192892 A1 | 9/2004 | Valladeau et al. | 530/350 |
| 2004/0258688 A1 | 12/2004 | Hawiger et al. | 424/144.1 |

(Continued)

FOREIGN PATENT DOCUMENTS

| | | |
|---|---|---|
| CN | 102227447 | 10/2011 |
| EP | 1 418 234 | 5/2004 |

(Continued)

OTHER PUBLICATIONS

Scott et al., 2012, Nat. Rev. pp. 278-287.*
Rose, et al., "MRC1 Mannose Receptor, C Type 1 [*Homo sapiens*]," *Journal of Immunology*, 1999. http://www.ncbi.nlm.nih.gov/gene/4360.
Kundig, et al., "Fibroblasts as Efficient Antigen-Presenting Cells in Lymphoid Organs," *Science*, 268; 1343-1347, 1995.
Ohyama, et al., "Counter-Antigen Presentation: Fibroblasts Produce Cytokines by Signalling Through HLA Class II Molecules Without Inducing T-Cell Proliferation," *Cytokine*, 17(4); 175-181, 2002.

(Continued)

*Primary Examiner* — Amy E Juedes
(74) *Attorney, Agent, or Firm* — Norton Rose Fulbright US LLP

(57) ABSTRACT

Described herein are compositions and methods for inhibiting an inflammatory or autoimmune response and for inducing immune tolerance in a subject in need thereof comprising administering to the subject a therapeutically effective amount of an antigen presenting cell (APC)-targeted antibody operatively linked to IL-10 or a fragment thereof. The compositions and methods described herein are useful for treating inflammatory and autoimmune disorders.

7 Claims, 8 Drawing Sheets
Specification includes a Sequence Listing.

(56) References Cited

U.S. PATENT DOCUMENTS

| | | |
|---|---|---|
| 2004/0265901 A1 | 12/2004 | Li .................................. 435/7.1 |
| 2005/0037001 A1 | 2/2005 | Germeraad ................ 424/141.1 |
| 2005/0064509 A1 | 3/2005 | Bradbury ....................... 435/7.1 |
| 2005/0106700 A1 | 5/2005 | Kanaya ......................... 435/226 |
| 2006/0257412 A1 | 11/2006 | Bowdish .................... 424/178.1 |
| 2006/0269949 A1 | 11/2006 | Halloran ..................... 435/6.16 |
| 2008/0206262 A1* | 8/2008 | Banchereau ....... A61K 51/1027 424/172.1 |
| 2008/0233140 A1 | 9/2008 | Banchereau et al. ...... 424/185.1 |
| 2008/0254044 A1 | 10/2008 | Zurawski ................... 424/178.1 |
| 2009/0186025 A1 | 7/2009 | Colaco ....................... 424/134.1 |
| 2011/0243841 A1* | 10/2011 | Chang ............... C07K 16/2803 424/1.49 |
| 2011/0256091 A1 | 10/2011 | Neri et al. |
| 2012/0039916 A1 | 2/2012 | Zurawski et al. ......... 424/182.1 |
| 2012/0121592 A1 | 5/2012 | Oh et al. .................... 424/134.1 |
| 2012/0231023 A1 | 9/2012 | Zurawski et al. ......... 424/178.1 |
| 2012/0237513 A1 | 9/2012 | Zurawski et al. ......... 424/134.1 |
| 2012/0244155 A1 | 9/2012 | Lecine et al. .............. 424/134.1 |
| 2012/0282281 A1 | 11/2012 | Banchereau et al. ...... 424/178.1 |
| 2012/0301465 A1 | 11/2012 | Dutartre et al. ........... 424/134.1 |
| 2012/0315269 A1 | 12/2012 | Klechevsky et al. ...... 424/133.1 |
| 2014/0044674 A1 | 2/2014 | Duerner et al. |
| 2016/0375126 A1 | 12/2016 | Oh et al. .................... 424/186.1 |

FOREIGN PATENT DOCUMENTS

| | | | |
|---|---|---|---|
| EP | 1 441 030 | 7/2004 | |
| FR | 2748479 | 11/1997 | |
| JP | 2000-157282 | 6/2000 | |
| JP | 2004-236504 | 8/2004 | |
| JP | 2006/521387 | 9/2006 | |
| JP | 2010/518024 | 5/2010 | |
| JP | 2013/525496 | 6/2013 | |
| JP | 2013/540162 | 10/2013 | |
| TW | 201219053 | 5/2012 | |
| WO | WO 1997/14789 | 4/1997 | |
| WO | WO 00/063251 | 10/2000 | |
| WO | WO 2000/63151 | 10/2000 | |
| WO | WO 2002/035242 | 5/2002 | |
| WO | WO 2003/036895 | 5/2003 | |
| WO | WO 2003/073827 | 9/2003 | |
| WO | WO 06/004663 | 1/2006 | |
| WO | WO 2006/107617 | 10/2006 | |
| WO | WO 2008/097817 | 8/2008 | |
| WO | WO-2010040105 A2 * | 4/2010 | ......... C07K 16/2827 |
| WO | WO 2011/044452 | 4/2011 | |
| WO | WO 2012/051291 | 4/2012 | |
| WO | WO 2012/122396 | 9/2012 | |
| WO | WO 2014/023673 | 2/2014 | |

OTHER PUBLICATIONS

Office Action issued in corresponding Japanese Patent Application No. 2017-512873 dated Feb. 28, 2019.
Extended European Search Report Issued in Corresponding European Application No. 15792154.5, dated Mar. 13, 2018.
Accession No. NP_498023, Nov. 2008, pp. 1-2.
Ahmad-Nejad, et al., "Bacterial CpG-DNA and Lipopolysaccharides Activate Toll-Like Receptors at Distinct Cellular Compartments," European J. Immunol., (2002), 32:1958-1968.
Arce, Ignacio et al., "The human C-type lectin CLECSF18 is a novel monocyte/macrophage endocytic receptor", European Journal of Immunology, 2004, vol. 34(1), pp. 210-220.
Asea, A., et al., "HSP70 Stimulates Cytokine Production Through a CD14-Dependant Pathway, Demonstrating its Dual Role as a Chaperone and Cytokine," Nat Med, (2000), 6:435-442.
Balazs, F., et al., "Blood Dendritic Cells Interact with Splenic Marginal Zone B Cells to Initiate T-Independent Immune Responses," Immunity, (2002), 17:341-352.
Balch, et al., *J Biol Chem.* 273(29): 18656-64, 1998.

Banchereau J., et al., "Immune and Clinical Responses in Patients with Metastatic Melanoma to CD34(+) Progenitor-Derived Dendritic Cell Vaccine," Cancer Res, (2001), 61(17):6451-8.
Banchereau, J., et al., "Dendritic Cells and the Control of Immunity," Nature, (1998), 392:245-252.
Banchereau, J., et al., "Dendritic Cells as Vectors for Thereapy," Cell, (2001), 106(3):271-4.
Banchereau, J., et al., "Immunobiology of Dendritic Cells," Annu Rev Immunol, (2000), 18:767-811.
Barak, Y. et al., "Matching Fusion Protein Systems for Affinity Analysis of Two Interacting Families of Proteins: the Cohesin-Dockerin Interaction", J. Mo. Recognit, 2005:18:491-501.
Barrios, et al., "Length of the Antibody Heavy Chain Complementarity Determining Region 3 as a Specificity-Determining Factor", J. Mol. Recognit. 2004: 17:332-338.
Bates, E. E., et al., "APCs Express DCIR, a Novel C-Type Lectin Surface Receptor Containing an Immunoreceptor Tyrosine-Based Inhibitory Motif," J Immunol, (1999), 163(4):1973-83.
Bausinger, H., et al., "Endotoxin-Free Heat-Shock Protein 70 Fails to Induce APC Activation," Eur J Immunol (2002), 32:3708-3713.
Bayer, et al., *Trends Biotechnol.* 12: 379-386, 1994.
Bendsten, J.D., et al., "Improved Prediction of Signal Peptides: SignaIP 3.0." J Mol Bioi, (2004), 340(4):783-95.
Berard, F., et al., "Cross-Priming of Naive CDS T Cells Against Melanoma Antigens Using Dendritic Cells Loaded with Killed Allogeneic Melanoma Cells," J Exp Med, (Dec. 2000), 192(11):1535-44.
Bergtold, A., et al., "Cell Surface Recycling of Internalized Antigen Permits Dendritic Cell Priming of B Cells," Immunity (2005), 23:503-514.
Bernasconi, N. L., et al., "Maintenance of Serological Memory by Polyclonal Activation of Human Memory B Cells," Science (2002), 298:2199-2202.
Beutler, B., et al., "Genetic Analysis of Host Resistance: Toll-Like Receptor Signaling and Immunity at Large," Annu Rev lmmunol (2006), 24:353-389.
Bonifaz, L.C., et al., "In Vivo Targeting of Antigens to Maturing Dendritic Cells via the DEC-205 Receptor Improves T Cell Caccination" J Exp Med, (Mar. 2004), 199(6):815-24.
Bonifaz, Laura, et al., "Efficient Targeting of Protein Antigen to the Dendritic Cell Receptor DEC-205 in the Steady 8 State Leads to Antigen Presentation on Major Histocompatibility Complex Class I Products and Peripheral CD8 T Cell D Tolerance," J. Exp. Med., Dec. 16, 2002, vol. 196, No. 12, pp. 1627-1638.
Brown, G. D., "Dectin-1: a signalling non-TLR pattern-recognition receptor," Nat Rev lmmunol (2006), 6:33-43.
Burgdorf et al., *J Immunol.* 176:6770-6, 2006.
Cambi, A., et al., "The C-type lectin DC-SIGN (CD209) is an antigenuptake receptor for Candida albicans on dendritic cells," Eur J lmmunol (2003), 33:532-538.
Carter, et al., "Preferential Induction of CD4+ T Cell Responses through In Vivo Targeting of Antigen to Dendritic Cell-Associated C-Type Lectin-1", J. of lmmunol., vol. 177, No. 4, 2006, pp. 2276-2284.
Carvalho, A.L., et al., "Cellulosome Assembly Reveal by the Crystal Structure of the Cohesin-Dockerin Complex." Proc Natl Acad Sci USA, (2003), 100(24):13809-14.
Chu. et al., "CpG Oligodeoxynucleotides Down-Regulate Macrophage Class II MHC Antigen Processing", J lmmunol 1999:163:1188-1194.
Colonna, M., et al., "Molecular Characterization of Two Novel C-Type Lectin-Like Receptors, one of which is Selectively Expressed in Human Dendritic Cells," Eur J lmmunol (2000), 30:697-704.
Cooper, A.M., et al., "Mice Lacking Bioactive IL-12 Can Generate Protective, Antigen-Specific Cellular Responses to Mycobacterial Infection Only if the IL-12 p40 Subunit is Present," J lmmunol (2002), 168:1322-1327.
Craig et al., 2006, J. Biotech. vol. 121: 165-173.
Craxton, A., et al., "Macrophage and Dendritic Cell-Dependent Regulation of Human B-Cell Proliferation Requires the TNF Family Ligand BAFF," Blood, (2003), 101:4464-4471.
Daly, et al., *Anal Lett.* 34:1799-1827, 2001.

(56) References Cited

OTHER PUBLICATIONS

Deineste, Y., G. et al., "Involvement of LOX-1 in Dendritic Cell-Mediated Antigen Cross-Presentation." Immunity (2002), 17(3):353-62.

Deyev, S.M. et al., "Design of multivalent complexes using the barnase-barstar module", Nature Biotechnology, vol. 21, No. 12, Dec. 2003, pp. 1486-1492.

Ding, et al., "A Scaffoldin of the Bacteriodes cellulosolvens Celluslosome That Contains 11 Type II Cohesins", J. Bacteriology 182(17):4915-4925, Sep. 2000.

Ding, et al.,"The Bacterial Scaffoldin: Structure, Function and Potential Applications in the Nanosciences", Genetic Engineering, vol. 25:209-225, (2003).

D'Ostiani, C. F., et al., "Dendritic Cells Discriminate between Yeasts and Hyphae of the Fungus *Candida albicans*: Implications for Initiation ofT Helper Cell Immunity In Vitro and In Vivo," J Exp Med {2000), 191:1661-1673.

Dubois, B., et al., "Dendritic cells directly modulate B cell growth and differentiation," J Leukoc Bioi (1999), 66:224-230.

Engering, et al., *Trends Immunol.* 23(10): 480-5, 2002.

Extended European Search Report for Application No. 08714180.0, dated Sep. 29, 2011, 14 pages.

Extended European Search Report for Application No. 08728767.8, dated Aug. 24, 2010, 11 pages.

Extended European Search Report for Application No. 08728868.4, dated Aug. 3, 2010, 10 pages.

Extended European Search Report for Application No. 08799678.1, dated Feb. 5, 2010, 12 pages.

Fierobe, H-P. et al., "Design and Production of Active Cellulosome Chimeras," J Bioi Chem (2001 ), 276:21257-21261.

Figdor, C. G., et al., "C-Type Lectin Receptors on Dendritic Cells and Langerhans Cells," Nat Rev lmmunol, (2002), 2{2}: 77-84.

Flamar, A.L. et al., "Antibody and Antigen Complexes Based on Cohesin and Dockerin Interaction are Versatile Tools for Eliciting and Monitoring Specific Immune Responses", Clinical Immunology, US Lnkd-DOI:1 0.1016/J. D Clim.2009.03.019, vol. 131, Jan. 1, 2009, pp. S9.

Flomes, L.M. et al., "Identification of Lectin-Like Receptors Expressed by Antigen Presenting Cells and Neutrophils and their Mapping to a Novel Gene Complex," Immunogenetics, (2004), vol. 56, pp. 506-517.

Fradin, C., et al., "~-1 ,2-Linked Oligomannosides from Candida albicans Bind to a 32-Kilodalton Macrophage Membrane Protein Homologous to the Mammalian Lectin Galectin-3," Infect lmmun (2000), 68:4391-4398.

Frankel, A. F., "Increased Sophistication of lmmunotoxins," Clin Can Res, {2002), 8:942-944.

Gantner, B. N., et al., "Collaborative Induction of Inflammatory Responses by Dectin-1 and Toll-like Receptor 2," J Exp Med (2003), 197:1107-1117.

Geijtenbeek, T. B., et al., "DC-SIGN-ICAM-2 Interaction Mediates Dendritic Cell Trafficking," Nat lmmunol {2000), 1:353-357.

Geijtenbeek, T. B., et al., "Identification of DC-SIGN, a Novel Dendritic Cell-Specific ICAM-3 Receptor that Supports Primary Immune Responses," Cell (2000), 100:575-585.

Geijtenbeek, T. B., et al., "Mycobacteria Target DC-SIGN to Suppress Dendritic Cell Function," J Exp Med (2003), 197:7-17.

Geijtenbeek, T.B., et al., "Self-and Nonself-Recognition by C-type Lectins on Dendritic Cells." Annu Rev lmmunol (2004), 22:33-54.

Gross, J. A., et al., "TACI and BCMA are Receptors for a TNF Homologue Implicated in B-cell Autoimmune Disease," Nature (2000), 404:995-999.

Grueneback, et al., "Human {h) Dectin-1 is a Member of C-Type-Lectin-Like Receptor Family that was Shown to be the Major Receptor for Fungal Beta-Giucans . . . "Abstract from 49th Annual Meeting of the American Society of Dematology, Dec. 2007, XP002563205, 2 pages.

Hayashida, K., et al., "Lectin-Like Oxidized LDL Receptor-1 (LOX-1) Supports Adhesion of Mononuclear Leukocytes and a Monocyte-Like Cell Line THP-1 Cells Under Static and Flow Conditions," FEBS Letters, (2002), 511:133-138.

Huang, et al., "Cloning and Characterization of a Novel ITIM Containing Lectin-like lmmunoreceptor LLIR and its Two Transmembrane Region Deletion Variants", Biochem. Biophys. Res. Commun., 281(1):131-140, (2001).

International search Report and Written Opinion for PCT/US08/52865, dated Aug. 13, 2008, 8 pages.

International Search Report and Written Opinion for PCT/US2008/052714, dated Jul. 8, 2008, 8 pages.

International Search Report and Written Opinion for PCT/US2008/054785, dated Sep. 25, 2008, 12 pages.

International Search Report and Written Opinion for PCT/US2008/054792, dated Aug. 13, 2008, 10 pages.

International Search Report and Written Opinion for PCT/US2008/054798, dated Dec. 8, 2008, 13 pages.

International Search Report and Written Opinion for PCT/US2008/52850, dated Sep. 24, 2008, 9 pages.

Janeway, et al., *Immunobiol.* 3:3-3: 4, 1997.

Jeannin, P., et al., "Complexity and Complementarity of Outer Membrane Protein A Recognition by Cellular and Humoral Innate Immunity Receptors," Immunity (2005), 22:551-560.

Jego, G., et al., "Plasmacytoid Dendritic Cells Induce Plasma Cell Differentiation through Type I Interferon and lnterleukin 6," Immunity (2003), 19:225-234.

Jiang, W., et al., Nature, 375, pp. 151-155, May 11, 1995.

Jindou, S. et al., "Interaction between a Type-11 Dockerin Domain and a Type-11 Cohesin Domain from Clostridium thermocellum Cellulosome", Biosci. Biotechnol. Biochem. 68(4):924-926,(2004).

Kakutani, M., et al., "A platelet-endothelium interaction mediated by lectin-like oxidized low-density lipoprotein receptor-1," PNAS (2000), 97:360-364.

Karni et al., Journal of Immunology vol. 177: 4196-4202, 2006.

Karpol, A. et al., "Engineering a Reversible, High-Affinity System for Efficient Protein Purification Based on the Cohesin-Dockerin Interaction", J. Mol. Recognit. 2009, vol. 22:91-98.

Kikuchi, T., et al., "Dendritic Cells Genetically Modified to Express CD40 Ligand and Pulsed with Antigen can Initiate Antigen-Specific Humoral Immunity Independent of CD4+ T Cells," Nat Med, (2000), 6:1154-1159.

Klimka et al., "Human Anti-CD30 Recombinant Antibodies by Guided Phage Antibody Selection Using Cell Planning", Brit. J. Cancer, vol. 83, 252-260, 2000.

Kobrin, et al., "A V Region Mutation in a Phosphocholine-Bindng Monoclonal Antibody Results in Loss of Antigen Binding", J. Immunology, 146:2017-2020 (1991).

Latz, et al., "TLR9 Signals After Translocating from the ER to CpG DNA in the Lysosome", Nat. lmmunol., (2004), vol. 5:190-198.

Lee, S. J., et al., "Mannose Receptor-Mediated Regulation of Serum Glycoprotein Homeostasis," Science (2002), 295:1898-1901.

Li et al., "Targeting self-and foreign antigens to dendritic cells via DC-ASGPR generates IL-10-producing suppressive CD4+ T cells," *J Exp. Med.* 2012; 209: 109-121.

Li, et al., *Clin Exp Immunol.* 162:251-61, 2010.

Luft, et al., *International Immunology* 14(4):367-380, 2002.

Ma, "Genome-Wide Analysis of Human Peripheral Leukocyte Gene Expression," PhD Thesis, p. 51 & 60, 2003.

MacLennan, C., et al., "Dendritic Cells, BAFF, and APRIL: Innate Players in Adaptive Antibody Responses," Immunity (2002), 17:235-238.

Maeda, N., et al., "The Cell Surface Receptor DC-SIGN Discriminates between *Mycobacterium* Species through Selective Recognition of the Mannose Caps on Lipoarabinomannan," J Bioi Chern, (2003), 278:5513-5513.

Marks et al., "By-Passing Immunization: Human Antibodies from V-gene Libraries Displayed on Phage", J. Mol. Bioi., (1991), 222:581-597.

Mechaly, A. et al., "Cohesin-Dockerin Interaction in Cellulosome Assembly", J. Biological Chemistry, Mar. 30, 2001, vol. 276, No. 13, pp. 9883-9888.

Mehta et al., "Lectin-like, oxidized low-density lipoprotein receptor-1 (LOX-1): a critical player in the development of aterosclerosis and related disorders", *Cardiovasc. Res.*, 69:36-45, 2006.

(56) References Cited

OTHER PUBLICATIONS

Mellman, I. et al., "Dendritic Cells: Specialized and Regulated Antigen Processing Machines," Cell, (2001), 106 (3):255-8.
Moore, P. A., et al., "BLyS: Member of the Tumor Necrosis Factor Family and B Lymphocyte Stimulator," Science (1999), 285:260-263.
Moriwaki, H., et al., "Expression of Lectin-Like Oxidized Low Density Lipoprotein Receptor-1 in Human and Murine Macrophages: Upregulated Expression by TN F-a," FEBS Letters, (1998), 440:29-32.
Neidhardt-Berard, E.M., et al., "Dendritic Cells Loaded with Killed Breast Cancer Cells Induce Differentiation of Tumor-Specific Cytotoxic T Lymphocytes" Breast Cancer Res, (2004), 6(4):R322-8.
Netea, M.G., et al., "CD40/CD40 Ligand Interactions in the Host Defense Against Disseminated Candida Albicans Infection: the Role of Macrophage-Derived Nitric Oxide," Eur J lmmunol, (2002), 32:1455-1463.
Office Communication in Israeli Patent Application No. 224539 dated Apr. 23, 2013.
Palucka, A.K., et al., "Human Dendritic Cell Subsets in NOD/SCID Mice Engrafted with CD34+ Hematopoieticprogenitors," Blood, (2003), 102(9):3302-1 0.
Proudfoot et al., "Receptor-Mediated Delivery of Antigens to Dendritic Cells: Anticancer Applications", Molec. Pharm., vol. 4, 2007, pp. 58-72.
Pyz, E., et al., "C-Type Lectin-Like Receptors on Myeloid Cells," Ann Med, (2006), 38:242-251.
Ql, H., et al., "Extrafollicular Activation of Lymph Node B Cells by Antigen-Bearing Dendritic Cells," Science (2006), 312:1672-1676.
Ramakrishna, et al., "Toll-like Receptor Activation Enhances Cell-Mediated Immunity Inducted by an Antibody Vaccine Targeting Human Dendritic Cells", Journal of Translational Medicine, vol. 5:5, pp. 1-14, Jan. 2007.
Ramakrishna, V., et al., "Mannose Receptor Targeting of Tumor Antigen PMEL 17 to Human Dendritic Cells Directs Antimelanoma T Cell Responses via Multiple HLA Molecules" J lmmunol, (2004), 172(5):2845-52.
Reddy, M.P., et al., "Elimination of FC Receptor-Dependent Effector Functions of a Modified lgG4 Monoclonal Antibody to Human CD4," J lmmunol ,(2000), 164(4):1925-33.
Riemer, et al., Mol Immunol. 42: 1121-4, 2005.
Rocca-Serra, et al., Nature. 304:353-355, 1983.
Rossi, E.A. et al., "Development of New Multivalent-bispecific Agents for Pretargeting Tumor Localization and Therapy", Clinical Cancer Research, vol. 9, Sep. 1, 2003, pp. 3886S-3896S.
Ruprecht, C. R., et al., "Toll-like Receptor Stimulation as a Third Signal Required for Activation of Human Naive B Cells," Eur J lmmunol, (2006), 36:810-816.
Saeland, S., "Langerin and the DC Asialoglycoprotein Receptor: Two Closely Related Endocytic Type-11 Lectins with Divergent Functions in Dendritic Cells," Journal of Investigative Dermatology, vol. 117, No. 4, Oct. 2001, p. 1003.
Sagoo et al., "Regulatory T cells and therapeutic cells," *Curr. Opin. Organ. Transplant*, 2008; 13: 645-653.
Schaft, Neils, et al., "Dendritic Cell Vaccination and Other Strategies to Tip the Balance of the Immune System," Cancer lmmunol. lmmunother, (2008), 57:913-928.
Shortman, Ken, et al., "Mouse and Human Dendritic Cell Subtypes," Nature Reviews, Immunology, vol. 2, Mar. 2002, pp. 454-465.

Smith, Daniel C., et al., "Lack of Dendritic Cell Maturation by the Plant Toxin Ricin," European J. lmmunol., (2004), 34:2149-2157.
Spooner, RA, et al., "Expression of Immunoglobulin Heavy Chain-Ricin a Chain Fusions in Mammalian Cells," Mol. lmmunol., Feb. 1994, 31(2):117-125.
Stancovski, et al., *PNAS.* 88:8691-5, 1991.
Starovasnik, Melissa A., et al., "Structural Mimicry of a Native Protein by a Minimized Binding Domain," Proc. Nat. Acad. Sci. USA, Sep. 1997, vol. 94, pp. 10080-10085.
Steinman, "In vitro production of antigen-activated dendritic cell precursor for use as an immunogen in a vaccine; application in juvenile diabetes, multiple sclerosis, myasrhenia gravis and atopic dermatitis therapy", Vaccine, 12(5):478, 1994.
Steinman, Ralph M., et al., "Active Immunization Against Cancer with Dendritic Cells: The Near Future," Int. J. Cancer, {2001), 94, 459-473.
Tacken, Paul J., et al., "Effective Induction of Naive and Recall T-Cell Responses by Targeting Antigen to Human Dendritic Cells via a Humanized Anti-DC-SIGN Antibody," Blood, May 5, 2005, 106:1278-1285.
Tailleux, L., et al., "DC-SIGN is the Major *Mycobacterium tuberculosis* Receptor on Human Dendritic Cells," J Exp Med (2003), 197:121-127.
Tan, et al., "Mannose Receptor-Mediated Uptake of Antigens Strongly Enhances HLA Class 11-Restricted Antigen Presentation by Cultured Dendritic Cells," Eur. J. lmmunol., 1997, 27:2426-2435.
Trombetia, E. Sergio, et al., "Cell Biology of Antigen Processing In Vitro and In Vivo," Annu. Rev. lmmunol., 2005, 23:975-1028.
Trumpfheller, Christine, et al., "Intensified and Protective CD4+ T Cell Immunity in Mice with Anti-Dendritic Cell HIV Gag Fusion Antibody Vaccine," Mar. 20, 2006, vol. 203, No. 3, pp. 607-617.
Valladeau, J., et al., "Immature Human Dendritic Cells Express Asialoglycoprotein Receptor lsoforms for Efficient Receptor-Mediated Endocytosis," J lmmunol (2001), 167:5767-5774.
Wang, Y., et al., "CD40 is a Cellular Receptor Mediating Mycobacterial Heat Shock Protein 70 Stimulation of CC-Chemokines," Immunity (2001), 15:971-983.
Wiley, K.N., et al., "The In-Vitro Inhibition of Rat Alloantigen Presentation by lmmunotoxins—IMplications for Allografting," Clin. Exp. lmmunol., (1989), 76:132-137.
Wykes, M. N., et al., "Dendritic cell-8-cell interaction: dendritic cells provide B cells with CD40-independent proliferation signals and CD40-dependent survival signals," Immunology (2000), 100:1-3.
Wykes, M. N., et al., "Dendritic cells and follicular dendritic cells express a novel ligand for CD38 which influences their maturation and antibody responses," Immunology (2004), 113:318-327.
Xie et al., "Generation of Anti-LOX-1 Cytotoxic T Lymphocytes by AAV Manipulation of Dendritic Cells towards Preventing Atheosclerosis", *Mol. Ther.*, 11(Suppl. 1):S362-S363, 2005.
Zhu, Zhenping, et al., "Inhibition of Tumor Grow1h and Metastasis by Targeting Rumor-Associated Angiogenesis with Antagonists to the Receptors of Vascular Endothelial Grow1h Factor," Investigational New Drugs, 1999, 17:195-212.
Zymosan, Dectin-1 Review, "A Major Receptor in Antifungal Immunity" 2008.
Office Action and Search Report Issued in Corresponding Chinese Patent Application No. 201580038844.8, dated Jan. 16, 2020.
Office Action and Search Report Issued in Corresponding Chinese Patent Application No. 201580038844.8, dated Sep. 2, 2020.

\* cited by examiner

SEQUENCE LISTING

```
<160> NUMBER OF SEQ ID NOS: 114

<210> SEQ ID NO 1
<211> LENGTH: 633
<212> TYPE: PRT
<213> ORGANISM: Homo sapiens

<400> SEQUENCE: 1

Val Gln Leu Gln Glu Ser Gly Pro Asp Leu Val Lys Pro Ser Gln Ser
1               5                   10                  15

Leu Ser Leu Thr Cys Thr Val Thr Gly Tyr Ser Ile Thr Ser Gly Tyr
            20                  25                  30

Ser Trp His Trp Ile Arg Gln Phe Pro Gly Asn Lys Leu Glu Trp Met
        35                  40                  45

Gly Tyr Ile Leu Phe Ser Gly Ser Thr Asn Tyr Asn Pro Ser Leu Lys
    50                  55                  60

Ser Arg Ile Ser Ile Thr Arg Asp Thr Ser Lys Asn Gln Phe Phe Leu
65                  70                  75                  80

Gln Leu Asn Ser Val Thr Thr Glu Asp Thr Ala Thr Tyr Phe Cys Ala
                85                  90                  95
```

```
Arg Ser Asn Tyr Gly Ser Phe Ala Ser Trp Gln Gly Thr Leu Val
            100                 105                 110
Thr Val Ser Ala Ala Lys Thr Thr Gly Pro Ser Val Phe Pro Leu Ala
        115                 120                 125
Pro Cys Ser Arg Ser Thr Ser Glu Ser Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Lys Thr Tyr Thr Cys Asn Val Asp His Lys Pro Ser Asn Thr
        195                 200                 205
Lys Val Asp Lys Arg Val Glu Ser Lys Tyr Gly Pro Pro Cys Pro Pro
    210                 215                 220
Cys Pro Ala Pro Glu Phe Glu Gly Gly Pro Ser Val Phe Leu Phe Pro
225                 230                 235                 240
Pro Lys Pro Lys Asp Thr Leu Met Ile Ser Arg Thr Pro Glu Val Thr
                245                 250                 255
Cys Val Val Val Asp Val Ser Gln Glu Asp Pro Glu Val Gln Phe Asn
            260                 265                 270
Trp Tyr Val Asp Gly Val Glu Val His Asn Ala Lys Thr Lys Pro Arg
        275                 280                 285
Glu Glu Gln Phe Asn Ser Thr Tyr Arg Val Val Ser Val Leu Thr Val
    290                 295                 300
Leu His Gln Asp Trp Leu Asn Gly Lys Glu Tyr Lys Cys Lys Val Ser
305                 310                 315                 320
Asn Lys Gly Leu Pro Ser Ser Ile Glu Lys Thr Ile Ser Lys Ala Lys
                325                 330                 335
Gly Gln Pro Arg Glu Pro Gln Val Tyr Thr Leu Pro Pro Ser Gln Glu
            340                 345                 350
Glu Met Thr Lys Asn Gln Val Ser Leu Thr Cys Leu Val Lys Gly Phe
        355                 360                 365
Tyr Pro Ser Asp Ile Ala Val Glu Trp Glu Ser Asn Gly Gln Pro Glu
    370                 375                 380
Asn Asn Tyr Lys Thr Thr Pro Pro Val Leu Asp Ser Asp Gly Ser Phe
385                 390                 395                 400
Phe Leu Tyr Ser Arg Leu Thr Val Asp Lys Ser Arg Trp Gln Glu Gly
                405                 410                 415
Asn Val Phe Ser Cys Ser Val Met His Glu Ala Leu His Asn His Tyr
            420                 425                 430
Thr Gln Lys Ser Leu Ser Leu Ser Leu Gly Lys Ala Ser Gln Thr Pro
        435                 440                 445
Thr Asn Thr Ile Ser Val Thr Pro Thr Asn Asn Ser Thr Pro Thr Asn
    450                 455                 460
Asn Ser Asn Pro Lys Pro Asn Pro Ala Ser Pro Gly Gln Gly Thr Gln
465                 470                 475                 480
Ser Glu Asn Ser Cys Thr His Phe Pro Gly Asn Leu Pro Asn Met Leu
                485                 490                 495
Arg Asp Leu Arg Asp Ala Phe Ser Arg Val Lys Thr Phe Phe Gln Met
            500                 505                 510
```

```
Lys Asp Gln Leu Asp Asn Leu Leu Leu Lys Glu Ser Leu Leu Glu Asp
            515                 520                 525
Phe Lys Gly Tyr Leu Gly Cys Gln Ala Leu Ser Glu Met Ile Gln Phe
    530                 535                 540
Tyr Leu Glu Glu Val Met Pro Gln Ala Glu Asn Gln Asp Pro Asp Ile
545                 550                 555                 560
Lys Ala His Val Asn Ser Leu Gly Glu Asn Leu Lys Thr Leu Arg Leu
                565                 570                 575
Arg Leu Arg Arg Cys His Arg Phe Leu Pro Cys Glu Asn Lys Ser Lys
            580                 585                 590
Ala Val Glu Gln Val Lys Asn Ala Phe Asn Lys Leu Gln Glu Lys Gly
        595                 600                 605
Ile Tyr Lys Ala Met Ser Glu Phe Asp Ile Phe Ile Asn Tyr Ile Glu
    610                 615                 620
Ala Tyr Met Thr Met Lys Ile Arg Asn
625                 630

<210> SEQ ID NO 2
<211> LENGTH: 445
<212> TYPE: PRT
<213> ORGANISM: Homo sapiens

<400> SEQUENCE: 2

Val Gln Leu Gln Glu Ser Gly Pro Asp Leu Val Lys Pro Ser Gln Ser
1               5                   10                  15
Leu Ser Leu Thr Cys Thr Val Thr Gly Tyr Ser Ile Thr Ser Gly Tyr
                20                  25                  30
Ser Trp His Trp Ile Arg Gln Phe Pro Gly Asn Lys Leu Glu Trp Met
            35                  40                  45
Gly Tyr Ile Leu Phe Ser Gly Ser Thr Asn Tyr Asn Pro Ser Leu Lys
        50                  55                  60
Ser Arg Ile Ser Ile Thr Arg Asp Thr Ser Lys Asn Gln Phe Phe Leu
65                  70                  75                  80
Gln Leu Asn Ser Val Thr Thr Glu Asp Thr Ala Thr Tyr Phe Cys Ala
                85                  90                  95
Arg Ser Asn Tyr Gly Ser Phe Ala Ser Trp Gly Gln Gly Thr Leu Val
            100                 105                 110
Thr Val Ser Ala Ala Lys Thr Thr Gly Pro Ser Val Phe Pro Leu Ala
        115                 120                 125
Pro Cys Ser Arg Ser Thr Ser Glu Ser Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Lys Thr Tyr Thr Cys Asn Val Asp His Lys Pro Ser Asn Thr
        195                 200                 205
Lys Val Asp Lys Arg Val Glu Ser Lys Tyr Gly Pro Pro Cys Pro Pro
    210                 215                 220
Cys Pro Ala Pro Glu Phe Glu Gly Gly Pro Ser Val Phe Leu Phe Pro
225                 230                 235                 240
Pro Lys Pro Lys Asp Thr Leu Met Ile Ser Arg Thr Pro Glu Val Thr
                245                 250                 255
```

-continued

Cys Val Val Asp Val Ser Gln Glu Asp Pro Glu Val Gln Phe Asn
                260                 265                 270

Trp Tyr Val Asp Gly Val Glu Val His Asn Ala Lys Thr Lys Pro Arg
            275                 280                 285

Glu Glu Gln Phe Asn Ser Thr Tyr Arg Val Val Ser Val Leu Thr Val
        290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys Ala Ser
        435                 440                 445

<210> SEQ ID NO 3
<211> LENGTH: 119
<212> TYPE: PRT
<213> ORGANISM: Homo sapiens

<400> SEQUENCE: 3

Gln Leu Gln Glu Ser Gly Pro Asp Leu Val Lys Pro Ser Gln Ser Leu
1               5                   10                  15

Ser Leu Thr Cys Thr Val Thr Gly Tyr Ser Ile Thr Ser Gly Tyr Ser
            20                  25                  30

Trp His Trp Ile Arg Gln Phe Pro Gly Asn Lys Leu Glu Trp Met Gly
        35                  40                  45

Tyr Ile Leu Phe Ser Gly Ser Thr Asn Tyr Asn Pro Ser Leu Lys Ser
    50                  55                  60

Arg Ile Ser Ile Thr Arg Asp Thr Ser Lys Asn Gln Phe Phe Leu Gln
65                  70                  75                  80

Leu Asn Ser Val Thr Thr Glu Asp Thr Ala Thr Tyr Phe Cys Ala Arg
                85                  90                  95

Ser Asn Tyr Gly Ser Phe Ala Ser Trp Gly Gln Gly Thr Leu Val Thr
            100                 105                 110

Val Ser Ala Ala Lys Thr Thr
        115

<210> SEQ ID NO 4
<211> LENGTH: 27
<212> TYPE: PRT
<213> ORGANISM: Homo sapiens

<400> SEQUENCE: 4

Gln Thr Pro Thr Asn Thr Ile Ser Val Thr Pro Thr Asn Asn Ser Thr
1               5                   10                  15

```
Pro Thr Asn Asn Ser Asn Pro Lys Pro Asn Pro
            20                  25

<210> SEQ ID NO 5
<211> LENGTH: 161
<212> TYPE: PRT
<213> ORGANISM: Homo sapiens

<400> SEQUENCE: 5

Ala Ser Pro Gly Gln Gly Thr Gln Ser Glu Asn Ser Cys Thr His Phe
1               5                   10                  15

Pro Gly Asn Leu Pro Asn Met Leu Arg Asp Leu Arg Asp Ala Phe Ser
            20                  25                  30

Arg Val Lys Thr Phe Phe Gln Met Lys Asp Gln Leu Asp Asn Leu Leu
        35                  40                  45

Leu Lys Glu Ser Leu Leu Glu Asp Phe Lys Gly Tyr Leu Gly Cys Gln
    50                  55                  60

Ala Leu Ser Glu Met Ile Gln Phe Tyr Leu Glu Glu Val Met Pro Gln
65                  70                  75                  80

Ala Glu Asn Gln Asp Pro Asp Ile Lys Ala His Val Asn Ser Leu Gly
                85                  90                  95

Glu Asn Leu Lys Thr Leu Arg Leu Arg Leu Arg Arg Cys His Arg Phe
            100                 105                 110

Leu Pro Cys Glu Asn Lys Ser Lys Ala Val Glu Gln Val Lys Asn Ala
        115                 120                 125

Phe Asn Lys Leu Gln Glu Lys Gly Ile Tyr Lys Ala Met Ser Glu Phe
    130                 135                 140

Asp Ile Phe Ile Asn Tyr Ile Glu Ala Tyr Met Thr Met Lys Ile Arg
145                 150                 155                 160

Asn

<210> SEQ ID NO 6
<211> LENGTH: 1959
<212> TYPE: DNA
<213> ORGANISM: Homo sapiens

<400> SEQUENCE: 6
atgagagcgc tgattctttt gtgcctgttc acagcctttc ctggtatcct gtctgatgtg      60
cagcttcagg agtcaggacc tgacctggtg aaaccttctc agtcactttc actcacctgc    120
actgtcactg gctactccat caccagtggt tatagctggc actggatccg gcagtttcca    180
ggaaacaaac tggaatggat gggctacata ctcttcagtg gtagcactaa ctacaaccca    240
tctctgaaaa gtcgaatctc tatcactcga gacacatcca agaaccagtt cttcctgcag    300
ttgaattctg tgactactga ggacacagcc acatatttct gtgcaagatc taactatggt    360
tcctttgctt cctggggcca agggactctg gtcactgtct ctgcagccaa acaacgggc     420 ccatccgtct tccccctggc gccctgctcc aggagcacct ccgagagcac agccgccctg    480
ggctgcctgg tcaaggacta cttccccgaa ccggtgacgg tgtcgtggaa ctcaggcgcc    540
ctgaccagcg gcgtgcacac cttcccggct gtcctacagt cctcaggact ctactccctc    600
agcagcgtgg tgaccgtgcc ctccagcagc ttgggcacga agacctacac ctgcaacgta    660
gatcacaagc ccagcaacac caaggtggac aagagagttg agtccaaata tggtccccca    720
tgcccacccc tgcccagcac ctgagttcga aggggaccat cagtcttcct gttccccca    780 aaacccaagg acactctcat gatctcccgg acccctgagg tcacgtgcgt ggtggtggac    840
```

```
gtgagccagg aagaccccga ggtccagttc aactggtacg tggatggcgt ggaggtgcat    900
aatgccaaga caaagccgcg ggaggagcag ttcaacagca cgtaccgtgt ggtcagcgtc    960
ctcaccgtcc tgcaccagga ctggctgaac ggcaaggagt acaagtgcaa ggtctccaac   1020
aaaggcctcc cgtcctccat cgagaaaacc atctccaaag ccaagggca gccccgagag    1080
ccacaggtgt acaccctgcc cccatcccag gaggagatga ccaagaacca ggtcagcctg   1140
acctgcctgg tcaaaggctt ctaccccagc gacatcgccg tggagtggga gagcaatggg   1200
cagccggaga caactacaa gaccacgcct cccgtgctgg actccgacgg ctccttcttc    1260
ctctacagca ggctaaccgt ggacaagagc aggtggcagg aggggaatgt cttctcatgc   1320
tccgtgatgc atgaggctct gcacaaccac tacacacaga gagcctctc cctgtctctg    1380
ggtaaagcta gtcagacccc caccaacacc atcagcgtga ccccaccaa caacagcacc    1440
cccaccaaca acagcaaccc caagcccaac cccgctagcc caggccaggg cacccagtct   1500
gagaacagct gcacccactt cccaggcaac ctgcctaaca tgcttcgaga tctccgagat   1560
gccttcagca gagtgaagac tttcttcaa atgaaggatc agctggacaa cttgttgtta    1620
aaggagtcct tgctggagga cttttaagggt tacctgggtt gccaagcctt gtctgagatg   1680
atccagtttt acctggagga ggtgatgccc caagctgaga accaagaccc agacatcaag   1740
gcgcatgtga actccctggg ggagaacctg aagaccctca ggctgaggct acggcgctgt   1800
catcgatttc ttccctgtga aaacaagagc aaggccgtgg agcaggtgaa gaatgccttt   1860
aataagctcc aagagaaagg catctacaaa gccatgagtg agtttgacat cttcatcaac   1920
tacatagaag cctacatgac aatgaagata cgaaactga                           1959
```

<210> SEQ ID NO 7
<211> LENGTH: 213
<212> TYPE: PRT
<213> ORGANISM: Homo sapiens

<400> SEQUENCE: 7

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser His Met
            20                  25                  30

His Trp Tyr Gln Gln Lys Ser Gly Thr Ser Pro Lys Arg Trp Ile Tyr
        35                  40                  45

Asp Thr Ser Arg Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser His Pro Trp Ser
            85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175
```

```
Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
        210

<210> SEQ ID NO 8
<211> LENGTH: 104
<212> TYPE: PRT
<213> ORGANISM: Homo sapiens

<400> SEQUENCE: 8

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser His Met
            20                  25                  30

His Trp Tyr Gln Gln Lys Ser Gly Thr Ser Pro Lys Arg Trp Ile Tyr
        35                  40                  45

Asp Thr Ser Arg Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser His Pro Trp Ser
                85                  90                  95

Phe Gly Gly Gly Thr Lys Leu Glu
            100

<210> SEQ ID NO 9
<211> LENGTH: 708
<212> TYPE: PRT
<213> ORGANISM: Homo sapiens

<400> SEQUENCE: 9

Ala Thr Gly Gly Ala Thr Thr Thr Cys Ala Ala Gly Thr Gly Cys
1               5                   10                  15

Ala Gly Ala Thr Thr Thr Thr Cys Ala Gly Cys Thr Thr Cys Cys Thr
            20                  25                  30

Gly Cys Thr Ala Ala Thr Cys Ala Gly Thr Gly Cys Cys Thr Cys Ala
        35                  40                  45

Gly Thr Cys Ala Thr Ala Ala Thr Ala Thr Cys Cys Ala Gly Ala Gly
    50                  55                  60

Gly Ala Cys Ala Ala Thr Thr Gly Thr Thr Cys Thr Cys Ala Cys Cys
65                  70                  75                  80

Cys Cys Ala Gly Thr Cys Thr Cys Cys Ala Gly Cys Ala Ala Thr Cys
                85                  90                  95

Ala Thr Gly Thr Cys Thr Gly Cys Ala Thr Cys Thr Cys Cys Ala Gly
            100                 105                 110

Gly Gly Gly Ala Gly Ala Ala Gly Gly Thr Cys Ala Cys Cys Ala Thr
        115                 120                 125

Gly Ala Cys Cys Thr Gly Cys Ala Gly Thr Gly Cys Cys Ala Gly Cys
    130                 135                 140

Thr Cys Ala Ala Gly Thr Gly Thr Ala Ala Gly Thr Cys Ala Cys Ala
145                 150                 155                 160

Thr Gly Cys Ala Cys Thr Gly Gly Thr Ala Cys Cys Ala Gly Cys Ala
                165                 170                 175
```

Gly Ala Ala Gly Thr Cys Ala Gly Gly Cys Ala Cys Thr Cys Cys
                180                 185                 190

Cys Cys Cys Ala Ala Ala Ala Gly Ala Thr Gly Gly Ala Thr Thr Thr
            195                 200                 205

Ala Thr Gly Ala Cys Ala Cys Ala Thr Cys Cys Ala Gly Ala Cys Thr
210                 215                 220

Gly Gly Cys Thr Thr Cys Thr Gly Gly Ala Gly Thr Cys Cys Cys Thr
225                 230                 235                 240

Gly Cys Thr Cys Gly Cys Thr Cys Ala Gly Thr Gly Gly Cys Ala
                245                 250                 255

Gly Thr Gly Gly Gly Thr Cys Thr Gly Gly Ala Cys Cys Thr Cys
                260                 265                 270

Thr Thr Ala Cys Thr Cys Thr Cys Ala Cys Ala Ala Thr Cys
        275                 280                 285

Ala Gly Cys Ala Gly Cys Ala Thr Gly Gly Ala Gly Gly Cys Thr Gly
        290                 295                 300

Ala Ala Gly Ala Thr Gly Cys Thr Gly Cys Cys Ala Cys Thr Thr Ala
305 310 315 320

Thr Thr Ala Cys Thr Gly Cys Cys Ala Gly Cys Ala Gly Thr Gly Gly
325 330 335

Ala Gly Thr Ala Gly Thr Cys Ala Cys Cys Cys Ala Thr Gly Gly Thr
340 345 350

Cys Gly Thr Thr Cys Gly Gly Thr Gly Gly Ala Gly Gly Cys Ala Cys
355 360 365

Cys Ala Ala Ala Cys Thr Cys Gly Ala Gly Ala Thr Cys Ala Ala Ala
370 375 380

Cys Gly Ala Ala Cys Thr Gly Thr Gly Gly Cys Thr Gly Cys Ala Cys
385 390 395 400

Cys Ala Thr Cys Thr Gly Thr Cys Thr Thr Cys Ala Thr Cys Thr Thr
405 410 415

Cys Cys Cys Gly Cys Cys Ala Thr Cys Thr Gly Ala Thr Gly Ala Gly
420 425 430

Cys Ala Gly Thr Thr Gly Ala Ala Ala Thr Cys Thr Gly Gly Ala Ala
435 440 445

Cys Thr Gly Cys Cys Thr Cys Thr Gly Thr Thr Gly Thr Gly Thr Gly
450 455 460

Cys Cys Thr Gly Cys Thr Gly Ala Ala Thr Ala Ala Cys Thr Thr Cys
465 470 475 480

Thr Ala Thr Cys Cys Cys Ala Gly Ala Gly Ala Gly Gly Cys Cys Ala
485 490 495

Ala Ala Gly Thr Ala Cys Ala Gly Thr Gly Gly Ala Ala Gly Gly Thr
500 505 510

Gly Gly Ala Thr Ala Ala Cys Gly Cys Cys Cys Thr Cys Cys Ala Ala
515 520 525

Thr Cys Gly Gly Gly Thr Ala Ala Cys Thr Cys Cys Cys Ala Gly Gly
530 535 540

Ala Gly Ala Gly Thr Gly Thr Cys Ala Cys Ala Gly Ala Gly Cys Ala
545 550 555 560

Gly Gly Ala Cys Ala Gly Cys Ala Ala Gly Gly Ala Cys Ala Gly Cys
565 570 575

Ala Cys Cys Thr Ala Cys Ala Gly Cys Cys Thr Cys Ala Gly Cys Ala
580 585 590

```
Gly Cys Ala Cys Cys Thr Gly Ala Cys Gly Cys Thr Gly Ala Gly
            595                 600                 605

Cys Ala Ala Ala Gly Cys Ala Gly Ala Cys Thr Ala Cys Gly Ala Gly
    610                 615                 620

Ala Ala Ala Cys Ala Cys Ala Ala Gly Thr Cys Thr Ala Thr Gly
625                 630                 635                 640

Cys Cys Thr Gly Cys Gly Ala Ala Gly Thr Cys Ala Cys Cys Ala
                645                 650                 655

Thr Cys Ala Gly Gly Cys Cys Thr Gly Ala Gly Cys Thr Cys Gly
            660                 665                 670

Cys Cys Cys Gly Thr Cys Ala Cys Ala Ala Gly Ala Gly Cys Thr
        675                 680                 685

Thr Cys Ala Ala Cys Ala Gly Gly Gly Ala Gly Ala Gly Thr Gly
        690                 695                 700

Thr Thr Ala Gly
705

<210> SEQ ID NO 10
<211> LENGTH: 635
<212> TYPE: PRT
<213> ORGANISM: Homo sapiens

<400> SEQUENCE: 10

Val Gln Leu Gln Glu Ser Gly Pro Asp Leu Val Lys Pro Ser Gln Ser
1               5                   10                  15

Leu Ser Leu Thr Cys Thr Val Thr Gly Tyr Ser Ile Thr Ser Asp Tyr
            20                  25                  30

Ser Trp His Trp Ile Arg Gln Phe Pro Gly Asn Lys Leu Glu Trp Met
        35                  40                  45

Gly Tyr Ile Tyr Tyr Ser Gly Ser Thr Asn Tyr Asn Pro Ser Leu Lys
    50                  55                  60

Ser Arg Ile Ser Ile Thr Arg Asp Thr Ser Lys Asn Gln Phe Phe Leu
65                  70                  75                  80

Gln Leu Asn Ser Val Thr Thr Glu Asp Ser Ala Thr Tyr Phe Cys Ala
                85                  90                  95

Arg Phe Tyr Tyr Gly Tyr Ser Phe Phe Asp Tyr Trp Gly Gln Gly Thr
            100                 105                 110

Thr Leu Thr Val Ser Ser Ala Lys Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Glu Gly Gly Pro Ser Val Phe Leu
225                 230                 235                 240

Phe Pro Pro Lys Pro Lys Asp Thr Leu Met Ile Ser Arg Thr Pro Glu
                245                 250                 255
```

Val Thr Cys Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys Ala Ser Gln
        435                 440                 445

Thr Pro Thr Asn Thr Ile Ser Val Thr Pro Thr Asn Asn Ser Thr Pro
    450                 455                 460

Thr Asn Asn Ser Asn Pro Lys Pro Asn Pro Ala Ser Pro Gly Gln Gly
465                 470                 475                 480

Thr Gln Ser Glu Asn Ser Cys Thr His Phe Pro Gly Asn Leu Pro Asn
                485                 490                 495

Met Leu Arg Asp Leu Arg Asp Ala Phe Ser Arg Val Lys Thr Phe Phe
            500                 505                 510

Gln Met Lys Asp Gln Leu Asp Asn Leu Leu Leu Lys Glu Ser Leu Leu
        515                 520                 525

Glu Asp Phe Lys Gly Tyr Leu Gly Cys Gln Ala Leu Ser Glu Met Ile
    530                 535                 540

Gln Phe Tyr Leu Glu Glu Val Met Pro Gln Ala Glu Asn Gln Asp Pro
545                 550                 555                 560

Asp Ile Lys Ala His Val Asn Ser Leu Gly Glu Asn Leu Lys Thr Leu
                565                 570                 575

Arg Leu Arg Leu Arg Arg Cys His Arg Phe Leu Pro Cys Glu Asn Lys
            580                 585                 590

Ser Lys Ala Val Glu Gln Val Lys Asn Ala Phe Asn Lys Leu Gln Glu
        595                 600                 605

Lys Gly Ile Tyr Lys Ala Met Ser Glu Phe Asp Ile Phe Ile Asn Tyr
    610                 615                 620

Ile Glu Ala Tyr Met Thr Met Lys Ile Arg Asn
625                 630                 635

<210> SEQ ID NO 11
<211> LENGTH: 447
<212> TYPE: PRT
<213> ORGANISM: Homo sapiens

<400> SEQUENCE: 11

```
Val Gln Leu Gln Glu Ser Gly Pro Asp Leu Val Lys Pro Ser Gln Ser
1               5                   10                  15
Leu Ser Leu Thr Cys Thr Val Thr Gly Tyr Ser Ile Thr Ser Asp Tyr
            20                  25                  30
Ser Trp His Trp Ile Arg Gln Phe Pro Gly Asn Lys Leu Glu Trp Met
        35                  40                  45
Gly Tyr Ile Tyr Tyr Ser Gly Ser Thr Asn Tyr Asn Pro Ser Leu Lys
    50                  55                  60
Ser Arg Ile Ser Ile Thr Arg Asp Thr Ser Lys Asn Gln Phe Phe Leu
65                  70                  75                  80
Gln Leu Asn Ser Val Thr Thr Glu Asp Ser Ala Thr Tyr Phe Cys Ala
                85                  90                  95
Arg Phe Tyr Tyr Gly Tyr Ser Phe Phe Asp Tyr Trp Gly Gln Gly Thr
            100                 105                 110
Thr Leu Thr Val Ser Ser Ala Lys Thr Lys Gly Pro Ser Val Phe Pro
        115                 120                 125
Leu Ala Pro Cys Ser Arg Ser Thr Ser Glu Ser Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Lys Thr Tyr Thr Cys Asn Val Asp His Lys Pro Ser
        195                 200                 205
Asn Thr Lys Val Asp Lys Arg Val Glu Ser Lys Tyr Gly Pro Pro Cys
    210                 215                 220
Pro Pro Cys Pro Ala Pro Glu Phe Glu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser Gln Glu Asp Pro Glu Val Gln
            260                 265                 270
Phe Asn Trp Tyr Val Asp Gly Val Glu Val His Asn Ala Lys Thr Lys
        275                 280                 285
Pro Arg Glu Glu Gln Phe Asn Ser Thr Tyr Arg Val Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Gly Leu Pro Ser Ser Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Gln Glu Glu Met Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Val Leu Asp Ser Asp Gly
385                 390                 395                 400
Ser Phe Phe Leu Tyr Ser Arg Leu Thr Val Asp Lys Ser Arg Trp Gln
                405                 410                 415
```

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys Ala Ser
            435                 440                 445

<210> SEQ ID NO 12
<211> LENGTH: 1965
<212> TYPE: DNA
<213> ORGANISM: Homo sapiens

<400> SEQUENCE: 12

| | | | | | |
|---|---|---|---|---|---|
| atgagagtgc | tgattctttt | gtgcctgttc | acagcctttc | ctggtatcct | gtctgatgtg | 60 |
| cagcttcagg | agtcaggacc | tgacctggtg | aaaccttctc | agtcactttc | actcacctgc | 120 |
| actgtcactg | gctactccat | caccagtgat | tatagctggc | actggatccg | gcagttccca | 180 |
| ggaaacaaac | tggaatggat | gggctacata | tattacagtg | gtagcactaa | ctacaaccca | 240 |
| tctctcaaaa | gtcgaatctc | tatcactcga | gacacatcca | agaaccagtt | cttcctgcag | 300 |
| ttgaattctg | tgactactga | ggactcagcc | acatatttct | gtgcaagatt | ttactacggt | 360 |
| tatagcttct | ttgactactg | gggccaaggc | accactctca | cagtctcctc | agccaaaaca | 420 |
| aagggcccat | ccgtcttccc | cctggcgccc | tgctccagga | gcacctccga | gagcacagcc | 480 |
| gccctgggct | gcctggtcaa | ggactacttc | cccgaaccgg | tgacggtgtc | gtggaactca | 540 |
| ggcgccctga | ccagcggcgt | gcacaccttc | ccggctgtcc | tacagtcctc | aggactctac | 600 |
| tccctcagca | gcgtggtgac | cgtgccctcc | agcagcttgg | gcacgaagac | ctacacctgc | 660 |
| aacgtagatc | acaagcccag | caacaccaag | gtggacaaga | gagttgagtc | caaatatggt | 720 |
| cccccatgcc | caccctgccc | agcacctgag | ttcgaagggg | gaccatcagt | cttcctgttc | 780 |
| cccccaaaac | ccaaggacac | tctcatgatc | tcccggaccc | ctgaggtcac | gtgcgtggtg | 840 |
| gtggacgtga | gccaggaaga | ccccgaggtc | cagttcaact | ggtacgtgga | tggcgtggag | 900 |
| gtgcataatg | ccaagacaaa | gccgcgggag | gagcagttca | acagcacgta | ccgtgtggtc | 960 |
| agcgtcctca | ccgtcctgca | ccaggactgg | ctgaacggca | aggagtacaa | gtgcaaggtc | 1020 |
| tccaacaaag | gcctcccgtc | ctccatcgag | aaaaccatct | ccaaagccaa | agggcagccc | 1080 |
| cgagagccac | aggtgtacac | cctgccccca | tcccaggagg | agatgaccaa | gaaccaggtc | 1140 |
| agcctgacct | gcctggtcaa | aggcttctac | cccagcgaca | tcgccgtgga | gtgggagagc | 1200 |
| aatgggcagc | cggagaacaa | ctacaagacc | acgcctcccg | tgctggactc | cgacggctcc | 1260 |
| ttcttcctct | acagcaggct | aaccgtggac | aagagcaggt | ggcaggaggg | gaatgtcttc | 1320 |
| tcatgctccg | tgatgcatga | ggctctgcac | aaccactaca | cacagaagag | cctctccctg | 1380 |
| tctctgggta | aagctagtca | gacccccacc | aacaccatca | gcgtgacccc | caccaacaac | 1440 |
| agcacccccca | ccaacaacag | caaccccaag | cccaacccg | ctagcccagg | ccagggcacc | 1500 |
| cagtctgaga | cagctgcac | ccacttccca | ggcaacctgc | taacatgct | tcgagatctc | 1560 |
| cgagatgcct | tcagcagagt | gaagactttc | tttcaaatga | aggatcagct | ggacaacttg | 1620 |
| ttgttaaagg | agtccttgct | ggaggacttt | aagggttacc | tgggttgcca | agccttgtct | 1680 |
| gagatgatcc | agtttaccct | ggaggaggtg | atgccccaag | ctgagaacca | agacccagac | 1740 |
| atcaaggcgc | atgtgaactc | cctggggag | aacctgaaga | ccctcaggct | gaggctacgg | 1800 |
| cgctgtcatc | gatttcttcc | ctgtgaaaac | aagagcaagg | ccgtggagca | ggtgaagaat | 1860 |
| gcctttaata | agctccaaga | gaaaggcatc | tacaaagcca | tgagtgagtt | tgacatcttc | 1920 | atcaactaca tagaagccta catgacaatg aagatacgaa actga           1965

<210> SEQ ID NO 13
<211> LENGTH: 215
<212> TYPE: PRT
<213> ORGANISM: Homo sapiens

<400> SEQUENCE: 13

Gln Ile Val Leu Thr Gln Ser Pro Ala Phe Met Ser Ala Ser Pro Gly
1               5                   10                  15

Glu Lys Val Thr Met Thr Cys Ser Ala Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Ala Ser
    210                 215

<210> SEQ ID NO 14
<211> LENGTH: 714
<212> TYPE: DNA
<213> ORGANISM: Homo sapiens

<400> SEQUENCE: 14 atggatttc aagtgcagat tttcagcttc ctgctaatca gtgcctcagt catagtatcc     60
agaggacaaa ttgttctcac ccagtctcca gcattcatgt ctgcatctcc aggggagaag    120
gtcaccatga cctgcagtgc cagctcaagt gtcagttaca tgcactggta ccagcagaag    180
tcaggcacct cccccaaaag atggatttat gacacatcca aactggcttc tggagtccct    240
gctcgcttca gtggcagtgg gtctgggacc tcttactctc tcacaatcag cagcatggag    300
gctgaagatg ctgccactta ttactgccag cagtggagta gtaacccact cacgttcggt    360
gctgggacca agctcgagat caaacgaact gtggctgcac catctgtctt catcttcccg    420
ccatctgatg agcagttgaa atctggaact gcctctgttg tgtgcctgct gaataacttc    480
tatcccagag aggccaaagt acagtggaag gtggataacg ccctccaatc gggtaactcc    540
caggagagtg tcacagagca ggacagcaag gacagcacct acagcctcag cagcaccctg    600
acgctgagca aagcagacta cgagaaacac aaagtctatg cctgcgaagt cacccatcag    660
ggcctgagct cgcccgtcac aaagagcttc aacaggggag agtgtgctag ctag    714

<210> SEQ ID NO 15
<211> LENGTH: 642
<212> TYPE: PRT
<213> ORGANISM: Homo sapiens

<400> SEQUENCE: 15

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Leu Ser Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Thr Ser Ser Asn Gln Val
65                  70                  75                  80

Phe Leu Lys Ile Thr Ile Val Asp Thr Ala Asp Ala Ala Thr Tyr Tyr
                85                  90                  95

Cys Ala Arg Ser Ser His Tyr Tyr Gly Tyr Gly Tyr Gly Tyr Phe
            100                 105                 110

Asp Val Trp Gly Ala Gly Thr Thr Val Thr Val Ser Ser Ala Lys Thr
            115                 120                 125

Lys Gly Pro Ser Val Phe Pro Leu Ala Pro Cys Ser Arg Ser Thr Ser
        130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Lys Thr Tyr Thr Cys
            195                 200                 205

Asn Val Asp His Lys Pro Ser Asn Thr Lys Val Asp Lys Arg Val Glu
        210                 215                 220

Ser Lys Tyr Gly Pro Pro Cys Pro Pro Cys Pro Ala Pro Glu Phe Glu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Met Thr Lys Asn Gln Val
            355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
                420                 425                 430

Met His Glu Ala Leu His Asn His Tyr Thr Gln Lys Ser Leu Ser Leu
            435                 440                 445

Ser Leu Gly Lys Ala Ser Gln Thr Pro Thr Asn Thr Ile Ser Val Thr
        450                 455                 460

Pro Thr Asn Asn Ser Thr Pro Thr Asn Asn Ser Asn Pro Lys Pro Asn
465                 470                 475                 480

Pro Ala Ser Pro Gly Gln Gly Thr Gln Ser Glu Asn Ser Cys Thr His
                485                 490                 495

Phe Pro Gly Asn Leu Pro Asn Met Leu Arg Asp Leu Arg Asp Ala Phe
                500                 505                 510

Ser Arg Val Lys Thr Phe Phe Gln Met Lys Asp Gln Leu Asp Asn Leu
            515                 520                 525

Leu Leu Lys Glu Ser Leu Leu Glu Asp Phe Lys Gly Tyr Leu Gly Cys
        530                 535                 540

Gln Ala Leu Ser Glu Met Ile Gln Phe Tyr Leu Glu Glu Val Met Pro
545                 550                 555                 560

Gln Ala Glu Asn Gln Asp Pro Asp Ile Lys Ala His Val Asn Ser Leu
                565                 570                 575

Gly Glu Asn Leu Lys Thr Leu Arg Leu Arg Leu Arg Arg Cys His Arg
                580                 585                 590

Phe Leu Pro Cys Glu Asn Lys Ser Lys Ala Val Glu Gln Val Lys Asn
            595                 600                 605

Ala Phe Asn Lys Leu Gln Glu Lys Gly Ile Tyr Lys Ala Met Ser Glu
        610                 615                 620

Phe Asp Ile Phe Ile Asn Tyr Ile Glu Ala Tyr Met Thr Met Lys Ile
625                 630                 635                 640

Arg Asn

<210> SEQ ID NO 16
<211> LENGTH: 454
<212> TYPE: PRT
<213> ORGANISM: Homo sapiens

<400> SEQUENCE: 16

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Leu Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Ser Asn Gln Val
65                  70                  75                  80

```
Phe Leu Lys Ile Thr Ile Val Asp Thr Ala Asp Ala Thr Tyr Tyr
             85                  90                  95
Cys Ala Arg Ser Ser His Tyr Tyr Gly Tyr Gly Tyr Gly Gly Tyr Phe
            100                 105                 110
Asp Val Trp Gly Ala Gly Thr Thr Val Thr Val Ser Ser Ala Lys Thr
            115                 120                 125
Lys Gly Pro Ser Val Phe Pro Leu Ala Pro Cys Ser Arg Ser Thr Ser
            130                 135                 140
Glu Ser Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
            180                 185                 190
Val Val Thr Val Pro Ser Ser Ser Leu Gly Thr Lys Thr Tyr Thr Cys
            195                 200                 205
Asn Val Asp His Lys Pro Ser Asn Thr Lys Val Asp Lys Arg Val Glu
            210                 215                 220
Ser Lys Tyr Gly Pro Pro Cys Pro Pro Cys Pro Ala Pro Glu Phe Glu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
                260                 265                 270
Gln Glu Asp Pro Glu Val Gln Phe Asn Trp Tyr Val Asp Gly Val Glu
            275                 280                 285
Val His Asn Ala Lys Thr Lys Pro Arg Glu Glu Gln Phe Asn Ser Thr
290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Gly Leu Pro Ser Ser
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Gln Glu Glu Met Thr Lys Asn Gln Val
            355                 360                 365
Ser Leu Thr Cys Leu Val Lys Gly Phe Tyr Pro Ser Asp Ile Ala Val
370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Arg Leu Thr
                405                 410                 415
Val Asp Lys Ser Arg Trp Gln Glu Gly Asn Val Phe Ser Cys Ser Val
            420                 425                 430
Met His Glu Ala Leu His Asn His Tyr Thr Gln Lys Ser Leu Ser Leu
            435                 440                 445
Ser Leu Gly Lys Ala Ser
    450

<210> SEQ ID NO 17
<211> LENGTH: 124
<212> TYPE: PRT
<213> ORGANISM: Homo sapiens

<400> SEQUENCE: 17
```

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
                20                  25                  30

Gly Met Gly Leu Ser Trp Ile Arg Gln Pro Ser Gly Lys Gly Leu Glu
            35                  40                  45

Trp Leu Ala His Ile Tyr Trp Asp Asp Lys Arg Tyr Asn Pro Ser
50                  55                  60

Leu Lys Ser Arg Leu Thr Ile Ser Lys Asp Thr Ser Ser Asn Gln Val
65                  70                  75                  80

Phe Leu Lys Ile Thr Ile Val Asp Thr Ala Asp Ala Thr Tyr Tyr
                85                  90                  95

Cys Ala Arg Ser Ser His Tyr Tyr Gly Tyr Gly Tyr Gly Tyr Phe
            100                 105                 110

Asp Val Trp Gly Ala Gly Thr Thr Val Thr Val Ser
            115                 120
```

<210> SEQ ID NO 18
<211> LENGTH: 27
<212> TYPE: PRT
<213> ORGANISM: Homo sapiens

<400> SEQUENCE: 18

```
Gln Thr Pro Thr Asn Thr Ile Ser Val Thr Pro Thr Asn Asn Ser Thr
1               5                   10                  15

Pro Thr Asn Asn Ser Asn Pro Lys Pro Asn Pro
            20                  25
```

<210> SEQ ID NO 19
<211> LENGTH: 161
<212> TYPE: PRT
<213> ORGANISM: Homo sapiens

<400> SEQUENCE: 19

```
Ala Ser Pro Gly Gln Gly Thr Gln Ser Glu Asn Ser Cys Thr His Phe
1               5                   10                  15

Pro Gly Asn Leu Pro Asn Met Leu Arg Asp Leu Arg Asp Ala Phe Ser
                20                  25                  30

Arg Val Lys Thr Phe Phe Gln Met Lys Asp Gln Leu Asp Asn Leu Leu
            35                  40                  45

Leu Lys Glu Ser Leu Leu Glu Asp Phe Lys Gly Tyr Leu Gly Cys Gln
50                  55                  60

Ala Leu Ser Glu Met Ile Gln Phe Tyr Leu Glu Glu Val Met Pro Gln
65                  70                  75                  80

Ala Glu Asn Gln Asp Pro Asp Ile Lys Ala His Val Asn Ser Leu Gly
                85                  90                  95

Glu Asn Leu Lys Thr Leu Arg Leu Arg Leu Arg Arg Cys His Arg Phe
            100                 105                 110

Leu Pro Cys Glu Asn Lys Ser Lys Ala Val Glu Gln Val Lys Asn Ala
            115                 120                 125

Phe Asn Lys Leu Gln Glu Lys Gly Ile Tyr Lys Ala Met Ser Glu Phe
130                 135                 140

Asp Ile Phe Ile Asn Tyr Ile Glu Ala Tyr Met Thr Met Lys Ile Arg
145                 150                 155                 160

Asn
```

<210> SEQ ID NO 20
<211> LENGTH: 487
<212> TYPE: DNA
<213> ORGANISM: Homo sapiens

<400> SEQUENCE: 20

| | | | | | | |
|---|---|---|---|---|---|---|
| cgctagccca | ggccagggca | cccagtctga | aacagctgc | acccacttcc | caggcaacct | 60 |
| gcctaacatg | cttcgagatc | tccgagatgc | cttcagcaga | gtgaagactt | tctttcaaat | 120 |
| gaaggatcag | ctggacaact | tgttgttaaa | ggagtccttg | ctggaggact | ttaagggtta | 180 |
| cctgggttgc | caagccttgt | ctgagatgat | ccagttttac | ctggaggagg | tgatgcccca | 240 |
| agctgagaac | caagacccag | acatcaaggc | gcatgtgaac | tccctggggg | agaacctgaa | 300 |
| gaccctcagg | ctgaggctac | ggcgctgtca | tcgatttctt | ccctgtgaaa | caagagcaa | 360 |
| ggccgtggag | caggtgaaga | atgcctttaa | taagctccaa | gagaaaggca | tctacaaagc | 420 |
| catgagtgag | tttgacatct | tcatcaacta | catagaagcc | tacatgacaa | tgaagatacg | 480 |
| aaactga | | | | | | 487 |

<210> SEQ ID NO 21
<211> LENGTH: 1986
<212> TYPE: DNA
<213> ORGANISM: Homo sapiens

<400> SEQUENCE: 21

| | | | | | | |
|---|---|---|---|---|---|---|
| atgaacaggc | ttacttcctc | attgctgctg | ctgattgtcc | ctgcatatgt | cctgtcccag | 60 |
| gttactctga | aagagtctgg | ccctgggata | ttgcagccct | cccagaccct | cagtctgact | 120 |
| tgttctttct | ctgggttttc | actgagcact | tctggtatgg | gtctgagctg | gattcgtcag | 180 |
| ccttcaggaa | agggtctgga | gtggctggca | cacatttact | gggatgatga | caagcgctat | 240 |
| aacccatccc | tgaagagccg | gctcacaatc | tccaaggata | cctccagcaa | ccaggttttc | 300 |
| ctcaagatca | ccattgtgga | cactgcagat | gctgccacat | actactgtgc | tcgaagctcc | 360 |
| cattactacg | gttatggcta | cggggggatac | ttcgatgtct | ggggcgcagg | gaccacggtc | 420 |
| accgtctcct | cagccaaaac | gaagggccca | tccgtcttcc | ccctggcgcc | ctgctccagg | 480 |
| agcacctccg | agagcacagc | cgccctgggc | tgcctggtca | aggactactt | ccccgaaccg | 540 |
| gtgacggtgt | cgtggaactc | aggcgccctg | accagcggcg | tgcacacctt | cccggctgtc | 600 |
| ctacagtcct | caggactcta | ctccctcagc | agcgtggtga | ccgtgccctc | cagcagcttg | 660 |
| ggcacgaaga | cctacacctg | caacgtagat | cacaagccca | gcaacaccaa | ggtggacaag | 720 |
| agagttgagt | ccaaatatgg | tcccccatgc | ccaccctgcc | cagcacctga | gttcgaaggg | 780 |
| ggaccatcag | tcttcctgtt | ccccccaaaa | cccaaggaca | ctctcatgat | ctcccggacc | 840 |
| cctgaggtca | cgtgcgtggt | ggtggacgtg | agccaggaag | accccgaggt | ccagttcaac | 900 |
| tggtacgtgg | atggcgtgga | ggtgcataat | gccaagacaa | agccgcggga | ggagcagttc | 960 |
| aacagcacgt | accgtgtggt | cagcgtcctc | accgtcctgc | accaggactg | gctgaacggc | 1020 |
| aaggagtaca | agtgcaaggt | ctccaacaaa | ggcctcccgt | cctccatcga | gaaaaccatc | 1080 |
| tccaaagcca | aagggcagcc | ccgagagcca | caggtgtaca | ccctgccccc | atcccaggag | 1140 |
| gagatgacca | agaaccaggt | cagcctgacc | tgcctggtca | aaggcttcta | ccccagcgac | 1200 |
| atcgccgtgg | agtgggagag | caatgggcag | ccggagaaca | actacaagac | cacgcctccc | 1260 |
| gtgctggact | ccgacggctc | cttcttcctc | tacagcaggc | taaccgtgga | caagagcagg | 1320 |
| tggcaggagg | ggaatgtctt | ctcatgctcc | gtgatgcatg | aggctctgca | caaccactac | 1380 |

```
acacagaaga gcctctccct gtctctgggt aaagctagtc agaccccccac caacaccatc    1440 agcgtgaccc ccaccaacaa cagcaccccc accaacaaca gcaacccccaa gcccaacccc    1500 gctagcccag gccagggcac ccagtctgag aacagctgca cccacttccc aggcaacctg    1560
cctaacatgc ttcgagatct ccgagatgcc ttcagcagag tgaagacttt ctttcaaatg    1620
aaggatcagc tggacaactt gttgttaaag gagtccttgc tggaggactt taagggttac    1680
ctgggttgcc aagccttgtc tgagatgatc cagttttacc tggaggaggt gatgccccaa    1740
gctgagaacc aagacccaga catcaaggcg catgtgaact ccctggggga gaacctgaag    1800
accctcaggc tgaggctacg gcgctgtcat cgatttcttc cctgtgaaaa caagagcaag    1860
gccgtggagc aggtgaagaa tgcctttaat aagctccaag agaaaggcat ctacaaagcc    1920
atgagtgagt ttgacatctt catcaactac atagaagcct acatgacaat gaagatacga    1980
aactga                                                               1986
```

<210> SEQ ID NO 22
<211> LENGTH: 218
<212> TYPE: PRT
<213> ORGANISM: Homo sapiens

<400> SEQUENCE: 22

```
Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Ile His Ser Tyr
            20                  25                  30

Gly Asn Ser Phe Leu His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 23
<211> LENGTH: 111
<212> TYPE: PRT
<213> ORGANISM: Homo sapiens

<400> SEQUENCE: 23

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Ile His Ser Tyr
            20                  25                  30

Gly Asn Ser Phe Leu His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Trp Thr Phe Gly Gly Gly Thr Lys Leu Glu Ile Lys
            100                 105                 110

<210> SEQ ID NO 24
<211> LENGTH: 333
<212> TYPE: DNA
<213> ORGANISM: Homo sapiens

<400> SEQUENCE: 24
aacattgtgc tgacccaatc tccagcttct ttggctgtgt ctctagggca gagggccacc      60
atatcctgca gagccagtga agtattcat agttatggca atagttttct gcactggtac     120
cagcagaaac aggacagcc acccaaactc ctcatctatc ttgcatccaa cctagaatct     180
ggggtccctg ccaggttcag cggcagtggg tctaggacag acttcaccct caccattgat     240
cctgtggagg ctgatgatgc tgcaacctat tactgtcagc aaaataatga ggatccgtgg     300
acgttcggtg gaggcaccaa gctcgagatc aaa                                 333

<210> SEQ ID NO 25
<211> LENGTH: 20
<212> TYPE: PRT
<213> ORGANISM: Homo sapiens

<400> SEQUENCE: 25

Met Glu Thr Asp Thr Leu Leu Leu Trp Val Leu Leu Leu Trp Val Pro
1               5                   10                  15

Gly Ser Thr Gly
            20

<210> SEQ ID NO 26
<211> LENGTH: 60
<212> TYPE: DNA
<213> ORGANISM: Homo sapiens

<400> SEQUENCE: 26
atggagacag acacactcct gctatgggtg ctgctgctct ggttccagg ttccacaggt      60

<210> SEQ ID NO 27
<211> LENGTH: 717
<212> TYPE: DNA
<213> ORGANISM: Homo sapiens

<400> SEQUENCE: 27
atggagacag acacactcct gctatgggtg ctgctgctct ggttccagg ttccacaggt      60 aacattgtgc tgacccaatc tccagcttct ttggctgtgt ctctagggca gagggccacc     120

-continued

```
atatcctgca gagccagtga aagtattcat agttatggca atagttttct gcactggtac    180
cagcagaaac caggacagcc acccaaactc ctcatctatc ttgcatccaa cctagaatct    240
ggggtccctg ccaggttcag cggcagtggg tctaggacag acttcaccct caccattgat    300
cctgtggagg ctgatgatgc tgcaacctat tactgtcagc aaaataatga ggatccgtgg    360
acgttcggtg gaggcaccaa gctcgagatc aaacgaactg tggctgcacc atctgtcttc    420
atcttcccgc catctgatga gcagttgaaa tctggaactg cctctgttgt gtgcctgctg    480
aataacttct atcccagaga ggccaaagta cagtggaagg tggataacgc cctccaatcg    540
ggtaactccc aggagagtgt cacagagcag gacagcaagg acagcaccta cagcctcagc    600
agcaccctga cgctgagcaa agcagactac gagaaacaca aagtctatgc ctgcgaagtc    660
acccatcagg gcctgagctc gcccgtcaca aagagcttca caggggaga gtgttag      717
```

```
<210> SEQ ID NO 28
<211> LENGTH: 636
<212> TYPE: PRT
<213> ORGANISM: Homo sapiens

<400> SEQUENCE: 28

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Asn Ser Gly Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
                85                  90                  95

Ala Arg Arg Gly Leu Pro Phe His Ala Met Asp Tyr Trp Gly Gln Gly
            100                 105                 110

Thr Ser Val Thr Val Ser Ser Ala Lys Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270
```

```
Gln Phe Asn Trp Tyr Val Asp Gly Val Glu Val His Asn Ala Lys Thr
            275                 280                 285
Lys Pro Arg Glu Glu Gln Phe Asn Ser Thr Tyr Arg Val Val Ser Val
        290                 295                 300
Leu Thr Val Leu His Gln Asp Trp Leu Asn Gly Lys Glu Tyr Lys Cys
305                 310                 315                 320
Lys Val Ser Asn Lys Gly Leu Pro Ser Ser Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Gln Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Arg Leu Thr Val Asp Lys Ser Arg Trp
                405                 410                 415
Gln Glu Gly Asn Val Phe Ser Cys Ser Val Met His Glu Ala Leu His
            420                 425                 430
Asn His Tyr Thr Gln Lys Ser Leu Ser Leu Ser Leu Gly Lys Ala Ser
        435                 440                 445
Gln Thr Pro Thr Asn Thr Ile Ser Val Thr Pro Thr Asn Asn Ser Thr
450                 455                 460
Pro Thr Asn Asn Ser Asn Pro Lys Pro Asn Pro Ala Ser Pro Gly Gln
465                 470                 475                 480
Gly Thr Gln Ser Glu Asn Ser Cys Thr His Phe Pro Gly Asn Leu Pro
                485                 490                 495
Asn Met Leu Arg Asp Leu Arg Asp Ala Phe Ser Arg Val Lys Thr Phe
            500                 505                 510
Phe Gln Met Lys Asp Gln Leu Asp Asn Leu Leu Leu Lys Glu Ser Leu
        515                 520                 525
Leu Glu Asp Phe Lys Gly Tyr Leu Gly Cys Gln Ala Leu Ser Glu Met
530                 535                 540
Ile Gln Phe Tyr Leu Glu Glu Val Met Pro Gln Ala Glu Asn Gln Asp
545                 550                 555                 560
Pro Asp Ile Lys Ala His Val Asn Ser Leu Gly Glu Asn Leu Lys Thr
                565                 570                 575
Leu Arg Leu Arg Leu Arg Arg Cys His Arg Phe Leu Pro Cys Glu Asn
            580                 585                 590
Lys Ser Lys Ala Val Glu Gln Val Lys Asn Ala Phe Asn Lys Leu Gln
        595                 600                 605
Glu Lys Gly Ile Tyr Lys Ala Met Ser Glu Phe Asp Ile Phe Ile Asn
610                 615                 620
Tyr Ile Glu Ala Tyr Met Thr Met Lys Ile Arg Asn
625                 630                 635

<210> SEQ ID NO 29
<211> LENGTH: 448
<212> TYPE: PRT
<213> ORGANISM: Homo sapiens

<400> SEQUENCE: 29

Glu Val Lys Leu Val Glu Ser Gly Gly Gly Leu Val Gln Pro Gly Gly
1               5                   10                  15
```

```
Ser Leu Lys Leu Ser Cys Ala Thr Ser Gly Phe Thr Phe Ser Asp Tyr
         20                  25                  30

Tyr Met Tyr Trp Val Arg Gln Thr Pro Glu Lys Arg Leu Glu Trp Val
         35                  40                  45

Ala Tyr Ile Asn Ser Gly Gly Gly Ser Thr Tyr Tyr Pro Asp Thr Val
 50                  55                  60

Lys Gly Arg Phe Thr Ile Ser Arg Asp Asn Ala Lys Asn Thr Leu Tyr
 65                  70                  75                  80

Leu Gln Met Ser Arg Leu Lys Ser Glu Asp Thr Ala Met Tyr Tyr Cys
                 85                  90                  95

Ala Arg Arg Gly Leu Pro Phe His Ala Met Asp Tyr Trp Gly Gln Gly
                100                 105                 110

Thr Ser Val Thr Val Ser Ser Ala Lys Thr Lys Gly Pro Ser Val Phe
                115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Lys Thr Tyr Thr Cys Asn Val Asp His Lys Pro
                195                 200                 205

Ser Asn Thr Lys Val Asp Lys Arg Val Glu Ser Lys Tyr Gly Pro Pro
210                 215                 220

Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
                275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
                420                 425                 430
```

```
Asn His Tyr Thr Gln Lys Ser Leu Ser Leu Ser Leu Gly Lys Ala Ser
            435                 440                 445
```

<210> SEQ ID NO 30
<211> LENGTH: 118
<212> TYPE: PRT
<213> ORGANISM: Homo sapiens

<400> SEQUENCE: 30

```
Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Asn Ser Gly Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
                85                  90                  95

Ala Arg Arg Gly Leu Pro Phe His Ala Met Asp Tyr Trp Gly Gln Gly
            100                 105                 110

Thr Ser Val Thr Val Ser
            115
```

<210> SEQ ID NO 31
<211> LENGTH: 11
<212> TYPE: PRT
<213> ORGANISM: Homo sapiens

<400> SEQUENCE: 31

```
Ser Ala Ser Gln Gly Ile Ser Asn Tyr Leu Asn
1               5                   10
```

<210> SEQ ID NO 32
<211> LENGTH: 17
<212> TYPE: PRT
<213> ORGANISM: Homo sapiens

<400> SEQUENCE: 32

```
Ala Tyr Ile Asn Ser Gly Gly Gly Ser Thr Tyr Tyr Pro Asp Thr Val
1               5                   10                  15

Lys
```

<210> SEQ ID NO 33
<211> LENGTH: 10
<212> TYPE: PRT
<213> ORGANISM: Homo sapiens

<400> SEQUENCE: 33

```
Arg Arg Gly Leu Pro Phe His Ala Met Asp
1               5                   10
```

<210> SEQ ID NO 34
<211> LENGTH: 1968
<212> TYPE: DNA
<213> ORGANISM: Homo sapiens

<400> SEQUENCE: 34

```
atgaacttgg ggctcagctt gattttcctt gtccttgttt taaaaggtgt ccagtgtgaa    60
```

```
gtgaagctgg tggagtctgg gggaggctta gtgcagcccg agggtccct gaaactctcc      120 tgtgcaacct ctggattcac tttcagtgac tattacatgt attgggttcg ccagactcca     180
gagaagaggc tggagtgggt cgcatacatt aattctggtg gtggtagcac ctattatcca    240
gacactgtaa agggccgatt caccatctcc agagacaatg ccaagaacac cctgtacctg    300
caaatgagcc ggctgaagtc tgaggacaca gccatgtatt actgtgcaag acggggtta    360 ccgttccatg ctatggacta ttggggtcaa ggaacctcag tcaccgtctc ctcagccaaa    420
acgaagggcc catccgtctt ccccctggcg ccctgctcca ggagcacctc cgagagcaca    480
gccgccctgg gctgcctggt caaggactac ttccccgaac cggtgacggt gtcgtggaac    540
tcaggcgccc tgaccagcgg cgtgcacacc ttcccggctg tcctacagtc ctcaggactc    600
tactccctca gcagcgtggt gaccgtgccc tccagcagct gggcacgaa gacctacacc     660 tgcaacgtag atcacaagcc cagcaacacc aaggtggaca gagagttga gtccaaatat     720 ggtcccccat gcccacctg cccagcacct gagttcgaag gggaccatc agtcttcctg      780 ttcccccaa acccaagga cactctcatg atctcccgga cccctgaggt cacgtgcgtg      840
gtggtggacg tgagccagga agaccccgag gtccagttca actggtacgt ggatggcgtg    900
gaggtgcata atgccaagac aaagccgcgg gaggagcagt tcaacagcac gtaccgtgtg    960
gtcagcgtcc tcaccgtcct gcaccaggac tggctgaacg gcaaggagta caagtgcaag   1020
gtctccaaca aaggcctccc gtcctccatc gagaaaacca tctccaaagc caaagggcag   1080
ccccgagagc cacaggtgta caccctgccc ccatcccagg aggagatgac caagaaccag   1140
gtcagcctga cctgcctggt caaaggcttc taccccagcg acatcgccgt ggagtgggag   1200
agcaatgggc agccggagaa caactacaag accacgcctc ccgtgctgga ctccgacggc   1260
tccttcttcc tctacagcag gctaaccgtg gacaagagca ggtggcagga ggggaatgtc   1320
ttctcatgct ccgtgatgca tgaggctctg cacaaccact acacacagaa gagcctctcc   1380
ctgtctctgg gtaaagctag tcagaccccc accaacacca tcagcgtgac cccaccaac    1440 aacagcaccc ccaccaacaa cagcaaccc aagcccaacc ccgctagccc aggccagggc    1500
acccagtctg agaacagctg cacccacttc ccaggcaacc tgcctaacat gcttcgagat   1560
ctccgagatg ccttcagcag agtgaagact ttctttcaaa tgaaggatca gctggacaac   1620
ttgttgttaa aggagtcctt gctggaggac tttaagggtt acctgggttg ccaagccttg   1680
tctgagatga tccagttta cctggaggag gtgatgcccc aagctgagaa ccaagaccca   1740
gacatcaagg cgcatgtgaa ctccctgggg gagaacctga gaccctcag gctgaggcta   1800 cggcgctgtc atcgatttct tccctgtgaa aacaagagca aggccgtgga gcaggtgaag   1860 aatgcctta ataagctcca agagaaaggc atctacaaag ccatgagtga gtttgacatc    1920
ttcatcaact acatagaagc ctacatgaca atgaagatac gaaactga                 1968
```

<210> SEQ ID NO 35
<211> LENGTH: 214
<212> TYPE: PRT
<213> ORGANISM: Homo sapiens

<400> SEQUENCE: 35

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

```
Leu Asn Trp Tyr Gln Gln Lys Pro Asp Gly Thr Val Lys Leu Leu Ile
        35                  40                  45

Tyr Tyr Thr Ser Ile Leu His Ser Gly Val Pro Ser Arg Phe Ser Gly
 50                  55                  60

Ser Gly Ser Gly Thr Asp Tyr Ser Leu Thr Ile Gly Asn Leu Glu Pro
 65                  70                  75                  80

Glu Asp Ile Ala Thr Tyr Tyr Cys Gln Gln Phe Asn Lys Leu Pro Pro
                 85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210
```

<210> SEQ ID NO 36
<211> LENGTH: 107
<212> TYPE: PRT
<213> ORGANISM: Homo sapiens

<400> SEQUENCE: 36

```
Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ile Leu His Ser Gly Val Pro Ser Arg Phe Ser Gly
 50                  55                  60

Ser Gly Ser Gly Thr Asp Tyr Ser Leu Thr Ile Gly Asn Leu Glu Pro
 65                  70                  75                  80

Glu Asp Ile Ala Thr Tyr Tyr Cys Gln Gln Phe Asn Lys Leu Pro Pro
                 85                  90                  95

Thr Phe Gly Gly Gly Thr Lys Leu Glu Ile Lys
            100                 105
```

<210> SEQ ID NO 37
<211> LENGTH: 11
<212> TYPE: PRT
<213> ORGANISM: Homo sapiens

<400> SEQUENCE: 37

```
Ser Ala Ser Gln Gly Ile Ser Asn Tyr Leu Asn
1               5                   10
```

<210> SEQ ID NO 38
<211> LENGTH: 7

```
<212> TYPE: PRT
<213> ORGANISM: Homo sapiens

<400> SEQUENCE: 38

Tyr Thr Ser Ile Leu His Ser
1               5

<210> SEQ ID NO 39
<211> LENGTH: 9
<212> TYPE: PRT
<213> ORGANISM: Homo sapiens

<400> SEQUENCE: 39

Gln Gln Phe Asn Lys Leu Pro Pro Thr
1               5

<210> SEQ ID NO 40
<211> LENGTH: 705
<212> TYPE: DNA
<213> ORGANISM: Homo sapiens

<400> SEQUENCE: 40
atgatgtcct ctgctcagtt ccttggtctc ctgttgctct gttttcaagg taccagatgt      60
gatatccaga tgacacagac tacatcctcc ctgtctgcct ctctaggaga cagagtcacc     120
atcagttgca gtgcaagtca gggcattagc aattatttaa actggtatca gcagaaacca     180
gatggaactg ttaaactcct gatctattac acatcaattt acactcagg  agtcccatca     240
aggttcagtg gcagtgggtc tgggacagat tattctctca ccatcggcaa cctggaacct     300
gaagatattg ccacttacta ttgtcagcag tttaataagc ttcctccgac gttcggtgga     360
ggcaccaaac tcgagatcaa acgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag caccctgacg     600
ctgagcaaag cagactacga gaaacacaaa gtctatgcct gcgaagtcac ccatcagggc     660
ctgagctcgc ccgtcacaaa gagcttcaac aggggagagt gttag                    705

<210> SEQ ID NO 41
<211> LENGTH: 637
<212> TYPE: PRT
<213> ORGANISM: Homo sapiens

<400> SEQUENCE: 41

Arg Leu Gln Leu Gln Glu Ser Gly Pro Gly Leu Leu Lys Pro Ser Val
1               5                   10                  15

Thr Leu Ser Leu Thr Cys Thr Val Ser Gly Asp Ser Val Ala Ser Ser
                20                  25                  30

Ser Tyr Tyr Trp Gly Trp Val Arg Gln Pro Pro Gly Lys Gly Leu Glu
            35                  40                  45

Trp Ile Gly Thr Ile Asn Phe Ser Gly Asn Met Tyr Tyr Ser Pro Ser
        50                  55                  60

Leu Arg Ser Arg Val Thr Met Ser Ala Asp Met Ser Glu Asn Ser Phe
65                  70                  75                  80

Tyr Leu Lys Leu Asp Ser Val Thr Ala Ala Asp Thr Ala Val Tyr Tyr
                85                  90                  95

Cys Ala Ala Gly His Leu Val Met Gly Phe Gly Ala His Trp Gly Gln
            100                 105                 110
```

```
Gly Lys Leu Val Ser Val Ser Pro Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
                195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
                275                 280                 285

Thr Lys Pro Arg Glu Glu Gln Phe Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys Ala
                435                 440                 445

Ser Gln Thr Pro Thr Asn Thr Ile Ser Val Thr Pro Thr Asn Asn Ser
            450                 455                 460

Thr Pro Thr Asn Asn Ser Asn Pro Lys Pro Asn Pro Ala Ser Pro Gly
465                 470                 475                 480

Gln Gly Thr Gln Ser Glu Asn Ser Cys Thr His Phe Pro Gly Asn Leu
                485                 490                 495

Pro Asn Met Leu Arg Asp Leu Arg Asp Ala Phe Ser Arg Val Lys Thr
                500                 505                 510

Phe Phe Gln Met Lys Asp Gln Leu Asp Asn Leu Leu Leu Lys Glu Ser
            515                 520                 525
```

```
Leu Leu Glu Asp Phe Lys Gly Tyr Leu Gly Cys Gln Ala Leu Ser Glu
    530                 535                 540

Met Ile Gln Phe Tyr Leu Glu Glu Val Met Pro Gln Ala Glu Asn Gln
545                 550                 555                 560

Asp Pro Asp Ile Lys Ala His Val Asn Ser Leu Gly Glu Asn Leu Lys
                565                 570                 575

Thr Leu Arg Leu Arg Leu Arg Arg Cys His Arg Phe Leu Pro Cys Glu
            580                 585                 590

Asn Lys Ser Lys Ala Val Glu Gln Val Lys Asn Ala Phe Asn Lys Leu
        595                 600                 605

Gln Glu Lys Gly Ile Tyr Lys Ala Met Ser Glu Phe Asp Ile Phe Ile
    610                 615                 620

Asn Tyr Ile Glu Ala Tyr Met Thr Met Lys Ile Arg Asn
625                 630                 635

<210> SEQ ID NO 42
<211> LENGTH: 1992
<212> TYPE: DNA
<213> ORGANISM: Homo sapiens

<400> SEQUENCE: 42
atggacctcc tgtgcaagaa catgaagcac ctgtggttct tcctcctgct ggtggcggct      60
cccagatggg tcctgtcccg gctgcagctg caggagtcgg gcccaggcct gctgaagcct     120
tcggtgaccc tgtccctcac ctgcactgtc tcgggtgact ccgtcgccag tagttcttat     180
tactggggct gggtccgtca gcccccaggg aagggactcg agtggatagg gactatcaat     240
tttagtggca atatgtatta tagtccgtcc ctcaggagtc gagtgaccat gtcggcagac     300
atgtccgaga actccttcta tctgaaattg actctgtgac cgcagcagac acggccgtc      360 tattattgtg cggcaggaca cctcgttatg ggatttgggg cccactgggg acagggaaaa     420
ctggtctccg tctctccagc ttccaccaag ggcccatccg tcttcccccct ggcgccctgc    480 tccaggagca cctccgagag cacagccgcc ctgggctgcc tggtcaagga ctacttcccc     540
gaaccggtga cggtgtcgtg gaactcaggc gccctgacca gcggcgtgca caccttcccg     600
gctgtcctac agtcctcagg actctactcc ctcagcagcg tggtgaccgt gccctccagc     660
agcttgggca cgaagaccta cacctgcaac gtagatcaca agcccagcaa caccaaggtg     720
gacaagagag ttgagtccaa atatggtccc ccatgcccac cctgcccagc acctgagttc     780
ctggggggac catcagtctt cctgttcccc ccaaaaccca aggacactct catgatctcc     840
cggacccctg aggtcacgtg cgtggtggtg gacgtgagcc aggaagaccc cgaggtccag     900
ttcaactggt acgtggatgg cgtggaggtg cataatgcca agacaaagcc gcgggaggag     960
cagttcaaca gcacgtaccg tgtggtcagc gtcctcaccg tcctgcacca ggactggctg    1020
aacggcaagg agtacaagtg caaggtctcc aacaaaggcc tcccgtcctc catcgagaaa    1080
accatctcca agcccaaagg gcagccccga gagccacagg tgtacaccct gcccccatcc    1140
caggaggaga tgaccaagaa ccaggtcagc ctgacctgcc tggtcaaagg cttctacccc    1200
agcgacatcg ccgtggagtg ggagagcaat gggcagccgg agaacaacta caagaccacg    1260
cctcccgtgc tggactccga cggctccttc ttcctctaca gcaggctaac cgtggacaag    1320
agcaggtggc aggagggga atgtcttctca tgctccgtga tgcatgaggc tctgcacaac    1380
cactacacac agaagagcct ctccctgtct ctgggtaaag ctagtcagac ccccaccaac    1440
accatcagcg tgacccccac caacaacagc acccccacca caacagcaa ccccaagccc    1500
```

```
aacccccgcta gcccaggcca gggcacccag tctgagaaca gctgcaccca cttcccaggc    1560
aacctgccta acatgcttcg agatctccga gatgccttca gcagagtgaa gactttcttt    1620
caaatgaagg atcagctgga caacttgttg ttaaaggagt ccttgctgga ggactttaag    1680
ggttacctgg gttgccaagc cttgtctgag atgatccagt tttacctgga ggaggtgatg    1740
ccccaagctg agaaccaaga cccagacatc aaggcgcatg tgaactccct ggggagaac    1800 ctgaagaccc tcaggctgag gctacggcgc tgtcatcgat ttcttccctg tgaaaacaag    1860
agcaaggccg tggagcaggt gaagaatgcc tttaataagc tccaagagaa aggcatctac    1920
aaagccatga gtgagtttga catcttcatc aactacatag aagcctacat gacaatgaag    1980
atacgaaact ga                                                        1992
```

<210> SEQ ID NO 43
<211> LENGTH: 214
<212> TYPE: PRT
<213> ORGANISM: Homo sapiens

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 44
<211> LENGTH: 705
<212> TYPE: DNA
<213> ORGANISM: Homo sapiens

<400> SEQUENCE: 44

```
atgagggtcc ccgctcagct cctggggctc ctgctactct ggctccgagg tgccagatgt      60
gacatccaga tgacccagtc tccatcctcc ctgtctgcat ctgtaggaga cagagtcacc     120
```

```
atcacttgcc gggcaagtca gagcattagc agctatttaa attggtatca gcagaaacca    180
gggaaagccc ctaagctcct gatctatgct gcatccagtt tgcaaagtgg ggtcccatca    240
aggttcagtg gcagtggatc tgggacagat ttcactctca ccatcagcag tctccaacct    300
gaagattttg caacttacta ctgtcaacag agttacagta ccccgtacac ttttggccag    360
gggaccaagc tggagatcaa acgaactgtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg ataacgccc tccaatcggg taactcccag    540
gagagtgtca cagagcagga cagcaaggac agcacctaca gcctcagcag caccctgacg    600
ctgagcaaag cagactacga gaaacacaaa gtctacgcct gcgaagtcac ccatcagggc    660
ctgagctcgc ccgtcacaaa gagcttcaac aggggagagt gttag                    705
```

<210> SEQ ID NO 45
<211> LENGTH: 447
<212> TYPE: PRT
<213> ORGANISM: Homo sapiens

<400> SEQUENCE: 45

```
Gln Val Gln Leu Lys Glu Ser Gly Pro Gly Leu Val Ala Pro Ser Gln
1               5                   10                  15

Ser Leu Ser Ile Thr Cys Ser Val Ser Gly Phe Ser Leu Ser Asn Tyr
            20                  25                  30

Asp Ile Ser Trp Ile Arg Gln Pro Pro Gly Lys Gly Leu Glu Trp Leu
        35                  40                  45

Gly Val Met Trp Thr Gly Gly Ala Asn Tyr Asn Ser Ala Phe Met
    50                  55                  60

Ser Arg Leu Ser Ile Asn Lys Asp Asn Ser Lys Ser Gln Val Phe Leu
65                  70                  75                  80

Lys Met Asn Asn Leu Gln Thr Asp Asp Thr Ala Ile Tyr Tyr Cys Val
                85                  90                  95

Arg Asp Ala Val Arg Tyr Trp Asn Phe Asp Val Trp Gly Ala Gly Thr
            100                 105                 110

Thr Val Thr Val Ser Ser Ala Lys Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Glu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270
```

```
Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys Ala Ser
        435                 440                 445

<210> SEQ ID NO 46
<211> LENGTH: 122
<212> TYPE: PRT
<213> ORGANISM: Homo sapiens

<400> SEQUENCE: 46

Gln Val Gln Leu Lys Glu Ser Gly Pro Gly Leu Val Ala Pro Ser Gln
1               5                   10                  15

Ser Leu Ser Ile Thr Cys Ser Val Ser Gly Phe Ser Leu Ser Asn Tyr
            20                  25                  30

Asp Ile Ser Trp Ile Arg Gln Pro Pro Gly Lys Gly Leu Glu Trp Leu
        35                  40                  45

Gly Val Met Trp Thr Gly Gly Ala Asn Tyr Asn Ser Ala Phe Met
    50                  55                  60

Ser Arg Leu Ser Ile Asn Lys Asp Asn Ser Lys Ser Gln Val Phe Leu
65                  70                  75                  80

Lys Met Asn Asn Leu Gln Thr Asp Asp Thr Ala Ile Tyr Tyr Cys Val
                85                  90                  95

Arg Asp Ala Val Arg Tyr Trp Asn Phe Asp Val Trp Gly Ala Gly Thr
            100                 105                 110

Thr Val Thr Val Ser Ser Ala Lys Thr Lys
        115                 120

<210> SEQ ID NO 47
<211> LENGTH: 213
<212> TYPE: PRT
<213> ORGANISM: Homo sapiens

<400> SEQUENCE: 47

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30
```

His Trp Tyr Gln Gln Lys Pro Gly Ser Ser Pro Lys Pro Trp Ile Tyr
            35                  40                  45

Ala Thr Ser His Leu Ala Ser Gly Val Pro Ala Arg Phe Ser Gly Ser
        50                  55                  60

Gly Ser Gly Thr Ser Tyr Ser Leu Thr Ile Ser Arg Val Glu Ala Glu
65                  70                  75                  80

Asp Thr Ala Thr Tyr Tyr Cys Gln Gln Trp Ser Ser Asn Pro Phe Thr
                85                  90                  95

Phe Gly Ser Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 48
<211> LENGTH: 102
<212> TYPE: PRT
<213> ORGANISM: Homo sapiens

<400> SEQUENCE: 48

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Tyr Gln Gln Lys Pro Gly Ser Ser Pro Lys Pro Trp Ile Tyr
            35                  40                  45

Ala Thr Ser His Leu Ala Ser Gly Val Pro Ala Arg Phe Ser Gly Ser
        50                  55                  60

Gly Ser Gly Thr Ser Tyr Ser Leu Thr Ile Ser Arg Val Glu Ala Glu
65                  70                  75                  80

Asp Thr Ala Thr Tyr Tyr Cys Gln Gln Trp Ser Ser Asn Pro Phe Thr
                85                  90                  95

Phe Gly Ser Gly Thr Lys
            100

<210> SEQ ID NO 49
<211> LENGTH: 450
<212> TYPE: PRT
<213> ORGANISM: Homo sapiens

<400> SEQUENCE: 49

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Thr Tyr
            20                  25                  30

```
Thr Met His Trp Val Lys Gln Arg Pro Gly Gln Gly Leu Glu Trp Ile
        35                  40                  45

Gly Tyr Ile Asn Pro Ser Ser Gly Tyr Thr Asn Tyr Asn Gln Lys Phe
        50                  55                  60

Lys Asp Lys Ala Thr Leu Thr Ala Asp Lys Ser Ser Ser Thr Ala Ser
65                  70                  75                  80

Met Gln Leu Ser Ser Leu Thr Ser Glu Asp Ser Ala Val Tyr Tyr Cys
                85                  90                  95

Ala Arg Glu Arg Ala Val Leu Val Pro Tyr Ala Met Asp Tyr Trp Gly
                100                 105                 110

Gln Gly Thr Ser Val Thr Val Ser Ser Ala Lys Thr Lys Gly Pro Ser
                115                 120                 125

Val Phe Pro Leu Ala Pro Cys Ser Arg Ser Thr Ser Glu Ser Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Lys Thr Tyr Thr Cys Asn Val Asp His
                195                 200                 205

Lys Pro Ser Asn Thr Lys Val Asp Lys Arg Val Glu Ser Lys Tyr Gly
            210                 215                 220

Pro Pro Cys Pro Pro Cys Pro Ala Pro Glu Phe Glu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
                260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445
```

Ala Ser
    450

<210> SEQ ID NO 50
<211> LENGTH: 125
<212> TYPE: PRT
<213> ORGANISM: Homo sapiens

<400> SEQUENCE: 50

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Thr Tyr
            20                  25                  30

Thr Met His Trp Val Lys Gln Arg Pro Gly Gln Gly Leu Glu Trp Ile
        35                  40                  45

Gly Tyr Ile Asn Pro Ser Ser Gly Tyr Thr Asn Tyr Asn Gln Lys Phe
    50                  55                  60

Lys Asp Lys Ala Thr Leu Thr Ala Asp Lys Ser Ser Ser Thr Ala Ser
65                  70                  75                  80

Met Gln Leu Ser Ser Leu Thr Ser Glu Asp Ser Ala Val Tyr Tyr Cys
                85                  90                  95

Ala Arg Glu Arg Ala Val Leu Val Pro Tyr Ala Met Asp Tyr Trp Gly
            100                 105                 110

Gln Gly Thr Ser Val Thr Val Ser Ser Ala Lys Thr Lys
        115                 120                 125

<210> SEQ ID NO 51
<211> LENGTH: 213
<212> TYPE: PRT
<213> ORGANISM: Homo sapiens

<400> SEQUENCE: 51

Gln Ile Val Leu Thr Gln Ser Pro Ala Val Met Ser Ala Ser Pro Gly
1               5                   10                  15

Glu Lys Val Thr Ile Thr Cys Thr Ala Ser Ser Ser Leu Ser Tyr Met
            20                  25                  30

His Trp Phe Gln Gln Lys Pro Gly Thr Ser Pro Lys Leu Trp Leu Tyr
        35                  40                  45

Ser Thr Ser Ile Leu Ala Ser Gly Val Pro Thr Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Pro Phe Thr
                85                  90                  95

Phe Gly Ser Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 52
<211> LENGTH: 102
<212> TYPE: PRT
<213> ORGANISM: Homo sapiens

<400> SEQUENCE: 52

Gln Ile Val Leu Thr Gln Ser Pro Ala Val Met Ser Ala Ser Pro Gly
1               5                   10                  15

Glu Lys Val Thr Ile Thr Cys Thr Ala Ser Ser Ser Leu Ser Tyr Met
            20                  25                  30

His Trp Phe Gln Gln Lys Pro Gly Thr Ser Pro Lys Leu Trp Leu Tyr
        35                  40                  45

Ser Thr Ser Ile Leu Ala Ser Gly Val Pro Thr Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Pro Phe Thr
                85                  90                  95

Phe Gly Ser Gly Thr Lys
            100

<210> SEQ ID NO 53
<211> LENGTH: 448
<212> TYPE: PRT
<213> ORGANISM: Homo sapiens

<400> SEQUENCE: 53

Glu Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Ser Asn Gly Lys Ser Leu Glu Trp Ile
        35                  40                  45

Gly Asn Ile Asp Pro Tyr Tyr Gly Asp Thr Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met His Leu Lys Ser Leu Thr Ser Glu Asp Ser Ala Val Tyr Tyr Cys
                85                  90                  95

Ala Arg Pro Tyr Gly Ser Glu Ala Tyr Phe Ala Tyr Trp Gly Gln Gly
            100                 105                 110

Thr Leu Val Thr Val Ser Ala Ala Lys Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys Ala Ser
        435                 440                 445

<210> SEQ ID NO 54
<211> LENGTH: 123
<212> TYPE: PRT
<213> ORGANISM: Homo sapiens

<400> SEQUENCE: 54

Glu Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Asn Gly Lys Ser Leu Glu Trp Ile
        35                  40                  45

Gly Asn Ile Asp Pro Tyr Tyr Gly Asp Thr Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met His Leu Lys Ser Leu Thr Ser Glu Asp Ser Ala Val Tyr Tyr Cys
                85                  90                  95

Ala Arg Pro Tyr Gly Ser Glu Ala Tyr Phe Ala Tyr Trp Gly Gln Gly
            100                 105                 110

Thr Leu Val Thr Val Ser Ala Ala Lys Thr Lys
            115                 120

<210> SEQ ID NO 55
<211> LENGTH: 214
<212> TYPE: PRT
<213> ORGANISM: Homo sapiens

<400> SEQUENCE: 55

```
Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ala Gln Ser Ile Ser Gly Ile Pro Ser Arg Phe Ser Gly
50                  55                  60

Ser Gly Ser Gly Ser Asp Phe Thr Leu Ser Ile Asn Gly Val Glu Pro
65                  70                  75                  80

Glu Asp Val Gly Val Tyr Tyr Cys Gln Asn Gly His Ser Phe Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 56
<211> LENGTH: 103
<212> TYPE: PRT
<213> ORGANISM: Homo sapiens

<400> SEQUENCE: 56

```
Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ala Gln Ser Ile Ser Gly Ile Pro Ser Arg Phe Ser Gly
50                  55                  60

Ser Gly Ser Gly Ser Asp Phe Thr Leu Ser Ile Asn Gly Val Glu Pro
65                  70                  75                  80

Glu Asp Val Gly Val Tyr Tyr Cys Gln Asn Gly His Ser Phe Pro Tyr
                85                  90                  95

Thr Phe Gly Gly Gly Thr Lys
            100
```

<210> SEQ ID NO 57
<211> LENGTH: 449
<212> TYPE: PRT
<213> ORGANISM: Homo sapiens

<400> SEQUENCE: 57

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Val Pro Gly Lys Gly Leu Arg Trp Met
        35                  40                  45

Gly Trp Met Asp Thr Phe Thr Gly Glu Pro Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Ser Leu Lys Asn Glu Asp Thr Ala Thr Tyr Phe Cys
                85                  90                  95

Ala Arg Gly Gly Ile Leu Arg Leu Asn Tyr Phe Asp Tyr Trp Gly Gln
            100                 105                 110

Gly Thr Thr Leu Thr Val Ser Ser Ala Lys Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
```

370                 375                 380
Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys Ala
        435                 440                 445

Ser

<210> SEQ ID NO 58
<211> LENGTH: 124
<212> TYPE: PRT
<213> ORGANISM: Homo sapiens

<400> SEQUENCE: 58

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Val Pro Gly Lys Gly Leu Arg Trp Met
        35                  40                  45

Gly Trp Met Asp Thr Phe Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Ser Leu Lys Asn Glu Asp Thr Ala Thr Tyr Phe Cys
                85                  90                  95

Ala Arg Gly Gly Ile Leu Arg Leu Asn Tyr Phe Asp Tyr Trp Gly Gln
            100                 105                 110

Gly Thr Thr Leu Thr Val Ser Ser Ala Lys Thr Lys
        115                 120

<210> SEQ ID NO 59
<211> LENGTH: 214
<212> TYPE: PRT
<213> ORGANISM: Homo sapiens

<400> SEQUENCE: 59

Asp Ile Gln Met Thr Gln Ser Ser Ser Ser Phe Ser Val Ser Leu Gly
1               5                   10                  15

Asp Arg Val Thr Ile Thr Cys Lys Ala Ser Glu Asp Ile Tyr Asn Arg
            20                  25                  30

Leu Gly Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Lys Asp Tyr Ala Leu Ser Ile Thr Ser Leu Gln Thr
65                  70                  75                  80

Glu Asp Leu Ala Thr Tyr Tyr Cys Gln Gln Cys Trp Thr Ser Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 60
<211> LENGTH: 106
<212> TYPE: PRT
<213> ORGANISM: Homo sapiens

<400> SEQUENCE: 60

Asp Ile Gln Met Thr Gln Ser Ser Ser Ser Phe Ser Val Ser Leu Gly
1               5                   10                  15

Asp Arg Val Thr Ile Thr Cys Lys Ala Ser Glu Asp Ile Tyr Asn Arg
                20                  25                  30

Leu Gly Trp Tyr Gln Gln Lys Pro Gly Asn Ala Pro Arg Leu Leu Ile
            35                  40                  45

Ser Gly Ala Thr Ser Leu Glu Thr Gly Val Pro Ser Arg Phe Ser Gly
        50                  55                  60

Ser Gly Ser Gly Lys Asp Tyr Ala Leu Ser Ile Thr Ser Leu Gln Thr
65                  70                  75                  80

Glu Asp Leu Ala Thr Tyr Tyr Cys Gln Gln Cys Trp Thr Ser Pro Tyr
                85                  90                  95

Thr Phe Gly Gly Gly Thr Lys Leu Glu Ile
                100                 105

<210> SEQ ID NO 61
<211> LENGTH: 445
<212> TYPE: PRT
<213> ORGANISM: Homo sapiens

<400> SEQUENCE: 61

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
                20                  25                  30

Tyr Met Lys Trp Val Lys Gln Ser His Gly Lys Ser Leu Glu Trp Ile
            35                  40                  45

Gly Asp Ile Asn Pro Asn Tyr Gly Asp Thr Phe Tyr Asn Gln Lys Phe
        50                  55                  60

Glu Gly Lys Ala Thr Leu Thr Val Asp Lys Ser Ser Arg Thr Ala Tyr
65                  70                  75                  80

Met Gln Leu Asn Ser Leu Thr Ser Glu Asp Ser Ala Val Tyr Tyr Cys
                85                  90                  95

Gly Arg Gly Asp Tyr Gly Tyr Phe Asp Val Trp Gly Ala Gly Thr Thr
                100                 105                 110

Val Thr Val Ser Ser Ala Lys Thr Lys Gly Pro Ser Val Phe Pro Leu
                115                 120                 125
```

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
                260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Leu Ser Leu Gly Lys Ala Ser
            435                 440                 445

<210> SEQ ID NO 62
<211> LENGTH: 121
<212> TYPE: PRT
<213> ORGANISM: Homo sapiens

<400> SEQUENCE: 62

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
                20                  25                  30

Tyr Met Lys Trp Val Lys Gln Ser His Gly Lys Ser Leu Glu Trp Ile
            35                  40                  45

Gly Asp Ile Asn Pro Asn Tyr Gly Asp Thr Phe Tyr Asn Gln Lys Phe

```
                    50                  55                  60
Glu Gly Lys Ala Thr Leu Thr Val Asp Lys Ser Ser Arg Thr Ala Tyr
 65                  70                  75                  80

Met Gln Leu Asn Ser Leu Thr Ser Glu Asp Ser Ala Val Tyr Tyr Cys
                 85                  90                  95

Gly Arg Gly Asp Tyr Gly Tyr Phe Asp Val Trp Gly Ala Gly Thr Thr
                100                 105                 110

Val Thr Val Ser Ser Ala Lys Thr Lys
            115                 120

<210> SEQ ID NO 63
<211> LENGTH: 214
<212> TYPE: PRT
<213> ORGANISM: Homo sapiens

<400> SEQUENCE: 63

Asp Ile Val Met Thr Gln Ser His Lys Phe Met Ser Thr Ser Val Gly
  1               5                  10                  15

Asp Arg Val Ser Ile Thr Cys Lys Ala Ser Gln Asp Val Gly Thr Ala
                 20                  25                  30

Val Ala Trp Tyr Gln Gln Lys Pro Gly Gln Ser Pro Lys Leu Leu Ile
             35                  40                  45

Tyr Trp Ala Ser Thr Arg His Thr Gly Val Pro Asp Arg Phe Thr Gly
 50                  55                  60

Ser Gly Ser Gly Thr Asp Phe Thr Leu Thr Ile Asn Asn Val Gln Ser
 65                  70                  75                  80

Glu Asp Leu Ala Asp Tyr Phe Cys Gln Gln Tyr Ser Ser Asn Pro Tyr
                 85                  90                  95

Met Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 64
<211> LENGTH: 106
<212> TYPE: PRT
<213> ORGANISM: Homo sapiens

<400> SEQUENCE: 64

Asp Ile Val Met Thr Gln Ser His Lys Phe Met Ser Thr Ser Val Gly
  1               5                  10                  15

Asp Arg Val Ser Ile Thr Cys Lys Ala Ser Gln Asp Val Gly Thr Ala
                 20                  25                  30

Val Ala Trp Tyr Gln Gln Lys Pro Gly Gln Ser Pro Lys Leu Leu Ile
```

```
              35                  40                  45
Tyr Trp Ala Ser Thr Arg His Thr Gly Val Pro Asp Arg Phe Thr Gly
 50                  55                  60

Ser Gly Ser Gly Thr Asp Phe Thr Leu Thr Ile Asn Asn Val Gln Ser
65                  70                  75                  80

Glu Asp Leu Ala Asp Tyr Phe Cys Gln Gln Tyr Ser Ser Asn Pro Tyr
                 85                  90                  95

Met Phe Gly Gly Gly Thr Lys Leu Glu Ile
             100                 105

<210> SEQ ID NO 65
<211> LENGTH: 447
<212> TYPE: PRT
<213> ORGANISM: Homo sapiens

<400> SEQUENCE: 65

Gln Leu Gln Gln Ser Gly Pro Glu Leu Val Lys Pro Gly Ala Ser Val
1               5                  10                  15

Lys Ile Ser Cys Lys Thr Ser Gly Tyr Thr Phe Thr Glu Tyr Thr Met
             20                  25                  30

His Trp Val Arg Gln Ser His Gly Lys Ser Leu Glu Trp Ile Gly Gly
         35                  40                  45

Ile Asn Pro Ile Asn Gly Gly Pro Thr Tyr Asn Gln Lys Phe Lys Gly
 50                  55                  60

Lys Ala Thr Leu Thr Val Asp Lys Ser Ser Thr Ala Tyr Met Glu
65                  70                  75                  80

Leu Arg Ser Leu Thr Ser Glu Asp Ser Ala Val Tyr Tyr Cys Ala Arg
                 85                  90                  95

Trp Asp Tyr Gly Ser Arg Asp Val Met Asp Tyr Trp Gly Gln Gly Thr
             100                 105                 110

Ser Val Thr Val Ser Ser Ala Lys Thr Lys Gly Pro Ser Val Phe Pro
         115                 120                 125

Leu Ala Pro Cys Ser Arg Ser Thr Ser Glu Ser Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
210                 215                 220

Pro Pro Cys Pro Ala Pro Glu Phe Glu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
290                 295                 300
```

```
Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
            405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys Ala Ser
            435                 440                 445
```

```
<210> SEQ ID NO 66
<211> LENGTH: 122
<212> TYPE: PRT
<213> ORGANISM: Homo sapiens

<400> SEQUENCE: 66
```

```
Gln Leu Gln Gln Ser Gly Pro Glu Leu Val Lys Pro Gly Ala Ser Val
1               5                   10                  15

Lys Ile Ser Cys Lys Thr Ser Gly Tyr Thr Phe Thr Glu Tyr Thr Met
            20                  25                  30

His Trp Val Arg Gln Ser His Gly Lys Ser Leu Glu Trp Ile Gly Gly
        35                  40                  45

Ile Asn Pro Ile Asn Gly Gly Pro Thr Tyr Asn Gln Lys Phe Lys Gly
    50                  55                  60

Lys Ala Thr Leu Thr Val Asp Lys Ser Ser Thr Ala Tyr Met Glu
65                  70                  75                  80

Leu Arg Ser Leu Thr Ser Glu Asp Ser Ala Val Tyr Tyr Cys Ala Arg
                85                  90                  95

Trp Asp Tyr Gly Ser Arg Asp Val Met Asp Tyr Trp Gly Gln Gly Thr
            100                 105                 110

Ser Val Thr Val Ser Ser Ala Lys Thr Lys
            115                 120
```

```
<210> SEQ ID NO 67
<211> LENGTH: 214
<212> TYPE: PRT
<213> ORGANISM: Homo sapiens

<400> SEQUENCE: 67
```

```
Asn Ile Val Met Thr Gln Ser Pro Lys Ser Met Ser Met Ser Val Gly
1               5                   10                  15

Glu Arg Val Thr Leu Ser Cys Lys Ala Ser Glu Asn Val Gly Thr Tyr
            20                  25                  30

Val Ser Trp Tyr Gln Gln Arg Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60
```

```
Ser Gly Ser Ala Thr Asp Phe Thr Leu Thr Ile Ser Ser Val Gln Ala
 65                  70                  75                  80

Glu Asp Leu Ala Asp Tyr His Cys Gly Gln Thr Tyr Ser Tyr Ile Phe
                 85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 68
<211> LENGTH: 105
<212> TYPE: PRT
<213> ORGANISM: Homo sapiens

<400> SEQUENCE: 68

Asn Ile Val Met Thr Gln Ser Pro Lys Ser Met Ser Met Ser Val Gly
  1               5                  10                  15

Glu Arg Val Thr Leu Ser Cys Lys Ala Ser Glu Asn Val Gly Thr Tyr
                 20                  25                  30

Val Ser Trp Tyr Gln Gln Arg Pro Glu Gln Ser Pro Lys Leu Leu Ile
             35                  40                  45

Tyr Gly Ala Ser Asn Arg Tyr Thr Gly Val Pro Asp Arg Phe Thr Gly
 50                  55                  60

Ser Gly Ser Ala Thr Asp Phe Thr Leu Thr Ile Ser Ser Val Gln Ala
 65                  70                  75                  80

Glu Asp Leu Ala Asp Tyr His Cys Gly Gln Thr Tyr Ser Tyr Ile Phe
                 85                  90                  95

Thr Phe Gly Ser Gly Thr Lys Leu Glu
            100                 105

<210> SEQ ID NO 69
<211> LENGTH: 446
<212> TYPE: PRT
<213> ORGANISM: Homo sapiens

<400> SEQUENCE: 69

Val Gln Leu Gln Gln Ser Gly Ala Glu Leu Val Arg Pro Gly Thr Ser
  1               5                  10                  15

Val Lys Met Ser Cys Glu Ala Ala Arg Phe Thr Phe Ser Asn Tyr Trp
                 20                  25                  30

Ile Gly Trp Val Lys Gln Arg Pro Gly His Gly Leu Glu Trp Ile Gly
             35                  40                  45

Asp Ile Phe Pro Gly Gly Asp Tyr Thr Asn Tyr Asn Lys Lys Phe Lys
 50                  55                  60
```

```
Asp Lys Ala Thr Leu Thr Ala Asp Thr Ser Ser Ser Thr Ala Tyr Met
 65                  70                  75                  80

Gln Leu Ser Ser Leu Thr Ser Glu Asp Ser Ala Ile Tyr Tyr Cys Ala
                 85                  90                  95

Arg Ser Asp Tyr Gly Gly Tyr Tyr Val Phe Asp Tyr Trp Gly Gln Gly
            100                 105                 110

Thr Thr Leu Thr Val Ser Ser Ala Lys Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 70
<211> LENGTH: 220
<212> TYPE: PRT
<213> ORGANISM: Homo sapiens

<400> SEQUENCE: 70
```

```
Asp Ile Val Met Ser Gln Ser Pro Ser Ser Leu Ala Val Ser Val Gly
1               5                   10                  15

Glu Lys Val Thr Met Ser Cys Lys Ser Ser Gln Asn Leu Leu Tyr Ser
                20                  25                  30

Ser Asn Gln Lys Asn Tyr Leu Ala Trp Tyr Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Tyr Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
210                 215                 220

<210> SEQ ID NO 71
<211> LENGTH: 445
<212> TYPE: PRT
<213> ORGANISM: Homo sapiens

<400> SEQUENCE: 71

Ala Gln Ile Gln Leu Val Gln Ser Gly Pro Glu Leu Lys Lys Pro Gly
1               5                   10                  15

Glu Thr Val Lys Ile Ser Cys Lys Ala Ser Gly Tyr Thr Phe Thr Asp
                20                  25                  30

Tyr Ser Val His Trp Val Lys Gln Ala Pro Gly Lys Gly Leu Lys Trp
            35                  40                  45

Met Gly Trp Ile Asn Thr Glu Thr Gly Glu Pro Thr Tyr Ala Asp Asp
    50                  55                  60

Leu Lys Gly Arg Phe Ala Phe Ser Leu Glu Thr Ser Ala Ser Thr Ala
65                  70                  75                  80

Tyr Leu Gln Ile Asn Asn Leu Lys Asn Glu Asp Thr Ala Thr Tyr Phe
                85                  90                  95

Cys Ala Lys Pro Thr Tyr Arg Phe Phe Asp Tyr Trp Gly Gln Gly Thr
            100                 105                 110

Thr Leu Thr Ala Ser Ser Ala Lys Thr Lys Gly Pro Ser Val Phe Pro
        115                 120                 125

Leu Ala Pro Cys Ser Arg Ser Thr Ser Glu Ser Thr Ala Ala Leu Gly
130                 135                 140

Cys Leu Val Lys Asp Tyr Phe Pro Glu Pro Val Thr Val Ser Trp Asn
```

```
                145                 150                 155                 160
Ser Gly Ala Leu Thr Ser Gly Val His Thr Phe Pro Ala Val Leu Gln
                165                 170                 175

Ser Ser Gly Leu Tyr Ser Leu Ser Ser Val Thr Val Pro Ser Ser
            180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
        210                 215                 220

Pro Pro Cys Pro Ala Pro Glu Phe Glu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 72
<211> LENGTH: 219
<212> TYPE: PRT
<213> ORGANISM: Homo sapiens

<400> SEQUENCE: 72

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80
```

-continued

```
Ile Ser Ser Val Gln Ala Glu Asp Leu Ala Val Tyr Tyr Cys Lys Gln
                85                  90                  95

Ser Tyr Asn Leu Trp Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 73
<211> LENGTH: 203
<212> TYPE: PRT
<213> ORGANISM: Homo sapiens

<400> SEQUENCE: 73

```
Met Glu Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Asp Tyr Val Leu His Trp Val Lys Gln Lys Pro Gly Gln Gly Leu
    50                  55                  60

Glu Trp Ile Gly Tyr Ile Asn Pro Tyr Asn Asp Gly Thr Lys Tyr Asn
65                  70                  75                  80

Glu Lys Phe Lys Gly Lys Ala Thr Leu Thr Ser Asp Lys Ser Ser Ser
                85                  90                  95

Thr Ala Tyr Met Glu Leu Ser Ser Leu Thr Ser Glu Asp Ser Ala Val
            100                 105                 110

Tyr Tyr Cys Ala Arg Gly Tyr Pro Ala Tyr Ser Gly Tyr Ala Met Asp
        115                 120                 125

Tyr Trp Gly Gln Gly Thr Ser Val Thr Val Ser Ser Ala Lys Thr Thr
    130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
            180                 185                 190

Phe Pro Ala Val Leu Gln Lys Gly Glu Phe Val
        195                 200
```

<210> SEQ ID NO 74
<211> LENGTH: 234
<212> TYPE: PRT
<213> ORGANISM: Homo sapiens

<400> SEQUENCE: 74

Met Met Ser Ser Ala Gln Phe Leu Gly Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Asn Tyr Leu Asn Trp Tyr Gln Gln Lys Pro Asp Gly Thr Val
    50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys His His Gly Asn
            100                 105                 110

Thr Leu Pro Trp Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
210                 215                 220

Ile Val Lys Ser Phe Asn Arg Asn Glu Cys
225                 230

<210> SEQ ID NO 75
<211> LENGTH: 235
<212> TYPE: PRT
<213> ORGANISM: Homo sapiens

<400> SEQUENCE: 75

Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Leu Ser Ala Ser Pro Gly Glu Lys Val Thr Met Thr Cys Ser Ala Ser
        35                  40                  45

Ser Ser Val Ser Tyr Met Tyr Arg Tyr Gln Gln Lys Pro Gly Ser Ser
    50                  55                  60

Pro Lys Pro Trp Ile Tyr Gly Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys Gln Gln Tyr
            100                 105                 110

His Ser Tyr Pro Leu Thr Phe Gly Ala Gly Thr Lys Leu Glu Leu Lys
        115                 120                 125

```
Arg Ala Asp Ala Ala Pro Thr Val Ser Ile Phe Pro Pro Ser Ser Glu
            130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
                195                 200                 205

Arg His Asn Ser Tyr Thr Cys Glu Ala Thr His Lys Thr Ser Thr Ser
            210                 215                 220

Pro Ile Val Lys Ser Phe Asn Arg Asn Glu Cys
225                 230                 235

<210> SEQ ID NO 76
<211> LENGTH: 196
<212> TYPE: PRT
<213> ORGANISM: Homo sapiens

<400> SEQUENCE: 76

Met Gly Trp Ser Trp Ile Phe Leu Phe Leu Leu Ser Gly Thr Ala Gly
1               5                   10                  15

Val Leu Ser Glu Val Gln Leu Gln Gln Ser Gly Pro Glu Leu Val Lys
                20                  25                  30

Pro Gly Ala Ser Val Lys Ile Ser Cys Lys Ala Ser Gly Tyr Ser Phe
            35                  40                  45

Thr Gly Tyr Tyr Met His Trp Val Lys Gln Ser His Val Lys Ser Leu
        50                  55                  60

Glu Trp Ile Gly Arg Ile Asn Pro Tyr Asn Gly Ala Thr Ser Tyr Asn
65                  70                  75                  80

Gln Asn Phe Lys Asp Lys Ala Ser Leu Thr Val Asp Lys Ser Ser Ser
                85                  90                  95

Thr Ala Tyr Met Glu Leu His Ser Leu Thr Ser Glu Asp Ser Ala Val
            100                 105                 110

Tyr Tyr Cys Ala Arg Glu Asp Tyr Val Tyr Trp Gly Gln Gly Thr Thr
        115                 120                 125

Leu Thr Val Ser Ser Ala Lys Thr Thr Pro Pro Ser Val Tyr Pro Leu
130                 135                 140

Ala Pro Gly Ser Ala Ala Gln Thr Asn Ser Met Val Thr Leu Gly Cys
145                 150                 155                 160

Leu Val Lys Gly Tyr Phe Pro Glu Pro Val Thr Val Thr Trp Asn Ser
                165                 170                 175

Gly Ser Leu Ser Ser Gly Val His Thr Phe Pro Ala Val Leu Gln Lys
            180                 185                 190

Gly Glu Phe Val
        195

<210> SEQ ID NO 77
<211> LENGTH: 238
<212> TYPE: PRT
<213> ORGANISM: Homo sapiens

<400> SEQUENCE: 77

Met Lys Leu Pro Val Arg Leu Leu Val Leu Met Phe Trp Ile Pro Ala
1               5                   10                  15
```

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Ala
                85                  90                  95

Leu Lys Ile Ser Arg Val Glu Ala Glu Asp Leu Gly Val Tyr Phe Cys
            100                 105                 110

Ser Gln Ser Thr His Val Pro Trp Thr Phe Gly Gly Gly Thr Lys Leu
        115                 120                 125

Glu Ile Lys Arg Ala Asp Ala Ala Pro Thr Val Ser Ile Phe Pro Pro
130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235

<210> SEQ ID NO 78
<211> LENGTH: 444
<212> TYPE: PRT
<213> ORGANISM: Homo sapiens

<400> SEQUENCE: 78

Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Ala Ile Tyr Pro Gly Asn Ser Asp Thr Thr Tyr Asn Gln Lys Phe
    50                  55                  60

Lys Gly Lys Ala Lys Leu Thr Ala Val Thr Ser Thr Ser Thr Ala Tyr
65                  70                  75                  80

Met Glu Leu Ser Ser Leu Thr Asn Glu Asp Ser Ala Val Tyr Tyr Cys
                85                  90                  95

Thr Pro Thr Tyr Tyr Phe Asp Tyr Trp Gly Gln Gly Thr Ser Leu Thr
            100                 105                 110

Val Ser Ser Ala Lys Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala

```
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
                180                 185                 190
Thr Lys Thr Tyr Thr Cys Asn Val Asp His Lys Pro Ser Asn Thr Lys
                195                 200                 205
Val Asp Lys Arg Val Glu Ser Lys Tyr Gly Pro Pro Cys Pro Pro Cys
210                 215                 220
Pro Ala Pro Glu Phe Glu Gly Gly Pro Ser Val Phe Leu Phe Pro Pro
225                 230                 235                 240
Lys Pro Lys Asp Thr Leu Met Ile Ser Arg Thr Pro Glu Val Thr Cys
                245                 250                 255
Val Val Val Asp Val Ser Gln Glu Asp Pro Glu Val Gln Phe Asn Trp
                260                 265                 270
Tyr Val Asp Gly Val Glu Val His Asn Ala Lys Thr Lys Pro Arg Glu
                275                 280                 285
Glu Gln Phe Asn Ser Thr Tyr Arg Val Val Ser Val Leu Thr Val Leu
                290                 295                 300
His Gln Asp Trp Leu Asn Gly Lys Glu Tyr Lys Cys Lys Val Ser Asn
305                 310                 315                 320
Lys Gly Leu Pro Ser Ser Ile Glu Lys Thr Ile Ser Lys Ala Lys Gly
                325                 330                 335
Gln Pro Arg Glu Pro Gln Val Tyr Thr Leu Pro Pro Ser Gln Glu Glu
                340                 345                 350
Met Thr Lys Asn Gln Val Ser Leu Thr Cys Leu Val Lys Gly Phe Tyr
                355                 360                 365
Pro Ser Asp Ile Ala Val Glu Trp Glu Ser Asn Gly Gln Pro Glu Asn
                370                 375                 380
Asn Tyr Lys Thr Thr Pro Pro Val Leu Asp Ser Asp Gly Ser Phe Phe
385                 390                 395                 400
Leu Tyr Ser Arg Leu Thr Val Asp Lys Ser Arg Trp Gln Glu Gly Asn
                405                 410                 415
Val Phe Ser Cys Ser Val Met His Glu Ala Leu His Asn His Tyr Thr
                420                 425                 430
Gln Lys Ser Leu Ser Leu Ser Leu Gly Lys Ala Ser
                435                 440

<210> SEQ ID NO 79
<211> LENGTH: 119
<212> TYPE: PRT
<213> ORGANISM: Homo sapiens

<400> SEQUENCE: 79

Glu Val Gln Leu Gln Gln Ser Gly Thr Val Leu Ala Arg Pro Gly Ala
1               5                   10                  15
Ser Val Lys Met Ser Cys Lys Ala Ser Gly Tyr Thr Phe Thr Ser Tyr
                20                  25                  30
Trp Met His Trp Val Lys Gln Arg Pro Gly Gln Gly Leu Glu Trp Ile
            35                  40                  45
Gly Ala Ile Tyr Pro Gly Asn Ser Asp Thr Thr Tyr Asn Gln Lys Phe
        50                  55                  60
Lys Gly Lys Ala Lys Leu Thr Ala Val Thr Ser Thr Ser Thr Ala Tyr
65                  70                  75                  80
```

Met Glu Leu Ser Ser Leu Thr Asn Glu Asp Ser Ala Val Tyr Tyr Cys
                85                  90                  95

Thr Pro Thr Tyr Tyr Phe Asp Tyr Trp Gly Gln Gly Thr Ser Leu Thr
            100                 105                 110

Val Ser Ser Ala Lys Thr Lys
        115

<210> SEQ ID NO 80
<211> LENGTH: 219
<212> TYPE: PRT
<213> ORGANISM: Homo sapiens

<400> SEQUENCE: 80

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Phe Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Trp Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 81
<211> LENGTH: 110
<212> TYPE: PRT
<213> ORGANISM: Homo sapiens

<400> SEQUENCE: 81

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Phe Leu Gln Arg Pro Gly Gln Ser
        35                  40                  45

Pro Lys Arg Leu Ile Tyr Leu Val Ser Lys Leu Asp Ser Gly Val Pro
    50                  55                  60

```
Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Trp Gln Gly
                 85                  90                  95

Thr His Phe Pro Trp Thr Phe Gly Gly Gly Thr Lys Leu Glu
            100                 105                 110

<210> SEQ ID NO 82
<211> LENGTH: 442
<212> TYPE: PRT
<213> ORGANISM: Homo sapiens

<400> SEQUENCE: 82

Gln Val Gln Leu Gln Gln Ser Gly Ala Glu Leu Met Lys Pro Gly Ala
  1               5                  10                  15

Ser Val Lys Ile Ser Cys Lys Ala Thr Gly Tyr Thr Phe Gly Ser Tyr
                 20                  25                  30

Trp Ile Glu Trp Val Lys Gln Arg Pro Gly His Gly Leu Glu Trp Ile
             35                  40                  45

Gly Glu Ile Leu Pro Gly Ser Gly Asn Thr Asn Tyr Asn Glu Asn Phe
 50                  55                  60

Lys Gly Lys Ala Thr Phe Thr Ala Asp Thr Ser Ser Asn Thr Ala Tyr
 65                  70                  75                  80

Met Gln Leu Thr Ser Leu Thr Ser Glu Asp Ser Ala Val Tyr Tyr Cys
                 85                  90                  95

Ala Arg Ala Gly Ile Tyr Trp Gly Gln Gly Thr Leu Val Thr Val Ser
                100                 105                 110

Ala Ala Lys Thr Lys Gly Pro Ser Val Phe Pro Leu Ala Pro Cys Ser
            115                 120                 125

Arg Ser Thr Ser Glu Ser Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
            195                 200                 205

Lys Arg Val Glu Ser Lys Tyr Gly Pro Pro Cys Pro Pro Cys Pro Ala
210                 215                 220

Pro Glu Phe Glu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335
```

```
Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Gln Gly Asn Val Phe
                405                 410                 415

Ser Cys Ser Val Met His Glu Ala Leu His Asn His Tyr Thr Gln Lys
                420                 425                 430

Ser Leu Ser Leu Ser Leu Gly Lys Ala Ser
        435                 440

<210> SEQ ID NO 83
<211> LENGTH: 117
<212> TYPE: PRT
<213> ORGANISM: Homo sapiens

<400> SEQUENCE: 83

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Gly Ser Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Asn Thr Asn Tyr Asn Glu Asn Phe
    50                  55                  60

Lys Gly Lys Ala Thr Phe Thr Ala Asp Thr Ser Ser Asn Thr Ala Tyr
65                  70                  75                  80

Met Gln Leu Thr Ser Leu Thr Ser Glu Asp Ser Ala Val Tyr Tyr Cys
                85                  90                  95

Ala Arg Ala Gly Ile Tyr Trp Gly Gln Gly Thr Leu Val Thr Val Ser
            100                 105                 110

Ala Ala Lys Thr Lys
        115

<210> SEQ ID NO 84
<211> LENGTH: 218
<212> TYPE: PRT
<213> ORGANISM: Homo sapiens

<400> SEQUENCE: 84

Asp Ile Val Leu Thr Gln Ser Pro Ala Phe Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Val Ala Ser Lys Gln Gly Ser Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95
```

```
Glu Val Pro Arg Thr Phe Gly Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 85
<211> LENGTH: 109
<212> TYPE: PRT
<213> ORGANISM: Homo sapiens

<400> SEQUENCE: 85

```
Asp Ile Val Leu Thr Gln Ser Pro Ala Phe Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Val Ala Ser Lys Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Arg Thr Phe Gly Gly Gly Thr Lys Leu Glu
            100                 105
```

<210> SEQ ID NO 86
<211> LENGTH: 449
<212> TYPE: PRT
<213> ORGANISM: Homo sapiens

<400> SEQUENCE: 86

```
Glu Ile Gln Leu Gln Gln Thr Gly Pro Glu Leu Val Lys Pro Gly Ala
1               5                   10                  15

Ser Val Lys Ile Ser Cys Lys Ala Ser Gly Tyr Pro Phe Thr Asp Tyr
            20                  25                  30

Ile Met Val Trp Val Lys Gln Ser His Gly Lys Ser Leu Glu Trp Ile
        35                  40                  45

Gly Asn Ile Ser Pro Tyr Tyr Gly Thr Thr Asn Tyr Asn Leu Lys Phe
    50                  55                  60

Lys Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95
```

-continued

```
Ala Arg Ser Pro Asn Trp Asp Gly Ala Trp Phe Ala His Trp Gly Gln
            100                 105                 110

Gly Ala Leu Val Thr Val Ser Ala Ala Lys Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys Ala
        435                 440                 445

Ser

<210> SEQ ID NO 87
<211> LENGTH: 124
<212> TYPE: PRT
<213> ORGANISM: Homo sapiens

<400> SEQUENCE: 87

Glu Ile Gln Leu Gln Gln Thr Gly Pro Glu Leu Val Lys Pro Gly Ala
1               5                   10                  15
```

```
Ser Val Lys Ile Ser Cys Lys Ala Ser Gly Tyr Pro Phe Thr Asp Tyr
            20                  25                  30

Ile Met Val Trp Val Lys Gln Ser His Gly Lys Ser Leu Glu Trp Ile
        35                  40                  45

Gly Asn Ile Ser Pro Tyr Tyr Gly Thr Thr Asn Tyr Asn Leu Lys Phe
 50                  55                  60

Lys Gly Lys Ala Thr Leu Thr Val Asp Lys Ser Ser Thr Ala Tyr
 65                  70                  75                  80

Met Gln Leu Asn Ser Leu Thr Ser Glu Asp Ser Ala Val Tyr Tyr Cys
                85                  90                  95

Ala Arg Ser Pro Asn Trp Asp Gly Ala Trp Phe Ala His Trp Gly Gln
            100                 105                 110

Gly Ala Leu Val Thr Val Ser Ala Ala Lys Thr Lys
        115                 120
```

<210> SEQ ID NO 88
<211> LENGTH: 218
<212> TYPE: PRT
<213> ORGANISM: Homo sapiens

<400> SEQUENCE: 88

```
Asp Ile Val Leu Thr Gln Ser Pro Ala Ser Leu Ala Val Ser Leu Gly
 1               5                  10                  15

Gln Arg Ala Thr Ile Ser Cys Lys Ala Ser Gln Ser Val Asp Tyr Asp
            20                  25                  30

Gly Asp Ser Tyr Met Asn Trp Phe Gln Gln Lys Pro Gly Gln Pro Pro
        35                  40                  45

Lys Leu Leu Ile Tyr Ala Ala Ser Asn Leu Glu Ser Gly Ile Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln Gln Ser Asn
                85                  90                  95

Glu Asp Pro Phe Thr Phe Gly Ser Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 89
<211> LENGTH: 109
<212> TYPE: PRT
<213> ORGANISM: Homo sapiens

<400> SEQUENCE: 89

-continued

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Phe Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Phe Thr Phe Gly Ser Gly Thr Lys Leu Glu
            100                 105

<210> SEQ ID NO 90
<211> LENGTH: 467
<212> TYPE: PRT
<213> ORGANISM: Homo sapiens

<400> SEQUENCE: 90

Met Asp Trp Leu Trp Asn Leu Leu Phe Leu Met Ala Ala Ala Gln Ser
1               5                   10                  15

Ala Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Ser Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Tyr Thr Gly Glu Ser Thr Tyr Ala
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Ser Asn Leu Lys Asn Glu Asp Met Ala Thr
            100                 105                 110

Tyr Phe Cys Ala Arg Gly Asp Phe Arg Tyr Tyr Phe Asp Tyr Trp
        115                 120                 125

Gly Gln Gly Thr Thr Leu Thr Gly Ser Ser Ala Lys Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Lys Thr Tyr Thr Cys Asn Val Asp
    210                 215                 220

His Lys Pro Ser Asn Thr Lys Val Asp Lys Arg Val Glu Ser Lys Tyr
225                 230                 235                 240

Gly Pro Pro Cys Pro Pro Cys Pro Ala Pro Glu Phe Glu Gly Gly Pro
                245                 250                 255

Ser Val Phe Leu Phe Pro Pro Lys Pro Lys Asp Thr Leu Met Ile Ser

```
                    260                 265                 270
Arg Thr Pro Glu Val Thr Cys Val Val Asp Val Ser Gln Glu Asp
                275                 280                 285

Pro Glu Val Gln Phe Asn Trp Tyr Val Asp Gly Val Glu Val His Asn
            290                 295                 300

Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Gly Leu Pro Ser Ser Ile Glu Lys
            340                 345                 350

Thr Ile Ser Lys Ala Lys Gly Gln Pro Arg Glu Pro Gln Val Tyr Thr
                355                 360                 365

Leu Pro Pro Ser Gln Glu Glu Met Thr Lys Asn Gln Val Ser Leu Thr
            370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Arg Leu Thr Val Asp Lys
            420                 425                 430

Ser Arg Trp Gln Glu Gly Asn Val Phe Ser Cys Ser Val Met His Glu
                435                 440                 445

Ala Leu His Asn His Tyr Thr Gln Lys Ser Leu Ser Leu Ser Leu Gly
            450                 455                 460

Lys Ala Ser
465

<210> SEQ ID NO 91
<211> LENGTH: 233
<212> TYPE: PRT
<213> ORGANISM: Homo sapiens

<400> SEQUENCE: 91

Met Ser Val Leu Thr Gln Val Leu Ala Leu Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Glu Thr Val Thr Ile Thr Cys Arg Ala Ser Gly Asn
        35                  40                  45

Ile His Asn Tyr Leu Ala Trp Tyr Gln Gln Lys Gln Gly Lys Ser Pro
    50                  55                  60

Gln Leu Leu Val Tyr Asn Ala Lys Thr Leu Ala Asp Gly Val Pro Ser
65                  70                  75                  80

Arg Phe Ser Gly Ser Gly Ser Gly Thr Gln Tyr Ser Leu Lys Ile Asn
                85                  90                  95

Thr Leu Gln Pro Glu Asp Phe Gly Ser Tyr Tyr Cys Gln His Phe Trp
            100                 105                 110

Asp Ser Trp Thr Phe Gly Gly Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160
```

```
Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 92
<211> LENGTH: 465
<212> TYPE: PRT
<213> ORGANISM: Homo sapiens

<400> SEQUENCE: 92

Met Glu Trp Thr Trp Val Phe Leu Phe Leu Leu Ser Val Thr Ala Gly
1               5                   10                  15

Val His Ser Gln Val Gln Leu Gln Gln Ser Gly Ala Glu Leu Met Lys
            20                  25                  30

Pro Gly Ala Ser Val Lys Ile Ser Cys Lys Ala Thr Gly Tyr Thr Phe
        35                  40                  45

Ser Ser Tyr Trp Ile Glu Trp Val Lys Gln Arg Pro Gly His Gly Leu
    50                  55                  60

Glu Trp Ile Gly Glu Ile Leu Pro Gly Ser Gly Arg Thr Asn Asp Asn
65                  70                  75                  80

Glu Lys Phe Lys Gly Lys Ala Thr Phe Thr Ala Asp Thr Ser Ser Lys
                85                  90                  95

Lys Ala Tyr Met Gln Leu Ser Ser Leu Thr Ser Glu Asp Ser Ala Val
            100                 105                 110

Tyr Tyr Cys Ala Arg Arg Gly Gly Tyr Ser Phe Ala Tyr Trp Gly Gln
        115                 120                 125

Gly Thr Leu Val Thr Val Ser Ala Ala Lys Thr Lys Gly Pro Ser Val
    130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Lys Thr Tyr Thr Cys Asn Val Asp His Lys
    210                 215                 220

Pro Ser Asn Thr Lys Val Asp Lys Arg Val Glu Ser Lys Tyr Gly Pro
225                 230                 235                 240

Pro Cys Pro Pro Cys Pro Ala Pro Glu Phe Glu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser Gln Glu Asp Pro Glu
        275                 280                 285

Val Gln Phe Asn Trp Tyr Val Asp Gly Val Glu Val His Asn Ala Lys
    290                 295                 300
```

-continued

```
Thr Lys Pro Arg Glu Glu Gln Phe Asn Ser Thr Tyr Arg Val Val Ser
305                 310                 315                 320

Val Leu Thr Val Leu His Gln Asp Trp Leu Asn Gly Lys Glu Tyr Lys
            325                 330                 335

Cys Lys Val Ser Asn Lys Gly Leu Pro Ser Ser Ile Glu Lys Thr Ile
        340                 345                 350

Ser Lys Ala Lys Gly Gln Pro Arg Glu Pro Gln Val Tyr Thr Leu Pro
    355                 360                 365

Pro Ser Gln Glu Glu Met Thr Lys Asn Gln Val Ser Leu Thr Cys Leu
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
            405                 410                 415

Asp Gly Ser Phe Phe Leu Tyr Ser Arg Leu Thr Val Asp Lys Ser Arg
        420                 425                 430

Trp Gln Glu Gly Asn Val Phe Ser Cys Ser Val Met His Glu Ala Leu
    435                 440                 445

His Asn His Tyr Thr Gln Lys Ser Leu Ser Leu Ser Leu Gly Lys Ala
    450                 455                 460

Ser
465

<210> SEQ ID NO 93
<211> LENGTH: 236
<212> TYPE: PRT
<213> ORGANISM: Homo sapiens

<400> SEQUENCE: 93

Met Thr Met Phe Ser Leu Ala Leu Leu Ser Leu Leu Leu Leu Leu Cys
1               5                   10                  15

Val Ser Asp Ser Arg Ala Glu Thr Thr Val Thr Gln Ser Pro Ala Ser
            20                  25                  30

Leu Ser Met Ala Ile Gly Glu Lys Val Thr Ile Arg Cys Val Thr Ser
        35                  40                  45

Thr Asp Ile Asp Asp Asp Val Asn Trp Tyr Gln Gln Lys Pro Gly Glu
    50                  55                  60

Pro Pro Lys Leu Leu Ile Ser Glu Gly Asn Thr Leu Arg Pro Gly Val
65                  70                  75                  80

Pro Ser Arg Phe Ser Ser Gly Tyr Gly Thr Asp Phe Val Phe Thr
            85                  90                  95

Ile Glu Asn Met Leu Ser Glu Asp Val Ala Asp Tyr Tyr Cys Leu Gln
            100                 105                 110

Ser Gly Asn Leu Pro Tyr Thr Phe Gly Gly Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
```

```
                195                 200                 205
Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 94
<211> LENGTH: 467
<212> TYPE: PRT
<213> ORGANISM: Homo sapiens

<400> SEQUENCE: 94

Met Ala Trp Val Trp Thr Leu Leu Phe Leu Met Ala Ala Ala Gln Ser
1               5                   10                  15

Ala Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Val Gly Trp Ile Asn Thr Phe Thr Gly Glu Pro Thr Tyr Val
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Gly Asn Phe Arg Tyr Tyr Tyr Phe Asp Tyr Trp
        115                 120                 125

Gly Gln Gly Thr Thr Leu Thr Val Ser Ser Ala Lys Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Lys Thr Tyr Thr Cys Asn Val Asp
    210                 215                 220

His Lys Pro Ser Asn Thr Lys Val Asp Lys Arg Val Glu Ser Lys Tyr
225                 230                 235                 240

Gly Pro Pro Cys Pro Pro Cys Pro Ala Pro Glu Phe Glu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser Gln Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
                325                 330                 335
```

```
Tyr Lys Cys Lys Val Ser Asn Lys Gly Leu Pro Ser Ser Ile Glu Lys
                340                 345                 350

Thr Ile Ser Lys Ala Lys Gly Gln Pro Arg Glu Pro Gln Val Tyr Thr
            355                 360                 365

Leu Pro Pro Ser Gln Glu Glu Met Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Arg Leu Thr Val Asp Lys
                420                 425                 430

Ser Arg Trp Gln Glu Gly Asn Val Phe Ser Cys Ser Val Met His Glu
            435                 440                 445

Ala Leu His Asn His Tyr Thr Gln Lys Ser Leu Ser Leu Ser Leu Gly
            450                 455                 460

Lys Ala Ser
465

<210> SEQ ID NO 95
<211> LENGTH: 234
<212> TYPE: PRT
<213> ORGANISM: Homo sapiens

<400> SEQUENCE: 95

Met Ser Val Leu Thr Gln Val Leu Ala Leu Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Glu Thr Val Thr Ile Thr Cys Arg Thr Ser Gly Asn
        35                  40                  45

Ile Arg Asn Tyr Leu Ala Trp Tyr Gln Gln Lys Gln Gly Lys Ser Pro
    50                  55                  60

Gln Leu Leu Val Tyr Asn Ala Lys Thr Leu Ala Asp Gly Val Pro Ser
65                  70                  75                  80

Arg Phe Gly Gly Ser Gly Ser Gly Thr Gln Tyr Ser Leu Lys Ile Asn
                85                  90                  95

Ser Leu Gln Pro Glu Asp Phe Gly Asn Tyr Tyr Cys Gln His Phe Trp
            100                 105                 110

Ser Ser Pro Tyr Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 96
<211> LENGTH: 469
<212> TYPE: PRT
<213> ORGANISM: Homo sapiens

<400> SEQUENCE: 96

```
Met Met Gly Trp Ser Tyr Ile Ile Leu Phe Leu Val Ala Thr Ala Thr
1               5                   10                  15

Asp Val His Ser Gln Val Gln Leu Gln Gln Pro Gly Ala Glu Leu Val
            20                  25                  30

Lys Pro Gly Ala Ser Val Lys Leu Ser Cys Lys Ala Ser Gly Tyr Thr
        35                  40                  45

Phe Thr Ser Tyr Trp Met His Trp Val Lys Gln Arg Pro Gly Glu Gly
    50                  55                  60

Leu Glu Trp Ile Gly Glu Ile Asn Pro Ser Tyr Gly Arg Thr Asp Tyr
65                  70                  75                  80

Asn Glu Lys Phe Lys Asn Lys Ala Thr Leu Thr Val Ala Lys Ser Ser
                85                  90                  95

Ser Thr Ala Tyr Met Gln Leu Ser Ser Leu Thr Ser Glu Asp Ser Ala
            100                 105                 110

Val Tyr Tyr Cys Ala Arg Gly Asp Tyr Tyr Gly Ser Ser Ser Phe Ala
        115                 120                 125

Tyr Trp Gly Gln Gly Thr Leu Val Thr Val Ser Ala Ala Lys Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Lys Thr Tyr Thr Cys Asn
    210                 215                 220

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Phe Glu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Gln
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Gln Glu Glu Met Thr Lys Asn Gln Val Ser
```

```
            370                 375                 380
Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Arg Leu Thr Val
                420                 425                 430

Asp Lys Ser Arg Trp Gln Glu Gly Asn Val Phe Ser Cys Ser Val Met
                435                 440                 445

His Glu Ala Leu His Asn His Tyr Thr Gln Lys Ser Leu Ser Leu Ser
                450                 455                 460

Leu Gly Lys Ala Ser
465

<210> SEQ ID NO 97
<211> LENGTH: 235
<212> TYPE: PRT
<213> ORGANISM: Homo sapiens

<400> SEQUENCE: 97

Met Asp Phe Gln Val Gln Ile Phe Ser Phe Leu Leu Met Ser Ala Ser
1               5                   10                  15

Val Ile Met Ser Arg Gly Gln Ile Val Leu Thr Gln Ser Pro Ala Leu
                20                  25                  30

Met Ser Ala Ser Pro Gly Glu Lys Val Thr Met Thr Cys Ser Ala Ser
                35                  40                  45

Ser Asn Ile Ser Tyr Met Tyr Trp Tyr Gln Gln Lys Pro Arg Ser Ser
            50                  55                  60

Pro Lys Pro Trp Ile Tyr Leu Thr Ser Asn Leu Ala Ser Gly Val Pro
65                  70                  75                  80

Ala Arg Phe Ser Gly Ser Gly Ser Gly Thr Ser Tyr Ser Leu Thr Thr
                85                  90                  95

Ser Ser Met Glu Ala Glu Asp Ala Ala Thr Tyr Cys Cys Gln Gln Trp
                100                 105                 110

Ser Ser Asn Pro Pro Thr Phe Gly Ala Gly Thr Lys Leu Glu Ile Lys
            115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
            210                 215                 220

Pro Val Thr Lys Ser Phe Asn Arg Gly Glu Cys
225                 230                 235

<210> SEQ ID NO 98
<211> LENGTH: 235
<212> TYPE: PRT
<213> ORGANISM: Homo sapiens
```

-continued

```
<400> SEQUENCE: 98

Met Asp Phe Arg Val Gln Ile Phe Ser Phe Leu Leu Met Ser Ala Ser
1               5                   10                  15

Val Ile Met Ser Arg Gly Gln Ile Val Leu Thr Gln Ser Pro Ala Leu
            20                  25                  30

Met Ser Ala Ser Pro Gly Glu Lys Val Thr Met Thr Cys Ser Ala Ser
        35                  40                  45

Ser Asn Ile Ser Tyr Met Tyr Trp Tyr Gln Lys Pro Arg Ser Ser
    50                  55                  60

Pro Lys Pro Trp Ile Tyr Leu Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys Gln Gln Trp
            100                 105                 110

Ser Ser Asn Pro Pro Thr Phe Gly Ala Gly Thr Lys Leu Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 99
<211> LENGTH: 465
<212> TYPE: PRT
<213> ORGANISM: Homo sapiens

<400> SEQUENCE: 99

Met Glu Cys Asn Trp Ile Leu Pro Phe Ile Leu Ser Val Ile Ser Gly
1               5                   10                  15

Val Tyr Ser Glu Val Gln Leu Gln Gln Ser Gly Thr Val Leu Ala Arg
            20                  25                  30

Pro Gly Ala Ser Val Asn Met Ser Cys Lys Ala Ala Gly Tyr Ser Phe
        35                  40                  45

Thr Ser Tyr Trp Val Tyr Trp Val Lys Gln Arg Pro Gly Gln Gly Leu
    50                  55                  60

Glu Trp Ile Gly Ala Ile Tyr Pro Lys Asn Ser Arg Thr Ser Tyr Asn
65                  70                  75                  80

Gln Lys Phe Gln Asp Lys Ala Thr Leu Thr Ala Val Thr Ser Ala Ser
                85                  90                  95

Thr Ala Tyr Met Glu Leu Ser Ser Leu Thr Asn Glu Asp Ser Ala Val
            100                 105                 110

Tyr Tyr Cys Thr Arg Pro His Tyr Asp Ser Phe Gly Tyr Trp Gly Gln
        115                 120                 125
```

```
Gly Thr Leu Val Thr Val Ser Ala Ala Lys Thr Lys Gly Pro Ser Val
    130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Lys Thr Tyr Thr Cys Asn Val Asp His Lys
    210                 215                 220

Pro Ser Asn Thr Lys Val Asp Lys Arg Val Glu Ser Lys Tyr Gly Pro
225                 230                 235                 240

Pro Cys Pro Pro Cys Pro Ala Pro Glu Phe Glu Gly Gly Pro Ser Val
                245                 250                 255

Phe Leu Phe Pro Pro Lys Pro Lys Asp Thr Leu Met Ile Ser Arg Thr
                260                 265                 270

Pro Glu Val Thr Cys Val Val Val Asp Val Ser Gln Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Gly Leu Pro Ser Ser Ile Glu Lys Thr Ile
            340                 345                 350

Ser Lys Ala Lys Gly Gln Pro Arg Glu Pro Gln Val Tyr Thr Leu Pro
        355                 360                 365

Pro Ser Gln Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Arg Leu Thr Val Asp Lys Ser Arg
            420                 425                 430

Trp Gln Glu Gly Asn Val Phe Ser Cys Ser Val Met His Glu Ala Leu
        435                 440                 445

His Asn His Tyr Thr Gln Lys Ser Leu Ser Leu Ser Leu Gly Lys Ala
    450                 455                 460

Ser
465

<210> SEQ ID NO 100
<211> LENGTH: 238
<212> TYPE: PRT
<213> ORGANISM: Homo sapiens

<400> SEQUENCE: 100

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30
```

```
Val Ser Leu Gly Gln Arg Ala Thr Ile Ser Cys Arg Ala Ser Glu Ser
            35                  40                  45

Val Asp Ser Tyr Gly Ile Ser Phe Met His Trp Tyr Gln Gln Lys Pro
 50                  55                  60

Gly Gln Pro Pro Lys Leu Leu Ile Tyr Arg Ala Ser Asn Gln Glu Ser
 65                  70                  75                  80

Gly Ile Pro Ala Arg Phe Ser Gly Ser Gly Ser Arg Thr Asp Phe Thr
                 85                  90                  95

Leu Thr Ile Asn Pro Val Glu Ala Asp Val Ala Thr Tyr Tyr Cys
            100                 105                 110

Gln Gln Ser Asn Glu Asp Pro Leu Thr Phe Gly Ala Gly Thr Lys Leu
            115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235

<210> SEQ ID NO 101
<211> LENGTH: 473
<212> TYPE: PRT
<213> ORGANISM: Homo sapiens

<400> SEQUENCE: 101

Asn Arg Leu Thr Ser Ser Leu Leu Leu Ile Val Pro Ala Tyr Val
 1               5                  10                  15

Leu Ser Gln Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu
            35                  40                  45

Ser Thr Ser Gly Met Gly Val Ser Trp Ile Arg Gln Pro Ser Gly Lys
 50                  55                  60

Gly Leu Glu Trp Leu Ala His Ile Tyr Trp Asp Asp Lys Arg Tyr
 65                  70                  75                  80

Asn Pro Ser Leu Lys Ser Arg Leu Thr Ile Phe Lys Asp Pro Ser Ser
                 85                  90                  95

Asn Gln Val Phe Leu Arg Ile Thr Ser Val Asp Thr Ala Asp Thr Ala
            100                 105                 110

Thr Tyr Tyr Cys Ala Arg Asn Ser His Tyr Tyr Gly Ser Thr Tyr Gly
            115                 120                 125

Gly Tyr Phe Asp Val Trp Gly Ala Gly Thr Thr Val Thr Val Ser Ser
            130                 135                 140

Ala Lys Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
```

```
                165                 170                 175
Phe Pro Glu Pro Val Thr Val Ser Trp Asn Ser Gly Ala Leu Thr Ser
                180                 185                 190

Gly Val His Thr Phe Pro Ala Val Leu Gln Ser Ser Gly Leu Tyr Ser
            195                 200                 205

Leu Ser Ser Val Val Thr Val Pro Ser Ser Ser Leu Gly Thr Lys Thr
        210                 215                 220

Tyr Thr Cys Asn Val Asp His Lys Pro Ser Asn Thr Lys Val Asp Lys
225                 230                 235                 240

Arg Val Glu Ser Lys Tyr Gly Pro Pro Cys Pro Pro Cys Pro Ala Pro
                245                 250                 255

Glu Phe Glu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser Gln Glu Asp Pro Glu Val Gln Phe Asn Trp Tyr Val Asp
    290                 295                 300

Gly Val Glu Val His Asn Ala Lys Thr Lys Pro Arg Glu Glu Gln Phe
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Gly Leu
            340                 345                 350

Pro Ser Ser Ile Glu Lys Thr Ile Ser Lys Ala Lys Gly Gln Pro Arg
        355                 360                 365

Glu Pro Gln Val Tyr Thr Leu Pro Pro Ser Gln Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Arg Leu Thr Val Asp Lys Ser Arg Trp Gln Glu Gly Asn Val Phe Ser
        435                 440                 445

Cys Ser Val Met His Glu Ala Leu His Asn His Tyr Thr Gln Lys Ser
    450                 455                 460

Leu Ser Leu Ser Leu Gly Lys Ala Ser
465                 470

<210> SEQ ID NO 102
<211> LENGTH: 238
<212> TYPE: PRT
<213> ORGANISM: Homo sapiens

<400> SEQUENCE: 102

Met Glu Thr Asp Thr Leu Leu Leu Trp Val Leu Leu Leu Gly Val Pro
1               5                   10                  15

Gly Ser Thr Gly Asn Ile Val Leu Thr Gln Ser Pro Thr Ser Phe Thr
            20                  25                  30

Val Ser Leu Gly Gln Arg Ala Thr Ile Ser Cys Arg Ala Ser Glu Ser
        35                  40                  45

Val His Ser Tyr Gly Asn Ser Phe Met His Trp Tyr Gln Gln Lys Pro
    50                  55                  60
```

Gly Gln Pro Pro Lys Leu Leu Ile Tyr Leu Ala Ser Asn Val Glu Ser
65                  70                  75                  80

Gly Val Pro Ala Arg Phe Ser Gly Ser Gly Ser Arg Thr Asp Phe Thr
                85                  90                  95

Leu Thr Ile Asp Pro Val Glu Ala Asp Asp Ala Ala Thr Tyr Tyr Cys
            100                 105                 110

Gln Gln Asn Ser Glu Asp Pro Trp Thr Phe Gly Gly Gly Thr Lys Leu
        115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235

<210> SEQ ID NO 103
<211> LENGTH: 465
<212> TYPE: PRT
<213> ORGANISM: Homo sapiens

<400> SEQUENCE: 103

Met Glu Trp Thr Trp Val Phe Leu Phe Leu Leu Ser Val Thr Ala Gly
1               5                   10                  15

Val His Ser Gln Val Gln Leu Gln Gln Ser Gly Thr Glu Leu Met Lys
            20                  25                  30

Pro Gly Ala Ser Val Lys Ile Ser Cys Lys Ala Thr Gly Tyr Thr Phe
        35                  40                  45

Ser Thr Tyr Trp Ile Glu Trp Val Lys Gln Arg Pro Gly His Gly Leu
50                  55                  60

Glu Trp Ile Gly Glu Ile Leu Pro Gly Ser Gly Arg Thr Asn Asp Asn
65                  70                  75                  80

Glu Lys Phe Lys Gly Lys Ala Thr Ile Thr Ala Asp Thr Ser Ser Lys
                85                  90                  95

Lys Ala Tyr Met Gln Leu Ser Ser Leu Thr Ser Glu Asp Ser Ala Val
            100                 105                 110

Tyr Tyr Cys Ala Arg Arg Gly Gly Tyr Ser Phe Ala Phe Trp Gly Gln
        115                 120                 125

Gly Thr Leu Val Ser Val Ser Ala Ala Lys Thr Lys Gly Pro Ser Val
130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

```
Ser Ser Ser Leu Gly Thr Lys Thr Tyr Thr Cys Asn Val Asp His Lys
    210                 215                 220

Pro Ser Asn Thr Lys Val Asp Lys Arg Val Glu Ser Lys Tyr Gly Pro
225                 230                 235                 240

Pro Cys Pro Pro Cys Pro Ala Pro Glu Phe Glu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser Gln Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Gly Leu Pro Ser Ser Ile Glu Lys Thr Ile
            340                 345                 350

Ser Lys Ala Lys Gly Gln Pro Arg Glu Pro Gln Val Tyr Thr Leu Pro
        355                 360                 365

Pro Ser Gln Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Arg Leu Thr Val Asp Lys Ser Arg
            420                 425                 430

Trp Gln Glu Gly Asn Val Phe Ser Cys Ser Val Met His Glu Ala Leu
        435                 440                 445

His Asn His Tyr Thr Gln Lys Ser Leu Ser Leu Ser Leu Gly Lys Ala
    450                 455                 460

Ser
465

<210> SEQ ID NO 104
<211> LENGTH: 236
<212> TYPE: PRT
<213> ORGANISM: Homo sapiens

<400> SEQUENCE: 104

Met Thr Met Phe Ser Leu Ala Leu Leu Leu Ser Leu Leu Leu Leu Cys
1               5                   10                  15

Val Ser Asp Ser Arg Ala Glu Thr Thr Val Thr Gln Ser Pro Ala Ser
            20                  25                  30

Leu Ser Met Ala Ile Gly Glu Lys Val Thr Ile Arg Cys Val Thr Ser
        35                  40                  45

Thr Asp Ile Asp Asp Asp Val Asn Trp Tyr Gln Gln Lys Pro Gly Glu
    50                  55                  60

Pro Pro Lys Leu Leu Ile Ser Glu Gly Asn Thr Leu Arg Ala Gly Val
65                  70                  75                  80

Pro Ser Arg Phe Ser Ser Gly Tyr Gly Thr Asp Phe Val Phe Thr
                85                  90                  95

Ile Glu Asn Met Leu Ser Glu Asp Val Ala Asp Tyr Tyr Cys Leu Gln
```

```
            100                 105                 110
Ser Gly Asn Leu Pro Tyr Thr Phe Gly Gly Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 105
<211> LENGTH: 467
<212> TYPE: PRT
<213> ORGANISM: Homo sapiens
<220> FEATURE:
<221> NAME/KEY: misc_feature
<222> LOCATION: (309)..(309)
<223> OTHER INFORMATION: Xaa can be any naturally occurring amino acid

<400> SEQUENCE: 105

Met Lys Cys Ser Trp Val Ile Phe Phe Leu Met Ala Val Val Thr Gly
1               5                   10                  15

Val Asn Ser Glu Val Gln Leu Gln Gln Ser Gly Ala Glu Leu Val Arg
            20                  25                  30

Pro Gly Ala Leu Val Lys Leu Ser Cys Lys Ala Ser Gly Phe Asn Ile
        35                  40                  45

Asn Asp Tyr Tyr Ile His Trp Val Lys Gln Arg Pro Glu Gln Gly Leu
    50                  55                  60

Glu Arg Ile Gly Trp Ile Asp Pro Asp Asn Gly Asn Thr Ile Tyr Asp
65                  70                  75                  80

Pro Lys Phe Gln Gly Lys Ala Ser Ile Thr Ala Asp Thr Ser Pro Asn
                85                  90                  95

Thr Ala Tyr Leu Gln Leu Ser Ser Leu Thr Ser Glu Asp Thr Ala Val
            100                 105                 110

Tyr Tyr Cys Ala Arg Thr Arg Ser Pro Met Val Thr Thr Gly Phe Val
        115                 120                 125

Tyr Trp Gly Gln Gly Thr Val Thr Val Ser Ala Ala Lys Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Lys Thr Tyr Thr Cys Asn
    210                 215                 220
```

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Phe Glu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Gln
        275                 280                 285

Glu Asp Pro Glu Val Gln Phe Asn Trp Tyr Val Asp Gly Val Glu Val
    290                 295                 300

His Asn Ala Lys Xaa Lys Pro Arg Glu Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Gln Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Arg Leu Thr Val
            420                 425                 430

Asp Lys Ser Arg Trp Gln Glu Gly Asn Val Phe Ser Cys Ser Val Met
        435                 440                 445

His Glu Ala Leu His Asn His Tyr Thr Gln Lys Ser Leu Ser Leu Ser
    450                 455                 460

Leu Gly Lys
465

<210> SEQ ID NO 106
<211> LENGTH: 238
<212> TYPE: PRT
<213> ORGANISM: Homo sapiens

<400> SEQUENCE: 106

Met Glu Thr Asp Thr Leu Leu Leu Trp Val Leu Leu Leu Trp Val Pro
1               5                   10                  15

Gly Ser Thr Gly Asp Ile Val Leu Ile Gln Ser Pro Ala Ser Leu Ala
            20                  25                  30

Val Ser Leu Gly Gln Arg Ala Thr Ile Ser Cys Arg Ala Ser Glu Ser
        35                  40                  45

Val Asp Ser Tyr Val Asn Ser Phe Met His Trp Tyr Gln Gln Lys Pro
    50                  55                  60

Gly Gln Pro Pro Lys Leu Leu Ile Tyr Arg Val Ser Asn Leu Glu Ser
65                  70                  75                  80

Gly Ile Pro Ala Arg Phe Ser Gly Ser Gly Ser Arg Thr Asp Phe Thr
                85                  90                  95

Leu Thr Ile Asn Pro Val Glu Ala Asp Asp Val Ala Thr Tyr Tyr Cys
            100                 105                 110

Gln Gln Ser Asn Glu Asp Pro Phe Thr Phe Gly Ser Gly Thr Lys Leu

```
            115                 120                 125
Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235

<210> SEQ ID NO 107
<211> LENGTH: 446
<212> TYPE: PRT
<213> ORGANISM: Homo sapiens

<400> SEQUENCE: 107

Gln Val Gln Leu Arg Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
                20                  25                  30

Val Ile Ser Trp Val Lys Gln Arg Thr Gly Gln Gly Leu Glu Trp Ile
            35                  40                  45

Gly Asp Ile Tyr Pro Gly Ser Gly Tyr Ser Phe Tyr Asn Glu Asn Phe
50                  55                  60

Lys Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Phe Cys
                85                  90                  95

Ala Thr Tyr Tyr Asn Tyr Pro Phe Ala Tyr Trp Gly Gln Gly Thr Leu
                100                 105                 110

Val Thr Val Ser Ala Ala Lys Thr Thr Gly Pro Ser Val Phe Pro Leu
            115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255
```

```
Thr Cys Val Val Val Asp Val Ser Gln Glu Asp Pro Glu Val Gln Phe
                260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys Ala Ser
                435                 440                 445

<210> SEQ ID NO 108
<211> LENGTH: 81
<212> TYPE: PRT
<213> ORGANISM: Homo sapiens

<400> SEQUENCE: 108

Ser Val Lys Met Ser Cys Lys Ala Ser Gly Tyr Thr Phe Thr Asp Tyr
1               5                   10                  15

Val Ile Ser Trp Val Lys Gln Arg Thr Gly Gln Gly Leu Glu Trp Ile
            20                  25                  30

Gly Asp Ile Tyr Pro Gly Ser Gly Tyr Ser Phe Tyr Asn Glu Asn Phe
        35                  40                  45

Lys Gly Lys Ala Thr Leu Thr Ala Asp Lys Ser Ser Thr Thr Ala Tyr
    50                  55                  60

Met Gln Leu Ser Ser Leu Thr Ser Glu Asp Ser Ala Val Tyr Phe Cys
65                  70                  75                  80

Ala

<210> SEQ ID NO 109
<211> LENGTH: 219
<212> TYPE: PRT
<213> ORGANISM: Homo sapiens

<400> SEQUENCE: 109

Asp Val Val Met Thr Gln Thr Pro Leu Ser Leu Pro Val Arg Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
```

```
                50                  55                  60
Asp Arg Phe Ser Gly Ser Gly Ser Gly Thr Asn Phe Thr Leu Lys Ile
 65                  70                  75                  80

Ser Arg Val Glu Ala Glu Asp Leu Gly Leu Tyr Phe Cys Ser Gln Ser
                 85                  90                  95

Thr His Val Pro Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 110
<211> LENGTH: 76
<212> TYPE: PRT
<213> ORGANISM: Homo sapiens

<400> SEQUENCE: 110

Ala Ser Ile Ser Cys Arg Ser Ser Gln Ser Leu Val His Ser Asn Gly
 1               5                  10                  15

Asn Thr Tyr Leu His Trp Tyr Leu Gln Lys Pro Gly Gln Ser Pro Lys
                20                  25                  30

Leu Leu Ile Tyr Lys Val Ser Asn Arg Phe Ser Gly Val Pro Asp Arg
            35                  40                  45

Phe Ser Gly Ser Gly Ser Gly Thr Asn Phe Thr Leu Lys Ile Ser Arg
        50                  55                  60

Val Glu Ala Glu Asp Leu Gly Leu Tyr Phe Cys Ser
 65                  70                  75

<210> SEQ ID NO 111
<211> LENGTH: 469
<212> TYPE: PRT
<213> ORGANISM: Homo sapiens

<400> SEQUENCE: 111

Met Thr Leu Asn Met Leu Gly Leu Arg Trp Val Phe Phe Val Val
 1               5                  10                  15

Phe Tyr Gln Gly Val His Cys Glu Val Gln Leu Val Glu Ser Gly Gly
                20                  25                  30

Gly Leu Val Gln Pro Lys Gly Ser Leu Lys Leu Ser Cys Ala Ala Ser
            35                  40                  45

Gly Leu Thr Phe Asn Ile Tyr Ala Met Asn Trp Val Arg Gln Ala Pro
        50                  55                  60

Gly Lys Gly Leu Glu Trp Val Ala Arg Ile Arg Asn Lys Ser Asn Asn
 65                  70                  75                  80

Tyr Ala Thr Tyr Tyr Ala Asp Ser Val Lys Asp Arg Phe Thr Ile Ser
```

```
            85                  90                  95
Arg Asp Asp Ser Gln Ser Leu Leu Tyr Leu Gln Met Asn Asn Leu Lys
            100                 105                 110

Thr Glu Asp Thr Ala Met Tyr Tyr Cys Val Gly Arg Asp Trp Phe Asp
            115                 120                 125

Tyr Trp Gly Gln Gly Thr Leu Val Thr Val Ser Ala Ala Lys Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
                195                 200                 205

Val Thr Val Pro Ser Ser Ser Leu Gly Thr Lys Thr Tyr Thr Cys Asn
    210                 215                 220

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Phe Glu Gly
                245                 250                 255

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser Gln
                275                 280                 285

Glu Asp Pro Glu Val Gln Phe Asn Trp Tyr Val Asp Gly Val Glu Val
            290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
                340                 345                 350

Glu Lys Thr Ile Ser Lys Ala Lys Gly Gln Pro Arg Glu Pro Gln Val
                355                 360                 365

Tyr Thr Leu Pro Pro Ser Gln Glu Glu Met Thr Lys Asn Gln Val Ser
            370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Arg Leu Thr Val
                420                 425                 430

Asp Lys Ser Arg Trp Gln Glu Gly Asn Val Phe Ser Cys Ser Val Met
                435                 440                 445

His Glu Ala Leu His Asn His Tyr Thr Gln Lys Ser Leu Ser Leu Ser
            450                 455                 460

Leu Gly Lys Ala Ser
465
```

<210> SEQ ID NO 112
<211> LENGTH: 82
<212> TYPE: PRT
<213> ORGANISM: Homo sapiens

<400> SEQUENCE: 112

Ser Leu Lys Leu Ser Cys Ala Ala Ser Gly Leu Thr Phe Asn Ile Tyr
1               5                   10                  15

Ala Met Asn Trp Val Arg Gln Ala Pro Gly Lys Gly Leu Glu Trp Val
            20                  25                  30

Ala Arg Ile Arg Asn Lys Ser Asn Asn Tyr Ala Thr Tyr Tyr Ala Asp
        35                  40                  45

Ser Val Lys Asp Arg Phe Thr Ile Ser Arg Asp Asp Ser Gln Ser Leu
    50                  55                  60

Leu Tyr Leu Gln Met Asn Asn Leu Lys Thr Glu Asp Thr Ala Met Tyr
65                  70                  75                  80

Tyr Cys

<210> SEQ ID NO 113
<211> LENGTH: 235
<212> TYPE: PRT
<213> ORGANISM: Homo sapiens

<400> SEQUENCE: 113

Met Ala Trp Ile Ser Leu Ile Leu Ser Leu Leu Ala Leu Ser Ser Gly
1               5                   10                  15

Ala Ile Ser Gln Ala Val Val Thr Gln Glu Ser Ala Leu Thr Thr Ser
            20                  25                  30

Pro Gly Glu Thr Val Thr Leu Thr Cys Arg Ser Ser Thr Gly Ala Val
        35                  40                  45

Thr Thr Ser Asn Tyr Ala Asn Trp Val Gln Glu Lys Pro Asp His Leu
    50                  55                  60

Phe Thr Gly Leu Ile Gly Gly Thr Asn Asn Arg Val Ser Gly Val Pro
65                  70                  75                  80

Ala Arg Phe Ser Gly Ser Leu Ile Gly Asp Lys Ala Ala Leu Thr Ile
                85                  90                  95

Thr Gly Ala Gln Thr Glu Asp Glu Ala Ile Tyr Phe Cys Ala Leu Trp
            100                 105                 110

Tyr Ser Asn His Trp Val Phe Gly Gly Gly Thr Lys Leu Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 114
<211> LENGTH: 74
<212> TYPE: PRT
<213> ORGANISM: Homo sapiens -continued

```
<400> SEQUENCE: 114

Val Thr Leu Thr Cys Arg Ser Ser Thr Gly Ala Val Thr Thr Ser Asn
1               5                   10                  15

Tyr Ala Asn Trp Val Gln Glu Lys Pro Asp His Leu Phe Thr Gly Leu
                20                  25                  30

Ile Gly Gly Thr Asn Asn Arg Val Ser Gly Val Pro Ala Arg Phe Ser
            35                  40                  45

Gly Ser Leu Ile Gly Asp Lys Ala Ala Leu Thr Ile Thr Gly Ala Gln
        50                  55                  60

Thr Glu Asp Glu Ala Ile Tyr Phe Cys Ala
65                  70
```

METHODS AND COMPOSITIONS FOR TREATING AUTOIMMUNE AND INFLAMMATORY CONDITIONS

This application is a national phase application under 35 U.S.C. § 371 of International Application No. PCT/US2015/031117, filed May 15, 2015, which claims the benefit of priority to U.S. Provisional Patent Application Ser. No. 61/994,239, filed May 16, 2014, and U.S. Provisional Patent Application Ser. No. 62/014,504, filed Jun. 19, 2014, the entire contents of each of which are hereby incorporated by reference in their entirety.

The invention was made with government support under Grant No. 1R56AI105066-01 and Grant No. 2. 1R01AI105066-01A1 awarded by the National Institute of Allergy and Infectious Disease/National Institutes of Health. The government has certain rights in the invention.

BACKGROUND OF THE INVENTION

1. Field of the Invention

The present invention relates generally to the field of medicine. More particularly, it concerns pharmaceutical compositions for enhancing tolerance to antigens and for treating inflammatory and autoimmune disorders.

2. Background

Autoimmune and inflammatory diseases arise from an abnormal immune response of the body against substances and tissues normally present in the body. This may be restricted to certain organs (e.g., in autoimmune thyroiditis) or involve a particular tissue in different places (e.g., Goodpasture's disease which may affect the basement membrane in both the lung and the kidney). Autoimmune and auto-inflammatory diseases affect up to 50 million people in America alone, and the cause of autoimmunity remains unknown.

The treatment of these diseases is typically with immunosuppression-medication that decreases the immune response. Conventional immunotherapies using immunosuppressants, such as cyclosporine, tacroliums, methotrexate or anti-TNFa/IL-6 non-specifically suppress the function of T cell including non-pathogenic T cells in the host. Therefore, treatment with these immunesuppressants often results in the development of severe infections and sometimes leads to the lethal consequences. There is a need in the art for therapeutics that treat autoimmune responses without global immunosuppression.

SUMMARY OF THE INVENTION

This disclosure fulfills a need in the art by providing methods and compositions for delivering the anti-inflammatory cytokine, IL-10, to antigen presenting cells (APCs) to suppress and alter the pathophysiologic functions of APCs in the subjects using APC-targeted antibody operatively linked to IL-10 or a fragment thereof. Targeted delivery of anti-inflammatory cytokines to the APCs in the patients is expected to result in more effective and pro-longed immune tolerance in the patients. Accordingly, aspects of the disclosure relate to a method for inhibiting an inflammatory or autoimmune response in a subject in need thereof comprising administering to the subject a therapeutically effective amount of an antigen presenting cell (APC)-targeted antibody operatively linked to IL-10 or a fragment thereof.

In some embodiments, the disclosure relates to a method for preventing or treating graft versus host disease in a subject in need thereof comprising administering to the subject a therapeutically effective amount of DC-ASGPR operatively linked to IL-10 or a fragment thereof.

Further aspects relate to a method of inducing immune tolerance in a subject in need thereof comprising administering to the subject a therapeutically effective amount of an APC-targeted antibody operatively linked to IL-10 or a fragment thereof. Other aspects relate to a method of suppressing a T cell response in a subject in a subject having or at risk of developing an inflammatory response by administering to the subject a therapeutically effective amount of an APC-targeted antibody operatively linked to IL-10 or a fragment thereof.

The term "operatively linked" refers to a situation where two components are combined to form the active complex prior to binding at the target site. For example, an antibody conjugated to one-half of a cohesin-dockerin complex and a cytokine (e.g. IL-10) or other molecule (e.g. antigen) complexed to the other one-half of the cohesin-dockerin complex are operatively linked through complexation of the cohesin and dockerin molecules. The term operatively linked is also intended to refer to covalent or chemical linkages that conjugate two molecules together.

Yet further aspects relate to methods and compositions for treating undesired and/or abnormal immune responses without non-specific suppression of the host immune system. In particular, an anti-DC-ASGPR antibody or antigen binding fragment thereof can be used in compositions and methods described herein for generating anti-pathogenic antigen-specific T regulatory cells and/or for decreasing pathogenic T cell responses.

The term "anti-pathogenic antigen-specific T regulatory cells" refers to T cells with beneficial and therapeutic properties. In one embodiment, the anti-pathogenic antigen-specific T regulatory cells are alloantigen-specific T regulatory cells. In another embodiment, the anti-pathogenic antigen-specific T regulatory cells is one that produces IL-10. The anti-pathogenic antigen-specific T regulatory cells may also be a CD4+ T cell.

The term pathogenic T cell responses refers to abnormal or undesired T cell responses that contribute to the pathology of autoimmune disease or to the pathology of graft versus host disease (GVHD) or graft rejection. In one embodiment, the pathogenic T cell response is an allogeneic T cell response. In a further embodiment, the pathogenic T cell response comprises allogeneic CD4+ and CD8+ T cells. In one embodiment, the pathogenic T cell response is one that comprises immune cells of the tissue graft.

A further aspect of the disclosure relates to a method for preventing or treating GVHD in a subject in need thereof comprising administering to the subject an anti-DC-ASGPR antibody or antigen binding fragment thereof.

Graft-versus-host disease (GVHD) is a common complication following an allogeneic tissue transplant. It is commonly associated with stem cell or bone marrow transplant but the term also applies to other forms of tissue graft. Immune cells (white blood cells) in the tissue (the graft) recognize the recipient (the host) as "foreign". The transplanted immune cells then attack the host's body cells. GVHD may also occur after a blood transfusion if the blood products used have not been irradiated.

In another instance, the disclosure describes a method for preventing or treating graft rejection in a subject in need thereof comprising administering to the subject an anti-DC-ASGPR antibody or antigen binding fragment thereof.

Graft rejection occurs when transplanted tissue is rejected by the recipient's immune system, which destroys the transplanted tissue. Graft rejection may also be referred to as transplant rejection or host versus graft disease.

In certain embodiments, the antibody or antigen binding fragment specifically binds to DC-ASGPR and activates DC-ASGPR. DC-asialoglycoprotein receptor (DC-ASGPR) is a scavenger receptor carrying an immunoreceptor tyrosine-based activation motiflike motif. ASGPR may also be known as ASGR1, ASGPR1, CLEC4H1, and HL-1. In one embodiment, the antibody or antigen binding fragment thereof binds to human DC-ASGPR.

In some embodiments, the APC-targeted antibody targets one or more APCs of the group Langerhans cells, macrophages, dendritic cells, B cells, and peripheral blood mononuclear cells. In further embodiments, the APC-targeted antibody is selected from an antibody that specifically binds to MHC class I, MHC class II, CD1d, CD2, CD3, CD4, CD8, CD11b, CD14, CD15, CD16, CD19, CD20, CD29, CD31, CD40, CD43, CD44, CD45, CD54, CD56, CD57, CD58, CD83, CD86, CMRF-44, CMRF-56, DCIR, DC-ASGPR, CLEC-6, CD40, BDCA-2, MARCO, DEC-205, mannose receptor, Langerin, DECTIN-1, B7-1, B7-2, IFN-γ receptor, IL-2 receptor, ICAM-1, Fc γ receptor, LOX-1, and ASPGR.

In other embodiments, the APC-targeted antibody targets Langerhans cells. One example of an APC-targeted antibody to Langerhans cells is anti-Langerin. In further embodiments, the APC-targeted antibody targets macrophages. For example, the APC-targeted antibody may be anti-MARCO.

In yet further embodiments, the APC-targeted antibody targets one or more APCs of the group dendritic cells, B cells, and macrophages. In specific embodiments, the APC-targeted antibody targets dendritic cells. In some embodiments, the APC-targeted antibody comprises anti-CD40. In further embodiments, the anti-CD40 antibody comprises anti-CD40 clone 12E12 or fragments thereof. As shown in Example 1, anti-CD40 (12E12)-IL-10 suppressed the expression of CD86. In some embodiments, the anti-CD40 antibody comprises one or more CDRs having a sequence of SEQ ID NOS:31-33 and 37-39. In other embodiments, the anti-CD40 antibody comprises a heavy chain comprising one or more CDRs of SEQ ID NOS:31-33. In further embodiments, the anti-CD40 antibody comprises a light chain comprising one or more CDRs of SEQ ID NOS:37-39.

In specific embodiments, the anti-CD40 antibody is a humanized antibody comprising a heavy chain comprising three CDRs, wherein CDR1 comprises SEQ ID NO:31, CDR2 comprises SEQ ID NO:32, and CDR3 comprises SEQ ID NO:33. In further embodiments, the anti-CD40 antibody is a humanized antibody comprising a light chain comprising three CDRs, wherein CDR1 comprises SEQ ID NO:37, CDR2 comprises SEQ ID NO:38, and CDR3 comprises SEQ ID NO:39.

In some embodiments, the APC-targeted antibody comprises anti-DC-ASGPR or anti-Dectin-1. The anti-DC-ASGRP or anti-Dectin-1 may be one known in the art or described herein. In some embodiments the antibody comprises a variable region comprising an amino acid sequence selected from the sequences of SEQ ID NOs: 3, 8, 62, 64, 66, or 68. In some embodiments, the antibody comprises a heavy or light chain with an amino acid sequence selected from the sequences of SEQ ID NOs: 1, 7, 61, 63, 65, 67, or 69-72. In some embodiments, the antibody comprises one or more CDRs from the variable region, heavy chain, or light chain of SEQ ID NOs: 1, 3, 7, 8, 61, 62, 63, 64, 65, 66, 67, or 68-72.

In some embodiments, the APC-targeted antibody comprises anti-DCIR. In specific embodiments, anti-DCIR antibody comprises anti-DCIR clone 9E8 or fragments thereof. In further embodiments, the anti-DCIR antibody comprises one or more CDRs having a sequence of SEQ ID NOS:18-20 or 24-26. In other embodiments, the anti-DCIR antibody comprises a heavy chain comprising one or more CDRs of SEQ ID NOS:18-20. In yet further embodiments, the anti-CD40 antibody comprises a light chain comprising one or more CDRs of SEQ ID NOS:24-26.

Certain aspects of the disclosure relate to a method for inhibiting an inflammatory or autoimmune response or for inducing tolerance in a subject in need thereof comprising administering to the subject a therapeutically effective amount of an anti-CD40 antibody operatively linked to IL-10 or a fragment thereof, wherein the anti-CD40 is a humanized antibody having three heavy chain CDRs comprising an amino acid sequence of SEQ ID NO:31 (CDR1), SEQ ID NO:32 (CDR2), and SEQ ID NO:33 (CDR3) and three light chain CDRs comprising an amino acid sequence of SEQ ID NO:37 (CDR1), SEQ ID NO:38 (CDR2), and SEQ ID NO:39 (CDR3).

Further aspects relate to a method for inhibiting an inflammatory or autoimmune response or for inducing tolerance in a subject in need thereof comprising administering to the subject a therapeutically effective amount of an anti-DCIR antibody operatively linked to IL-10 or a fragment thereof, wherein the anti-DCIR is a humanized antibody having three heavy chain CDRs from the variable region of anti-DCIR 9E8 heavy chain (SEQ ID NO:17) and three light chain CDRs from the variable region of anti-DCIR 9E8 light chain (SEQ ID NO:23).

Further aspects relate to a method for inhibiting an inflammatory or autoimmune response in a subject in need thereof comprising administering to the subject a therapeutically effective amount of an anti-DC-ASGPR antibody operatively linked to IL-10 or a fragment thereof, wherein the anti-DC-ASGPR antibody is a humanized antibody having three heavy chain CDRs and three light chain CDRs from the variable regions of an anti-DC-ASGPR heavy chain and light chain pair selected from SEQ ID NO:3 and 8; SEQ ID NO:58 and 60; SEQ ID NO:62 and 64; or SEQ ID NO:66 and 68; or is a humanized antibody having three heavy chain CDRs and three light chain CDRs from the heavy and light chains of an anti-DC-ASGPR heavy chain and light chain pair selected from SEQ ID NO:69 and 70 and SEQ ID NO:71 and 72.

In some embodiments, the APC-targeted antibody or antibody conjugate or antigen binding fragment thereof comprises an amino acid sequence that is at least or at most 70%, 75%, 80%, 85%, 90%, 95%, 96%, 97%, 98%, or 99% identical or similar (or any derivable range therein) to an APC-targeted antibody or antigen binding fragment of any of SEQ ID NOS:1, 2, 3, 7, 8, 10, 11, 13, 15-20, 22-26, 28-33, 35-39, or 45-114 (or any range derivable therein). In further embodiments, the APC-targeted antibody conjugate or antigen binding fragment thereof comprises a variable region comprising an amino acid sequence that is at least or at most 70%, 75%, 80%, 85%, 90%, 95%, 96%, 97%, 98%, or 99% (or any range derivable therein) identical or similar to the APC-targeted antibody variable region described herein as SEQ ID NOS: 3, 8, 17, 23, 30, 36, 46, 48, 50, 52, 54, 56, 58, 60, 62, 64, 66, 68, 79, 81, 83, 85, 87, 89, 108, 110, 112, and 114. In further embodiments, the antibody comprises a CDR having an amino acid sequence corresponding to a CDR in any one of SEQ ID NOS: 2, 3, 7, 8, 11, 13, 16, 17-20, 22-26, 29-33, 35-39, or 45-114 (or any derivable range therein). In some embodiments, the antibody comprises the CDRs of SEQ ID NOS:18-20, 24-26, 31-33, or 37-39. In further embodiments, the APC-targeted antibody or antigen binding fragment thereof comprises a heavy or light chain amino acid sequence that is at least or at most 70%, 75%, 80%, 85%, 90%, 95%, 96%, 97%, 98%, or 99% (or any range derivable therein) identical or similar to the APC-targeted antibody or antigen binding fragment of any of SEQ ID NOs:1, 2, 7, 10, 11, 13, 15, 16, 22, 28, 29, 35, 45, 47, 49, 51, 53, 55, 57, 59, 61, 63, 65, 67, 69-78, 80, 82, 84, 86, 88, 90-107, 109, 111, or 113. In certain embodiments, the antibody conjugate or antigen binding fragment thereof comprises CDR1, CDR2, and/or CDR3 from the heavy and/or light chain variable region of a APC-targeted antibody described herein. In certain embodiments, the antibody conjugate or antigen binding fragment thereof comprises all three CDRs from the light chain variable region and/or all three CDRs from the heavy chain variable region of a APC-targeted antibody described herein.

In certain embodiments, the antibody or antigen binding fragment specifically binds to DC-ASGPR and activates DC-ASGPR. DC-asialoglycoprotein receptor (DC-ASGPR) is a scavenger receptor carrying an immunoreceptor tyrosine-based activation motiflike motif. ASGPR may also me known as ASGR1, ASGPR1, CLEC4H1, and HL-1. In one embodiment, the antibody or antigen binding fragment thereof binds to human DC-ASGPR.

In some embodiments, the antibody or antigen binding fragment of the methods and compositions described herein is an anti-DC-ASGPR antibody and comprises an amino acid sequence that is at least or at most 70%, 75%, 80%, 85%, 90%, 95%, 96%, 97%, 98%, or 99% (or any derivable range therein) identical or similar to the DC-ASGPR antibody or antigen binding fragment of any of SEQ ID NO: 2, 3, 7, 8, and 61-72 (or any range derivable therein). In a further embodiment, the DC-ASGPR antibody or antigen binding fragment thereof may include a polypeptide, peptide, or protein that is, is at least, or is at most 70%, 75%, 80%, 85%, 90%, 95%, 96%, 97%, 98%, or 99% (or any range derivable therein) identical or similar to an ASGPR binding polypeptide, such as Anti-ASGPR_49C11_7H (heavy chain), SEQ ID NO:2; Anti-ASGPR_49C11_7K (light chain), SEQ ID NO:7; anti-hASGPR_6.3H9.1D11H (heavy chain), SEQ ID NO:69; anti-hASGPR_6.3H9.1D11K (light chain), SEQ ID NO:70; anti-hASGPR_5H8.1D4H (heavy chain), SEQ ID NO:71; anti-hASGPR_5H8.1D4K (light chain), SEQ ID NO: 72; Anti-ASGPR_4G2.2_ (heavy chain), SEQ ID NO: 57; Anti-ASGPR_4 G2.2_ (light chain), SEQ ID NO: 59; Anti-ASGPR-5F10H (heavy chain), SEQ ID NO:61; Anti-ASGPR-5F10H (light chain), SEQ ID NO: 63; Anti-ASGPR1H11 (heavy chain), SEQ ID NO: 65; or Anti-ASGPR1H11 (light chain). SEQ ID NO: 67. In further embodiments, the DC-ASGPR antibody or antigen binding fragment thereof comprises a variable region comprising an amino acid sequence that is at least or at most 70%, 75%, 80%, 85%, 90%, 95%, 96%, 97%, 98%, or 99% identical or similar to the DC-ASGPR antibody or antigen binding fragment of any of SEQ ID NOs: 3, 8, 62, 64, 66, and 68. In some embodiments, the antibody comprises at least or exactly one, two, or all three CDRs of a variable region from a heavy or light chain amino acid sequence selected from SEQ ID NO:2, 7, 57, 59, 61, 63, 65, 67, and 69-72. In some embodiments, the antibody comprises at least or exactly one, two, or all three CDRs of a variable region from a heavy or light chain variable region amino acid sequence selected from SEQ ID NO:3, 8, 58, 60, 62, 64, 66, and 68. In further embodiments, the antibody comprises at least or exactly 1, 2, 3, 4, 5, or 6 (or any derivable range therein) CDRs from a heavy and light chain antibody fragment selected from SEQ ID NOS: 2 and 7, SEQ ID NOS: 57 and 59; SEQ ID NOS: 61 and 63; SEQ ID NOS: 65 and 67; SEQ ID NOS: 69 and 70; or SEQ ID NOS: 71 and 72. In some embodiments, the antibody comprises at least or exactly 1, 2, 3, 4, 5, or 6 (or any derivable range therein) CDRs from a heavy and light chain variable region antibody fragment selected from SEQ ID NOS: 3 and 8, SEQ ID NOS: 58 and 60; SEQ ID NOS: 62 and 64; or SEQ ID NOS: 66 and 68.

The ASGPR antibody or antigen binding fragments described herein may include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more variant amino acids within at least, or at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein, of SEQ ID NO: 2, 3, 7, 8, and 61-72.

The APC-targeted antibody conjugate or antigen binding fragments described herein may include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more variant amino acids (or any range derivable therein) within at least, or at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein, of any of SEQ ID NOs:1-5, 7-8, 10-11, 13, 15-20, 22-26, 28-33, 35-39, or 45-114.

Embodiments are provided in which the APC-targeted antibody or antigen binding fragments comprises one or more CDR domains from an antibody that specifically binds to an antigen presenting cell surface protein. In particular embodiments, the APC-targeted antibody or antigen binding fragment thereof comprises one, two, three, four, five, six, or more CDR domains from among the VH or VL domain of the monoclonal antibodies listed herein in SEQ ID NOS: 3, 8, 17, 23, 30, 36, 46, 48, 50, 52, 54, 56, 58, 60, 62, 64, 66, 68, 79, 81, 83, 85, 87, 89, 108, 110, 112, and 114. In certain aspects, the APC-targeted antibody or antigen binding fragment thereof comprises six CDR domains from among the VH or VL domains of the monoclonal antibodies: anti-Dectin-1 clone 11B6.4, 15E2.5, or 2D8.2D4; ASGPR clone 49C11, 4G2.2, 5F10, 1H11, 6.3H9.1D11, or 5H8.1D4; anti-CD40 clone 12E12, 12B4.2C10, 24A3, or 11B6.1C3; anti-Lox-1 clone 11C8, 10F9, or 15C4; anti-DCIR clone 24A5.4A5, 24E7.3H9, 29E9.2E2, 29G10.3D9, 31A6.IF5, 3C2.2D9, 6C8.1G9, 9E8, or 2C9; or anti-Langrin clone 15B10 or 2G3. In some embodiments, the APC-targeted antibody or antigen binding fragment thereof comprises a sequence at least or at most 70%, 75%, 80%, 85%, 90%, 95%, or 99% (or any range derivable therein) identical to the VH or VL domain of the monoclonal antibodies: anti-Dectin-1 clone 11B6.4, 15E2.5, or 2D8.2D4; ASGPR clone 49C11, 4G2.2, 5F10, 1H11, 6.3H9.1D11, or 5H8.1D4; anti-CD40 clone 12E12, 12B4.2C10, 24A3, or 11B6.1C3; anti-Lox-1 clone 11C8, 10F9, or 15C4; anti-DCIR clone 24A5.4A5, 24E7.3H9, 29E9.2E2, 29G10.3D9, 31A6.IF5, 3C2.2D9, 6C8.1G9, 9E8, or 2C9; or anti-Langrin clone 15B10 or 2G3. Embodiments are provided in which the APC-targeted antibody or antigen binding fragment thereof comprises the VH domain from the monoclonal antibodies listed herein and/or the VL domain from the monoclonal antibodies listed herein. In further embodiments, the monoclonal antibody is selected from: anti-Dectin-1 clone 11B6.4, 15E2.5, or 2D8.2D4; ASGPR clone 49C11, 4G2.2, 5F10, 1H11, 6.3H9.1D11, or 5H8.1D4; anti-CD40 clone 12E12, 12B4.2C10, 24A3, or 11B6.1C3; anti-Lox-1 clone 11C8, 10F9, or 15C4; anti-DCIR clone 24A5.4A5, 24E7.3H9, 29E9.2E2, 29G10.3D9, 31A6.IF5, 3C2.2D9, 6C8.1G9, 9E8, or 2C9; or anti-Langrin clone 15B10 or 2G3.

In certain embodiments, the APC-targeted antibody or antigen binding fragment thereof is recombinant. In certain aspects, the recombinant polypeptide comprises at least 90%, 95%, or 99% of one or more CDR domains from the VH or VL domain of the anti-Dectin-1 clone 11B6.4, 15E2.5, or 2D8.2D4; ASGPR clone 49C11, 4G2.2, 5F10, 1H11, 6.3H9.1D11, or 5H8.1D4; anti-CD40 clone 12E12, 12B4.2C10, 24A3, or 11B6.1C3; anti-Lox-1 clone 11C8, 10F9, or 15C4; anti-DCIR clone 24A5.4A5, 24E7.3H9, 29E9.2E2, 29G10.3D9, 31A6.IF5, 3C2.2D9, 6C8.1G9, 9E8, or 2C9; or anti-Langrin clone 15B10 or 2G3 monoclonal antibodies. In some embodiments, the recombinant polypeptide comprises two, three, four, five, six, or more CDR domains from the VH or VL domain of the anti-Dectin-1 clone 11B6.4, 15E2.5, or 2D8.2D4; ASGPR clone 49C11, 4G2.2, 5F10, 1H11, 6.3H9.1D11, or 5H8.1D4; anti-CD40 clone 12E12, 12B4.2C10, 24A3, or 11B6.1C3; anti-Lox-1 clone 11C8, 10F9, or 15C4; anti-DCIR clone 24A5.4A5, 24E7.3H9, 29E9.2E2, 29G10.3D9, 31A6.IF5, 3C2.2D9, 6C8.1G9, 9E8, or 2C9; or anti-Langrin clone 15B10 or 2G3 monoclonal antibodies.

In some embodiments, a recombinant polypeptide comprises i) CDR1 (SEQ ID NO:37), CDR2 (SEQ ID NO:38), and/or CDR3 (SEQ ID NO:39) from the variable light chain of anti-CD40 12E12; and/or ii) CDR1 (SEQ ID NO:31), CDR2 (SEQ ID NO:32), and/or CDR3 (SEQ ID NO:33) from the variable heavy chain of 12E12. In some embodiments, a recombinant polypeptide comprises i) CDR1, CDR2, and/or CDR3 from the variable light chain of anti-DCIR 9E8; and/or ii) CDR1, CDR2, and/or CDR3 from the variable heavy chain of 9E8.

Certain aspects are directed to methods of inhibiting an inflammatory response or inducing tolerance in a subject in need thereof comprising administering to the subject an effective amount of one or more APC-targeted antibody or antigen binding fragment thereof operatively linked to IL-10. The antibody can be a purified polyclonal antibody, a purified monoclonal antibody, a recombinant polypeptide, or a fragment thereof. In certain aspects the antibody is humanized or human. In still further aspects the antibody is a recombinant antibody segment. In certain aspects a monoclonal antibody includes one or more of anti-Dectin-1 clone 11B6.4, 15E2.5, or 2D8.2D4; ASGPR clone 49C11, 4G2.2, 5F10, 1H11, 6.3H9.1D11, or 5H8.1D4; anti-CD40 clone 12E12, 12B4.2C10, 24A3, or 11B6.1C3; anti-Lox-1 clone 11C8, 10F9, or 15C4; anti-DCIR clone 24A5.4A5, 24E7.3H9, 29E9.2E2, 29G10.3D9, 31A6.IF5, 3C2.2D9, 6C8.1G9, 9E8, or 2C9; or anti-Langrin clone 15B10 or 2G3. An antibody can be administered at a dose of 0.1, 0.5, 1, 5, 10, 50, 100 mg or µg/kg to 5, 10, 50, 100, 500 mg or µg/kg, or any range derivable therein.

The methods described herein provide a dose sparing effect such that the targeted delivery of IL-10 requires a smaller amount or dose to achieve the same effect as a non-targeted IL-10. In certain embodiments, the therapeutically effective amount of the APC-targeted antibodies operatively linked to IL-10 is at least 5, 10, 20, 50, 100, 500, or 1000 fold less than the dose of non-targeted IL-10. In further embodiments, the therapeutically effective amount of the APC-targeted antibodies operatively linked to IL-10 is greater than 50%, greater than 75%, greater than 80%, greater than 90% or greater than 99% less than the effective amount of the dose of non-targeted IL-10. The therapeutically effective amount of non-targeted IL-10 is known in the art, and may vary depending on the disease to be treated. In certain embodiments, the effective amount of non-targeted IL-10 is 1, 5, 10, or 20 µg/kg. In one embodiment, the effective amount of non-targeted IL-10 is 5 µg/kg. In other embodiments, the therapeutically effective amount of the APC-targeted antibodies operatively linked to IL-10 is at least 5 fold less than the dose of non-targeted IL-10.

In certain embodiments, the antibody is a human antibody, humanized antibody, recombinant antibody, bi-specific antibody, chimeric antibody, a nanobody, a DARPin, an antibody derivative, a veneered antibody, a diabody, a monoclonal antibody, or a polyclonal antibody. In a specific embodiment, the antibody is a humanized antibody.

In certain embodiments, the antibody is a non-naturally occurring antibody. In some embodiments, the antibody is non-naturally occurring since it comprises at least two polypeptide segments from different sources. The different sources may be different mammals, such as human and mouse, for example.

In some embodiments of the methods described herein, the subject is a human subject. The term "subject," "individual" or "patient" is used interchangeably herein and refers to a vertebrate, for example a primate, a mammal or preferably a human. Mammals include, but are not limited to equines, canines, bovines, ovines, murines, rats, simians, humans, farm animals, sport animals and pets.

In some embodiments, the subject is one that has an autoimmune disease or an inflammatory disorder. The autoimmune disease or inflammatory disorder may be one known in the art and/or described herein. In some embodiments, the autoimmune disease or inflammatory disorder is selected from rheumatoid arthritis, allergy, asthma, systemic onset juvenile arthritis, inflammatory bowel disease, systemic lupus erythematosus, multiple sclerosis, type 1 diabetes, graft rejection, graft versus host disease, colitis, and Crohn's disease.

In some embodiments, the subject is at risk for the development of a disease mediated by a pathogenic T cell response. In further embodiments, the subject is one that is suffering from or at risk of suffering from an autoimmune disease or an auto-inflammatory disease. In a specific embodiment, the autoimmune disease or auto-inflammatory disease is selected from rheumatoid arthritis, allergy, asthma, systemic onset juvenile arthritis, inflammatory bowel disease, systemic lupus erythematosus, multiple sclerosis, type 1 diabetes, graft rejection, graft versus host disease, colitis, and Crohn's disease.

In some embodiments, the subject is one that will receive or has received transplanted tissues. In a related embodiment, the transplanted tissue is an allograft. An allograft (also known as allotransplantation, allogeneic transplant, or homograft) is the transplantation of cells, tissues, or organs, to a recipient from a genetically non-identical donor of the same species. In a related embodiment, the subject is one that has a complication from the transplanted tissue, wherein the complication is graft rejection or GVHD.

In some embodiments, the APC-targeted antibody is administered prior to tissue transplantation. When the antibody or antigen binding fragment thereof is administered prior to tissue transplantation, the method may further comprise the prevention of a complication relating to the transplanted tissue, wherein the complication comprises GVHD or graft rejection.

In some embodiments, the APC-targeted antibody is administered after tissue transplantation. When the antibody or antigen binding fragment thereof is administered after tissue transplantation, the method may further comprise treating a complication from the transplanted tissue, wherein the complication comprises GVHD or graft rejection.

The tissue used in transplantation may be any tissue known in the art to be therapeutically useful for transplantation. Non-limiting examples of tissue transplantations include anterior cruciate ligament (ACL); joint reconstruction in the knee and ankle; meniscal replacement; reconstruction due to cancer or trauma; ridge augmentation in dental procedures; shoulder repair; spinal fusion; urological tissues; skin transplants; corneal transplants; heart transplants; heart valves; lung transplantation; intestinal transplantation such as isolated small bowel, intestine, or multivisceral; liver transplants; kidney transplants; bone marrow transplants; bone allograft; and ligament or tendon allograft.

In one embodiment, the transplanted tissue comprises immune cells. The term immune cells includes cells of the immune system that are involved in defending the body against both infectious disease and foreign materials. Immune cells may include, for example, neutorphils, eosinophils, basophils, lymphocytes such as b cells and t cells, and monocytes. T cells may include, for example, CD4+, CD8+, T helper cells, cytotoxic T cells, γδ T cells, regulatory T cells, suppressor T cells, and natural killer cells.

In another embodiment, the transplanted tissue comprises stem cells. Stem cell types are known in the art. Non-limiting examples of stem cells include hematopoietic stem cells, neural stem cells, and embryonic stem cells. In one embodiment, the stem cells are hematopoietic stem cells. In a further embodiment, the transplanted tissue comprises bone marrow. In a yet further embodiment, the transplanted tissue comprises blood. In another embodiment, the transplanted tissue comprises skin cells.

In some embodiments, the APC-targeted antibody operatively linked to IL-10 or a fragment thereof is administered in an amount effect for the maintenance of pathogen-specific immunity in the subject.

The IL-10 polypeptide may be a polypeptide or fragment of an IL-10 protein known in the art or described herein by accession number NP_000563.1. In some embodiments, the IL-10 polypeptide comprises SEQ ID NO:5. In some embodiments, IL-10 is covalently linked to the antibody. In some embodiments, the covalent linkage is through a peptide bond. The IL-10 polypeptide may also be linked to the antibody through binding polypeptides. In one embodiment, the binding polypeptides are dockerin and cohesin.

In some embodiments, the method further comprises administration of an antigen or allergen. The antigen or allergen may be operatively linked to the APC-targeted antibody or to IL-10. In some embodiments, the antigen or allergen is covalently linked (i.e. by a peptide bond) to the APC-targeted antibody, antigen binding fragment thereof, or IL-10. When the antigen or allergen is operatively linked to the APC-targeted antibody, antigen binding fragment thereof, or IL-10, it may be linked through binding polypeptides. Binding peptides include, for example, dockerin and cohesin.

In further embodiments, the compositions or methods do not comprise an antigen or allergen or the administration of an allergy or antigen. For example, an antigen or allergen is not operatively (either directly or indirectly) linked to the APC-targeted antibody. In some embodiments, the compositions consists essentially of an antigen presenting cell (APC)-targeted antibody operatively linked to IL-10 or a fragment thereof.

In further embodiments, the compositions or methods do not comprise a TLR molecule or the administration of a TLR molecule.

In some embodiments, the antibody may comprise a γ4 constant region. In a related embodiment, the γ4 constant region comprises a substitution of glutamic acid for leucine at residue 235. In another embodiment, γ4 constant region comprises a substitution of proline for serine at residue 228 in the hinge region.

In certain embodiments, the methods comprises multiple administrations of the composition. The administrations may be days, weeks, months, years, or decades apart. The compositions comprising the conjugate described herein may be administered orally, intravenously, subcutaneously, intradermally, intramuscularly, intranasally, by injection, by inhalation, mucosally, and/or by using a nebulizer.

In certain embodiments of the methods described herein, the anti-DC-ASGPR antibody or antigen binding fragment is administered in a therapeutically effective amount. In certain embodiments, the antibody or antigen binding fragment is administered in an amount that increases production of IL-10 in the subject. In a further embodiment, the antibody or antigen binding fragment is administered in an amount whereby the subject maintains pathogen-specific immunity after administration of the antibody or antigen binding fragment.

In some embodiments, the anti-DC-ASGPR antibody or antigen binding fragment thereof may be administered in a pharmaceutical composition. In some embodiments, the pharmaceutical composition does not contain an antigen or does not contain detectable amounts of an antigen. In a further embodiment, the pharmaceutical composition consists essentially of an anti-DC-ASGPR antibody. In further embodiments, the antibody or antigen binding fragment thereof is not conjugated to an antigen or is not is not conjugated to a dockerin or cohesion molecule. In yet further embodiments, the antibody is not covalently or operatively linked to an antigen.

The term "operatively linked" refers to a situation where two components are combined to form the active complex prior to binding at the target site. For example, an antibody conjugated to one-half of a cohesion-docerin complex and an antigen complexed to the other one-half of the cohesion-docerin complex are operatively linked through complexation of the cohesion and docerin molecules.

Also disclosed herein are compositions comprising the antibodies and antibody conjugates as described herein.

Aspects of the disclosure relate to APC-targeted antibodies and APC-targeted antibodies conjugated to IL-10 in pharmaceutical compositions and for use in the preparation of medicaments for treating an autoimmune and/or inflammatory condition described herein.

Aspects also relate to an APC-targeted antibody or an APC-targeted antibody conjugated to IL-10 in pharmaceutical compositions and for use in the preparation of medicaments for inducing immune tolerance or suppressing a T cell response in a subject having or at risk of developing an autoimmune or inflammatory response, wherein the autoimmune or inflammatory response is caused by an autoimmune or inflammatory disease described herein.

As used herein the specification, "a" or "an" may mean one or more. As used herein in the claim(s), when used in conjunction with the word "comprising", the words "a" or "an" may mean one or more than one. A composition with the words "consisting essentially of" is intended to exclude any active ingredients not specifically recited in the composition. Examples of active ingredients include cytokines, TLRs, antigens, adjuvants, etc. . . . . In any of the embodiments described herein, embodiments consisting essentially of the recited elements is also contemplated.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
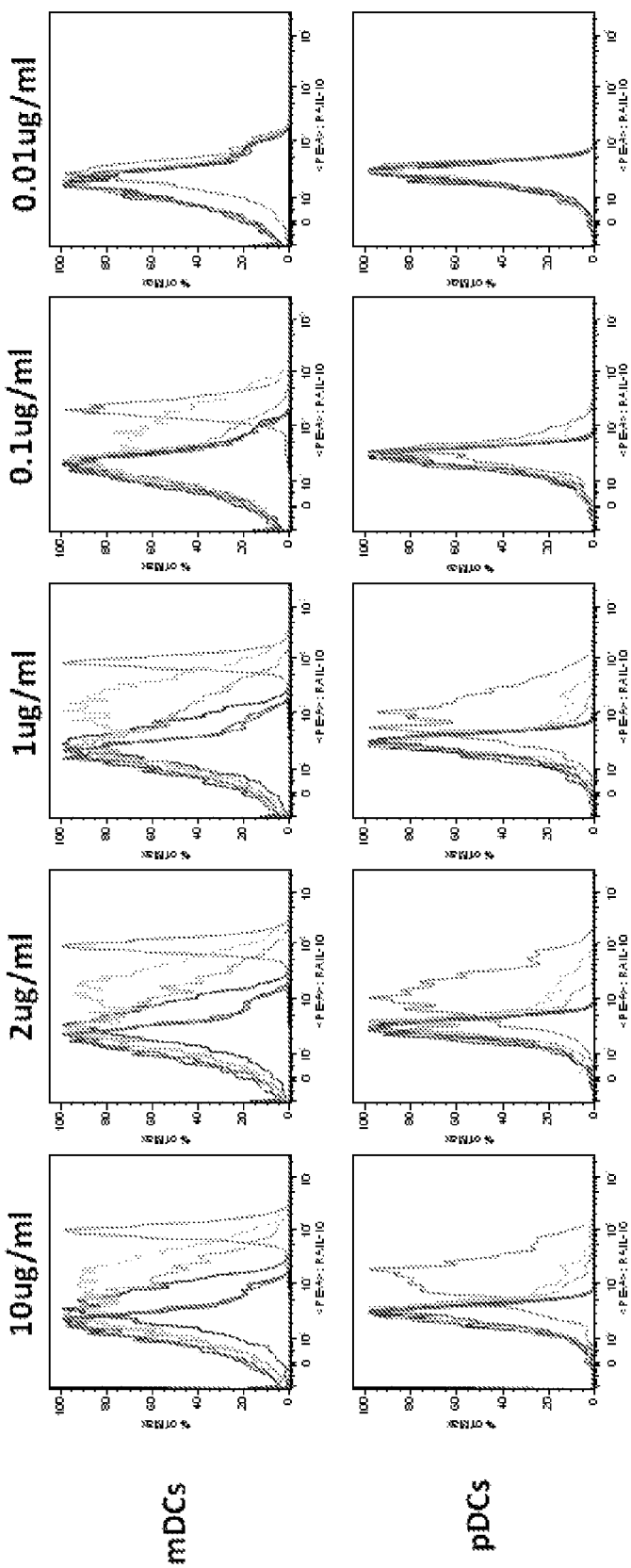
FIG. 1 shows that recombinant fusion proteins of antibody and IL-10 target human APCs.

Methods and compositions described herein can be used to treat or prevent inflammatory and/or autoimmune disorders or for inducing immune tolerance. It was discovered that delivering the anti-inflammatory cytokine, IL-10, to human antigen presenting cells (APCs) can suppress and alter the pathophysiologic functions of APCs in the patients. It is contemplated that targeted delivery of anti-inflammatory cytokines to the APCs in the patients is expected to result in more effective and pro-longed immune tolerance in the patients. Delivering IL-10 to APCs can directly suppress ongoing inflammatory reaction in a short term period and can also induce regulatory T cells which can prolong the effectiveness of the treatment. Furthermore, the methods described herein provide a dose sparing effect such that the targeted delivery of IL-10 requires a smaller amount or dose to achieve the same effect as a non-targeted IL-10.

I. ANTIBODIES

Methods and compositions of the disclosure relate to APC-targeted antibodies and antibody binding fragments thereof. In some embodiments, the antibodies are operatively linked to IL-10. As used herein, an "antibody" includes whole antibodies and any antigen binding fragment or a single chain thereof. Thus the term "antibody" includes any protein or peptide-containing molecule that comprises at least a portion of an immunoglobulin molecule. Examples of such include, but are not limited to a complementarity determining region (CDR) of a heavy or light chain or a ligand binding portion thereof, a heavy chain or light chain variable region, a heavy chain or light chain constant region, a framework (FR) region or any portion thereof or at least one portion of a binding protein.

The antibody can be any of the various antibodies described herein, non-limiting, examples of such include a polyclonal antibody, a monoclonal antibody, a chimeric antibody, a recombinant antibody, a human antibody, a veneered antibody, a diabody, a humanized antibody, an antibody derivative, a recombinant humanized antibody, or a derivative or fragment of each thereof.

Antibodies can be generated using conventional techniques known in the art and are well-described in the literature. Several methodologies exist for production of polyclonal antibodies. For example, polyclonal antibodies are typically produced by immunization of a suitable mammal such as, but not limited to, chickens, goats, guinea pigs, hamsters, horses, mice, rats, and rabbits. An antigen is injected into the mammal, induces the B-lymphocytes to produce immunoglobulins specific for the antigen. Immunoglobulins may be purified from the mammal's serum. Common variations of this methodology include modification of adjuvants, routes and site of administration, injection volumes per site and the number of sites per animal for optimal production and humane treatment of the animal. For example, adjuvants typically are used to improve or enhance an immune response to antigens. Most adjuvants provide for an injection site antigen depot, which allows for a stow release of antigen into draining lymph nodes. Other adjuvants include surfactants which promote concentration of protein antigen molecules over a large surface area and immunostimulatory molecules. Non-limiting examples of adjuvants for polyclonal antibody generation include Freund's adjuvants, Ribi adjuvant system, and Titermax. Polyclonal antibodies can be generated using methods known in the art some of which are described in U.S. Pat. Nos. 7,279,559; 7,119,179; 7,060,800; 6,709,659; 6,656,746; 6,322,788; 5,686,073; and 5,670,153.

Unless specified otherwise, the antibodies can be polyclonal or monoclonal and can be isolated from any suitable biological source, e.g., murine, rat, sheep or canine.

In a specific embodiment, the antibody is a monoclonal antibody. As used herein, "monoclonal antibody" refers to an antibody obtained from a substantially homogeneous antibody population. Monoclonal antibodies are highly specific, as each monoclonal antibody is directed against a single determinant on the antigen. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like.

Monoclonal antibodies can be generated using conventional hybridoma techniques known in the art and well-described in the literature. For example, a hybridoma is produced by fusing a suitable immortal cell line (e.g., a myeloma cell line such as, but not limited to, Sp2/0, Sp2/0-AG14, NSO, NS1, NS2, AE-1, L.5, P3X63Ag8,653, Sp2 SA3, Sp2 MAI, Sp2 SS1, Sp2 SA5, U397, MIA 144, ACT IV, MOLT4, DA-1, JURKAT, WEHI, K-562, COS, RAJI, NIH 313, HL-60, MLA 144, NAMAIWA, NEURO 2A, CHO, PerC.6, YB2/O) or the like, or heteromyelomas, fusion products thereof, or any cell or fusion cell derived there from, or any other suitable cell line as known in the art, with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. Antibody producing cells can also be obtained from the peripheral blood or, preferably the spleen or lymph nodes, of humans or other suitable animals that have been immunized with the antigen of interest. Any other suitable host cell can also be used for expressing-heterologous or endogenous nucleic acid encoding an antibody, specified fragment or variant thereof. The fused cells (hybridomas) or recombinant cells can be isolated using selective culture conditions or other suitable known methods, and cloned by limiting dilution or cell sorting, or other known methods.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, cDNA, or the like, display library; e.g., as available from various commercial vendors such as MorphoSys (Martinsried/Planegg, Del.), BioInvent (Lund, Sweden), Affitech (Oslo, Norway) using methods known in the art. Art known methods are described in the patent literature some of which include U.S. Pat. Nos. 4,704,692; 5,723,323; 5,763,192; 5,814,476; 5,817,483; 5,824,514; 5,976,862. Alternative methods rely upon immunization of transgenic animals (e.g., SCID mice, Nguyen et al. (1977) Microbiol. Immunol. 41:901-907 (1997); Sandhu et al. (1996) Crit, Rev. Biotechnol. 16:95-118; Eren et al. (1998) Mumma 93:154-161 that are capable of producing a repertoire of human antibodies, as known in the art and/or as described herein. Such techniques, include, but are not limited to, ribosome display Wanes et al. (1997) Proc. Natl. Acad. Sci. USA, 94:4937-4942; Hanes et al, (1998) Proc. Natl. Acad. Sci. USA 95:14130-14135); single cell antibody producing technologies (e.g., selected lymphocyte antibody method ("SLAM") (U.S. Pat. No. 5,627,052, Wen et al, (1987) J. Immunol 17:887-892; Babcook et al. (1996) Proc. Natl. Acad. Sci. USA 93:7843-7848); gel microdroplet and flow cytometry (Powell et al. (1990) Biotechnol. 8:333-337; One Cell Systems, (Cambridge, Mass.); Gray et al. (1995) J. Imm. Meth. 182:155-163; and Kenny et al, (1995) Bio. Technol. 13:787-790); B-cell selection (Steenbakkers et al. (1994) Molec. Biol. Reports 19:125-134).

The terms "polyclonal antibody" or "polyclonal antibody composition" as used herein refer to a preparation of antibodies that are derived from different B-cell lines. They are a mixture of immunoglobulin molecules secreted against a specific antigen, each recognizing a different epitope.

The term "mouse antibody" as used herein, is intended to include antibodies having variable and constant regions derived from mouse germline immunoglobulin sequences.

As used herein, chimeric antibodies are antibodies whose light and heavy chain genes have been constructed, typically by genetic engineering, from antibody variable and constant region genes belonging to different species. In one embodiment, the antibody is a mouse/human chimeric antibody.

In further embodiments, the antibody comprises a modification and is an "antibody derivative." The term "antibody derivative" includes post-translational modification to linear polypeptide sequence of the antibody or fragment. For example, U.S. Pat. No. 6,602,684 B1 describes a method for the generation of modified glycol-forms of antibodies, including whole antibody molecules, antibody fragments, or fusion proteins that include a region equivalent to the Fc region of an immunoglobulin, having enhanced Fc-mediated cellular toxicity, and glycoproteins so generated.

The antibodies provided herein also include derivatives that are modified by the covalent attachment of any type of molecule to the antibody such that covalent attachment does not prevent the antibody from generating an anti-idiotypic response. Antibody derivatives include, but are not limited to, antibodies that have been modified by glycosylation, acetylation, pegylation, phosphorylation, amidation, derivatization by known protecting/blocking groups, proteolytic cleavage, linkage to a cellular ligand or other protein, etc. Additionally, the derivatives may contain one or more non-classical amino acids.

Antibody derivatives can also be prepared by delivering a polynucleotide encoding an antibody to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873,316; 5,849,992; 5,994,616; 5,565,362; and 5,304,489.

Antibody derivatives also can be prepared by delivering a polynucleotide to provide transgenic plants and cultured plant cells (e.g., but not limited to tobacco, maize, and duckweed) that produce such antibodies, specified portions or variants in the plant parts or in cells cultured therefrom. Antibody derivatives have also been produced in large amounts from transgenic plant seeds including antibody fragments, such as single chain antibodies (scFv's), including tobacco seeds and potato tubers. See, e.g., Conrad et al. (1998) Plant Mol. Biol. 38:101-109 and references cited therein. Thus, antibodies can also be produced using transgenic plants, according to know methods.

Antibody derivatives also can be produced, for example, by adding exogenous sequences to modify immunogenicity or reduce, enhance or modify binding, affinity, on-rate, off-rate, avidity, specificity, half-life, or any other suitable characteristic. Generally part or all of the non-human or human CDR sequences are maintained while the non-human sequences of the variable and constant regions are replaced with human or other amino acids.

The term "variable region" refers to a portion of the antibody that gives the antibody its specificity for binding antigen. The variable region is typically located at the ends of the heavy and light chains. Variable loops of β-strands, three each on the light (VL) and heavy (VH) chains are responsible for binding to the antigen. These loops are referred to as the "complementarity determining regions" (CDRs).

In general, the CDR residues are directly and most substantially involved in influencing antigen binding. Humanization or engineering of antibodies can be performed using any known method such as, but not limited to, those described in U.S. Pat. Nos. 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567.

The term "constant region" refers to a portion of the antibody that is identical in all antibodies of the same isotype. The constant region differs in antibodies of different isotypes.

In one embodiment, the antibody is a humanized antibody. As used herein, the term "humanized antibody" or "humanized immunoglobulin" refers to a human/non-human chimeric antibody that contains a minimal sequence derived from non-human immunoglobulin. For the most part, humanized antibodies are human immunoglobulins (recipient antibody) in which residues from a variable region of the recipient are replaced by residues from a variable region of a non-human species (donor antibody) such as mouse, rat, rabbit, or non-human primate having the desired specificity, affinity and capacity. Humanized antibodies may comprise residues that are not found in the recipient antibody or in the donor antibody. The humanized antibody can optionally also comprise at least a portion of an immunoglobulin constant region (Fc), typically that of a human immunoglobulin, a non-human antibody containing one or more amino acids in a framework region, a constant region or a CDR, that have been substituted with a correspondingly positioned amino acid from a human antibody. In general, humanized antibodies are expected to produce a reduced immune response in a human host, as compared to a non-humanized version of the same antibody. The humanized antibodies may have conservative amino acid substitutions which have substantially no effect on antigen binding or other antibody functions. Conservative substitutions groupings include: glycine-alanine, valine-leucine-isoleucine, phenylalanine-tyrosine, lysine-arginine, alanine-valine, serine-threonine and asparagine-glutamine.

Chimeric, humanized or primatized antibodies can be prepared based on the sequence of a reference monoclonal antibody prepared using standard molecular biology techniques. DNA encoding the heavy and light chain immunoglobulins can be obtained from the hybridoma of interest and engineered to contain non-reference (e.g., human) immunoglobulin sequences using standard molecular biology techniques. For example, to create a chimeric antibody, the murine variable regions can be linked to human constant regions using methods known in the art (U.S. Pat. No. 4,816,567). To create a humanized antibody, the murine CDR regions can be inserted into a human framework using methods known in the art (U.S. Pat. Nos. 5,225,539 and 5,530,101; 5,585,089; 5,693,762 and 6,180,370). Similarly, to create a primatized antibody the murine CDR regions can be inserted into a primate framework using methods known in the art (WO 93/02108 and WO 99/55369). Methods of determining CDRs from the sequence of a variable region are known in the art (see, for example, Zhao and Lu, "A germline knowledge based computational approach for determining antibody complementarity determining regions." Mol. Immunol., (2010) 47(4):694-700, which is herein incorporated by reference).

Techniques for making partially to fully human antibodies are known in the art and any such techniques can be used. According to one embodiment, fully human antibody sequences are made in a transgenic mouse which has been engineered to express human heavy and light chain antibody genes. Multiple strains of such transgenic mice have been made which can produce different classes of antibodies. B cells from transgenic mice which are producing a desirable antibody can be fused to make hybridoma cell lines for continuous production of the desired antibody. (See for example, Russel et al. (2000) Infection and Immunity April 2000:1820-1826; Gallo et al. (2000) European J. of Immun. 30:534-540; Green (1999) J. of Immun. Methods 231:11-23; Yang et al. (1999A) J. of Leukocyte Biology 66:401-410; Yang (1999B) Cancer Research 59(6):1236-1243; Jakobovits (1998) Advanced Drug Reviews 31:33-42; Green and Jakobovits (1998) J. Exp. Med. 188(3):483-495; Jakobovits (1998) Exp. Opin. Invest. Drugs 7(4):607-614; Tsuda et al. (1997) Genomics 42:413-421; Sherman-Gold (1997) Genetic Engineering News 17(14); Mendez et al. (1997)

Nature Genetics 15:146-156; Jakobovits (1996) Weir's Handbook of Experimental Immunology, The Integrated Immune System Vol. IV, 194.1-194.7; Jakobovits (1995) Current Opinion in Biotechnology 6:561-566; Mendez et al, (1995) Genomics 26:294-307; Jakobovits (1994) Current Biology 4(8):761-763; Arbones et al. (1994):Immunity 1(4): 247-260; Jakobovits (1993) Nature 362(6417):255-258; Jakobovits et al. (1993) Proc. Natl. Acad. Sci. USA 90(6): 2551-2555; and U.S. Pat. No. 6,075,181.)

Antibodies also can be modified to create chimeric antibodies. Chimeric antibodies are those in which the various domains of the antibodies' heavy and light chains are coded for by DNA from more than one species. See, e.g., U.S. Pat. No. 4,816,567.

Alternatively, antibodies can also be modified to create veneered antibodies. Veneered antibodies are those in which the exterior amino acid residues of the antibody of one species are judiciously replaced or "veneered" with those of a second species so that the antibodies of the first species will not be immunogenic in the second species thereby reducing the immunogenicity of the antibody. Since the antigenicity of a protein is primarily dependent on the nature of its surface, the immunogenicity of an antibody could be reduced by replacing the exposed residues which differ from those usually found in another mammalian species antibodies. This judicious replacement of exterior residues should have little, or no, effect on the interior domains, or on the interdomain contacts. Thus, ligand binding properties should be unaffected as a consequence of alterations which are limited to the variable region framework residues. The process is referred to as "veneering" since only the outer surface or skin of the antibody is altered, the supporting residues remain undisturbed.

The procedure for "veneering" makes use of the available sequence data for human antibody variable domains compiled by Kabat et al. (1987) Sequences of Proteins of Immunological interest, 4th ed., Bethesda, Md., National Institutes of Health, updates to this database, and other accessible U.S. and foreign databases (both nucleic acid and protein). Non-limiting examples of the methods used to generate veneered antibodies include EP 519596; U.S. Pat. No. 6,797,492; and described in Padlan et al. (1991) Mol. Immunol. 28(4-5):489-498.

The term "antibody derivative" also includes "diabodies" which are small antibody fragments with two antigen-binding sites, wherein fragments comprise a heavy chain variable domain (VH) connected to a light chain variable domain (VL) in the same polypeptide chain. (See for example, EP 404,097; WO 93/11161; and Hollinger et al. (1993) Proc. Natl. Acad. Sci. USA 90:6444-6448.) By using a linker that is too short to allow pairing between the two domains on the same chain, the domains are forced to pair with the complementary domains of another chain and create two antigen-binding sites. (See also, U.S. Pat. No. 6,632,926 to Chen et al, which discloses antibody variants that have one or more amino acids inserted into a hypervariable region of the parent antibody and a binding affinity for a target antigen which is at least about two fold stronger than the binding affinity of the parent antibody for the antigen).

The term "antibody derivative" further includes engineered antibody molecules, fragments and single domains such as scFv, dAbs, nanobodies, minibodies, Unibodies, and Affibodies & Hudson (2005) Nature Biotech 23(9):1126-36; U.S. Patent Publication US 2006/0211088; PCT Publication WO2007/059782; U.S. Pat. No. 5,831,012).

The term "antibody derivative" further includes "linear antibodies". The procedure for making linear antibodies is known in the art and described in Zapata et al. (1995) Protein Eng. 8(10):1057-1062. Briefly, these antibodies comprise a pair of tandem Ed segments (V$_H$-C$_H$1-VH-C$_H$1) which form a pair of antigen binding regions. Linear antibodies can be bispecific or monospecific.

Antibodies can be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

It also is possible to determine without undue experimentation, whether an antibody has the same specificity as antibodies contemplated herein by determining whether the antibody being tested prevents an antibody from binding the protein or polypeptide with which the antibody is normally reactive. If the antibody being tested competes with an antibody used in embodiments described herein as shown by a decrease in binding by the monoclonal antibody, then it is likely that the two antibodies bind to the same or a closely related epitope. Alternatively, one can pre-incubate an antibody for use in embodiments with a protein with which it is normally reactive, and determine if the antibody being tested is inhibited in its ability to bind the antigen. If the antibody being tested is inhibited then, in all likelihood, it has the same, or a closely related, epitopic specificity as the antibody for use in embodiments described herein.

The term "antibody" also is intended to include antibodies of all immunoglobulin isotypes and subclasses unless specified otherwise. An isotype refers to the genetic variations or differences in the constant regions of the heavy and light chains of an antibody. In humans, there are five heavy chain isotypes: IgA, IgD, IgG, IgE, and IgM and two light chain isotypes: kappa and lambda. The IgG class is divided into four isotypes: IgG1, IgG2, IgG3 and IgG4 in humans, and IgG1, IgG2a, IgG2b and IgG3 in mice. They share more than 95% homology in the amino acid sequences of the Fc regions but show major differences in the amino acid composition and structure of the hinge region. Particular isotypes of a monoclonal antibody can be prepared either directly by selecting from an initial fusion, or prepared secondarily, from a parental hybridoma secreting a monoclonal antibody of different isotype by using the sib selection technique to isolate class switch variants using the procedure described in Steplewski et al. (1985) Proc. Natl. Acad. Sci. USA 82:8653 or Spira et al, (1984) J. Immunol. Methods 74:307. Alternatively, recombinant DNA techniques may be used.

The isolation of other monoclonal antibodies with the specificity of the monoclonal antibodies described herein can also be accomplished by one of ordinary skill in the art by producing anti-idiotypic antibodies. Herlyn et al. (1986) Science 232:100. An anti-idiotypic antibody is an antibody which recognizes unique determinants present on the monoclonal antibody of interest.

In some aspects, it will be useful to detectably or therapeutically label the antibody. Methods for conjugating antibodies to these agents are known in the art. For the purpose of illustration only, antibodies can be labeled with a detectable moiety such as a radioactive atom, a chromophore, a fluorophore, or the like. Such labeled antibodies can be used for diagnostic techniques, either in vivo, or in an isolated test sample.

In certain embodiments, the antibody or antigen binding fragment further comprises a modification. The modification may be a conservative amino acid mutation within the VH and/or VL CDR 1, CDR 2 and/or CDR 3 regions, of conservative amino acid mutations in the Fc hinge region, pegylation, conjugation to a serum protein, conjugation to human serum albumin, conjugation to a detectable label, conjugation to a diagnostic agent, conjugation to an enzyme, conjugation to a fluorescent, luminescent, or bioluminescent material, conjugation to a radioactive material, or conjugation to a therapeutic agent.

As used herein, the term "label" intends a directly or indirectly detectable compound or composition that is conjugated directly or indirectly to the composition to be detected, e.g., polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g. radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component.

Examples of luminescent labels that produce signals include, but are not limited to bioluminescence and chemiluminescence. Detectable luminescence response generally comprises a change in, or an occurrence of, a luminescence signal. Suitable methods and luminophores for luminescently labeling assay components are known in the art and described for example in Haugland, Richard P. (1996) Handbook of Fluorescent Probes and Research Chemicals (6.sup.th ed.). Examples of luminescent probes include, but are not limited to, aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals (6.sup.th ed.).

In another aspect, the fluorescent label is functionalized to facilitate covalent attachment to a cellular component present in or on the surface of the cell or tissue such as a cell surface marker. Suitable functional groups, including, but not are not limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

Attachment of the fluorescent label may be either directly to the cellular component or compound or alternatively, can by via a linker. Suitable binding pairs for use in indirectly linking the fluorescent label to the intermediate include, but are not limited to, antigens/antibodies, e.g., rhodamine/anti-rhodamine, biotin/avidin and biotin/strepavidin.

The coupling of antibodies to low molecular weight haptens can increase the sensitivity of the antibody in an assay. The haptens can then be specifically detected by means of a second reaction. For example, it is common to use haptens such as biotin, which reacts avidin, or dinitrophenol, pyridoxal, and fluorescein, which can react with specific anti-hapten antibodies. See, Harlow and Lane (1988) supra.

The variable region of an antibody can be modified by mutating amino acid residues within the VH and/or VL CDR 1, CDR 2 and/or CDR 3 regions to improve one or more binding properties (e.g., affinity) of the antibody. Mutations may be introduced by site-directed mutagenesis or PCR-mediated mutagenesis and the effect on antibody binding, or other functional property of interest, can be evaluated in appropriate in vitro or in vivo assays. Preferably conservative modifications are introduced and typically no more than one, two, three, four or five residues within a CDR region are altered. The mutations may be amino acid substitutions, additions or deletions.

Framework modifications can be made to the antibodies to decrease immunogenicity, for example, by "backmutating" one or more framework residues to the corresponding germline sequence.

In addition, an antibody may be engineered to include modifications within the Fc region to alter one or more functional properties of the antibody, such as serum half-fife, complement fixation, Fc receptor binding, and/or antigen-dependent cellular cytotoxicity. Such modifications include, but are not limited to, alterations of the number of cysteine residues in the hinge region to facilitate assembly of the light and heavy chains or to increase or decrease the stability of the antibody (U.S. Pat. No. 5,677,425) and amino acid mutations in the Fc hinge region to decrease die biological half life of the antibody (U.S. Pat. No. 6,165,745).

Additionally, one or more antibodies may be chemically modified. Glycosylation of an antibody can be altered, for example, by modifying one or more sites of glycosylation within the antibody sequence to increase the affinity of the antibody for antigen (U.S. Pat. Nos. 5,714,350 and 6,350,861). Alternatively, to increase antibody-dependent cell-mediated cytotoxicity, a hypofucosylated antibody having reduced amounts of fucosyl residues or an antibody having increased bisecting GlcNac structures can be obtained by expressing the antibody in a host cell.sub.—with altered glycosylation mechanism (Shields, R. L. et al., 2002 J. Biol. Chem. 277:26733-26740; Umana et al., 1999 Nat. Biotech. 17:176-180).

Antibodies can be pegylated to increase biological half-life by reacting the antibody or fragment thereof with polyethylene glycol (PEG) or a reactive ester or aldehyde derivative of PEG, under conditions in which one or more PEG groups become attached to the antibody or antibody fragment. Antibody pegylation may be carried out by an acylation reaction or an alkylation reaction with a reactive PEG molecule (or an analogous reactive watersoluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. The antibody to be pegylated can be an aglycosylated antibody. Methods for pegylating proteins are known in the art and can be applied to one or more antibodies (EP 0 154 316 and EP 0 401 384).

Additionally, antibodies may be chemically modified by conjugating or fusing the antigen-binding region of the antibody to serum protein, such as human serum albumin, to increase half-life of the resulting molecule. Such approach is for example described in EP 0322094 and EP 0 486 525.

The antibodies or fragments thereof may be conjugated to a diagnostic agent and used diagnostically, for example, to monitor the development or progression of a disease and determine the efficacy of a given treatment regimen. Examples of diagnostic agents include enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody or fragment thereof, or indirectly, through a 1 inker using techniques known in the art. Examples of suitable enzymes include horseradish peroxidase, alkaline phosphatase, beta-galactosidase, or acetylcholinesterase. Examples of suitable prosthetic group complexes include streptavidin/biotin and avidin/biotin. Examples of suitable fluorescent materials include umbelliferone, fluorescein, fluorescein isothiocyanate, rhodamine, dichlorotriazinylamine fluorescein, dansyl chloride or phycoerythrin. An example of a luminescent material includes luminol. Examples of bioluminescent materials include luciferase, luciferin, and aequorin. Examples of suitable radioactive material include.sup.125I, .sup.131I, Indium-111, Lutetium-171, Bismuth-212, Bismuth-213, Astatine-211, Copper-62, Copper-64, Copper-67, Yttrium-90, Iodine-125, Iodine-131, Phosphorus-32, Phosphorus-33, Scandium-47, Silver-111, Gallium-67, Praseodymium-142, Samarium-153, Terbium-161, Dysprosium-166, Holmium-166, Rhenium-186, Ithenium-188, Rhenium-189, Lead-212, Radium-223, Actinium-225, Iron-59, Selenium-75, Arsenic-77, Strontium-89, Molybdenum-99, Rhodium-1105, Palladium-109, Praseodymium-143, Promethium-149, Erbium-169, Iridium-194, Gold-198, Gold-199, and Lead-211. Monoclonal antibodies may be indirectly conjugated with radiometal ions through the use of bifunctional chelating agents that are covalently linked to the antibodies. Chelating agents may be attached through amities (Meares et al., 1984 Anal. Biochem. 142: 68-78); sulfhydral groups (Koyama 1994 Chem. Abstr. 120: 217262t) of amino acid residues and carbohydrate groups (Rodwell et al. 1986 PNAS USA 83: 2632-2636; Quadri et al. 1993 Nucl. Med. Biol. 20: 559-570).

Additional suitable conjugated molecules include ribonuclease (RNase), DNase I, an antisense nucleic acid, an inhibitory RNA molecule such as a siRNA molecule, an immunostimulatory nucleic acid, aptamers, ribozymes, triplex forming molecules, and external guide sequences. Aptamers are small nucleic acids ranging from 15-50 bases in length that fold into defined secondary and tertiary structures, such as stern-loops or G-quartets, and can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Ribozymes are nucleic acid molecules that are capable of catalyzing a chemical reaction, either intramolecularly or intermolecularly. Ribozymes typically cleave nucleic acid substrates through recognition and binding of the target substrate with subsequent cleavage. Triplex forming function nucleic acid molecules can interact with double-stranded or single-stranded nucleic acid by forming a triplex, in which three strands of DNA form a complex dependant on both Watson-Crick and Hoogsteen base-pairing. Triplex molecules can bind target regions with high affinity and specificity.

The functional nucleic acid molecules may act as effectors, inhibitors, modulators, and stimulators of a specific activity possessed by a target molecule, or the functional nucleic acid molecules may possess a de novo activity independent of any other molecules. In one embodiment, the antibody is a stimulator of dendritic cells The conjugated agents can be linked to the antibody directly or indirectly, using any of a large number of available methods. For example, an agent can be attached at the hinge region of the reduced antibody component via disulfide bond formation, using cross-linkers such as N-succinyl 3-(2-pyridyldithio)proprionate (SPDP), or via a carbohydrate moiety in the Fc region of the antibody (Yu et al. 1994 Int. J. Cancer 56: 244; Upeslacis et al., "Modification of Antibodies by Chemical Methods," in Monoclonal antibodies: principles and applications, Birch et al. (eds.), pages 187-230 (Wiley-Liss, Inc. 1995); Price, "Production and Characterization of Synthetic Peptide-Derived Antibodies," in Monoclonal antibodies: Production, engineering and clinical application, Ritter et al. (eds.), pages 60-84 (Cambridge University Press 1995)).

Techniques for conjugating agents to antibodies are well known (Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al, (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeted Antibody in Cancer Therapy", in Monoclonal Antibodies For Cancer Detection And Therapy, Baldwin et al. (eds.), pp. 303-16 (Academic Press 1985), and Thorpe et al., The Preparation And Cytotoxic Properties Of Antibody-Toxin Conjugates" 1982 Immunol. Rev. 62:119-58), Antibodies or antigen-binding regions thereof can be linked to another functional molecule such as another antibody or ligand for a receptor to generate a bi-specific or multi-specific molecule that binds to at least two or more different binding sites or target molecules. Linking of the antibody to one or more other binding molecules, such as another antibody, antibody fragment, peptide or binding mimetic, can be done, for example, by chemical coupling, genetic fusion, or noncovalent association. Multi-specific molecules can further include a third binding specificity, in addition to the first and second target epitope.

Bi-specific and multi-specific molecules can be prepared using methods known in the art. For example, each binding unit of the hi-specific molecule can be generated separately and then conjugated to one another. When the binding molecules are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitroberizoic acid) (DTNB), o-phenylenedimaleimide (oRDM), N-succinimidyl-3-(2-pyridyldithio) propionate (SPDP), and sulfosuccinimidyl 4-(N-maleimidomethyl)cyclohaxane-I-carboxylate (sulfo-SMCC) (Karpovsky et al., 1984 J. Exp. Med. 160:1686; Liu et al., 1985 Proc. Natl. Acad. Sci. USA 82:8648). When the binding molecules are antibodies, they can be conjugated by sulfhydryl bonding of the C-terminus hinge regions of the two heavy chains.

The antibodies or fragments thereof may be linked to a moiety that is toxic to a cell to which the antibody is bound to form "depleting" antibodies. These antibodies are particularly useful in applications where it is desired to deplete an NK cell.

The antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

The antibodies also can be bound to many different carriers. Thus, compositions are also provided containing the antibodies and another substance, active or inert. Examples of well-known carriers include glass, polystyrene, polypropylene, polyethylene, dextran, nylon, amylase, natural and modified cellulose, polyacrylamide, agarose, and magnetite. The nature of the carrier can be either soluble or insoluble for purposes of embodiments described herein. Those skilled in the art will know of other suitable carriers for binding monoclonal antibodies, or will be able to ascertain such, using routine experimentation.

II. CONSTRUCTS

All examples of H chain constructs are typically used in co-transfection of CHO cells with matching L chain vectors. Also, in some embodiments immunotherapeutics will have humanized variable regions.

The following depicts APC-targeted antibodies and antibody-IL10 fusion proteins useful in the methods and compositions described herein.

Anti-ASGPR-49C11-hIL-10

SEQ ID NO:1 shows a fusion protein of the heavy chain of the anti-ASGPR 49C11 antibody fused through a linker to human IL-10. The linker is underlined and the IL-10 amino acid sequence is in bold italics.

mAnti-ASGPR_49C11_7H-LV-hIgG4H-C-Flex-v1-hIL-10]antibody, SEQ ID NO:1:

```
                                                 (SEQ ID NO: 1)
VQLQESGPDLVKPSQSLSLTCTVTGYSITSGYSWHWIRQFPGNKLEWMGY

ILFSGSTNYNPSLKSRISITRDTSKNQFFLQLNSVTTEDTATYFCARSNY

GSFASWGQGTLVTVSAAKTTGPSVFPLAPCSRSTSESTAALGCLVKDYFP

EPVTVSWNSGALTSGVHTFPAVLQSSGLYSLSSVVTVPSSSLGTKTYTCN

VDHKPSNTKVDKRVESKYGPPCPPCPAPEFEGGPSVFLFPPKPKDTLMIS

RTPEVTCVVVDVSQEDPEVQFNWYVDGVEVHNAKTKPREEQFNSTYRVVS

VLTVLHQDWLNGKEYKCKVSNKGLPSSIEKTISKAKGQPREPQVYTLPPS

QEEMTKNQVSLTCLVKGFYPSDIAVEWESNGQPENNYKTTPPVLDSDGSF

FLYSRLTVDKSRWQEGNVFSCSVMHEALHNHYTQKSLSLSLGKASQTPTN

TISVTPTNNSTPTNNSNPKPNPASPGQGTQSENSCTHFPGNLPNMLRDLRDA

FSRVKTFFQMKDQLDNLLLKESLLEDFKGYLGCQALSEMIQF
```

YLEEVMPQAENQDPDIKAHVNSLGENLKTLRLRLRRCHRFLPCENKSKAVEQVKNA

FNKLQEKGIYKAMSEFDIFINYIEAYMTMKIRN.

The heavy chain of the anti-ASGPR 49C11 antibody from above is SEQ ID NO:2:

```
                                                 (SEQ ID NO: 2)
VQLQESGPDLVKPSQSLSLTCTVTGYSITSGYSWHWIRQFPGNKLEWMGY

ILFSGSTNYNPSLKSRISITRDTSKNQFFLQLNSVTTEDTATYFCARSNY

GSFASWGQGTLVTVSAAKTTGPSVFPLAPCSRSTSESTAALGCLVKDYFP

EPVTVSWNSGALTSGVHTFPAVLQSSGLYSLSSVVTVPSSSLGTKTYTCN

VDHKPSNTKVDKRVESKYGPPCPPCPAPEFEGGPSVFLFPPKPKDTLMIS

RTPEVTCVVVDVSQEDPEVQFNWYVDGVEVHNAKTKPREEQFNSTYRVVS

VLTVLHQDWLNGKEYKCKVSNKGLPSSIEKTISKAKGQPREPQVYTLPPS

QEEMTKNQVSLTCLVKGFYPSDIAVEWESNGQPENNYKTTPPVLDSDGSF

FLYSRLTVDKSRWQEGNVFSCSVMHEALHNHYTQKSLSLSLGKAS.
```

The H chain variable region of anti-ASGPR 49C11 is shown in SEQ ID NO.:3:

```
                                                 (SEQ ID NO: 3)
QLQESGPDLVKPSQSLSLTCTVTGYSITSGYSWHWIRQFPGNKLEWMGYI

LFSGSTNYNPSLKSRISITRDTSKNQFFLQLNSVTTEDTATYFCARSNYG

SFASWGQGTLVTVSAAKTT.
```

The linker shown above is SEQ ID NO:4:

```
                                                 (SEQ ID NO: 4)
QTPTNTISVTPTNNSTPTNNSNPKPNP.
```

The hIL-10 amino acid sequence from the Anti-ASGPR-49C11-hIL-10 is shown in SEQ ID NO:5:

```
                                                 (SEQ ID NO: 5)
ASPGQGTQSENSCTHFPGNLPNMLRDLRDAFSRVKTFFQMKDQLDNLLLK

ESLLEDFKGYLGCQALSEMIQFYLEEVMPQAENQDPDIKAHVNSLGENLK

TLRLRLRRCHRFLPCENKSKAVEQVKNAFNKLQEKGIYKAMSEFDIFINY

IEAYMTMKIRN.
```

The DNA sequence of the mAnti-ASGPR_49C11_7H-LV-hIgG4H-C-Flex-v1-hIL-10 antibody is shown in SEQ ID NO:6:

```
                                                 (SEQ ID NO: 6)
ATGAGAGCGCTGATTCTTTTGTGCCTGTTCACAGCCTTTCCTGGTATCCT

GTCTGATGTGCAGCTTCAGGAGTCAGGACCTGACCTGGTGAAACCTTCTC

AGTCACTTTCACTCACCTGCACTGTCACTGGCTACTCCATCACCAGTGGT

TATAGCTGGCACTGGATCCGGCAGTTTCCAGGAAACAAACTGGAATGGAT

GGGCTACATACTCTTCAGTGGTAGCACTAACTACAACCCATCTCTGAAAA

GTCGAATCTCTATCACTCGAGACACATCCAAGAACCAGTTCTTCCTGCAG

TTGAATTCTGTGACTACTGAGGACACAGCCACATATTTCTGTGCAAGATC

TAACTATGGTTCCTTTGCTTCCTGGGGCCAAGGGACTCTGGTCACTGTCT
```

-continued

```
CTGCAGCCAAAACAACGGGCCCATCCGTCTTCCCCCTGGCGCCCTGCTCC

AGGAGCACCTCCGAGAGCACAGCCGCCCTGGGCTGCCTGGTCAAGGACTA

CTTCCCCGAACCGGTGACGGTGTCGTGGAACTCAGGCGCCCTGACCAGCG

GCGTGCACACCTTCCCGGCTGTCCTACAGTCCTCAGGACTCTACTCCCTC

AGCAGCGTGGTGACCGTGCCCTCCAGCAGCTTGGGCACGAAGACCTACAC

CTGCAACGTAGATCACAAGCCCAGCAACACCAAGGTGGACAAGAGAGTTG

AGTCCAAATATGGTCCCCCATGCCCACCCTGCCCAGCACCTGAGTTCGAA

GGGGGACCATCAGTCTTCCTGTTCCCCCCAAAACCCAAGGACACTCTCAT

GATCTCCCGGACCCCTGAGGTCACGTGCGTGGTGGTGGACGTGAGCCAGG

AAGACCCCGAGGTCCAGTTCAACTGGTACGTGGATGGCGTGGAGGTGCAT

AATGCCAAGACAAAGCCGCGGGAGGAGCAGTTCAACAGCACGTACCGTGT

GGTCAGCGTCCTCACCGTCCTGCACCAGGACTGGCTGAACGGCAAGGAGT

ACAAGTGCAAGGTCTCCAACAAAGGCCTCCCGTCCTCCATCGAGAAAACC

ATCTCCAAAGCCAAAGGGCAGCCCCGAGAGCCACAGGTGTACACCCTGCC

CCCATCCCAGGAGGAGATGACCAAGAACCAGGTCAGCCTGACCTGCCTGG

TCAAAGGCTTCTACCCCAGCGACATCGCCGTGGAGTGGGAGAGCAATGGG

CAGCCGGAGAACAACTACAAGACCACGCCTCCCGTGCTGGACTCCGACGG

CTCCTTCTTCCTCTACAGCAGGCTAACCGTGGACAAGAGCAGGTGGCAGG

AGGGGAATGTCTTCTCATGCTCCGTGATGCATGAGGCTCTGCACAACCAC

TACACACAGAAGAGCCTCTCCCTGTCTCTGGGTAAAGCTAGTCAGACCCC

CACCAACACCATCAGCGTGACCCCCACCAACAACAGCACCCCCACCAACA

ACAGCAACCCCAAGCCCAACCCCGCTAGCCCAGGCCAGGGCACCCAGTCT

GAGAACAGCTGCACCCACTTCCCAGGCAACCTGCCTAACATGCTTCGAGA

TCTCCGAGATGCCTTCAGCAGAGTGAAGACTTTCTTTCAAATGAAGGATC

AGCTGGACAACTTGTTGTTAAAGGAGTCCTTGCTGGAGGACTTTAAGGGT

TACCTGGGTTGCCAAGCCTTGTCTGAGATGATCCAGTTTTACCTGGAGGA

GGTGATGCCCCAAGCTGAGAACCAAGACCCAGACATCAAGGCGCATGTGA

ACTCCCTGGGGGAGAACCTGAAGACCCTCAGGCTGAGGCTACGGCGCTGT

CATCGATTTCTTCCCTGTGAAAACAAGAGCAAGGCCGTGGAGCAGGTGAA

GAATGCCTTTAATAAGCTCCAAGAGAAAGGCATCTACAAAGCCATGAGTG

AGTTTGACATCTTCATCAACTACATAGAAGCCTACATGACAATGAAGATA

CGAAACTGA.
```

The corresponding light chain amino acid sequence, mAnti-ASGPR_49C11_7K-LV-hIgGK-C, is shown in SEQ ID NO:7:

(SEQ ID NO: 7)
QIVLTQSPAIMSASPGEKVTMTCSASSSVSHMHWYQQKSGTSPKRWIYD

TSRLASGVPARFSGSGSGTSYSLTISSMEAEDAATYYCQQWSSHPWSFG

GGTKLEIKRTVAAPSVFIFPPSDEQLKSGTASVVCLLNNFYPREAKVQW

KVDNALQSGNSQESVTEQDSKDSTYSLSSTLTLSKADYEKHKVYACEVT

HQGLSSPVTKSFNRGEC.

The L chain variable region of anti-ASGPR 49C11 is shown in SEQ ID NO.:8:

(SEQ ID NO: 8)
QIVLTQSPAIMSASPGEKVTMTCSASSSVSHMHWYQQKSGTSPKRWIYD

TSRLASGVPARFSGSGSGTSYSLTISSMEAEDAATYYCQQWSSHPWSFG

GGTKLE

The DNA sequence of mAnti-ASGPR_49C11_7K-LV-hIgGK-C is shown in SEQ ID NO:9:

(SEQ ID NO: 9)
ATGGATTTTCAAGTGCAGATTTTCAGCTTCCTGCTAATCAGTGCCTCAGT

CATAATATCCAGAGGACAAATTGTTCTCACCCAGTCTCCAGCAATCATGT

CTGCATCTCCAGGGGAGAAGGTCACCATGACCTGCAGTGCCAGCTCAAGT

GTAAGTCACATGCACTGGTACCAGCAGAAGTCAGGCACTTCCCCCAAAAG

ATGGATTTATGACACATCCAGACTGGCTTCTGGAGTCCCTGCTCGCTTCA

GTGGCAGTGGGTCTGGGACCTCTTACTCTCTCACAATCAGCAGCATGGAG

GCTGAAGATGCTGCCACTTATTACTGCCAGCAGTGGAGTAGTCACCCATG

GTCGTTCGGTGGAGGCACCAAACTCGAGATCAAACGAACTGTGGCTGCAC

CATCTGTCTTCATCTTCCCGCCATCTGATGAGCAGTTGAAATCTGGAACT

GCCTCTGTTGTGTGCCTGCTGAATAACTTCTATCCCAGAGAGGCCAAAGT

ACAGTGGAAGGTGGATAACGCCCTCCAATCGGGTAACTCCCAGGAGAGTG

TCACAGAGCAGGACAGCAAGGACAGCACCTACAGCCTCAGCAGCACCCTG

ACGCTGAGCAAAGCAGACTACGAGAAACACAAAGTCTATGCCTGCGAAGT

CACCCATCAGGGCCTGAGCTCGCCCGTCACAAAGAGCTTCAACAGGGGAG

AGTGTTAG.

Anti-CD40-24A3-hIL-10

SEQ ID NO:10 shows a fusion protein of the heavy chain of the anti-CD40 24A3 antibody fused through a linker to human IL-10. The linker is underlined and the IL-10 amino acid sequence is in bold italics.

manti-hCD40_24A3.3F1_H-LV-hIgG4H-C-Flex-v1-hIL-10 antibody, SEQ ID NO:10:

(SEQ ID NO: 10)
VQLQESGPDLVKPSQSLSLTCTVTGYSITSDYSWHWIRQFPGNKLEWMG

YIYYSGSTNYNPSLKSRISITRDTSKNQFFLQLNSVTTEDSATYFCARF

YYGYSFFDYWGQGTTLTVSSAKTKGPSVFPLAPCSRSTSESTAALGCLV

KDYFPEPVTVSWNSGALTSGVHTFPAVLQSSGLYSLSSVVTVPSSSLGT

KTYTCNVDHKPSNTKVDKRVESKYGPPCPPCPAPEFEGGPSVFLFPPKP

KDTLMISRTPEVTCVVVDVSQEDPEVQFNWYVDGVEVHNAKTKPREEQF

NSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTT

PPVLDSDGSFFLYSRLTVDKSRWQEGNVFSCSVMHEALHNHYTQKSLSL

SLGKASQTPTNTISVTPTNNSTPTNNSNPKPNP*ASPGQGTQSENSCTH*

*FPGNLPNMLRDLRDAFSRVKTFFQMKDQLDNLLLKESLLEDFKGYLGCQALSEMIQF*

*YLEEVMPQAENQDPDIKAHVNSLGENLKTLRLRLRRCHRFLPCENKSKAVEQVKN*

*AFNKLQEKGIYKAMSEFDIFINYIEAYMTMKIRN*

The heavy chain of the anti-CD40 24A3 antibody from above is SEQ ID NO:11:

(SEQ ID NO: 11)
VQLQESGPDLVKPSQSLSLTCTVTGYSITSDYSWHWIRQFPGNKLEWMGY
IYYSGSTNYNPSLKSRISITRDTSKNQFFLQLNSVTTEDSATYFCARFYY
GYSFFDYWGQGTTLTVSSAKTKGPVFPLAPCSRSTSESTAALGCLVKDYF
PEPVTVSWNSGALTSGVHTFPAVLQSSGLYSLSSVVTVPSSSLGTKTYTC
NVDHKPSNTKVDKRVESKYGPPCPPCPAPEFEGGPSVFLFPPKPKDTLMI
SRTPEVTCVVVDVSQEDPEVQFNWYVDGVEVHNAKTKPREEQFNSTYRVV
SVLTVLHQDWLNGKEYKCKVSNKGLPSSIEKTISKAKGQPREPQVYTLPP
SQEEMTKNQVSLTCLVKGFYPSDIAVEWESNGQPENNYKTTPPVLDSDGS
FFLYSRLTVDKSRWQEGNVFSCSVMHEALHNHYTQKSLSLSLGKAS.

The linker shown above is SEQ ID NO:4 and the IL-10 amino acid sequence is shown as SEQ ID NO:5.

The DNA sequence of the manti-hCD40_24A3.3F1_H-LV-hIgG4H-C-Flex-v1-hIL-10 antibody is shown in SEQ ID NO:12:

(SEQ ID NO: 12)
ATGAGAGTGCTGATTCTTTTGTGCCTGTTCACAGCCTTTCCTGGTATCCT
GTCTGATGTGCAGCTTCAGGAGTCAGGACCTGACCTGGTGAAACCTTCTC
AGTCACTTTCACTCACCTGCACTGTCACTGGCTACTCCATCACCAGTGAT
TATAGCTGGCACTGGATCCGGCAGTTCCCAGGAAACAAACTGGAATGGAT
GGGCTACATATATTACAGTGGTAGCACTAACTACAACCCATCTCTCAAAA
GTCGAATCTCTATCACTCGAGACACATCCAAGAACCAGTTCTTCCTGCAG
TTGAATTCTGTGACTACTGAGGACTCAGCCACATATTTCTGTGCAAGATT
TTACTACGGTTATAGCTTCTTTGACTACTGGGGCCAAGGCACCACTCTCA
CAGTCTCCTCAGCCAAAACAAAGGGCCCATCCGTCTTCCCCCTGGCGCCC
TGCTCCAGGAGCACCTCCGAGAGCACAGCCGCCCTGGGCTGCCTGGTCAA
GGACTACTTCCCCGAACCGGTGACGGTGTCGTGGAACTCAGGCGCCCTGA
CCAGCGGCGTGCACACCTTCCCGGCTGTCCTACAGTCCTCAGGACTCTAC
TCCCTCAGCAGCGTGGTGACCGTGCCCTCCAGCAGCTTGGGCACGAAGAC
CTACACCTGCAACGTAGATCACAAGCCCAGCAACACCAAGGTGGACAAGA
GAGTTGAGTCCAAATATGGTCCCCCATGCCCACCCTGCCCAGCACCTGAG
TTCGAAGGGGGACCATCAGTCTTCCTGTTCCCCCCAAAACCCAAGGACAC
TCTCATGATCTCCCGGACCCCTGAGGTCACGTGCGTGGTGGTGGACGTGA
GCCAGGAAGACCCCGAGGTCCAGTTCAACTGGTACGTGGATGGCGTGGAG
GTGCATAATGCCAAGACAAAGCCGCGGGAGGAGCAGTTCAACAGCACGTA
CCGTGTGGTCAGCGTCCTCACCGTCCTGCACCAGGACTGGCTGAACGGCA
AGGAGTACAAGTGCAAGGTCTCCAACAAAGGCCTCCCGTCCTCCATCGAG
AAAACCATCTCCAAAGCCAAAGGGCAGCCCCGAGAGCCACAGGTGTACAC
CCTGCCCCCATCCCAGGAGGAGATGACCAAGAACCAGGTCAGCCTGACCT
GCCTGGTCAAAGGCTTCTACCCCAGCGACATCGCCGTGGAGTGGGAGAGC
AATGGGCAGCCGGAGAACAACTACAAGACCACGCCTCCCGTGCTGGACTC
CGACGGCTCCTTCTTCCTCTACAGCAGGCTAACCGTGGACAAGAGCAGGT
GGCAGGAGGGGAATGTCTTCTCATGCTCCGTGATGCATGAGGCTCTGCAC
AACCACTACACACAGAAGAGCCTCTCCCTGTCTCTGGGTAAAGCTAGTCA
GACCCCCACCAACACCATCAGCGTGACCCCCACCAACAACAGCACCCCCA
CCAACAACAGCAACCCCAAGCCCAACCCCGCTAGCCCAGGCCAGGGCACC
CAGTCTGAGAACAGCTGCACCCACTTCCCAGGCAACCTGCCTAACATGCT
TCGAGATCTCCGAGATGCCTTCAGCAGAGTGAAGACTTTCTTTCAAATGA
AGGATCAGCTGGACAACTTGTTGTTAAAGGAGTCCTTGCTGGAGGACTTT
AAGGGTTACCTGGGTTGCCAAGCCTTGTCTGAGATGATCCAGTTTTACCT
GGAGGAGGTGATGCCCCAAGCTGAGAACCAAGACCCAGACATCAAGGCGC
ATGTGAACTCCCTGGGGGAGAACCTGAAGACCCTCAGGCTGAGGCTACGG
CGCTGTCATCGATTTCTTCCCTGTGAAAACAAGAGCAAGGCCGTGGAGCA
GGTGAAGAATGCCTTTAATAAGCTCCAAGAGAAAGGCATCTACAAAGCCA
TGAGTGAGTTTGACATCTTCATCAACTACATAGAAGCCTACATGACAATG
AAGATACGAAACTGA.

The corresponding light chain amino acid sequence, manti-hCD40_24A3.3F1_K-LV-hIgGK-C, is shown in SEQ ID NO:13:

(SEQ ID NO: 13)
QIVLTQSPAFMSASPGEKVTMTCSASSSVSYMHWYQQKSGTSPKRWIYDT
SKLASGVPARFSGSGSGTSYSLTISSMEAEDAATYYCQQWSSNPLTFGAG
TKLEIKRTVAAPSVFIFPPSDEQLKSGTASVVCLLNNFYPREAKVQWKVD
NALQSGNSQESVTEQDSKDSTYSLSSTLTLSKADYEKHKVYACEVTHQGL
SSPVTKSFNRGECAS.

The DNA sequence of manti-hCD40_24A3.3F1_K-LV-hIgGK-C is shown in SEQ ID NO:14:

(SEQ ID NO: 14)
ATGGATTTTCAAGTGCAGATTTTCAGCTTCCTGCTAATCAGTGCCTCAG
TCATAGTATCCAGAGGACAAATTGTTCTCACCCAGTCTCCAGCATTCAT
GTCTGCATCTCCAGGGGAGAAGGTCACCATGACCTGCAGTGCCAGCTCA
AGTGTCAGTTACATGCACTGGTACCAGCAGAAGTCAGGCACCTCCCCCA
AAAGATGGATTTATGACACATCCAAACTGGCTTCTGGAGTCCCTGCTCG
CTTCAGTGGCAGTGGGTCTGGGACCTCTTACTCTCTCACAATCAGCAGC
ATGGAGGCTGAAGATGCTGCCACTTATTACTGCCAGCAGTGGAGTAGTA
ACCCACTCACGTTCGGTGCTGGGACCAAGCTCGAGATCAAACGAACTGT
GGCTGCACCATCTGTCTTCATCTTCCCGCCATCTGATGAGCAGTTGAAA
TCTGGAACTGCCTCTGTTGTGTGCCTGCTGAATAACTTCTATCCCAGAG
AGGCCAAAGTACAGTGGAAGGTGGATAACGCCCTCCAATCGGGTAACTC
CCAGGAGAGTGTCACAGAGCAGGACAGCAAGGACAGCACCTACAGCCTC
AGCAGCACCCTGACGCTGAGCAAAGCAGACTACGAGAAACACAAAGTCT

```
ATGCCTGCGAAGTCACCCATCAGGGCCTGAGCTCGCCCGTCACAAAGAG

CTTCAACAGGGGAGAGTGTGCTAGCTAG.
```

Anti-DCIR-9E8-hIL-10

SEQ ID NO:15 shows a fusion protein of the heavy chain of the anti-DCIR 9E8 antibody fused through a linker to human IL-10. The linker is underlined and the IL-10 amino acid sequence is in bold italics.

mAnti-DCIR_9E8_H-LV-hIgG4H-C-<u>Flex-v1</u>-hIL-10 antibody, SEQ ID NO:15:

```
                                          (SEQ ID NO: 15)
QVTLKESGPGILQPSQTLSLTCSFSGFSLSTSGMGLSWIRQPSGKGLEWL

AHIYWDDDKRYNPSLKSRLTISKDTSSNQVFLKITIVDTADAATYYCARS

SHYYGYGYGGYFDVWGAGTTVTVSSAKTKGPSVFPLAPCSRSTSESTAAL

GCLVKDYFPEPVTVSWNSGALTSGVHTFPAVLQSSGLYSLSSVVTVPSSS

LGTKTYTCNVDHKPSNTKVDKRVESKYGPPCPPCPAPEFEGGPSVFLFPP

KPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSL

GKAS<u>QTPTNTISVTPTNNSTPTNNSNPKPNP</u>*ASPGQGTQSENSCTH*

*FPGNLPNMLRDLRDAFSRVKTFFQMKDQLDNLLLKESLLEDFKGYLG*

*CQALSEMIQFYLEEVMPQAENQDPDIKAHVNSLGENLKTLRLRLRRCHRFLPCENKS*

*KAVEQVKNAFNKLQEKGIYKAMSEFDIFINYIEAYMTMKIRN*
```

The heavy chain of the anti-DCIR 9E8 antibody from above is SEQ ID NO:16:

```
                                          (SEQ ID NO: 16)
QVTLKESGPGILQPSQTLSLTCSFSGFSLSTSGMGLSWIRQPSGKGLEWL

AHIYWDDDKRYNPSLKSRLTISKDTSSNQVFLKITIVDTADAATYYCARS

SHYYGYGYGGYFDVWGAGTTVTVSSAKTKGPSVFPLAPCSRSTSESTAAL

GCLVKDYFPEPVTVSWNSGALTSGVHTFPAVLQSSGLYSLSSVVTVPSSS

LGTKTYTCNVDHKPSNTKVDKRVESKYGPPCPPCPAPEFEGGPSVFLFPP

KPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSL

GKAS.
```

The H chain variable region of anti-DCIR 9E8 is shown in SEQ ID NO.:17:

```
QVTLKESGPGILQPSQTLSLTCSFSGFSLSTSGMGLSWIRQPSGKGLEWL

AHIYWDDDKRYNPSLKSRLTISKDTSSNQVFLKITIVDTADAATYYCARS

SHYYGYGYGGYFDVWGAGTTVTVS.
```

The linker shown above is SEQ ID NO:18:

```
                                          (SEQ ID NO: 18)
QTPTNTISVTPTNNSTPTNNSNPKPNP.
```

The IL-10 amino acid sequence is shown as SEQ ID NO:19:

```
                                          (SEQ ID NO: 19)
ASPGQGTQSENSCTHFPGNLPNMLRDLRDAFSRVKTFFQMKDQLDNLLLK

ESLLEDFKGYLGCQALSEMIQFYLEEVMPQAENQDPDIKAHVNSLGENLK

TLRLRLRRCHRFLPCENKSKAVEQVKNAFNKLQEKGIYKAMSEFDIFINY

IEAYMTMKIRN.
```

The corresponding DNA sequence for the IL-10 gene is shown as SEQ ID NO:20:

```
                                          (SEQ ID NO: 20)
CGCTAGCCCAGGCCAGGGCACCCAGTCTGAGAACAGCTGCACCCACTTCC

CAGGCAACCTGCCTAACATGCTTCGAGATCTCCGAGATGCCTTCAGCAGA

GTGAAGACTTTCTTTCAAATGAAGGATCAGCTGGACAACTTGTTGTTAAA

GGAGTCCTTGCTGGAGGACTTTAAGGGTTACCTGGGTTGCCAAGCCTTGT

CTGAGATGATCCAGTTTTACCTGGAGGAGGTGATGCCCCAAGCTGAGAAC

CAAGACCCAGACATCAAGGCGCATGTGAACTCCCTGGGGGAGAACCTGAA

GACCCTCAGGCTGAGGCTACGGCGCTGTCATCGATTTCTTCCCTGTGAAA

ACAAGAGCAAGGCCGTGGAGCAGGTGAAGAATGCCTTTAATAAGCTCCAA

GAGAAAGGCATCTACAAAGCCATGAGTGAGTTTGACATCTTCATCAACTA

CATAGAAGCCTACATGACAATGAAGATACGAAACTGA.
```

The DNA sequence of mAnti-DCIR_9E8_H-LV-hIgG4H-C-<u>Flex-v1</u>-hIL-10 antibody is shown in SEQ ID NO:21:

```
                                          (SEQ ID NO: 21)
ATGAACAGGCTTACTTCCTCATTGCTGCTGCTGATTGTCCCTGCATATGT

CCTGTCCCAGGTTACTCTGAAAGAGTCTGGCCCTGGGATATTGCAGCCCT

CCCAGACCCTCAGTCTGACTTGTTCTTTCTCTGGGTTTTCACTGAGCACT

TCTGGTATGGGTCTGAGCTGGATTCGTCAGCCTTCAGGAAAGGGTCTGGA

GTGGCTGGCACACATTTACTGGGATGATGACAAGCGCTATAACCCATCCC

TGAAGAGCCGGCTCACAATCTCCAAGGATACCTCCAGCAACCAGGTTTTC

CTCAAGATCACCATTGTGGACACTGCAGATGCTGCCACATACTACTGTGC

TCGAAGCTCCCATTACTACGGTTATGGCTACGGGGGATACTTCGATGTCT

GGGGCGCAGGGACCACGGTCACCGTCTCCTCAGCCAAAACGAAGGGCCCA

TCCGTCTTCCCCCTGGCGCCCTGCTCCAGGAGCACCTCCGAGAGCACAGC

CGCCCTGGGCTGCCTGGTCAAGGACTACTTCCCCGAACCGGTGACGGTGT

CGTGGAACTCAGGCGCCCTGACCAGCGGCGTGCACACCTTCCCGGCTGTC

CTACAGTCCTCAGGACTCTACTCCCTCAGCAGCGTGGTGACCGTGCCCTC

CAGCAGCTTGGGCACGAAGACCTACACCTGCAACGTAGATCACAAGCCCA

GCAACACCAAGGTGGACAAGAGAGTTGAGTCCAAATATGGTCCCCCATGC
```

-continued
```
CCACCCTGCCCAGCACCTGAGTTCGAAGGGGGACCATCAGTCTTCCTGTT

CCCCCCAAAACCCAAGGACACTCTCATGATCTCCCGGACCCCTGAGGTCA

CGTGCGTGGTGGTGGACGTGAGCCAGGAAGACCCCGAGGTCCAGTTCAAC

TGGTACGTGGATGGCGTGGAGGTGCATAATGCCAAGACAAAGCCGCGGGA

GGAGCAGTTCAACAGCACGTACCGTGTGGTCAGCGTCCTCACCGTCCTGC

ACCAGGACTGGCTGAACGGCAAGGAGTACAAGTGCAAGGTCTCCAACAAA

GGCCTCCCGTCCTCCATCGAGAAAACCATCTCCAAAGCCAAAGGGCAGCC

CCGAGAGCCACAGGTGTACACCCTGCCCCCATCCCAGGAGGAGATGACCA

AGAACCAGGTCAGCCTGACCTGCCTGGTCAAAGGCTTCTACCCCAGCGAC

ATCGCCGTGGAGTGGGAGAGCAATGGGCAGCCGGAGAACAACTACAAGAC

CACGCCTCCCGTGCTGGACTCCGACGGCTCCTTCTTCCTCTACAGCAGGC

TAACCGTGGACAAGAGCAGGTGGCAGGAGGGGAATGTCTTCTCATGCTCC

GTGATGCATGAGGCTCTGCACAACCACTACACACAGAAGAGCCTCTCCCT

GTCTCTGGGTAAAGCTAGTCAGACCCCCACCAACACCATCAGCGTGACCC

CCACCAACAACAGCACCCCCACCAACAACAGCAACCCCAAGCCCAACCCC

GCTAGCCCAGGCCAGGGCACCCAGTCTGAGAACAGCTGCACCCACTTCCC

AGGCAACCTGCCTAACATGCTTCGAGATCTCCGAGATGCCTTCAGCAGAG

TGAAGACTTTCTTTCAAATGAAGGATCAGCTGGACAACTTGTTGTTAAAG

GAGTCCTTGCTGGAGGACTTTAAGGGTTACCTGGGTTGCCAAGCCTTGTC

TGAGATGATCCAGTTTTACCTGGAGGAGGTGATGCCCCAAGCTGAGAACC

AAGACCCAGACATCAAGGCGCATGTGAACTCCCTGGGGGAGAACCTGAAG

ACCCTCAGGCTGAGGCTACGGCGCTGTCATCGATTTCTTCCCTGTGAAAA

CAAGAGCAAGGCCGTGGAGCAGGTGAAGAATGCCTTTAATAAGCTCCAAG

AGAAAGGCATCTACAAAGCCATGAGTGAGTTTGACATCTTCATCAACTAC

ATAGAAGCCTACATGACAATGAAGATACGAAACTGA.
```

The corresponding light chain amino acid sequence, mAnti-DCIR_9E8_K-LV-hIgGK-C, is shown in SEQ ID NO:22:

```
(SEQ ID NO: 22)
NIVLTQSPASLAVSLGQRATISCRASESIHSYGNSFLHWYQQKPGQPPKL

LIYLASNLESGVPARFSGSGSRTDFTLTIDPVEADDAATYYCQQNNEDPW

TFGGGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC.
```

The L chain variable region of anti-DCIR 9E8 is shown in SEQ ID NO.:23:

```
NIVLTQSPASLAVSLGQRATISCRASESIHSYGNSFLHWYQQKPGQPPKL

LIYLASNLESGVPARFSGSGSRTDFTLTIDPVEADDAATYYCQQNNEDPW

TFGGGTKLEIK.
```

The DNA sequence of the L chain variable region of the anti-DCIR 9E8 is shown in SEQ ID NO:24:

```
(SEQ ID NO: 24)
AACATTGTGCTGACCCAATCTCCAGCTTCTTTGGCTGTGTCTCTAGGGCA

GAGGGCCACCATATCCTGCAGAGCCAGTGAAAGTATTCATAGTTATGGCA

ATAGTTTTCTGCACTGGTACCAGCAGAAACCAGGACAGCCACCCAAACTC

CTCATCTATCTTGCATCCAACCTAGAATCTGGGGTCCCTGCCAGGTTCAG

CGGCAGTGGGTCTAGGACAGACTTCACCCTCACCATTGATCCTGTGGAGG

CTGATGATGCTGCAACCTATTACTGTCAGCAAAATAATGAGGATCCGTGG

ACGTTCGGTGGAGGCACCAAGCTCGAGATCAAA.
```

The leader sequence prior to the light chain amino acid sequence comprises: METDTLLLWVLLLWVPGSTG (SEQ ID NO:25).

The corresponding DNA sequence of the leader sequence comprises:

```
(SEQ ID NO: 26)
ATGGAGACAGACACACTCCTGCTATGGGTGCTGCTGCTCTGGGTTCCAGG

TTCCACAGGT.
```

The DNA sequence of mAnti-DCIR_9E8_K-LV-hIgGK-C is shown in SEQ ID NO:27:

```
(SEQ ID NO: 27)
ATGGAGACAGACACACTCCTGCTATGGGTGCTGCTGCTCTGGGTTCCAGG

TTCCACAGGTAACATTGTGCTGACCCAATCTCCAGCTTCTTTGGCTGTGT

CTCTAGGGCAGAGGGCCACCATATCCTGCAGAGCCAGTGAAAGTATTCAT

AGTTATGGCAATAGTTTTCTGCACTGGTACCAGCAGAAACCAGGACAGCC

ACCCAAACTCCTCATCTATCTTGCATCCAACCTAGAATCTGGGGTCCCTG

CCAGGTTCAGCGGCAGTGGGTCTAGGACAGACTTCACCCTCACCATTGAT

CCTGTGGAGGCTGATGATGCTGCAACCTATTACTGTCAGCAAAATAATGA

GGATCCGTGGACGTTCGGTGGAGGCACCAAGCTCGAGATCAAACGAACTG

TGGCTGCACCATCTGTCTTCATCTTCCCGCCATCTGATGAGCAGTTGAAA

TCTGGAACTGCCTCTGTTGTGTGCCTGCTGAATAACTTCTATCCCAGAGA

GGCCAAAGTACAGTGGAAGGTGGATAACGCCCTCCAATCGGGTAACTCCC

AGGAGAGTGTCACAGAGCAGGACAGCAAGGACAGCACCTACAGCCTCAGC

AGCACCCTGACGCTGAGCAAAGCAGACTACGAGAAACACAAAGTCTATGC

CTGCGAAGTCACCCATCAGGGCCTGAGCTCGCCCGTCACAAAGAGCTTCA

ACAGGGGAGAGTGTTAG.
```

Anti-CD40-12E12-hIL-10

SEQ ID NO:28 shows a fusion protein of the heavy chain of the anti-DCIR 9E8 antibody fused through a linker to human IL-10. The linker is underlined and the IL-10 amino acid sequence is in bold italics.

mAnti-CD40_12E12.3F3_H-LV-hIgG4H-C-Flex-v1-hIL-10 antibody, SEQ ID NO:28:

(SEQ ID NO: 28)
EVKLVESGGGLVQPGGSLKLSCATSGFTFSDYYMYWVRQTPEKRLEWVAY

INSGGGSTYYPDTVKGRFTISRDNAKNTLYLQMSRLKSEDTAMYYCARRG

LPFHAMDYWGQGTSVTVSSAKTKGPSVFPLAPCSRSTSESTAALGCLVKD

YFPEPVTVSWNSGALTSGVHTFPAVLQSSGLYSLSSVVTVPSSSLGTKTY

TCNVDHKPSNTKVDKRVESKYGPPCPPCPAPEFEGGPSVFLFPPKPKDTL

MISRTPEVTCVVVDVSQEDPEVQFNWYVDGVEVHNAKTKPREEQFNSTYR

VVSVLTVLHQDWLNGKEYKCKVSNKGLPSSIEKTISKAKGQPREPQVYTL

PPSQEEMTKNQVSLTCLVKGFYPSDIAVEWESNGQPENNYKTTPPVLDSD

GSFFLYSRLTVDKSRWQEGNVFSCSVMHEALHNHYTQKSLSLSLGKAS<u>QT</u>

<u>PTNTISVTPTNNSTPTNNSNPKPNP</u>ASPGQGTQSENSCTHF

PGNLPNMLRDLRDAFSRVKTFFQMKDQLDNLLLKESLLEDFKGYLGCQA

LSEMIQFYLEEVMPQAENQDPDIKAHVNSLGENLKTLRLRLR

RCHRFLPCENKSKAVEQVKNAFNKLQEKGIYKAMSEFDIFINYI

EAYMTMKIRN.

The heavy chain of the anti-CD40 12E12 antibody from above is SEQ ID NO:29:

(SEQ ID NO: 29)
EVKLVESGGGLVQPGGSLKLSCATSGFTFSDYYMYWVRQTPEKRLEWVAY

INSGGGSTYYPDTVKGRFTISRDNAKNTLYLQMSRLKSEDTAMYYCARRG

LPFHAMDYWGQGTSVTVSSAKTKGPSVFPLAPCSRSTSESTAALGCLVKD

YFPEPVTVSWNSGALTSGVHTFPAVLQSSGLYSLSSVVTVPSSSLGTKTY

TCNVDHKPSNTKVDKRVESKYGPPCPPCPAPEFEGGPSVFLFPPKPKDTL

MISRTPEVTCVVVDVSQEDPEVQFNWYVDGVEVHNAKTKPREEQFNSTYR

VVSVLTVLHQDWLNGKEYKCKVSNKGLPSSIEKTISKAKGQPREPQVYTL

PPSQEEMTKNQVSLTCLVKGFYPSDIAVEWESNGQPENNYKTTPPVLDSD

GSFFLYSRLTVDKSRWQEGNVFSCSVMHEALHNHYTQKSLSLSLGKAS.

The H chain variable region of anti-CD40 12E12 is shown in SEQ ID NO.:30:

EVKLVESGGGLVQPGGSLKLSCATSGFTFSDYYMYWVRQTPEKRLEWVAY

INSGGGSTYYPDTVKGRFTISRDNAKNTLYLQMSRLKSEDTAMYYCARRG

LPFHAMDYWGQGTSVTVS.

The CDRs of the The H chain variable of anti-CD40 12E12 are:

(SEQ ID NO: 31)
CDR1: SASQGISNYLN, (SEQ ID NO: 32)
CDR2: AYINSGGGSTYYPDTVK,
and (SEQ ID NO: 33)
CDR3: RRGLPFHAMD.

The linker shown above is SEQ ID NO:4 and the IL-10 amino acid sequence is shown as SEQ ID NO:5.

The DNA sequence of mAnti-CD40_12E12.3F3_H-LV-hIgG4H-C-Flex-v1-hIL-10 antibody is shown in SEQ ID NO:34:

(SEQ ID NO: 34)
ATGAACTTGGGGCTCAGCTTGATTTTCCTTGTCCTTGTTTTAAAAGGTGT

CCAGTGTGAAGTGAAGCTGGTGGAGTCTGGGGGAGGCTTAGTGCAGCCCG

GAGGGTCCCTGAAACTCTCCTGTGCAACCTCTGGATTCACTTTCAGTGAC

TATTACATGTATTGGGTTCGCCAGACTCCAGAGAAGAGGCTGGAGTGGGT

CGCATACATTAATTCTGGTGGTGGTAGCACCTATTATCCAGACACTGTAA

AGGGCCGATTCACCATCTCCAGAGACAATGCCAAGAACACCCTGTACCTG

CAAATGAGCCGGCTGAAGTCTGAGGACACAGCCATGTATTACTGTGCAAG

ACGGGGGTTACCGTTCCATGCTATGGACTATTGGGGTCAAGGAACCTCAG

TCACCGTCTCCTCAGCCAAAACGAAGGGCCCATCCGTCTTCCCCCTGGCG

CCCTGCTCCAGGAGCACCTCCGAGAGCACAGCCGCCCTGGGCTGCCTGGT

CAAGGACTACTTCCCCGAACCGGTGACGGTGTCGTGGAACTCAGGCGCCC

TGACCAGCGGCGTGCACACCTTCCCGGCTGTCCTACAGTCCTCAGGACTC

TACTCCCTCAGCAGCGTGGTGACCGTGCCCTCCAGCAGCTTGGGCACGAA

GACCTACACCTGCAACGTAGATCACAAGCCCAGCAACACCAAGGTGGACA

AGAGAGTTGAGTCCAAATATGGTCCCCCATGCCCACCCTGCCCAGCACCT

GAGTTCGAAGGGGGACCATCAGTCTTCCTGTTCCCCCCAAAACCCAAGGA

CACTCTCATGATCTCCCGGACCCCTGAGGTCACGTGCGTGGTGGTGGACG

TGAGCCAGGAAGACCCCGAGGTCCAGTTCAACTGGTACGTGGATGGCGTG

GAGGTGCATAATGCCAAGACAAAGCCGCGGGAGGAGCAGTTCAACAGCAC

GTACCGTGTGGTCAGCGTCCTCACCGTCCTGCACCAGGACTGGCTGAACG

GCAAGGAGTACAAGTGCAAGGTCTCCAACAAAGGCCTCCCGTCCTCCATC

GAGAAAACCATCTCCAAAGCCAAAGGGCAGCCCCGAGAGCCACAGGTGTA

CACCCTGCCCCCATCCCAGGAGGAGATGACCAAGAACCAGGTCAGCCTGA

CCTGCCTGGTCAAAGGCTTCTACCCCAGCGACATCGCCGTGGAGTGGGAG

AGCAATGGGCAGCCGGAGAACAACTACAAGACCACGCCTCCCGTGCTGGA

CTCCGACGGCTCCTTCTTCCTCTACAGCAGGCTAACCGTGGACAAGAGCA

GGTGGCAGGAGGGGAATGTCTTCTCATGCTCCGTGATGCATGAGGCTCTG

CACAACCACTACACACAGAAGAGCCTCTCCCTGTCTCTGGGTAAAGCTAG

TCAGACCCCCACCAACACCATCAGCGTGACCCCCACCAACAACAGCACCC

CCACCAACAACAGCAACCCCAAGCCCAACCCCGCTAGCCCAGGCCAGGGC

ACCCAGTCTGAGAACAGCTGCACCCACTTCCCAGGCAACCTGCCTAACAT

GCTTCGAGATCTCCGAGATGCCTTCAGCAGAGTGAAGACTTTCTTTCAAA

TGAAGGATCAGCTGGACAACTTGTTGTTAAAGGAGTCCTTGCTGGAGGAC

TTTAAGGGTTACCTGGGTTGCCAAGCCTTGTCTGAGATGATCCAGTTTTA

CCTGGAGGAGGTGATGCCCCAAGCTGAGAACCAAGACCCAGACATCAAGG

CGCATGTGAACTCCCTGGGGGAGAACCTGAAGACCCTCAGGCTGAGGCTA

CGGCGCTGTCATCGATTTCTTCCCTGTGAAAACAAGAGCAAGGCCGTGGA

-continued

```
GCAGGTGAAGAATGCCTTTAATAAGCTCCAAGAGAAAGGCATCTACAAAG
CCATGAGTGAGTTTGACATCTTCATCAACTACATAGAAGCCTACATGACA
ATGAAGATACGAAACTGA.
```

The corresponding light chain amino acid sequence, mAnti-CD40_12E12.3F3_K-V-hIgGK-C, is shown in SEQ ID NO:35:

```
                                          (SEQ ID NO: 35)
DIQMTQTTSSLSASLGDRVTISCSASQGISNYLNWYQQKPDGTVKLLIYY

TSILHSGVPSRFSGSGSGTDYSLTIGNLEPEDIATYYCQQFNKLPPTFGG

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.
```

The L chain variable region of anti-CD40 12E12 is shown in SEQ ID NO.:36:

```
                                          (SEQ ID NO: 36)
DIQMTQTTSSLSASLGDRVTISCSASQGISNYLNWYQQKPDGTVKLLIYY

TSILHSGVPSRFSGSGSGTDYSLTIGNLEPEDIATYYCQQFNKLPPTFGG

GTKLEIK.
```

The CDRs of the L chain variable of anti-CD40 12E12 are CDR1: SASQGISNYLN (SEQ ID NO:37), CDR2: YTSILHS (SEQ ID NO:38), and CDR3: QQFNKLPPT (SEQ ID NO:39).

The DNA sequence of mAnti-CD40_12E12.3F3_K-V-hIgGK-C is shown in SEQ ID NO:40:

```
                                          (SEQ ID NO: 40)
ATGATGTCCTCTGCTCAGTTCCTTGGTCTCCTGTTGCTCTGTTTTCAA

GGTACCAGATGTGATATCCAGATGACACAGACTACATCCTCCCTGTCT

GCCTCTCTAGGAGACAGAGTCACCATCAGTTGCAGTGCAAGTCAGGGC

ATTAGCAATTATTTAAACTGGTATCAGCAGAAACCAGATGGAACTGTT

AAACTCCTGATCTATTACACATCAATTTTACACTCAGGAGTCCCATCA

AGGTTCAGTGGCAGTGGGTCTGGGACAGATTATTCTCTCACCATCGGC

AACCTGGAACCTGAAGATATTGCCACTTACTATTGTCAGCAGTTTAAT

AAGCTTCCTCCGACGTTCGGTGGAGGCACCAAACTCGAGATCAAACGA

ACTGTGGCTGCACCATCTGTCTTCATCTTCCCGCCATCTGATGAGCAG

TTGAAATCTGGAACTGCCTCTGTTGTGTGCCTGCTGAATAACTTCTAT

CCCAGAGAGGCCAAAGTACAGTGGAAGGTGGATAACGCCCTCCAATCG

GGTAACTCCCAGGAGAGTGTCACAGAGCAGGACAGCAAGGACAGCACC

TACAGCCTCAGCAGCACCCTGACGCTGAGCAAAGCAGACTACGAGAAA

CACAAAGTCTATGCCTGCGAAGTCACCCATCAGGGCCTGAGCTCGCCC

GTCACAAAGAGCTTCAACAGGGGAGAGTGTTAG.
```

IgG-hIL10 Control

SEQ ID NO:41 shows a fusion protein of the heavy chain of the IgG control antibody fused through a linker to human IL-10. The linker is underlined and the IL-10 amino acid sequence is in bold italics.

hIgG4H-Flex-v1-hIL-10 antibody, SEQ ID NO:41:

```
                                          (SEQ ID NO: 41)
RLQLQESGPGLLKPSVTLSLTCTVSGDSVASSSYYWGWVRQPPGKGLE

WIGTINFSGNMYYSPSLRSRVTMSADMSENSFYLKLDSVTAADTAVYY

CAAGHLVMGFGAHWGQGKLVSVSPASTKGPSVFPLAPCSRSTSESTAA

LGCLVKDYFPEPVTVSWNSGALTSGVHTFPPAVLQSSGLYSLSSVVTVP

SSSLGTKTYTCNVDHKPSNTKVDKRVESKYGPPCPPCPAPEFEGGPSV

FLFPPKPKDTLMISRTPEVTCVVVDVSQEDPEVQFNWYVDGVEVHNAK

TKPREEQFNSTYRVVSVLTVLHQDWLNGKEYKCKVSNKGLPSSIEKTI

SKAKGQPREPQVYTLPPSQEEMTKNQVSLTCLVKGFYPSDIAVEWESN

GQPENNYKTTPPVLDSDGSFFLYSRLTVDKSRWQEGNVFSCSVMHEAL

HNHYTQKSLSLSLGKASQTPTNTISVTPTNNSTPTNNSNPKPNP

ASPGQGTQSENSCTHFPGNLPNMLRDLRDAFSRVKTYFQMKDQLDNLLL

KESLLEDFKGYLGCQALSEMIQFYLEEVMPQAENQDPDIKAHVNSLGENLKTLRLRL

RRCHRFLPCENKSKAVEQVKNAFNKLQEKGIYKAMSEFDIFIN

YIEAYMTMKIRN.
```

The linker shown above is SEQ ID NO:4 and the IL-10 amino acid sequence is shown as SEQ ID NO:5.

The DNA sequence of hIgG4H-Flex-v1-hIL-10 antibody antibody is shown in SEQ ID NO:42:

```
                                          (SEQ ID NO: 42)
ATGGACCTCCTGTGCAAGAACATGAAGCACCTGTGGTTCTTCCTCCTG

CTGGTGGCGGCTCCCAGATGGGTCCTGTCCCGGCTGCAGCTGCAGGAG

TCGGGCCCAGGCCTGCTGAAGCCTTCGGTGACCCTGTCCCTCACCTGC

ACTGTCTCGGGTGACTCCGTCGCCAGTAGTTCTTATTACTGGGGCTGG

GTCCGTCAGCCCCCAGGGAAGGGACTCGAGTGGATAGGGACTATCAAT

TTTAGTGGCAATATGTATTATAGTCCGTCCCTCAGGAGTCGAGTGACC

ATGTCGGCAGACATGTCCGAGAACTCCTTCTATCTGAAATTGGACTCT

GTGACCGCAGCAGACACGGCCGTCTATTATTGTGCGGCAGGACACCTC

GTTATGGGATTTGGGGCCCACTGGGGACAGGGAAAACTGGTCTCCGTC

TCTCCAGCTTCCACCAAGGGCCCATCCGTCTTCCCCCTGGCGCCCTGC

TCCAGGAGCACCTCCGAGAGCACAGCCGCCCTGGGCTGCCTGGTCAAG

GACTACTTCCCCGAACCGGTGACGGTGTCGTGGAACTCAGGCGCCCTG

ACCAGCGGCGTGCACACCTTCCCGGCTGTCCTACAGTCCTCAGGACTC

TACTCCCTCAGCAGCGTGGTGACCGTGCCCTCCAGCAGCTTGGGCACG

AAGACCTACACCTGCAACGTAGATCACAAGCCCAGCAACACCAAGGTG

GACAAGAGAGTTGAGTCCAAATATGGTCCCCCATGCCCACCCTGCCCA

GCACCTGAGTTCGAAGGGGACCATCAGTCTTCCTGTTCCCCCCAAAA

CCCAAGGACACTCTCATGATCTCCCGGACCCCTGAGGTCACGTGCGTG

GTGGTGGACGTGAGCCAGGAAGACCCCGAGGTCCAGTTCAACTGGTAC

GTGGATGGCGTGGAGGTGCATAATGCCAAGACAAAGCCGCGGGAGGAG

CAGTTCAACAGCACGTACCGTGTGGTCAGCGTCCTCACCGTCCTGCAC
```

```
CAGGACTGGCTGAACGGCAAGGAGTACAAGTGCAAGGTCTCCAACAAA

GGCCTCCCGTCCTCCATCGAGAAAACCATCTCCAAAGCCAAAGGGCAG

CCCCGAGAGCCACAGGTGTACACCCTGCCCCCATCCCAGGAGGAGATG

ACCAAGAACCAGGTCAGCCTGACCTGCCTGGTCAAAGGCTTCTACCCC

AGCGACATCGCCGTGGAGTGGGAGAGCAATGGGCAGCCGGAGAACAAC

TACAAGACCACGCCTCCCGTGCTGGACTCCGACGGCTCCTTCTTCCTC

TACAGCAGGCTAACCGTGGACAAGAGCAGGTGGCAGGAGGGGAATGTC

TTCTCATGCTCCGTGATGCATGAGGCTCTGCACAACCACTACACACAG

AAGAGCCTCTCCCTGTCTCTGGGTAAAGCTAGTCAGACCCCCACCAAC

ACCATCAGCGTGACCCCCACCAACAACAGCACCCCCACCAACAACAGC

AACCCCAAGCCCAACCCCGCTAGCCCAGGCCAGGGCACCCAGTCTGAG

AACAGCTGCACCCACTTCCCAGGCAACCTGCCTAACATGCTTCGAGAT

CTCCGAGATGCCTTCAGCAGAGTGAAGACTTTCTTTCAAATGAAGGAT

CAGCTGGACAACTTGTTGTTAAAGGAGTCCTTGCTGGAGGACTTTAAG

GGTTACCTGGGTTGCCAAGCCTTGTCTGAGATGATCCAGTTTTACCTG

GAGGAGGTGATGCCCCAAGCTGAGAACCAAGACCCAGACATCAAGGCG

CATGTGAACTCCCTGGGGGAGAACCTGAAGACCCTCAGGCTGAGGCTA

CGGCGCTGTCATCGATTTCTTCCCTGTGAAAACAAGAGCAAGGCCGTG

GAGCAGGTGAAGAATGCCTTTAATAAGCTCCAAGAGAAAGGCATCTAC

AAAGCCATGAGTGAGTTTGACATCTTCATCAACTACATAGAAGCCTAC

ATGACAATGAAGATACGAAACTGA.
```

The corresponding light chain amino acid sequence hIgGK, is shown in SEQ ID NO:43:

```
                                    (SEQ ID NO: 43)
DIQMTQSPSSLSASVGDRVTITCRASQSISSYLNWYQQKPGKAPKLLI

YAASSLQSGVPSRFSGSGSGTDFTLTISSLQPEDFATYYCQQSYSTPY

TFGQGTKLEIKRTVAAPSVFIFPPSDEQLKSGTASVVCLLNNFYPREA

KVQWKVDNALQSGNSQESVTEQDSKDSTYSLSSTLTLSKADYEKHKVY

ACEVTHQGLSSPVTKSFNRGEC.
```

The DNA sequence of hIgGK is shown in SEQ ID NO:44:

```
                                    (SEQ ID NO: 44)
ATGAGGGTCCCCGCTCAGCTCCTGGGGCTCCTGCTACTCTGGCTCCGA

GGTGCCAGATGTGACATCCAGATGACCCAGTCTCCATCCTCCCTGTCT

GCATCTGTAGGAGACAGAGTCACCATCACTTGCCGGGCAAGTCAGAGC

ATTAGCAGCTATTTAAATTGGTATCAGCAGAAACCAGGGAAAGCCCCT

AAGCTCCTGATCTATGCTGCATCCAGTTTGCAAAGTGGGGTCCCATCA

AGGTTCAGTGGCAGTGGATCTGGGACAGATTTCACTCTCACCATCAGC

AGTCTCCAACCTGAAGATTTTGCAACTTACTACTGTCAACAGAGTTAC

AGTACCCCGTACACTTTTGGCCAGGGGACCAAGCTGGAGATCAAACGA

ACTGTGGCTGCACCATCTGTCTTCATCTTCCCGCCATCTGATGAGCAG

TTGAAATCTGGAACTGCCTCTGTTGTGTGCCTGCTGAATAACTTCTAT

CCCAGAGAGGCCAAAGTACAGTGGAAGGTGGATAACGCCCTCCAATCG

GGTAACTCCCAGGAGAGTGTCACAGAGCAGGACAGCAAGGACAGCACC

TACAGCCTCAGCAGCACCCTGACGCTGAGCAAAGCAGACTACGAGAAA

CACAAAGTCTACGCCTGCGAAGTCACCCATCAGGGCCTGAGCTCGCCC

GTCACAAAGAGCTTCAACAGGGGAGAGTGTTAG.
```

Shown below are further examples of antibodies and antibody fragments useful in the methods and compositions described herein.

Anti-Dectin-1 mAbs manti-Dectin-1-11B6.4-H-V-hIgG4H-C]; SEQ ID NO:45:

```
                                    (SEQ ID NO: 45)
QVQLKESGPGLVAPSQSLSITCSVSGFSLSNYDISWIRQPPGKGLEWL

GVMWTGGGANYNSAFMSRLSINKDNSKSQVFLKMNNLQTDDTAIYYCV

RDAVRYWNFDVWGAGTTVTVSSAKTKGPSVFPLAPCSRSTSESTAALG

CLVKDYFPEPVTVSWNSGALTSGVHTFPAVLQSSGLYSLSSVVTVPSS

SLGTKTYTCNVDHKPSNTKVDKRVESKYGPPCPPCPAPEFEGGPSVFL

FPPKPKDTLMISRTPEVTCVVVDVSQEDPEVQFNWYVDGVEVHNAKTK

PREEQFNSTYRVVSVLTVLHQDWLNGKEYKCKVSNKGLPSSIEKTISK

AKGQPREPQVYTLPPSQEEMTKNQVSLTCLVKGFYPSDIAVEWESNGQ

PENNYKTTPPVLDSDGSFFLYSRLTVDKSRWQEGNVFSCSVMHEALHN

HYTQKSLSLSLGKAS.
```

The above sequence is a chimera between the H chain variable region of the mAb 11B6.4 and the C region of hIgG4.

The H chain variable region of the mAb 11B6.4 is shown in SEQ ID NO:46:

```
                                    (SEQ ID NO: 46)
QVQLKESGPGLVAPSQSLSITCSVSGFSLSNYDISWIRQPPGKGLEWL

GVMWTGGGANYNSAFMSRLSINKDNSKSQVFLKMNNLQTDDTAIYYCV

RDAVRYWNFDVWGAGTTVTVSSAKTK.
```

[manti-Dectin-1-11B6.4-K-LV-hIgGK-C] is the corresponding L chain chimera; SEQ ID NO:47:

```
                                    (SEQ ID NO: 47)
QIVLSQSPAILSASPGEKVTMTCRASSSVSYIHWYQQKPGSSPKPWIY

ATSHLASGVPARFSGSGSGTSYSLTISRVEAEDTATYYCQQWSSNPFT

FGSGTKLEIKRTVAAPSVFIFPPSDEQLKSGTASVVCLLNNFYPREAK

VQWKVDNALQSGNSQESVTEQDSKDSTYSLSSTLTLSKADYEKHKVYA

CEVTHQGLSSPVTKSFNRGEC.
```

The L chain variable region of the manti-Dectin-1-11B6.4-K-LV-hIgGK-C is shown in SEQ ID NO:48:

(SEQ ID NO: 48)
QIVLSQSPAILSASPGEKVTMTCRASSSVSYIHWYQQKPGSSPKPWIY

ATSHLASGVPARFSGSGSGTSYSLTISRVEAEDTATYYCQQWSSNPFT

FGSGTK.

manti-Dectin-1-15E2.5-H-V-hIgG4H-C]; SEQ ID NO:49:

(SEQ ID NO: 49)
QVQLQQSGAELARPGASVKMSCKASGYTFTTYTMHWVKQRPGQGLEWI

GYINPSSGYTNYNQKFKDKATLTADKSSSTASMQLSSLTSEDSAVYYC

ARERAVLVPYAMDYWGQGTSVTVSSAKTKGPSVFPLAPCSRSTSESTA

ALGCLVKDYFPEPVTVSWNSGALTSGVHTFPAVLQSSGLYSLSSVVTV

PSSSLGTKTYTCNVDHKPSNTKVDKRVESKYGPPCPPCPAPEFEGGPS

VFLFPPKPKDTLMISRTPEVTCVVVDVSQEDPEVQFNWYVDGVEVHNA

KTKPREEQFNSTYRVVSVLTVLHQDWLNGKEYKCKVSNKGLPSSIEKT

ISKAKGQPREPQVYTLPPSQEEMTKNQVSLTCLVKGFYPSDIAVEWES

NGQPENNYKTTPPVLDSDGSFFLYSRLTVDKSRWQEGNVFSCSVMHEA

LHNHYTQKSLSLSLGKAS.

The above sequence is a chimera between the H chain variable region of the mAb 15E2.5 and the C region of hIgG4.

The H chain variable region of the mAb 15E2.5 is shown in SEQ ID NO:50:

(SEQ ID NO: 50)
QVQLQQSGAELARPGASVKMSCKASGYTFTTYTMHWVKQRPGQGLEWI

GYINPSSGYTNYNQKFKDKATLTADKSSSTASMQLSSLTSEDSAVYYC

ARERAVLVPYAMDYWGQGTSVTVSSAKTK.

[manti-Dectin-1-15E2.5-K-V-hIgGK-C] is the corresponding L chain chimera; SEQ ID NO:51:

(SEQ ID NO: 51)
QIVLTQSPAVMSASPGEKVTITCTASSSLSYMHWFQQKPGTSPKLWLY

STSILASGVPTRFSGSGSGTSYSLTISRMEAEDAATYYCQQRSSSPFT

FGSGTKLEIKRTVAAPSVFIFPPSDEQLKSGTASVVCLLNNFYPREAK

VQWKVDNALQSGNSQESVTEQDSKDSTYSLSSTLTLSKADYEKHKVYA

CEVTHQGLSSPVTKSFNRGEC.

The L chain variable region of the manti-Dectin-1-15E2.5-K-V-hIgGK-C is shown in SEQ ID NO:52:

(SEQ ID NO: 52)
QIVLTQSPAVMSASPGEKVTITCTASSSLSYMHWFQQKPGTSPKLWLY

STSILASGVPTRFSGSGSGTSYSLTISRMEAEDAATYYCQQRSSSPFT

FGSGTK.

manti-Dectin-1-2D8.2D4-H-V-hIgG4H-C]; SEQ ID NO:53:

(SEQ ID NO: 53)
EVQLQQSGPELEKPGASVKISCKASGYSFTGYNMNWVKQSNGKSLEWI

GNIDPYYGDTNYNQKFKGKATLTVDKSSSTAYMHLKSLTSEDSAVYYC

ARPYGSEAYFAYWGQGTLVTVSAAKTKGPSVFPLAPCSRSTSESTAAL

GCLVKDYFPEPVTVSWNSGALTSGVHTFPAVLQSSGLYSLSSVVTVPS

SSLGTKTYTCNVDHKPSNTKVDKRVESKYGPPCPPCPAPEFEGGPSVF

LFPPKPKDTLMISRTPEVTCVVVDVSQEDPEVQFNWYVDGVEVHNAKT

KPREEQFNSTYRVVSVLTVLHQDWLNGKEYKCKVSNKGLPSSIEKTIS

KAKGQPREPQVYTLPPSQEEMTKNQVSLTCLVKGFYPSDIAVEWESNG

QPENNYKTTPPVLDSDGSFFLYSRLTVDKSRWQEGNVFSCSVMHEALH

NHYTQKSLSLSLGKAS.

The above sequence is a chimera between the H chain variable region of the mAb 2D8.2D4 and the C region of hIgG4.

The H chain variable region of the mAb 2D8.2D4 is shown in SEQ ID NO:54:

(SEQ ID NO: 54)
EVQLQQSGPELEKPGASVKISCKASGYSFTGYNMNWVKQSNGKSLEWI

GNIDPYYGDTNYNQKFKGKATLTVDKSSSTAYMHLKSLTSEDSAVYYC

ARPYGSEAYFAYWGQGTLVTVSAAKTK.

[manti-Dectin-1-2D8.2D4-K-V-hIgGK-C] is the corresponding L chain chimera; SEQ ID NO:55:

(SEQ ID NO: 55)
DIVMTQSPATLSVTPGDRVSLSCRASQSISDYLHWYQQKSHESPRLLIK

YAAQSISGIPSRFSGSGSGSDFTLSINGVEPEDVGVYYCQNGHSFPYTF

GGGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC.

The L chain variable region of the manti-Dectin-1-2D8.2D4-K-V-hIgGK-C is shown in SEQ ID NO:56:

(SEQ ID NO: 56)
DIVMTQSPATLSVTPGDRVSLSCRASQSISDYLHWYQQKSHESPRLLIK

YAAQSISGIPSRFSGSGSGSDFTLSINGVEPEDVGVYYCQNGHSFPYTF

GGGTK.

Anti-DC ASGPR mAbs
[mAnti-ASGPR-4G2.2-Hv-V-hIgG4H-C]; SEQ ID NO.:57:

(SEQ ID NO: 57)
QIQLVQSGPELKKPGETVKISCKASGYTFTNYGMNWVKQVPGKGLRWMG

WMDTFTGEPTYADDFKGRFAFSLETSASTAYLQINSLKNEDTATYFCAR

GGILRLNYFDYWGQGTTLTVSSAKTKGPSVFPLAPCSRSTSESTAALGC

-continued
LVKDYFPEPVTVSWNSGALTSGVHTFPAVLQSSGLYSLSSVVTVPSSSL

GTKTYTCNVDHKPSNTKVDKRVESKYGPPCPPCPAPEFEGGPSVFLFPP

KPKDTLMISRTPEVTCVVVDVSQEDPEVQFNWYVDGVEVHNAKTKPREE

QFNSTYRVVSVLTVLHQDWLNGKEYKCKVSNKGLPSSIEKTISKAKGQP

REPQVYTLPPSQEEMTKNQVSLTCLVKGFYPSDIAVEWESNGQPENNYK

TTPPVLDSDGSFFLYSRLTVDKSRWQEGNVFSCSVMHEALHNHYTQKSL

SLSLGKAS.

The above sequence is a chimera between the H chain variable of the mAb 4G2.2 and the C region of hIgG4.

The H chain variable of the mAb 4G2.2 is shown in SEQ ID NO.:58:

(SEQ ID NO: 58)
QIQLVQSGPELKKPGETVKISCKASGYTFTNYGMNWVKQVPGKGLRWMG

WMDTFTGEPTYADDFKGRFAFSLETSASTAYLQINSLKNEDTATYFCAR

GGILRLNYFDYWGQGTTLTVSSAKTK.

[mAnti-ASGPR-4G2.2-Kv-V-hIgGK-C] is the corresponding L chain chimera; SEQ ID NO.:59:

(SEQ ID NO: 59)
DIQMTQSSSSFSVSLGDRVTITCKASEDIYNRLGWYQQKPGNAPRLLIS

GATSLETGVPSRFSGSGSGKDYALSITSLQTEDLATYYCQQCWTSPYTF

GGGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC.

The L chain variable region of the mAnti-ASGPR-4G2.2-Kv-V-hIgGK-C is shown in SEQ ID NO.:60:

(SEQ ID NO: 60)
DIQMTQSSSSFSVSLGDRVTITCKASEDIYNRLGWYQQKPGNAPRLLIS

GATSLETGVPSRFSGSGSGKDYALSITSLQTEDLATYYCQQCWTSPYTF

GGGTKLEI.

[mAnti-ASGPR-5F10H-LV-hIgG4H-C] (SEQ ID NO.: 61):

(SEQ ID NO: 61)
EVQLQQSGPELVKPGASVKMSCKASGYTFTDYYMKWVKQSHGKSLEWIG

DINPNYGDTFYNQKFEGKATLTVDKSSRTAYMQLNSLTSEDSAVYYCGR

GDYGYFDVWGAGTTVTVSSAKTKGPSVFPLAPCSRSTSESTAALGCLVK

DYFPEPVTVSWNSGALTSGVHTFPAVLQSSGLYSLSSVVTVPSSSLGTK

TYTCNVDHKPSNTKVDKRVESKYGPPCPPCPAPEFEGGPSVFLFPPKPK

DTLMISRTPEVTCVVVDVSQEDPEVQFNWYVDGVEVHNAKTKPREEQFN

STYRVVSVLTVLHQDWLNGKEYKCKVSNKGLPSSIEKTISKAKGQPREP

QVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLLSL

GKAS.

The above sequence is a chimera between the H chain variable of the mAb 5F10 and the C region of hIgG4.

The H chain variable of the mAb 5F10 is shown in SEQ ID NO.:62:

(SEQ ID NO: 62)
EVQLQQSGPELVKPGASVKMSCKASGYTFTDYYMKWVKQSHGKSLEWIG

DINPNYGDTFYNQKFEGKATLTVDKSSRTAYMQLNSLTSEDSAVYYCGR

GDYGYFDVWGAGTTVTVSSAKTK.

[mAnti-ASGPR-5F10K-LV-hIgGK-C] is the corresponding L chain chimera; SEQ ID NO.:63:

(SEQ ID NO: 63)
DIVMTQSHKFMSTSVGDRVSITCKASQDVGTAVAWYQQKPGQSPKLLIY

WASTRHTGVPDRFTGSGSGTDFTLTINNVQSEDLADYFCQQYSSNPYMF

GGGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC.

The L chain variable region of the mAnti-ASGPR-5F10K-LV-hIgGK-C is shown in SEQ ID NO.:64:

(SEQ ID NO: 64)
DIVMTQSHKFMSTSVGDRVSITCKASQDVGTAVAWYQQKPGQSPKLLIY

WASTRHTGVPDRFTGSGSGTDFTLTINNVQSEDLADYFCQQYSSNPYMF

GGGTKLEI.

[mAnti-ASGPR-1H11H-V-hIgG4H-C] (SEQ ID NO.: 65):

(SEQ ID NO: 65)
QLQQSGPELVKPGASVKISCKTSGYTFTEYTMHWVRQSHGKSLEWIGGI

NPINGGPTYNQKFKGKATLTVDKSSSTAYMELRSLTSEDSAVYYCARWD

YGSRDVMDYWGQGTSVTVSSAKTKGPSVFPLAPCSRSTSESTAALGCLV

KDYFPEPVTVSWNSGALTSGVHTFPAVLQSSGLYSLSSVVTVPSSSLGT

KTYTCNVDHKPSNTKVDKRVESKYGPPCPPCPAPEFEGGPSVFLFPPKP

KDTLMISRTPEVTCVVVDVSQEDPEVQFNWYVDGVEVHNAKTKPREEQF

NSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTT

PPVLDSDGSFFLYSRLTVDKSRWQEGNVFSCSVMHEALHNHYTQKSLSL

SLGKAS.

The above sequence is a chimera between the H chain variable of the mAb 1H11 and the C region of hIgG4.

The H chain variable of the mAb 1H11 is shown in SEQ ID NO.:66:

(SEQ ID NO: 66)
QLQQSGPELVKPGASVKISCKTSGYTFTEYTMHWVRQSHGKSLEWIGGI

NPINGGPTYNQKFKGKATLTVDKSSSTAYMELRSLTSEDSAVYYCARWD

YGSRDVMDYWGQGTSVTVSSAKTK.

[mAnti-ASGPR-1H11K-LV-hIgGK-C] is the corresponding L chain chimera, SEQ ID NO.:67:

(SEQ ID NO: 67)
NIVMTQSPKSMSMSVGERVTLSCKASENVGTYVSWYQQRPEQSPKLLIY

GASNRYTGVPDRFTGSGSATDFTLTISSVQAEDLADYHCGQTYSYIFTF

GSGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC.

The L chain variable region of the mAnti-ASGPR-1H11K-LV-hIgGK-C is shown in SEQ ID NO.:68:

(SEQ ID NO: 68)
NIVMTQSPKSMSMSVGERVTLSCKASENVGTYVSWYQQRPEQSPKLLIY

GASNRYTGVPDRFTGSGSATDFTLTISSVQAEDLADYHCGQTYSYIFTF

GSGTKLE.

manti-hASGPR-6.3H9.1D11H (heavy chain) SEQ ID NO: 69:

(SEQ ID NO: 69)
VQLQQSGAELVRPGTSVKMSCEAARFTFSNYWIGWVKQRPGHGLEWIGD

IFPGGDYTNYNKKFKDKATLTADTSSSTAYMQLSSLTSEDSAIYYCARS

DYGGYYVFDYWGQGTTLTVSSAKTKGPSVFPLAPCSRSTSESTAALGCL

VKDYFPEPVTVSWNSGALTSGVHTFPAVLQSSGLYSLSSVVTVPSSSLG

TKTYTCNVDHKPSNTKVDKRVESKYGPPCPPCPAPEFEGGPSVFLFPPK

PKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPR

EPQVYTLPPSQEEMTKNQVSLTCLVKGFYPSDIAVEWESNGQPENNYKT

TPPVLDSDGSFFLYSRLTVDKSRWQEGNVFSCSVMHEALHNHYTQKSLS

LSLGK.

manti-hASGPR_6.3H9.1D11K (light chain) SEQ ID NO: 70:

(SEQ ID NO: 70)
DIVMSQSPSSLAVSVGEKVTMSCKSSQNLLYSSNQKNYLAWYQQKPGQS

PKLLIYWASTRESGVPDRFTGSGSGTDFTLTISSVKAEDLAVYYCQQYY

SYPYTFGGGTKLEIKRTVAAPSVFIFPPSDEQLKSGTASVVCLLNNFYP

REAKVQWKVDNALQSGNSQESVTEQDSKDSTYSLSSTLTLSKADYEKHK

VYACEVTHQGLSSPVTKSFNRGEC.

manti-hASGPR-5H8.1D4H (heavy chain) SEQ ID NO: 71:

(SEQ ID NO: 71)
AQIQLVQSGPELKKPGETVKISCKASGYTFTDYSVHWVKQAPGKGLKWM

GWINTETGEPTYADDLKGRFAFSLETSASTAYLQINNLKNEDTATYFCA

KPTYRFFDYWGQGTTLTASSAKTKGPSVFPLAPCSRSTSESTAALGCLV

KDYFPEPVTVSWNSGALTSGVHTFPAVLQSSGLYSLSSVVTVPSSSLGT

KTYTCNVDHKPSNTKVDKRVESKYGPPCPPCPAPEFEGGPSVFLFPPKP

KDTLMISRTPEVTCVVVDVSQEDPEVQFNWYVDGVEVHNAKTKPREEQF

NSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTT

PPVLDSDGSFFLYSRLTVDKSRWQEGNVFSCSVMHEALHNHYTQKSLSL

SLGK.

manti-hASGPR-5H8.1D4K (light chain) SEQ ID NO: 72:

(SEQ ID NO: 72)
DIVMSQSPSSLAVSAGEKVTMSCKSSQSLLNSRTRKNYLAWYQQKPGQS

PKLLIYWASTRESGVPDRFTGSGSGTDFTLTISSVQAEDLAVYYCKQSY

NLWTFGGGTKLEIKRTVAAPSVFIFPPSDEQLKSGTASVVCLLNNFYPR

EAKVQWKVDNALQSGNSQESVTEQDSKDSTYSLSSTLTLSKADYEKHKV

YACEVTHQGLSSPVTKSFNRGEC.

anti-CD40 mAbs
anti-CD40-12B4.2C10, heavy chain, (SEQ ID NO:73:

(SEQ ID NO: 73)
MEWSWIFLFLLSGTAGVHSEVQLQQSGPELVKPGASVKMSCKASGYTFT

DYVLHWVKQKPGQGLEWIGYINPYNDGTKYNEKFKGKATLTSDKSSSTA

YMELSSLTSEDSAVYYCARGYPAYSGYAMDYWGQGTSVTVSSAKTTPPS

VYPLAPGSAAQTNSMVTLGCLVKGYFPEPVTVTWNSGSLSSGVHTFPAV

LQKGEFV.

anti-CD40-12B4.2C10, light chain, SEQ ID NO:74:

(SEQ ID NO: 74)
MMSSAQFLGLLLLCFQGTRCDIQMTQTTSSLSASLGDRVTISCRASQDI

SNYLNWYQQKPDGTVKLLIYYTSRLHSGVPSRFSGSGSGTDYSLTISNL

EQEDIATYFCHHGNTLPWTFGGGTKLEIKRADAAPTVSIFPPSSEQLTS

GGASVVCFLNNFYPKDINVKWKIDGSERQNGVLNSWTDQDSKDSTYSMS

STLTLTKDEYERHNSYTCEATHKTSTSPIVKSFNRNEC.

anti-CD40-12B4.2C10, light chain—alternative clone (17K6), SEQ ID NO:75:

(SEQ ID NO: 75)
MDFQVQIFSFLLISASVIIVISRGQIVLTQSPAILSASPGEKVTMTCSA

SSSVSYMYRYQQKPGSSPKPWIYGTSNLASGVPARFSGSGSGTSYSLTI

SSMEAEDAATYYCQQYHSYPLTFGAGTKLELKRADAAPTVSIFPPSSEQ

LTSGGASVVCFLNNFYPKDINVKWKIDGSERQNGVLNSWTDQDSKDSTY

SMSSTLTLTKDEYERHNSYTCEATHKTSTSPIVKSFNRNEC.

anti-CD40_11B6.1C3, heavy chain, SEQ ID NO:76:

(SEQ ID NO: 76)
MGWSWIFLFLLSGTAGVLSEVQLQQSGPELVKPGASVKISCKASGYSFT

GYYMHWVKQSHVKSLEWIGRINPYNGATSYNQNFKDKASLTVDKSSSTA

-continued

YMELHSLTSEDSAVYYCAREDYVYWGQGTTLTVSSAKTTPPSVYPLAPG

SAAQTNSMVTLGCLVKGYFPEPVTVTWNSGSLSSGVHTFPAVLQKGEFV.

anti-CD40_11B6.1C3, light chain, SEQ ID NO:77:

(SEQ ID NO: 77)
MKLPVRLLVLMFWIPASSSDVVMTQTPLSLPVSLGDQASISCRSSQSL

VHSNGNTYLHWYLQKPGQSPKLLIYKVSNRFSGVPDRFSGSGSGTDFAL

KISRVEAEDLGVYFCSQSTHVPWTFGGGTKLEIKRADAAPTVSIFPPSS

EQLTSGGASVVCFLNNFYPKDINVKWKIDGSERQNGVLNSWTDQDSKDS

TYSMSSTLTLTKDEYERHNSYTCEATHKTSTSPIVKSFNRNEC.

anti-LOX-1 Abs

[mAnti-LOX-1-11C8H-LV-hIgG4H-C], heavy chain, SEQ ID NO:78:

(SEQ ID NO: 78)
EVQLQQSGTVLARPGASVKMSCKASGYTFTSYWMHWVKQRPGQGLEWIG

AIYPGNSDTTYNQKFKGKAKLTAVTSTSTAYMELSSLTNEDSAVYYCTP

TYYFDYWGQGTSLTVSSAKTKGPSVFPLAPCSRSTSESTAALGCLVKDY

FPEPVTVSWNSGALTSGVHTFPAVLQSSGLYSLSSVVTVPSSSLGTKTY

TCNVDHKPSNTKVDKRVESKYGPPCPPCPAPEFEGGPSVFLFPPKPKDT

LMISRTPEVTCVVVDVSQEDPEVQFNWYVDGVEVHNAKTKPREEQFNST

YRVVSVLTVLHQDWLNGKEYKCKVSNKGLPSSIEKTISKAKGQPREPQV

YTLPPSQEEMTKNQVSLTCLVKGFYPSDIAVEWESNGQPENNYKTTPPV

LDSDGSFFLYSRLTVDKSRWQEGNVFSCSVMHEALHNHYTQKSLSLSLG

KAS.

The H chain variable of the Ab 11C8 is shown in SEQ ID NO:79:

(SEQ ID NO: 79)
EVQLQQSGTVLARPGASVKMSCKASGYTFTSYWMHWVKQRPGQGLEWI
GAIYPGNSDTTYNQKFKGKAKLTAVTSTSTAYMELSSLTNEDSAVYYC
TPTYYFDYWGQGTSLTVSSAKTK.

[mAnti-LOX-1-11C8K-LV-hIgGK-C], light chain, SEQ ID NO:80:

(SEQ ID NO: 80)
DVVMTQTPLTLSVTIGQPASISCKSSQSLLDSDGKTYLNWFLQRPGQS

PKRLIYLVSKLDSGVPDRFTGSGSGTDFTLKISRVEAEDLGVYYCWQG

THFPWTFGGGTKLEIKRTVAAPSVFIFPPSDEQLKSGTASVVCLLNNF

YPREAKVQWKVDNALQSGNSQESVTEQDSKDSTYSLSSTLTLSKADYE

KHKVYACEVTHQGLSSPVTKSFNRGEC.

The L chain variable of the Ab 11C8 is shown in SEQ ID NO:81:

(SEQ ID NO: 81)
DVVMTQTPLTLSVTIGQPASISCKSSQSLLDSDGKTYLNWFLQRPGQ
SPKRLIYLVSKLDSGVPDRFTGSGSGTDFTLKISRVEAEDLGVYYCW
QGTHFPWTFGGGTKLE

[mAnti-LOX-1-10F9H-LV-hIgG4H-C], heavy chain, SEQ ID NO:82:

(SEQ ID NO: 82)
QVQLQQSGAELMKPGASVKISCKATGYTFGSYWIEWVKQRPGHGLEW

IGEILPGSGNTNYNENFKGKATFTADTSSNTAYMQLTSLTSEDSAVY

YCARAGIYWGQGTLVTVSSAAKTKGPSVFPLAPCSRSTSESTAALGCL

VKDYFPEPVTVSWNSGALTSGVHTFPAVLQSSGLYSLSSVVTVPSSS

LGTKTYTCNVDHKPSNTKVDKRVESKYGPPCPPCPAPEFEGGPSVFL

FPPKPKDTLMISRTPEVTCVVVDVSQEDPEVQFNWYVDGVEVHNAKT

KPREEQFNSTYRVVSVLTVLHQDWLNGKEYKCKVSNKGLPSSIEKTI

SKAKGQPREPQVYTLPPSQEEMTKNQVSLTCLVKGFYPSDIAVEWES

NGQPENNYKTTPPVLDSDGSFFLYSRLTVDKSRWQEGNVFSCSVMHE

ALHNHYTQKSLSLSLGKAS.

The H chain variable of the Ab 10F9 is shown in SEQ ID NO:83:

(SEQ ID NO: 83)
QVQLQQSGAELMKPGASVKISCKATGYTFGSYWIEWVKQRPGHGLE
WIGEILPGSGNTNYNENFKGKATFTADTSSNTAYMQLTSLTSEDSA
VYYCARAGIYWGQGTLVTVSSAAKTK.

[mAnti-LOX-1-10F9K-LV-hIgGK-C], light chain, SEQ ID NO:84:

(SEQ ID NO: 84)
DIVLTQSPAFLAVSLGQRATISCRASESVDNYGISFMNWFQQKPGQ

PPKLLIYVASKQGSGVPARFSGSGSGTDFSLNIHPMEEDDTAMYFC

QQSKEVPRTFGGGTKLEIKRTVAAPSVFIFPPSDEQLKSGTASVVC

LLNNFYPREAKVQWKVDNALQSGNSQESVTEQDSKDSTYSLSSTLT

LSKADYEKHKVYACEVTHQGLSSPVTKSFNRGEC.

The L chain variable of the Ab 10F9 is shown in SEQ ID NO:85:

(SEQ ID NO: 85)
DIVLTQSPAFLAVSLGQRATISCRASESVDNYGISFMNWFQQKPGQPPKL
LIYVASKQGSGVPARFSGSGSGTDFSLNIHPMEEDDTAMYFCQQSKEVPR
TFGGGTKLE.

[mAnti-LOX-1-15C4H-LV-hIgG4H-C], heavy chain, SEQ ID NO:86:

(SEQ ID NO: 86)
EIQLQQTGPELVKPGASVKISCKASGYPFTDYEVIVWVKQSHGKSLEWIG

NISPYYGTTNYNLKFKGKATLTVDKSSSTAYMQLNSLTSEDSAVYYCARS

PNWDGAWFAHWGQGALVTVSAAKTKGPSVFPLAPCSRSTSESTAALGCLV

KDYFPEPVTVSWNSGALTSGVHTFPAVLQSSGLYSLSSVVTVPSSSLGTK

TYTCNVDHKPSNTKVDKRVESKYGPPCPPCPAPEFEGGPSVFLFPPKPKD

TLMISRTPEVTCVVVDVSQEDPEVQFNWYVDGVEVHNAKTKPREEQFNST

YRVVSVLTVLHQDWLNGKEYKCKVSNKGLPSSIEKTISKAKGQPREPQVY

The H chain variable of the Ab 15C4 is shown in SEQ ID NO:87:

(SEQ ID NO: 87)
EIQLQQTGPELVKPGASVKISCKASGYPFTDYIMVWVKQSHGKSLEWIG
NISPYYGTTNYNLKFKGKATLTVDKSSSTAYMQLNSLTSEDSAVYYCAR
SPNWDGAWFAHWGQGALVTVSAAKTK.

[mAnti-LOX-1-15C4K-LV-hIgGK-C], light chain, SEQ ID NO: 88:

(SEQ ID NO: 88)
DIVLTQSPASLAVSLGQRATISCKASQSVDYDGDSYMNWFQQKPGQPPKL
LIYAASNLESGIPARFSGSGSGTDFTLNIHPVEEEDAATYYCQQSNEDPF
TFGSGTKLEIKRTVAAPSVFIFPPSDEQLKSGTASVVCLLNNFYPREAKV
QWKVDNALQSGNSQESVTEQDSKDSTYSLSSTLTLSKADYEKHKVYACEV
THQGLSSPVTKSFNRGEC.

The L chain variable of the Ab 15C4 is shown in SEQ ID NO:89:

(SEQ ID NO: 89)
DIVLTQSPASLAVSLGQRATISCKASQSVDYDGDSYMNWFQQKPGQPPKL
LIYAASNLESGIPARFSGSGSGTDFTLNIHPVEEEDAATYYCQQSNEDPF
TFGSGTKLE.

Anti-DCIR Abs

Anti-DCIR_24A5.4A5_H-V-hIgG4H-C, heavy chain, SEQ ID NO:90:

(SEQ ID NO: 90)
MDWLWNLLFLMAAAQSAQAQIQLVQSGPELKKPGETVKISCKASGYSFT
NYGMNWVKQAPGKGLKWMGWINTYTGESTYADDFKGRFAFSLETSASTA
YLQISNLKNEDMATYFCARGDFRYYYFDYWGQGTTLTGSSAKTKGPSVF
PLAPCSRSTSESTAALGCLVKDYFPEPVTVSWNSGALTSGVHTFPAVLQ
SSGLYSLSSVVTVPSSSLGTKTYTCNVDHKPSNTKVDKRVESKYGPPCP
PCPAPEFEGGPSVFLFPPKPKDTLMISRTPEVTCVVVDVSQEDPEVQFN
WYVDGVEVHNAKTKPREEQFNSTYRVVSVLTVLHQDWLNGKEYKCKVSN
KGLPSSIEKTISKAKGQPREPQVYTLPPSQEEMTKNQVSLTCLVKGFYP
SDIAVEWESNGQPENNYKTTPPVLDSD
GSFFLYSRLTVDKSRWQEGNVFSCSVMHEALHNHYTQKSLSLSLGKAS.

Anti-DCIR_24A5.4A5_K-V-hIgGK-C, light chain, SEQ ID NO:91:

(SEQ ID NO: 91)
MSVLTQVLALLLLWLTGARCDIQMTQSPASLSASVGETVTITCRASGNI
HNYLAWYQQKQGKSPQLLVYNAKTLADGVPSRFSGSGSGTQYSLKINTL
QPEDFGSYYCQHFWDSWTFGGGTKLEIKRTVAAPSVFIFPPSDEQLKSG
TASVVCLLNNFYPREAKVQWKVDNALQSGNSQESVTEQDSKDSTYSLSS
TLTLSKADYEKHKVYACEVTHQGLSSPVTKSFNRGEC.

Anti-DCIR_24E7.3H9_H-V-hIgG4H-C, heavy chain, SEQ ID NO:92:

(SEQ ID NO: 92)
MEWTWVFLFLLSVTAGVHSQVQLQQSGAELMKPGASVKISCKATGYTFS
SYWIEWVKQRPGHGLEWIGEILPGSGRTNDNEKFKGKATFTADTSSKKA
YMQLSSLTSEDSAVYYCARRGGYSFAYWGQGTLVTVSAAKTKGPSVFPL
APCSRSTSESTAALGCLVKDYFPEPVTVSWNSGALTSGVHTFPAVLQSS
GLYSLSSVVTVPSSSLGTKTYTCNVDHKPSNTKVDKRVESKYGPPCPPC
PAPEFEGGPSVFLFPPKPKDTLMISRTPEVTCVVVDVSQEDPEVQFNWY
VDGVEVHNAKTKPREEQFNSTYRVVSVLTVLHQDWLNGKEYKCKVSNKG
LPSSIEKTISKAKGQPREPQVYTLPPSQEEMTKNQVSLTCLVKGFYPSD
IAVEWESNGQPENNYKTTPPVLDSDGSFFLYSRLTVDKSRWQEGNVFSC
SVMHEALHNHYTQKSLSLSLGKAS.

Anti-DCIR_24E7.3H9_K-V-hIgGK-C, light chain, SEQ ID NO:93:

(SEQ ID NO: 93)
MTMFSLALLLSLLLLCVSDSRAETTVTQSPASLSMAIGEKVTIRCVTST
DIDDDVNWYQQKPGEPPKLLISEGNTLRPGVPSRFSSSGYGTDFVFTIE
NMLSEDVADYYCLQSGNLPYTFGGGTKLEIKRTVAAPSVFIFPPSDEQL
KSGTASVVCLLNNFYPREAKVQWKVDNALQSGNSQESVTEQDSKDSTYS
LSSTLTLSKADYEKHKVYACEVTHQGLSSPVTKSFNRGEC.

Anti-DCIR_29E9.2E2_H-VhIgG4H-C, heavy chain, SEQ ID NO:94:

(SEQ ID NO: 94)
MAWVWTLLFLMAAAQSAQAQIQLVQSGPELKKPGETVKISCKASGYTFTN
YGMNWVKQAPGKGLKWVGWINTFTGEPTYVDDFKGRFAFSLETSASTAYL
QINNLKNEDTATYFCARGNFRYYYFDYWGQGTTLTVSSAKTKGPSVFPLA
PCSRSTSESTAALGCLVKDYFPEPVTVSWNSGALTSGVHTFPAVLQSSGL
YSLSSVVTVPSSSLGTKTYTCNVDHKPSNTKVDKRVESKYGPPCPPCPAP
EFEGGPSVFLFPPKPKDTLMISRTPEVTCVVVDVSQEDPEVQFNWYVDGV
EVHNAKTKPREEQFNSTYRVVSVLTVLHQDWLNGKEYKCKVSNKGLPSSI
EKTISKAKGQPREPQVYTLPPSQEEMTKNQVSLTCLVKGFYPSDIAVEWE
SNGQPENNYKTTPPVLDSDGSFFLYSRLTVDKSRWQEGNVFSCSVMHEAL
HNHYTQKSLSLSLGKAS.

Anti-DCIR_29E9.2E2_K-V-hIgGK-C, light chain, SEQ ID NO:95:

(SEQ ID NO: 95)
MSVLTQVLALLLLWLTGARCDIQMTQSPASLSASVGETVTITCRTSGNIR
NYLAWYQQKQGKSPQLLVYNAKTLADGVPSRFGGSGSGTQYSLKINSLQP

EDFGNYYCQHFWSSPYTFGGGTKLEIKRTVAAPSVFIFPPSDEQLKSGTA
SVVCLLNNFYPREAKVQWKVDNALQSGNSQESVTEQDSKDSTYSLSSTLT
LSKADYEKHKVYACEVTHQGLSSPVTKSFNRGEC.

Anti-DCIR_29 G10.3D9_H-V-hIgG4H-C, heavy chain, SEQ ID NO:96:

(SEQ ID NO: 96)
MMGWSYIILFLVATATDVHSQVQLQQPGAELVKPGASVKLSCKASGYTF
TSYWMHWVKQRPGEGLEWIGEINPSYGRTDYNEKFKNKATLTVAKSSST
AYMQLSSLTSEDSAVYYCARGDYYGSSSFAYWGQGTLVTVSAAKTKGPS
VFPLAPCSRSTSESTAALGCLVKDYFPEPVTVSWNSGALTSGVHTFPAV
LQSSGLYSLSSVVTVPSSSLGTKTYTCNVDHKPSNTKVDKRVESKYGPP
CPPCPAPEFEGGPSVFLFPPKPKDTLMISRTPEVTCVVVDVSQEDPEVQ
FNWYVDGVEVHNAKTKPREEQFNSTYRVVSVLTVLHQDWLNGKEYKCKV
SNKGLPSSIEKTISKAKGQPREPQVYTLPPSQEEMTKNQVSLTCLVKGF
YPSDIAVEWESNGQPENNYKTTPPVLDSDGSFFLYSRLTVDKSRWQEGN
VFSCSVMHEALHNHYTQKSLSLSLGKAS

Anti-DCIR_29 G10.3D9_K-Var1-V-hIgGK-C, light chain, SEQ ID NO:97:

(SEQ ID NO: 97)
MDFQVQIFSFLLMSASVEVISRGQIVLTQSPALMSASPGEKVTMTCSASS
NISYMYWYQQKPRSSPKPWIYLTSNLASGVPARFSGSGSGTSYSLTTSSM
EAEDAATYYCQQWSSNPPTFGAGTKLEIKRTVAAPSVFIFPPSDEQLKSG
TASVVCLLNNFYPREAKVQWKVDNALQSGNSQESVTEQDSKDSTYSLSST
LTLSKADYEKHKVYACEVTHQGLSSPVTKSFNRGEC.

Anti-DCIR_29 G10.3D9_K-Var2-V-hIgGK-C, light chain, SEQ ID NO:98:

(SEQ ID NO: 98)
MDFRVQIFSFLLMSASVEVISRGQIVLTQSPALMSASPGEKVTMTCSAS
SNISYMYWYQQKPRSSPKPWIYLTSNLASGVPARFSGSGSGTSYSLTIS
SMEAEDAATYYCQQWSSNPPTFGAGTKLEIKRTVAAPSVFIFPPSDEQL
KSGTASVVCLLNNFYPREAKVQWKVDNALQSGNSQESVTEQDSKDSTYS
LSSTLTLSKADYEKHKVYACEVTHQGLSSPVTKSFNRGEC.

Anti-DCIR_31A6.1F5_H-var2-V-hIgG4H-C, heavy chain, SEQ ID NO:99:

(SEQ ID NO: 99)
MECNWILPFILSVISGVYSEVQLQQSGTVLARPGASVNMSCKAAGYSFTS
YWVYWVKQRPGQGLEWIGAIYPKNSRTSYNQKFQDKATLTAVTSASTAYM
ELSSLTNEDSAVYYCTRPHYDSFGYWGQGTLVTVSAAKTKGPSVFPLAPC
SRSTSESTAALGCLVKDYFPEPVTVSWNSGALTSGVHTFPAVLQSSGLYS
LSSVVTVPSSSLGTKTYTCNVDHKPSNTKVDKRVESKYGPPCPPCPAPEF
EGGPSVFLFPPKPKDTLMISRTPEVTCVVVDVSQEDPEVQFNWYVDGVEV
HNAKTKPREEQFNSTYRVVSVLTVLHQDWLNGKEYKCKVSNKGLPSSIEK
TISKAKGQPREPQVYTLPPSQEEMTKNQVSLTCLVKGFYPSDIAVEWESN
GQPENNYKTTPPVLDSDGSFFLYSRLTVDKSRWQEGNVFSCSVMHEALHN
HYTQKSLSLSLGKAS.

Anti-DCIR_31A6.1F5_K-var2-V-hIgGK-C, light chain, SEQ ID NO:100:

(SEQ ID NO: 100)
METDTLLLWVLLLWVPGSTGDIVLTQSPASLAVSLGQRATISCRASESV
DSYGISFMHWYQQKPGQPPKLLIYRASNQESGIPARFSGSGSRTDFTLT
INPVEADDVATYYCQQSNEDPLTFGAGTKLEIKRTVAAPSVFIFPPSDE
QLKSGTASVVCLLNNFYPREAKVQWKVDNALQSGNSQESVTEQDSKDST
YSLSSTLTLSKADYEKHKVYACEVTHQGLSSPVTKSFNRGEC.

Anti-DCIR_3C2.2D9_H-LV-hIgG4H-C, heavy chain, SEQ ID NO:101:

(SEQ ID NO: 101)
NRLTSSLLLLIVPAYVLSQQVTLKESGPGILQPSQTLSLTCSFSGFSLS
TSGMGVSWIRQPSGKGLEWLAHIYWDDDKRYNPSLKSRLTIFKDPSSNQ
VFLRITSVDTADTATYYCARNSHYYGSTYGGYFDVWGAGTTVTVSSAKT
KGPSVFPLAPCSRSTSESTAALGCLVKDYFPEPVTVSWNSGALTSGVHT
FPAVLQSSGLYSLSSVVTVPSSSLGTKTYTCNVDHKPSNTKVDKRVESK
YGPPCPPCPAPEFEGGPSVFLFPPKPKDTLMISRTPEVTCVVVDVSQED
PEVQFNWYVDGVEVHNAKTKPREEQFNSTYRVVSVLTVLHQDWLNGKEY
KCKVSNKGLPSSIEKTISKAKGQPREPQVYTLPPSQEEMTKNQVSLTCL
VKGFYPSDIAVEWESNGQPENNYKTTPPVLDSDGSFFLYSRLTVDKSRW
QEGNVFSCSVMHEALHNHYTQKSLSLSLGKAS.

Anti-DCIR_3C2.2D9_K-LV-hIgGK-C, light chain, SEQ ID NO:102:

(SEQ ID NO: 102)
METDTLLLWVLLLGVPGSTGNIVLTQSPTSFTVSLGQRATISCRASESV
HSYGNSFMHWYQQKPGQPPKLLIYLASNVESGVPARFSGSGSRTDFTLT
IDPVEADDAATYYCQQNSEDPWTFGGGTKLEIKRTVAAPSVFIFPPSDE
QLKSGTASVVCLLNNFYPREAKVQWKVDNALQSGNSQESVTEQDSKDST
YSLSSTLTLSKADYEKHKVYACEVTHQGLSSPVTKSFNRGEC.

Anti-DCIR_6C8.1G9_H-V-hIgG4H-C, heavy chain, SEQ ID NO:103:

(SEQ ID NO: 103)
MEWTWVFLFLLSVTAGVHSQVQLQQSGTELMKPGASVKISCKATGYTFS
TYWIEWVKQRPGHGLEWIGEILPGSGRTNDNEKFKGKATITADTSSKKA
YMQLSSLTSEDSAVYYCARRGGYSFAFWGQGTLVSVSAAKTKGPSVFPL
APCSRSTSESTAALGCLVKDYFPEPVTVSWNSGALTSGVHTFPAVLQSS
GLYSLSSVVTVPSSSLGTKTYTCNVDHKPSNTKVDKRVESKYGPPCPPC

PAPEFEGGPSVFLFPPKPKDTLMISRTPEVTCVVVDVSQEDPEVQFNWY
VDGVEVHNAKTKPREEQFNSTYRVVSVLTVLHQDWLNGKEYKCKVSNKG
LPSSIEKTISKAKGQPREPQVYTLPPSQEEMTKNQVSLTCLVKGFYPSD
IAVEWESNGQPENNYKTTPPVLDSDGSFFLYSRLTVDKSRWQEGNVFSC
SVMHEALHNHYTQKSLSLSLGKAS.

Anti-DCIR_6C8.1G9_K-V-hIgGK-C, light chain, SEQ ID NO:104:

(SEQ ID NO: 104)
MTMFSLALLLSLLLLCVSDSRAETTVTQSPASLSMAIGEKVTIRCVTST
DIDDDVNWYQQKPGEPPKLLISEGNTLRAGVPSRFSSSGYGTDFVFTIE
NMLSEDVADYYCLQSGNLPYTFGGGTKLEIKRTVAAPSVFIFPPSDEQL
KSGTASVVCLLNNFYPREAKVQWKVDNALQSGNSQESVTEQDSKDSTYS
LSSTLTLSKADYEKHKVYACEVTHQGLSSPVTKSFNRGEC.

Anti-DCIR2C9H-LV-hIgG4H-V-hIgG4H-C, heavy chain, SEQ ID NO:105:

(SEQ ID NO: 105)
MKCSWVIFFLMAVVTGVNSEVQLQQSGAELVRPGALVKLSCKASGFNIN
DYYIHWVKQRPEQGLERIGWIDPDNGNTIYDPKFQGKASITADTSPNTA
YLQLSSLTSEDTAVYYCARTRSPMVTTGFVYWGQGTVVTVSAAKTKGPS
VFPLAPCSRSTSESTAALGCLVKDYFPEPVTVSWNSGALTSGVHTFPAV
LQSSGLYSLSSVVTVPSSSLGTKTYTCNVDHKPSNTKVDKRVESKYGPP
CPPCPAPEFEGGPSVFLFPPKPKDTLMISRTPEVTCVVVDVSQEDPEVQ
FNWYVDGVEVHNAKXKPREEQFNSTYRVVSVLTVLHQDWLNGKEYKCKV
SNKGLPSSIEKTISKAKGQPREPQVYTLPPSQEEMTKNQVSLTCLVKGF
YPSDIAVEWESNGQPENNYKTTPPVLDSDGSFFLYSRLTVDKSRWQEGN
VFSCSVMHEALHNHYTQKSLSLSLGK.

Anti-DCIR_2C9K-V-hIgGK-C, light chain, SEQ ID NO:106:

(SEQ ID NO: 106)
METDTLLLWVLLLWVPGSTGDIVLIQSPASLAVSLGQRATISCRASESV
DSYVNSFMHWYQQKPGQPPKLLIYRVSNLESGIPARFSGSGSRTDFTLT
INPVEADDVATYYCQQSNEDPFTFGSGTKLEIKRTVAAPSVFIFPPSDE
QLKSGTASVVCLLNNFYPREAKVQWKVDNALQSGNSQESVTEQDSKDST
YSLSSTLTLSKADYEKHKVYACEVTHQGLSSPVTKSFNRGEC.

Anti-Langerin Abs
Anti-Langerin-15B10H-LV-hIgG4H-C, heavy chain, SEQ ID NO:107:

(SEQ ID NO: 107)
QVQLRQSGPELVKPGASVKMSCKASGYTFTDYVISWVKQRTGQGLEWIG
DIYPGSGYSFYNENFKGKATLTADKSSTTAYMQLSSLTSEDSAVYFCAT
YYNYPFAYWGQGTLVTVSAAKTTGPSVFPLAPCSRSTSESTAALGCLVK
DYFPEPVTVSWNSGALTSGVHTFPAVLQSSGLYSLSSVVTVPSSSLGTK
TYTCNVDHKPSNTKVDKRVESKYGPPCPPCPAPEFEGGPSVFLFPPKPK
DTLMISRTPEVTCVVVDVSQEDPEVQFNWYVDGVEVHNAKTKPREEQFN
STYRVVSVLTVLHQDWLNGKEYKCKVSNKGLPSSIEKTISKAKGQPREP
QVYTLPPSQEEMTKNQVSLTCLVKGFYPSDIAVEWESNGQPENNYKTTP
PVLDSDGSFFLYSRLTVDKSRWQEGNVFSCSVMHEALHNHYTQKSLSLS
LGKAS.

The H chain variable of the Ab 15B10 is shown in SEQ ID NO:108:

(SEQ ID NO: 108)
SVKMSCKASGYTFTDYVISWVKQRTGQGLEWIGDIYPGSGYSFYNENFK
GKATLTADKSSTTAYMQLSSLTSEDSAVYFCA.

Anti-Langerin-15B10K-LV-hIgGK-C, light chain, SEQ ID NO:109:

(SEQ ID NO: 109)
DVVMTQTPLSLPVRLGDQASISCRSSQSLVHSNGNTYLHWYLQKPGQSP
KLLIYKVSNRFSGVPDRFSGSGSGTNFTLKISRVEAEDLGLYFCSQSTH
VPYTFGGGTKLEIKRTVAAPSVFIFPPSDEQLKSGTASVVCLLNNFYPR
EAKVQWKVDNALQSGNSQESVTEQDSKDSTYSLSSTLTLSKADYEKHKV
YACEVTHQGLSSPVTKSFNRGEC.

The L chain variable of the Ab 15B10 is shown in SEQ ID NO:110:

(SEQ ID NO: 110)
ASISCRSSQSLVHSNGNTYLHWYLQKPGQSPKLLIYKVSNRFSGVPDRF
SGSGSGTNFTLKISRVEAEDLGLYFCS.

Anti-Langerin-2G3H-LV-hIgG4H-C, heavy chain, SEQ ID NO:111:

(SEQ ID NO: 111)
MTLNMLLGLRWVFFVVFYQGVHCEVQLVESGGGLVQPKGSLKLSCAASG
LTFNIYAMNWVRQAPGKGLEWVARIRNKSNNYATYYADSVKDRFTISRD
DSQSLLYLQMNNLKTEDTAMYYCVGRDWFDYWGQGTLVTVSAAKTKGPS
VFPLAPCSRSTSESTAALGCLVKDYFPEPVTVSWNSGALTSGVHTFPAV
LQSSGLYSLSSVVTVPSSSLGTKTYTCNVDHKPSNTKVDKRVESKYGPP
CPPCPAPEFEGGPSVFLFPPKPKDTLMISRTPEVTCVVVDVSQEDPEVQ
FNWYVDGVEVHNAKTKPREEQFNSTYRVVSVLTVLHQDWLNGKEYKCKV
SNKGLPSSIEKTISKAKGQPREPQVYTLPPSQEEMTKNQVSLTCLVKGF
YPSDIAVEWESNGQPENNYKTTPPVLDSDGSFFLYSRLTVDKSRWQEGN
VFSCSVMHEALHNHYTQKSLSLSLGKAS.

The H chain variable of the Ab 2G3 is shown in SEQ ID NO:112:

```
                                           (SEQ ID NO: 112)
SLKLSCAASGLTFNIYAMNWVRQAPGKGLEWVARIRNKSNNYATYYADS

VKDRFTISRDDSQSLLYLQMNNLKTEDTAMYYC.
```

Anti-Langerin-2G3L-LV-hIgGK-C, light chain, SEQ ID NO:113:

```
                                           (SEQ ID NO: 113)
MAWISLILSLLALSSGAISQAVVTQESALTTSPGETVTLTCRSSTGAVT

TSNYANWVQEKPDHLFTGLIGGTNNRVSGVPARFSGSLIGDKAALTITG

AQTEDEAIYFCALWYSNHWVFGGGTKLEIKRTVAAPSVFIFPPSDEQLK

SGTASVVCLLNNFYPREAKVQWKVDNALQSGNSQESVTEQDSKDSTYSL

SSTLTLSKADYEKHKVYACEVTHQGLSSPVTKSFNRGEC.
```

The L chain variable of the Ab 2G3 is shown in SEQ ID NO:114:

```
                                           (SEQ ID NO: 114)
VTLTCRSSTGAVTTSNYANWVQEKPDHLFTGLIGGTNNRVSGVPARFSG

SLIGDKAALTITGAQTEDEAIYFCA.
```

III. INTERLEUKIN 10 (IL-10)

Interleukin-10 (IL-10), also known as human cytokine synthesis inhibitory factor (CSIF), is an anti-inflammatory cytokine. In humans, IL-10 is encoded by the IL10 gene. The mRNA sequence of human IL-10 is represented by accession No.: NM_000572.2. The amino acid sequence of human IL-10 is represented by accession No.: NP_000563.1 and SEQ ID NO:5. The sequence associated with these accession numbers is incorporated by reference for all purposes.

In some embodiments, the APC-targeted antibody or fragment thereof is operatively linked to an IL-10 polypeptide comprising a sequence corresponding to a protein sequence of an NCBI accession number NP_000563.1. In some embodiments, the IL-10 polypeptide comprises the amino acid sequence of SEQ ID NO:5 or a fragment thereof:

IV. ANTIGENS

Certain aspects of the disclosure include methods and compositions concerning antigenic components including segments, fragments, or epitopes of polypeptides, peptides, nucleic acids, carbohydrates, lipids and other molecules that provoke or induce an antigenic response, generally referred to as antigens. In one embodiment, the antigen is a peptide. In particular, antigens, or antigenic segments or fragments of such antigens, which lead to the destruction of a cell via an immune response, can be identified and used in the methods and compositions described herein.

Antigens associated with various diseases and disorders are known in the art. It is contemplated that any antigen may be used in the methods and compositions described herein. In certain aspects, the antigen is one that is involved in the etiology of an autoimmune, allergic, or inflammatory disease known in the art and/or described herein.

In certain aspects, the antigen is one known in the art to be involved in rheumatoid arthritis, allergy, asthma, systemic onset juvenile arthritis, inflammatory bowel disease, systemic lupus erythematosus, type 1 diabetes, and Crohn's disease.

V. PEPTIDE COMPONENTS AND PROTEINACEOUS COMPOSITIONS

Polypeptides and peptides may be modified by various amino acid deletions, insertions, and/or substitutions. In particular embodiments, modified polypeptides and/or peptides are capable of modulating an immune response in a subject. As used herein, a "protein" or "polypeptide" or "peptide" refers to a molecule comprising at least five amino acid residues. In some embodiments, a wild-type version of a protein or peptide are employed, however, in many embodiments, a modified protein or polypeptide is employed to generate the antibody conjugates described herein. A "modified protein" or "modified polypeptide" or "modified peptide" refers to a protein or polypeptide whose chemical structure, particularly its amino acid sequence, is altered with respect to the wild-type protein or polypeptide.

Peptides include peptides that are found to be specific to cancerous or pre-cancerous cells in the body. These peptides may be associated with the APC-targeted antibodies described herein. Administration of combinations of these peptides includes administering a population of antibody conjugates having multiple peptides attached and/or administering multiple conjugate populations, each having a specific peptide attached or a combination of such conjugates that includes nanoparticles with 1, 2, 3, 4, 5, 6, or more peptides attached to the APC-targeted antibody, antigen binding fragment thereof, or IL-10 protein.

Proteinaceous compositions may be made by any technique known to those of skill in the art, including (i) the expression of proteins, polypeptides, or peptides through standard molecular biological techniques, (ii) the isolation of proteinaceous compounds from natural sources, or (iii) the chemical synthesis of proteinaceous materials. The nucleotide as well as the protein, polypeptide, and peptide sequences for various genes have been previously disclosed, and may be found in the recognized computerized databases. One such database is the National Center for Biotechnology Information's GenBank and GenPept databases (on the World Wide Web at ncbi.nlm.nih.gov/). The all or part of the coding regions for these genes may be amplified and/or expressed using the techniques disclosed herein or as would be known to those of ordinary skill in the art.

Amino acid sequence variants of antigenic epitopes and other polypeptides of these compositions can be substitutional, insertional, or deletion variants. A modification in a polypeptide may affect 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500 or more non-contiguous or contiguous amino acids of a peptide or polypeptide, as compared to wild-type. A peptide or polypeptide that results in an immune response is contemplated for use in embodiments.

Deletion variants typically lack one or more residues of the native or wild-type amino acid sequence. Individual residues can be deleted or a number of contiguous amino acids can be deleted. A stop codon may be introduced (by substitution or insertion) into an encoding nucleic acid sequence to generate a truncated protein. Insertional mutants typically involve the addition of material at a non-terminal point in the polypeptide. This may include the insertion of one or more residues. Terminal additions, called fusion proteins, may also be generated.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of a polypeptide or peptide is affected, such as avidity or affinity for a cellular receptor(s). Non-conservative changes typically involve substituting a residue with one that is chemically dissimilar, such as a polar or charged amino acid for a nonpolar or uncharged amino acid, and vice versa.

Proteins may be recombinant, or synthesized in vitro. Alternatively, a recombinant protein may be isolated from bacteria or other host cell.

The term "functionally equivalent codon" is used herein to refer to codons that encode the same amino acid, such as the six codons for arginine or serine, and also refers to codons that encode biologically equivalent amino acids.

It also will be understood that amino acid and nucleic acid sequences may include additional residues, such as additional N- or C-terminal amino acids, or 5' or 3' nucleic acid sequences, respectively, and yet still be essentially as set forth in one of the sequences disclosed herein, so long as the sequence meets the criteria set forth above, including the maintenance of biological protein activity (e.g., immunogenicity). The addition of terminal sequences particularly applies to nucleic acid sequences that may, for example, include various non-coding sequences flanking either of the 5' or 3' portions of the coding region.

It is contemplated that in composition embodiments, there is between about 0.001 mg and about 10 mg of total protein per ml. Thus, the concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 50, 100 .mu.g/ml or mg/ml or more (or any range derivable therein).

Embodiments include in some cases the administration of an APC-targeted antibody. In some embodiments, the methods and compositions further comprise an antigen. U.S. Pat. No. 4,554,101 (Hopp), which is incorporated herein by reference, teaches the identification and preparation of antigenic epitopes from primary amino acid sequences on the basis of hydrophilicity. Through the methods disclosed in Hopp, one of skill in the art would be able to identify potential antigenic epitopes from within an amino acid sequence and confirm their immunogenicity. Numerous scientific publications have also been devoted to the prediction of secondary structure and to the identification of epitopes, from analyses of amino acid sequences (Chou & Fasman, 1974a,b; 1978a,b; 1979). Any of these may be used, if desired, to supplement the teachings of Hopp in U.S. Pat. No. 4,554,101.

VI. PHARMACEUTICAL COMPOSITIONS

Embodiments include methods and compositions for increasing immune responses in a subject in need thereof. They include compositions that can be used to induce or modify an immune response against an antigen e.g., a polypeptide, a peptide, a carbohydrate, a lipid or other molecule or molecular fragment and against developing a condition or disease associated with such antigen.

It is contemplated that the APC-targeted antibody or antigen binding fragment thereof (and optionally antigen and optionally linked to IL-10) may be administered with additional adjuvants known in the art such as TLR agonists. TLR agonists may include an agonist to TLR1 (e.g. peptidoglycan or triacyl lipoproteins), TLR2 (e.g. lipoteichoic acid; peptidoglycan from *Bacillus subtilis*, *E. coli* 0111:B4, *Escherichia coli* K12, or *Staphylococcus aureus*; atypical lipopolysaccharide (LPS) such as *Leptospirosis* LPS and *Porphyromonas gingivalis* LPS; a synthetic diacylated lipoprotein such as FSL-1 or Pam2CSK4; lipoarabinomannan or lipomannan from *M. smegmatis*; triacylated lipoproteins such as Pam3CSK4; lipoproteins such as MALP-2 and MALP-404 from *mycoplasma; Borrelia burgdorferi* OspA; Porin from *Neisseria meningitidis* or *Haemophilus influenza; Propionibacterium acnes* antigen mixtures; *Yersinia* LcrV; lipomannan from *Mycobacterium* or *Mycobacterium tuberculosis; Trypanosoma cruzi* GPI anchor; *Schistosoma mansoni* lysophosphatidylserine; *Leishmania major* lipophosphoglycan (LPG); *Plasmodium falciparum* glycophosphatidylinositol (GPI); zymosan; antigen mixtures from *Aspergillus fumigatus* or *Candida albicans*; and measles hemagglutinin), TLR3 (e.g. double-stramded RNA, polyadenylic-polyuridylic acid (Poly(A:U)); polyinosine-polycytidylic acid (Poly(I:C)); polyinosine-polycytidylic acid high molecular weight (Poly(I:C) HMW); and polyinosine-polycytidylic acid low molecular weight (Poly (I:C) LMW)), TLR4 (e.g. LPS from *Escherichia coli* and *Salmonella* species); TLR5 (e.g. Flagellin from *B. subtilis, P. aeruginosa*, or *S. typhimurium*), TLR8 (e.g. single stranded RNAs such as ssRNA with 6UUAU repeats, RNA homopolymer (ssPolyU naked), HIV-1 LTR-derived ssRNA (ssRNA40), or ssRNA with 2 GUCCUUCAA repeats (ssRNA-DR)), TLR7 (e.g. imidazoquinoline compound imiquimod, Imiquimod VacciGrade™, Gardiquimod VacciGrade™, or Gardiquimod™; adenine analog CL264; base analog CL307; guanosine analog loxoribine; TLR7/8 (e.g. thiazoquinoline compound CL075; imidazoquinoline compound CL097, R848, or R848 VacciGrade™), TLR9 (e.g. CpG ODNs); and TLR11 (e.g. *Toxoplasma gondii* Profilin). In certain embodiments, the TLR agonist is a specific agonist listed above. In further embodiments, the TLR agonist is one that agonizes either one TLR or two TLRs specifically.

In certain embodiments, the methods and compositions specifically exclude the administration of a TLR ligand and/or agonist.

Administration of the compositions will typically be via any common route. This includes, but is not limited to oral, parenteral, orthotopic, intradermal, subcutaneous, intramuscular, intraperitoneal, intranasal, by inhalation, by using a nebulizer, or by intravenous injection. In certain embodiments, a vaccine composition may be inhaled (e.g., U.S. Pat. No. 6,651,655, which is specifically incorporated by reference). Additional formulations which are suitable for other modes of administration include oral formulations. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, preferably about 25% to about 70%.

Typically, compositions are administered in a manner compatible with the dosage formulation, and in such amount as will be therapeutically effective and immune modifying. The quantity to be administered depends on the subject to be treated. Precise amounts of active ingredient required to be administered depend on the judgment of the practitioner.

The manner of application may be varied widely. Any of the conventional methods for administration of an antibody are applicable. These are believed to include oral application on a solid physiologically acceptable base or in a physiologically acceptable dispersion, parenterally, by injection and the like. The dosage of the pharmaceutical composition will depend on the route of administration and will vary according to the size and health of the subject.

In many instances, it will be desirable to have multiple administrations of at most about or at least about 3, 4, 5, 6, 7, 8, 9, 10 or more. The administrations may range from 2 day to twelve week intervals, more usually from one to two week intervals. The course of the administrations may be followed by assays for reactive immune responses and T cell activity.

The phrases "pharmaceutically acceptable" or "pharmacologically acceptable" refer to molecular entities and compositions that do not produce an adverse, allergic, or other untoward reaction when administered to an animal, or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated.

The antibodies or antigen binding fragments can be formulated for parenteral administration, e.g., formulated for injection via the intravenous, intradermal, intramuscular, sub-cutaneous, or even intraperitoneal routes. In a specific embodiment, the composition is administered by intradermal injection. In further embodiments, the composition is administered by intravenous injection. The preparation of an aqueous composition that contains a APC-targeted antibody that modifies the subject's immune condition will be known to those of skill in the art in light of the present disclosure. Typically, such compositions can be prepared as injectables, either as liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active ingredients in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the result and/or protection desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition. Upon formulation, solutions will be administered in a manner compatible with the dosage formulation and in such amount as is therapeutically or prophylactically effective. The formulations are easily administered in a variety of dosage forms, such as the type of injectable solutions described above.

VII. IN VITRO OR EX VIVO ADMINISTRATION

As used herein, the term in vitro administration refers to manipulations performed on cells removed from or outside of a subject, including, but not limited to cells in culture. The term ex vivo administration refers to cells which have been manipulated in vitro, and are subsequently administered to a subject. The term in vivo administration includes all manipulations performed within a subject, including administrations.

In certain aspects, the compositions may be administered either in vitro, ex vivo, or in vivo. In certain in vitro embodiments, isolated immune cells are incubated with compositions described herein. For example, isolated APCs may be incubated with the antibody or antibody conjugates as described herein. The cells can then be used for in vitro analysis, or alternatively for ex vivo administration.

VIII. THERAPEUTIC APPLICATIONS

Methods include treatment of inflammatory and autoimmune disorders Methods may be employed with respect to individuals who has tested positive for such disorders or who are deemed to be at risk for developing such a condition or related condition.

The antibody or antigen binding fragment of the disclosure (in some embodiments, conjugated to IL-10) can be given to induce or modify an immune response in a person having, suspected of having, or at risk of developing an autoimmune condition or complication relating to an allograft. Methods may be employed with respect to individuals who have tested positive for autoreactivity or alloreactivity or who are deemed to be at risk for developing such a condition or related condition.

The methods described herein are particularly useful in treating or preventing disorders for which antigenic determinants are poorly characterized. Such disorders include, for example, rheumatoid arthritis, allergy, asthma, systemic onset juvenile arthritis, inflammatory bowel disease, and Crohn's disease. The methods described herein are also particularly useful for disorders such as GVHD and graft rejection since the antigenic determinants of such diseases may not be known or may be different depending on the tissue and/or individual from which the tissue was obtained from.

It is contemplated that targeting dendritic cells (e.g. with an anti-DC-ASGPR antibody) inhibits autoimmune diseases but does not interfere with pathogen-specific T cell responses.

Embodiments can be used to treat or ameliorate a number of immune-mediated, inflammatory, or autoimmune-inflammatory diseases, e.g., allergies, asthma, diabetes (e.g. type 1 diabetes), graft rejection, etc. Examples of such diseases or disorders also include, but are not limited to arthritis (rheumatoid arthritis such as acute arthritis, chronic rheumatoid arthritis, gout or gouty arthritis, acute gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, and systemic juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, atopy including atopic diseases such as hay fever and Job's syndrome, dermatitis including contact dermatitis, chronic contact dermatitis, exfoliative dermatitis, allergic dermatitis, allergic contact dermatitis, dermatitis herpetiformis, nummular dermatitis, seborrheic dermatitis, non-specific dermatitis, primary irritant contact dermatitis, and atopic dermatitis, x-linked hyper IgM syndrome, allergic intraocular inflammatory diseases, urticaria such as chronic allergic urticaria and chronic idiopathic urticaria, including chronic autoimmune urticaria, myositis, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, ataxic sclerosis, neuromyelitis optica (NMO), inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), bowel inflammation, pyoderma gangrenosum, erythema nodosum, primary sclerosing cholangitis, respiratory distress syndrome, including adult or acute respiratory distress syndrome (ARDS), meningitis, inflammation of all or part of the uvea, iritis, choroiditis, an autoimmune hematological disorder, rheumatoid spondylitis, rheumatoid synovitis, hereditary angioedema, cranial nerve damage as in meningitis, herpes gestationis, pemphigoid gestationis, pruritis scroti, autoimmune premature ovarian failure, sudden hearing loss due to an autoimmune condition, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, non-granulomatous uveitis, phacoantigenic uveitis, posterior uveitis, or autoimmune uveitis, glomerulonephritis (GN)

with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, proliferative nephritis, autoimmune polyglandular endocrine failure, balanitis including balanitis circumscripta plasmacellularis, balanoposthitis, erythema annulare centrifugum, erythema dyschromicum perstans, eythema multiform, granuloma annulare, lichen nitidus, lichen sclerosus et atrophicus, lichen simplex chronicus, lichen spinulosus, lichen planus, lamellar ichthyosis, epidermolytic hyperkeratosis, premalignant keratosis, pyoderma gangrenosum, allergic conditions and responses, allergic reaction, eczema including allergic or atopic eczema, asteatotic eczema, dyshidrotic eczema, and vesicular palmoplantar eczema, asthma such as asthma bronchiale, bronchial asthma, and auto-immune asthma, conditions involving infiltration of T cells and chronic inflammatory responses, immune reactions against foreign antigens such as fetal A-B-O blood groups during pregnancy, chronic pulmonary inflammatory disease, autoimmune myocarditis, leukocyte adhesion deficiency, lupus, including lupus nephritis, lupus cerebritis, pediatric lupus, non-renal lupus, extra-renal lupus, discoid lupus and discoid lupus erythematosus, alopecia lupus, systemic lupus erythematosus (SLE) such as cutaneous SLE or subacute cutaneous SLE, neonatal lupus syndrome (NLE), and lupus erythematosus disseminatus, juvenile onset (Type I) diabetes mellitus, including pediatric insulin-dependent diabetes mellitus (IDDM), and adult onset diabetes mellitus (Type II diabetes) and autoimmune diabetes. Also contemplated are immune responses associated with acute and delayed hypersensitivity mediated by cytokines and T-lymphocytes, sarcoidosis, granulomatosis including lymphomatoid granulomatosis, Wegener's granulomatosis, agranulocytosis, vasculitides, including vasculitis, large-vessel vasculitis (including polymyalgia rheumatica and gianT cell (Takayasu's) arteritis), medium-vessel vasculitis (including Kawasaki's disease and polyarteritis nodosa/periarteritis nodosa), microscopic polyarteritis, immunovasculitis, CNS vasculitis, cutaneous vasculitis, hypersensitivity vasculitis, necrotizing vasculitis such as systemic necrotizing vasculitis, and ANCA-associated vasculitis, such as Churg-Strauss vasculitis or syndrome (CSS) and ANCA-associated small-vessel vasculitis, temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), Addison's disease, autoimmune neutropenia, pancytopenia, leukopenia, diseases involving leukocyte diapedesis, CNS inflammatory disorders, Alzheimer's disease, Parkinson's disease, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Behcet's disease/syndrome, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, thermal injury, preeclampsia, an immune complex disorder such as immune complex nephritis, antibody-mediated nephritis, polyneuropathies, chronic neuropathy such as IgM polyneuropathies or IgM-mediated neuropathy, autoimmune or immune-mediated thrombocytopenia such as idiopathic thrombocytopenic purpura (ITP) including chronic or acute ITP, scleritis such as idiopathic cerato-scleritis, episcleritis, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), experimental autoimmune encephalomyelitis, myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, gianT cell hepatitis, chronic active hepatitis or autoimmune chronic active hepatitis, lymphoid interstitial pneumonitis (LIP), bronchiolitis obliterans (non-transplant) vs NSIP, Guillain-Barre syndrome, Berger's disease (IgA nephropathy), idiopathic IgA nephropathy, linear IgA dermatosis, acute febrile neutrophilic dermatosis, subcorneal pustular dermatosis, transient acantholytic dermatosis, cirrhosis such as primary biliary cirrhosis and pneumonocirrhosis, autoimmune enteropathy syndrome, Celiac or Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, polychondritis such as refractory or relapsed or relapsing polychondritis, pulmonary alveolar proteinosis, Cogan's syndrome/nonsyphilitic interstitial keratitis, Bell's palsy, Sweet's disease/syndrome, rosacea autoimmune, zoster-associated pain, amyloidosis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal or segmental or focal segmental glomerulosclerosis (FSGS), endocrine opthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, Dressler's syndrome, alopecia greata, alopecia totalis, CREST syndrome (calcinosis, Raynaud's phenomenon, esophageal dysmotility, sclerodactyl), and telangiectasia), male and female autoimmune infertility, e.g., due to anti-spermatozoan antibodies, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, parasitic diseases such as leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, pulmonary fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis (acute or chronic), or Fuch's cyclitis, Henoch-Schonlein purpura, human immunodeficiency virus (HIV) infection, SCID, acquired immune deficiency syndrome (AIDS), echovirus infection, sepsis, endotoxemia, pancreatitis, thyroxicosis, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, gianT cell polymyalgia, chronic hypersensitivity pneumonitis, keratoconjunctivitis sicca, epidemic keratoconjunctivitis, idiopathic nephritic syndrome, minimal change nephropathy, benign familial and ischemia-reperfusion injury, transplant organ reperfusion, retinal autoimmunity, joint inflammation, bronchitis, chronic obstructive airway/pulmonary disease, silicosis, aphthae, aphthous stomatitis, arteriosclerotic disorders, aserniogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired spenic atrophy, non-malignant thymoma, vitiligo, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, autoimmune polyglandular syndrome type I, adult-onset idiopathic hypoparathyroidism (AOIH), cardiomyopathy such as dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia syndrome, angiectasis, autoimmune disorders associated with collagen disease, rheumatism, neurological disease, lymphadenitis, reduction in blood pressure response, vascular dysfunction, tissue injury, cardiovascular ischemia, hyperalgesia, renal ischemia, cerebral ischemia, and disease accompanying vascularization, allergic hypersensitivity disorders, glomerulonephritides, reperfusion injury, ischemic re-perfusion disorder, reperfusion injury of myocardial or other tissues, lymphomatous tracheobronchitis, inflammatory dermatoses, dermatoses with acute inflammatory components, multiple organ failure, bullous diseases, renal cortical necrosis, acute purulent meningitis or other central nervous system inflammatory disorders, ocular and orbital inflammatory disorders, granulocyte transfusion-associated syndromes, cytokine-induced toxicity, narcolepsy, acute serious inflammation, chronic intractable inflammation, pyelitis, endarterial hyperplasia, peptic ulcer, valvulitis, graft versus host disease, contact hypersensitivity, asthmatic airway hyperreaction, and endometriosis.

Embodiments can be used to prevent, treat or ameliorate a number of allergic disorders. Non-limiting examples include asthma, type 1 diabetes, chronic obstructive pulmonary disease, interstitial lung disease, chronic obstructive lung disease, chronic bronchitis, eosinophilic bronchitis, eosinophilic pneumonia, pneumonia, inflammatory bowel disease, atopic dermatitis, atopy, allergy, allergic rhinitis, idiopathic pulmonary fibrosis, scleroderma, emphysema, breast cancer, and ulcerative colitis. Non-limiting examples of allergic disorders include allergic atopy and dermatitis, allergic rhinitis, allergic asthma, allergic responses to food (e.g. milk, egg, wheat, nut, fish, shellfish, sulfite, soy, and casein), environmental allergens (e.g. plant and animal allergens such as dander, dust mites, pollen, cedar, poison ivy, poison oak, poison sumac, etc. . . . ), insect bites (e.g. bee, wasp, yellow jacket, hornet, or fire ant stings), hay fever, allergic conjunctivitis, hives, mold, medication allergies (e.g. aspirin and penicillin), and cosmetic allergies.

In some embodiments, the compositions and methods described herein are used to treat an inflammatory component of a disorder listed herein and/or known in the art. Accordingly, the methods and compositions described herein can be used to treat a subject suffering from inflammation. In some embodiments, the inflammation is acute. In other embodiments, the inflammation is chronic. In further embodiments, the compositions and methods described herein are used to treat or prevent a cancer by treating or preventing an inflammatory component associated with the cancer. In some embodiments, the cancer is breast cancer.

IX. COMBINATION THERAPY

The compositions and related methods disclosed herein, particularly administration of an APC-targeted antibody or antigen binding fragment may also be used in combination with the administration of traditional therapies. These include, but are not limited to, the administration of immunosuppressive or modulating therapies or treatments. Non-limiting examples of existing immunosuppressive therapies include administration of immunosuppressive compounds such as cyclosporine A, cyclophosphamide, FK506, tacrolimus, corticosteroids, azathioprine, mycophenolate mofetil, sirolimus, rapamycin, rapamycin analogs, deoxyspergualin, and prednisone In one aspect, it is contemplated that an APC-targeted antibody or antigen binding fragment is used in conjunction with a cytokine treatment. Alternatively, antibody administration may precede or follow the other treatment by intervals ranging from minutes to weeks. In embodiments where the other agents are administered separately, one would generally ensure that a significant period of time did not expire between the time of each delivery, such that the agent and antibody would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several weeks (1, 2, 3, 4, 5, 6, 7 or 8) lapse between the respective administrations.

Administration of the anti-DC-ASGPR antibody or antigen binding fragment compositions to a patient/subject will follow general protocols for the administration of such compounds, taking into account the toxicity, if any. It is expected that the treatment cycles would be repeated as necessary. It also is contemplated that various standard therapies, such as hydration, may be applied in combination with the described therapy.

X. EXAMPLES

The following examples are included to demonstrate certain embodiments. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Targeting IL-10 to Antigen Presenting Cells

With targeted in vivo delivery of IL-10 to APCs followed by alterations of pathogenic functions of APC as well as the enhancement of regulatory T cell responses, this therapeutic strategy can be more effective and durable than non-targeted anti-inflammatory cytokines. Compared to non-targeted methods, targeted method described herein requires much less amount of IL-10 to show the same or similar effects. With the dose-sparing-effect along with the delivery of IL-10 to subsets of patient's APCs, this strategy is expected to significantly reduce side effects of anti-inflammatory cytokine treatment, but with better effects.

To study the effects of APC-targeted IL-10, recombinant fusion protein of antibody and human IL-10 were made. Monoclonal antibodies (anti-CD40 clone 12E12, anti-CD40 clone 24A3, anti-DCIR clone 9E8, anti-DC-ASGPR clone 49C11, and control IgG4) and human IL-10 fusion proteins were made.

It was found that different antibodies fused to human IL-10 can target subsets of human DCs in distinct patterns. The ability of antibody-IL-10 fusion proteins to bind to human DCs was measured. Both myeloid DC (mDCs) and plasmacytoid DCs (pDCs) were purified from human blood. DCs were incubated for 20 min in ice in the presence of different concentrations of recombinant fusion proteins of antibody and IL-10 (FIG. 1). After vigorous washing, DCs were further stained with anti-human IL-10 to detect surface bound antibody-IL-10 fusion proteins using flow cytometry. As shown in FIG. 1, all the recombinant fusion proteins of antibody-IL-10 (except for the control IgG4-IL-10) could bind to mDCs. However, binding patterns of the individual proteins to mDCs were not the same. For example, anti-DCIR (9E8)-IL-10 binds to mDCs more efficiently than do the others. In addition, anti-CD40 (12E12)-IL-10 shows better binding to mDCs than anti-CD40 (24A3)-IL-10. Although both anti-CD40 (12E12)-IL-10 and anti-CD40 (24A3)-IL-10 bind to pDCs, anti-DCIR (9E8)-IL-10 shows the besting binding to pDCs.

Taken together, these data indicate that anti-inflammatory cytokines (including IL-10) fused to different antibodies can target different subsets of human APCs in different levels, which can result in different outcomes of immune responses.

Figure 2:
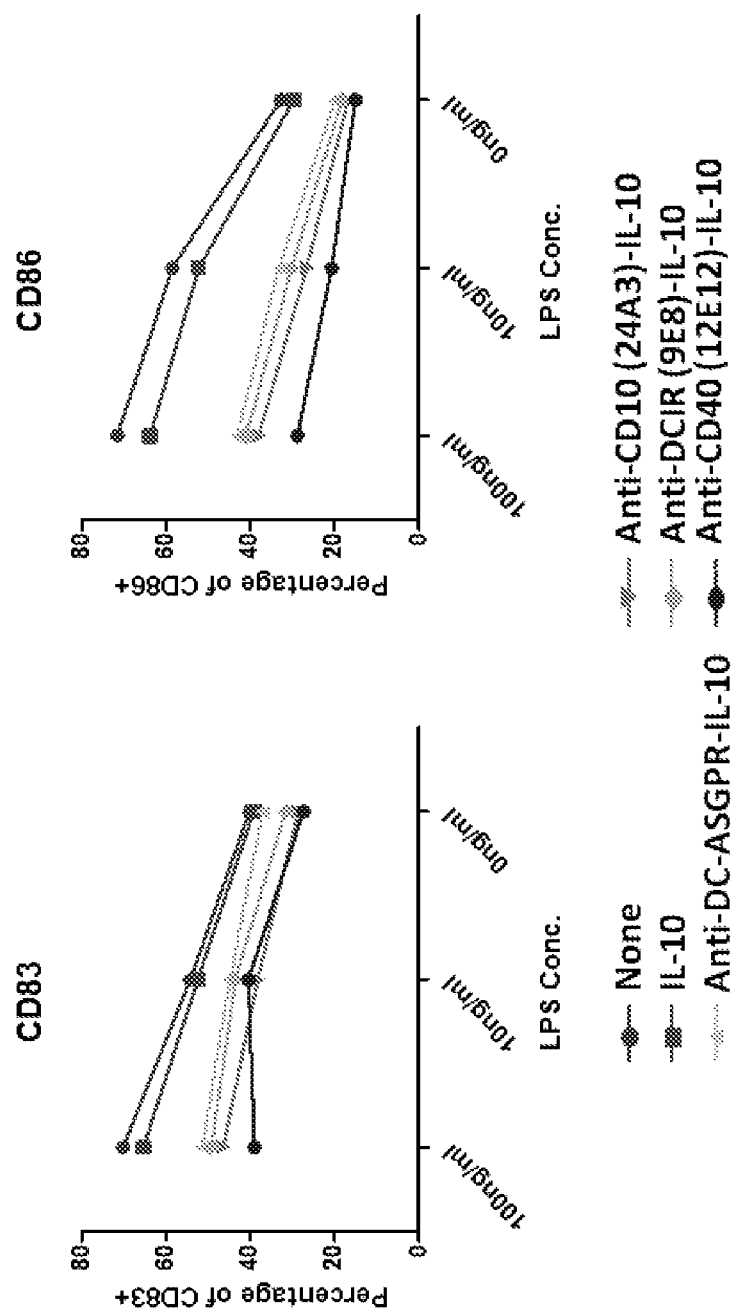
FIG. 2 shows that antibody-IL-10 fusion proteins inhibit DC maturation induced by *E. coli* lipopolysaccharide.

It was also found that antibody-IL-10 fusion proteins can suppress DC maturation. DCs are the major APCs that can induce and direct host immune responses toward either immunity or tolerance. It is also known that matured DCs induce immunity whereas immatured DCs induce immune tolerance. Therefore, the effectiveness of antibody-IL-10 fusion proteins on the maturation of DCs induced by *Escherichia coli* lipopolysaccharide (LPS: toll-like receptor 4 ligand) was tested. Purified blood mDCs were cultured overnight with 0, 10, and 100 ng/ml LPS in the presence or absence of 10 µg recombinant fusion proteins indicated or the same molar concentration of recombinant IL-10. mDCs were then stained with anti-CD83 and anti-CD86 to measure the expression levels of these two surface molecules (indicators for DC maturation) using flow cytometry. FIG. 2 shows that untargeted human IL-10 slightly decreased CD83 and CD86 expression. Compared to untargeted IL-10, targeted delivery of IL-10 using recombinant fusion proteins of antibody and IL-10 were far more efficient to suppress the LPS-induced DC maturation. Anti-CD40 (12E12)-IL-10 was slightly more efficient than others to suppress the expression of CD86.

These data demonstrate that recombinant fusion proteins of antibody and IL-10 can efficiently target human DCs and thus can effectively suppress DC maturation. This indicates that targeted delivery of anti-inflammatory cytokines to human APCs can efficiently suppress ongoing inflammatory responses by the inhibition of APC, including DCs, maturation.

Figure 3:
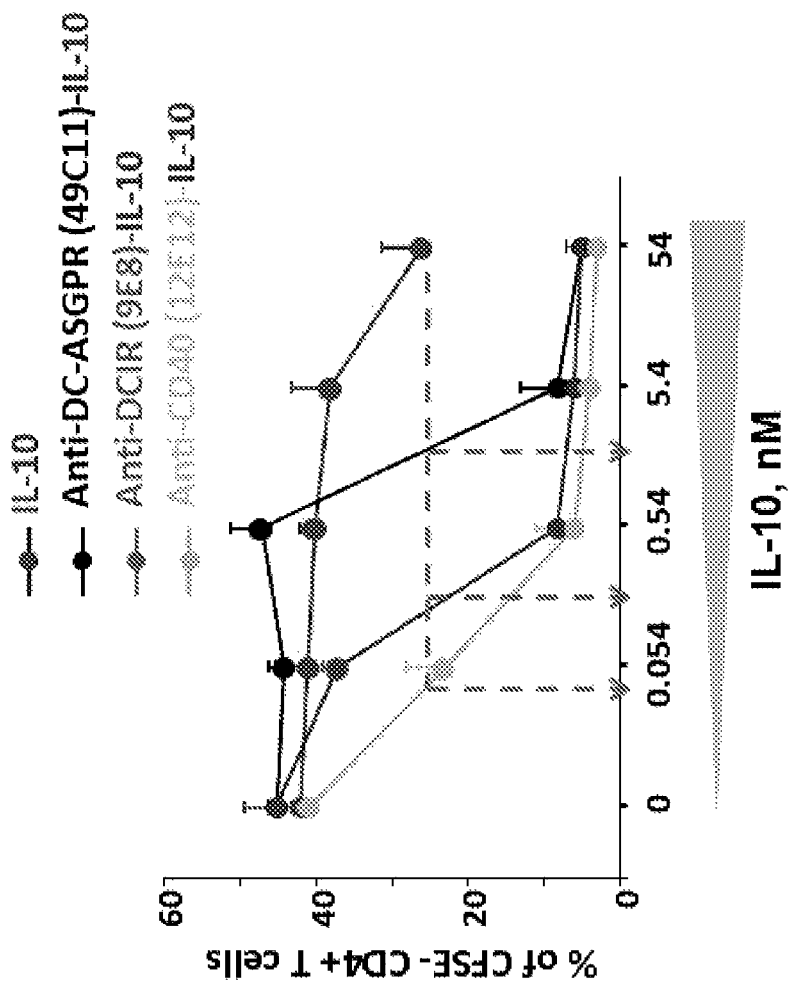
FIG. 3 demonstrates the dose sparing effects of the targeted IL-10 fustion proteins.

It was next found that targeted delivery of IL-10 to DCs using recombinant fusion proteins of antibody and IL-10 can efficiently suppress T cell responses. The effectiveness of recombinant fusion proteins of antibody and IL-10 in T cell responses (FIG. 3) was further assessed. Purified mDCs were incubated for 2 h with different concentrations of either recombinant human IL-10 or fusion proteins of antibody and IL-10. CFSE-labeled allogeneic CD4+ T cells were co-cultured for 5 days and T cell proliferation was assessed by measuring CFSE dilution with flow cytometry. Compared to IL-10 alone, recombinant fusion proteins of antibody and IL-10 were far more efficient to suppress the allogeneic CD4+ T cell proliferation. To result in 50% inhibition of T cell proliferation, 54 nM IL-10 was required, while only less than 5.4-0.054 nM (IL-10) was required to result in similar effect on T cell proliferation when IL-10 was delivered to DCs in a targeted fashion.

Taken together, the data (FIGS. 1, 2, 3) demonstrate that 1) recombinant fusion proteins of antibody and anti-inflammatory cytokines can effectively target human APCs with different patterns, depending on APC subsets (FIG. 1); 2) they can suppress human APCs (including DCs) activation and maturation; and 3) can effectively suppress T cell responses.

Example 2: Treating GVHD with Anti-DC-ASGPR

Tolerance to specific antigens is the ultimate goal for the success of transplantation. Over the past several decades, a large array of immunosuppressive agents has been developed and is being used for patients. However, immunosuppression does not guarantee the prevention of alloreaction over time in patients who receive organs, tissues, and hematopoietic stem cell (HPSC) transplantation. As a consequence, patients succumb to graft-versus-host disease (GVHD) as well as serious side effects due to life-long immunosuppression. T cell depletion also compromises the graft-versus-leukemia (GVL) effects in alloHPSC transplantation. Furthermore, controlling GVHD with nonspecific immunosuppression neither spares pre-existing memory cells nor discriminates between alloreactive and non-alloreactive T cells. Thus, although GVHD could be controlled to some degree by immunosuppression, it is at the cost of increased incidence of graft failure, leukemia relapse, and compromised immunity to post-transplant infections, such as cytomegalovirus (CMV). Therefore, a new therapeutic strategy that can prevent GVHD while preserving host immunity to infections will bring great benefit to patients.

Dendritic cells (DCs), major antigen presenting cells (APCs), can induce host immune responses. DCs also display functional plasticity to control immune responses. The ability of DCs, as immune controllers, is in part by the expression of pattern-recognition receptors (PRRs), including lectins. It was discovered that a lectin expressed on human DCs, DC-asialoglycoprotein receptor (DC-ASGPR), shows a unique ability to generate antigen-specific IL-10-producing regulatory T cells (Tregs). This applies to both self (prostate specific antigen) and foreign antigens (influenza HA1), as demonstrated in human in vitro and non-human primates in vivo. DC-ASGPR-induced antigen-specific Tregs efficiently suppress effector T cell proliferation and inflammatory cytokine expression. It was further discovered that signals via DC-ASGPR induce DCs to express IL-10, and this IL-10 promotes the generation of antigen-specific Tregs. Applicants sought out to test whether activation of DCs via DC-ASGPR can generate alloantigen-specific Tregs and thus can prevent GVHD and allograft transplantation. Data shows that targeting DC-ASGPR with anti-DC-ASGPR antibody results in decreased allogeneic T cell responses. These T cells can also secrete high level of IL-10 during their reactivation in response to alloantigens. Thus, Applicants surmise that DC-ASGPR can be a novel therapeutic target to inhibit such unwanted types of immune responses in patients who undergo transplantation surgery. This strategy is focusing on the induction of alloantigen-specific Tregs and thus may not interfere with host immunity to post-transplantation infections. Therefore, it was hypothesized that targeting DC-ASGPR with an anti-DC-ASGPR antibody not fused to an antigen prevents GVHD and allograft rejection but does not interfere with host immunity to infections.

Establishment of alloantigen-specific immune tolerance is an ultimate goal for the success of transplantation. The novel immunotherapeutic strategy described herein may eventually permit the production of alloantigen-specific Tregs in patients without interfering with host immunity to post-transplantation infections. Therefore, this study has a high significance in both medical and immunological implications.

The approach to controlling GVHD and transplant rejection by targeting DC-ASGPR is highly novel and innovative in the aspects of both basic immunology and medical implications.

DC-ASGPR has a specialized function to generate antigen-specific Tregs. DC-ASGPR, a scavenger receptor (Li, et al., 2012; Valladeau, et al., 2001), is expressed on subsets of human DCs (blood myeloid DCs: mDCs and skin dermal DCs but not plasmacytoid DCs: pDCs or Langerhans cells: LCs), monocytes, macrophages, and B cells (Li, et al., 2012). Endothelial cells express ASGPR, but not DC-ASGPR. DC-ASGPR is expressed in non-human primates (NHPs) (Li, et al., 2012), but not in mice. Mice have two closely linked genes called Mgl-1 and Mgl-2 which are distantly related to human DC-ASGPR, the former having a closer tissue distribution profile to the single human gene (not shown).

A. Anti-DC-ASGPR Antibody Treatment Suppresses Allogeneic CD4+ and CD8+ T Cell Proliferation To study the immunological function of DC-ASGPR, mouse monoclonal antibodies (mAbs) specific for human DC-ASGPR were first generated (Li, et al., 2012). To abolish their non-specific bindings to FcRs, recombinant mAbs carrying mouse variable region chimeras with human κ chain and human IgG4 carrying two site mutations (Reddy, et al., 2000) were made (Li, et al., 2012). Recombinant control mAb was also made in the same way.

It is important to note that both DC-ASGPR and Dectin-1 (Ni, et al., 2010) carry an immunoreceptor tyrosine-based activation motif (ITAM) and can induce IL-10 expression in DCs. However, DC-ASGPR is superior to Dectin-1 to generate Tregs (data not shown). In addition, anti-DC-ASGPR mAb does not induce DCs to express IL-1β, IL-23 or IL-12, while anti-Dectin-1 mAb does induce these cytokines, as previously described (Ni, et al., 2010).

Figure 4:
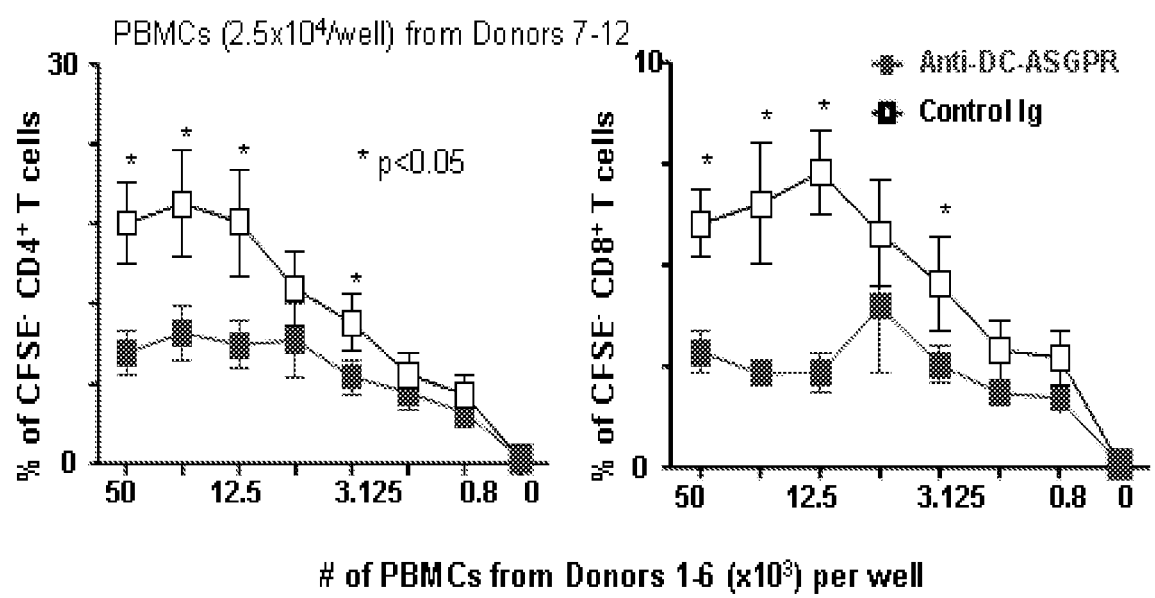
FIG. 4 shows that treatment of PBMCs from healthy donors with anti-DC-ASGPR mAb reduces the proliferation of $CD4^+$ and $CD8^+$ T cells from MHC-mismatched donors. Summary of data generated with PBMCs from 6 pairs of MHC-mismatched healthy donors (Mean±SD).

Anti-DC-ASGPR mAb can suppress MHC-mismatched allogeneic T cell responses: The effects of anti-DC-ASGPR mAb in MHC-mismatched allogeneic T cell responses was tested (FIG. 4). Different numbers of PKH25-labeled PBMCs from healthy donors were incubated overnight in the presence of anti-DC-ASGPR or control mAb, and then CFSE-labeled PBMCs from MHC-mismatched donors (total 6 pairs of MHC-mismatched donors) were co-cultured for 5 days. The percents of CFSE$^-$CD4$^+$ and CFSE$^-$CD8$^+$ T cells are presented. In the presence of control mAb, both CD4$^+$ and CD8$^+$ T cell proliferations were correlated with the numbers of stimulators (PBMCs from other donors). However, anti-DC-ASGPR mAb significantly decreased allogeneic CD4$^+$ and CD8$^+$ T cell proliferation, particularly when the number of stimulators (X-axis) was greater than 12.5× 10$^3$/well. Interestingly, total numbers of CD4$^+$ and CD8$^+$ T cells counted at the end of cultures were similar in both groups (control and anti-DC-ASGPR mAb-treated groups) (not shown).

Figure 5:
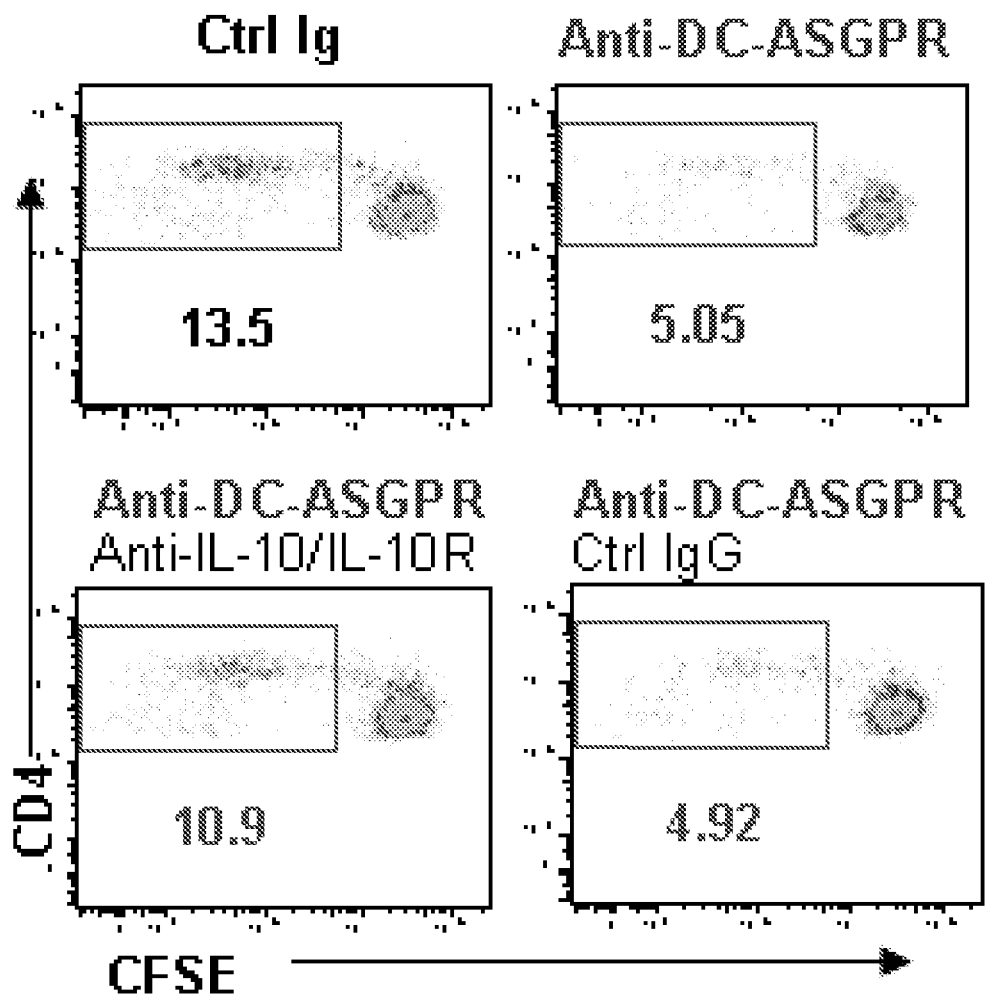
FIG. 5 shows that blocking IL-10 partially recovers allogeneic CD4+ T cells proliferation induced by anti-DC-ASGPR-activated PBMCs.

B. IL-10 Secreted from PBMC Activated with Anti-DC-ASGPR Contributes to the Suppression of Allogeneic CD4+ and CD8+ T Cell Responses Applicants further found that the decreased allogeneic T cell proliferation by anti-DC-ASGPR mAb was recovered (~60-70%) by neutralizing IL-10 on day 1 (2 h before adding MHC-mismatched PBMCs to the culture) (FIG. 5). This suggests that IL-10 secreted from anti-DC-ASGPR-activated APCs contributes to the decreased proliferation of T cells from MHC-mismatched donors.

Figure 6:
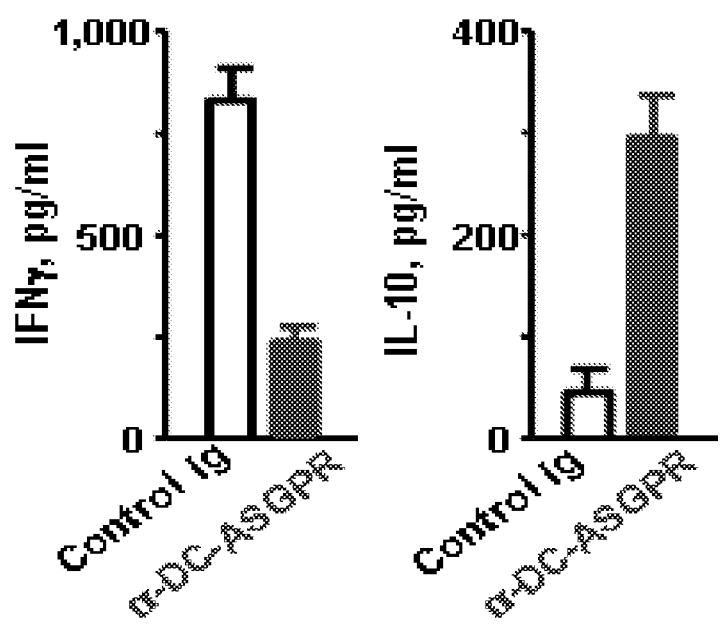
FIG. 6 shows that allogeneic CD4+ T cells cultured with anti-DC-ASGPR-activated PBMCs secrete decreased IFNγ but increased IL-10 during restimulation.

C. Anti-DC-ASGPR Antibody Treatment Results in Decreased IFNg-Producing, but Increased IL-10-Producing Regulatory T Cell Responses On day 8 of the co-culture of PBMCs from MHC-mismatched healthy donors, CFSE$^{low}$CD4$^+$ T cells were FACS-sorted, and then restimulated for 48 h with T cell-depleted PBMCs (from stimulators). The amounts of IL-10 and IFNγ in the supernatants were measured (FIG. 6). MHC-mismatched CD4$^+$ T cells co-cultured anti-DC-ASGPR-treated PBMCs secreted decreased amount of IFNγ but increased amount of IL-10 compared to CD4$^+$ T cells co-cultured with the same PBMC treated with control mAb. This suggests that treatment of PBMCs with anti-DC-ASGPR mAb promote the induction of alloantigen-specific Tregs which could play important roles in the inhibition of GVHD and allograft rejection in vivo.

Figure 7:
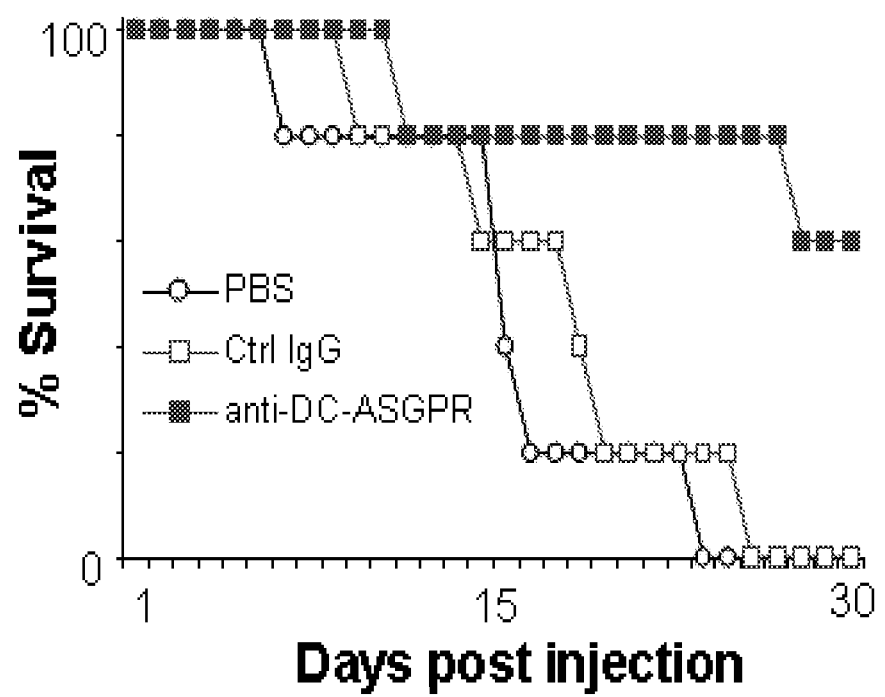
FIG. 7 demonstrates the effect of anti-DC-ASGPR mAb on delay of xenogenic GVHD in NOG mice.

D. Anti-DC-ASGPR Antibody Treatment Results in the Suppression of GVHD In Vivo Applicants further assessed the in vivo effects of anti-DC-ASGPR mAb. NOD/SCID/γc$^{-/-}$ (NOG) mice (5 mice/group) were injected intravenously (i.v.) on day 0 with 50×10$^6$ PBMCs from healthy donors. Animals also received 3 i.v. doses of antibodies (250 μg/dose) or PBS on days 0, 2, and 4. FIG. 7 shows that anti-DC-ASGPR treatment resulted in enhanced survival of animals (p<0.001) compared to control IgG or PBS treatment.

Taken together, this data demonstrates that targeting DC-ASGPR with anti-DC-ASGPR mAb promotes antigen-specific Treg responses. It is contemplated that this could also apply to the in vivo establishment of alloantigen-specific Tregs. This data and methodology described herein is useful in the research and development of a novel therapeutic that can efficiently inhibit GVHD and allograft rejection without interfering with host immune responses to infections.

Figure 8:
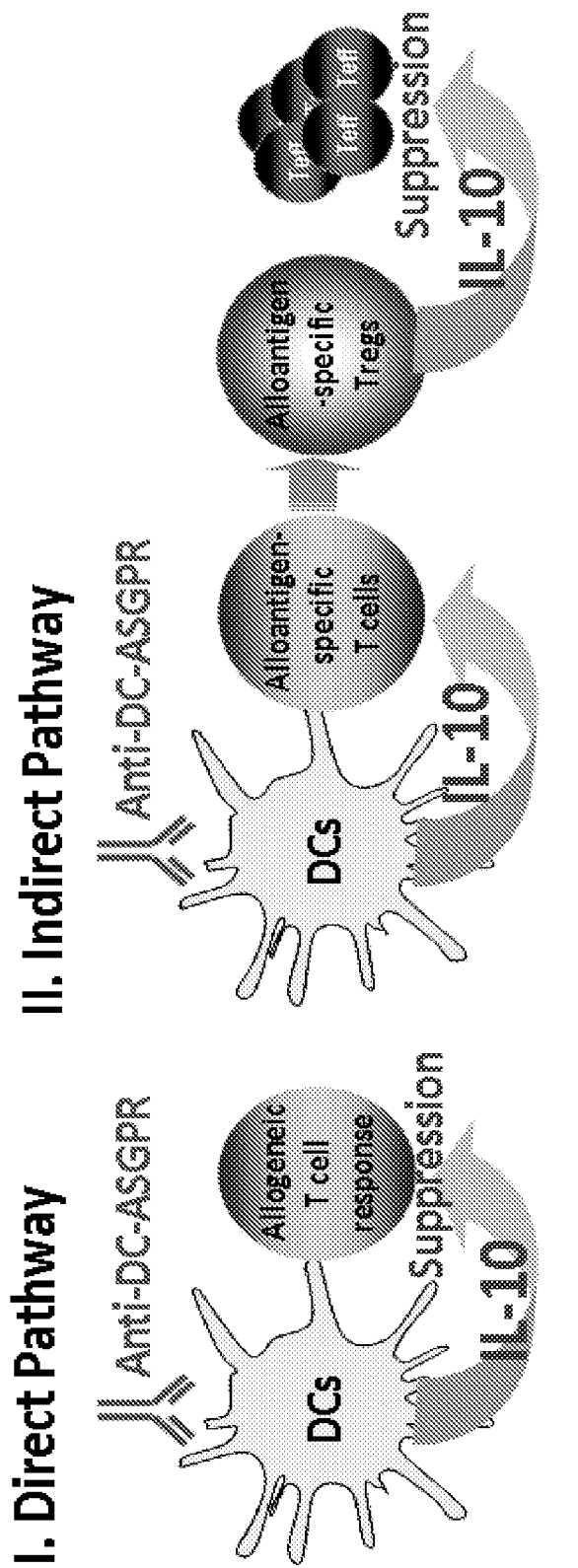
FIG. 8 shows the hypothetical pathways of DC-ASGPR-induced suppression of allogeneic T cell responses.

Applicants focused on novel antibodies that bind the DC-ASGPR that can induce DCs to secrete IL-10 and to induce IL-10-producing alloantigen-specific Tregs in the presence of alloantigens. Therefore, the strategy to inhibit GVHD and allograft rejection is based on two distinct but compensatory mechanisms (FIG. 8). First (Direct Pathway), IL-10 secreted from DC-ASGPR-activated DCs will directly inhibit allogeneic T cell responses in the early time point, as shown in FIG. 5. Second (Indirect Pathway), DC-ASGPR-induced IL-10 can contribute to the induction of IL-10-producing alloantigen-specific Tregs, as shown in FIG. 6. These two pathways could result in the enhanced survival of human PBMC-transferred NOG mice (FIG. 7). Such alloantigen-specific Tregs express IL-10 when they are activated at the place where alloantigens are available in vivo (Sagoo, et al., 2011).

It is specifically contemplated that embodiments of the invention may include one or more elements listed or exclude one or more elements listed throughout the specification. For example, specific embodiments may include one specific item listed (e.g. antibody framework) as described herein or embodiments of the invention may encompass multiple items from a specific list, such as 2, 3, 4, 5, 6, 7, 8, 9, 10, 20, 30, 40, or more. The invention may also exclude one or more listed elements, for example, some embodiments exclude 2, 3, 4, 5, 6, 7, 8, 9, 10, 20, 30, 40, or more elements listed. Furthermore, when ranges or numerical values are provided, it is specifically contemplated that certain ranges or numerical values may be excluded from the invention. Last, when the inventions is described in terms of including a particular feature, it is specifically contemplated that the invention may also exclude such feature.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

---

What is claimed is:

1. A method for preventing or treating graft versus host disease (GVHD) in a subject in need thereof comprising administering to the subject a pharmaceutical composition comprising a therapeutically effective amount of an anti-DC-ASGPR antibody or antigen binding fragment thereof operatively linked to IL-10; wherein the pharmaceutical composition does not comprise an antigen associated with an autoimmune disease or inflammatory condition.

2. The method of claim 1, wherein the anti-DC-ASGPR antibody or antigen binding fragment thereof comprises three heavy chain CDRs and three light chain CDRs from the variable regions of an anti-DC-ASGPR heavy chain and light chain variable region pair selected from SEQ ID NO:3 and 8; SEQ ID NO:58 and 60; SEQ ID NO:62 and 64; or SEQ ID NO:66 and 68.

3. The method of claim 1, wherein the anti-DC-ASGPR antibody or antigen binding fragment thereof comprises a γ4 constant region comprising a substitution of glutamic acid at residue 235 and/or a substitution of proline at residue 228 in the hinge region.

4. The method of claim 1, wherein the subject has been diagnosed as having GVHD.

5. The method of claim 1, wherein the subject is one that will receive or has received transplanted tissue.

6. The method of claim 1, wherein the method comprises administering to the subject an anti-DC-ASGPR antibody.

7. The method of claim 1, wherein the anti-DC-ASGPR antibody or antigen binding fragment thereof is administered intravenously.

* * * * *